US006077664A

United States Patent [19]
Slater et al.

[11] Patent Number: 6,077,664
[45] Date of Patent: *Jun. 20, 2000

[54] **THERMOPHILIC DNA POLYMERASES FROM *THERMOTOGA NEAPOLITANA***

[75] Inventors: Michael R. Slater; Fen Huang, both of Madison; James R. Hartnett, Fitchburg, all of Wis.; Elena Bolchakova, Foster City, Calif.; Douglas R. Storts; Paul Otto, both of Madison, Wis.; Katharine M. Miller, Verona, Wis.; Alexander Novikov, Foster City, Calif.; Galina A. Velikodvorskaya, Moscow, Russian Federation

[73] Assignee: Promega Corporation, Madison, Wis.

[*] Notice: This patent is subject to a terminal disclaimer.

[21] Appl. No.: 08/656,664

[22] Filed: May 31, 1996

Related U.S. Application Data

[63] Continuation-in-part of application No. 08/484,661, Jun. 7, 1995, Pat. No. 6,001,645.

[51] Int. Cl.[7] .............................. C12Q 1/68; C12P 19/34; C07H 21/04; C12N 9/00
[52] U.S. Cl. ........................ 435/6; 435/91.1; 435/91.2; 435/183; 435/320.1; 530/350; 536/23.2; 536/23.7
[58] Field of Search .............................. 435/183, 320.1, 435/6, 91.1, 91.2; 530/350; 536/23.2, 23.7

[56] References Cited

U.S. PATENT DOCUMENTS

| | | |
|---|---|---|
| 4,683,195 | 7/1987 | Mullis et al. .............................. 435/6 |
| 4,683,202 | 7/1987 | Mullis ...................................... 435/91 |
| 4,889,818 | 12/1989 | Gelfand et al. ......................... 435/194 |
| 4,962,020 | 10/1990 | Tabor ........................................ 435/6 |
| 4,965,188 | 10/1990 | Mullis et al. .............................. 435/6 |
| 5,075,216 | 12/1991 | Innis et al. ................................ 435/6 |
| 5,079,352 | 1/1992 | Gelfand et al. ......................... 536/27 |
| 5,210,036 | 5/1993 | Comb et al. ............................ 435/194 |
| 5,219,751 | 6/1993 | Starnes et al. .......................... 435/233 |
| 5,322,770 | 6/1994 | Gelfand ...................................... 435/6 |
| 5,322,785 | 6/1994 | Comb et al. ............................ 435/194 |
| 5,324,637 | 6/1994 | Thompson et al. ..................... 435/68.1 |
| 5,338,671 | 8/1994 | Scalice ................................... 435/91.2 |
| 5,352,600 | 10/1994 | Gelfand et al. ......................... 435/194 |
| 5,374,553 | 12/1994 | Gelfand ................................. 435/252.3 |
| 5,405,774 | 4/1995 | Abramson ............................. 435/252.3 |
| 5,409,811 | 4/1995 | Tabor ........................................ 435/6 |
| 5,420,029 | 5/1995 | Gelfand ................................. 435/194 |
| 5,455,170 | 10/1995 | Abramson ............................. 435/252.3 |
| 5,466,591 | 11/1995 | Abramson ............................. 435/194 |
| 5,491,086 | 2/1996 | Gelfand ................................. 435/194 |
| 5,498,523 | 3/1996 | Tabor et al. .............................. 435/6 |
| 5,614,365 | 3/1997 | Tabor et al. .............................. 435/6 |
| 5,656,497 | 8/1997 | Zeikus et al. .......................... 435/320.1 |
| 5,912,155 | 6/1999 | Chatterjee et al. ..................... 435/194 |
| 5,939,301 | 8/1999 | Hughes, Jr. et al. ................... 435/194 |
| 5,948,614 | 9/1999 | Chatterjee ................................ 435/6 |
| 6,001,645 | 12/1999 | Slater et al. ........................... 435/320.1 |

FOREIGN PATENT DOCUMENTS

| | | | |
|---|---|---|---|
| 02127188 | 6/1994 | Canada ............................ C12N 15/10 |
| 0 258 017 | 3/1988 | European Pat. Off. ......... C12N 15/00 |
| 0 371 437 | 11/1989 | European Pat. Off. .......... C12Q 1/68 |
| 655506 | 11/1994 | European Pat. Off. .......... C12Q 1/68 |
| WO 89/06691 | 7/1989 | WIPO .............................. C12N 15/54 |
| WO 91/09944 | 7/1991 | WIPO .............................. C12N 15/10 |
| WO 91/09950 | 7/1991 | WIPO .............................. C12N 15/54 |
| WO 92/03556 | 3/1992 | WIPO .............................. C12N 15/54 |
| WO 92/06188 | 4/1992 | WIPO .............................. C12N 15/00 |
| WO 92/06200 | 4/1992 | WIPO .............................. C12N 15/54 |
| WO 92/06202 | 4/1992 | WIPO .............................. C12N 15/54 |
| WO 92/09689 | 6/1992 | WIPO .............................. C12N 15/00 |
| WO 93/25706 | 12/1993 | WIPO ............................... C12Q 1/68 |
| WO 94/05797 | 3/1994 | WIPO .............................. C12P 19/34 |
| WO 94/26766 | 11/1994 | WIPO .............................. C07H 21/04 |
| WO 96/10640 | 4/1996 | WIPO .............................. C12N 15/54 |

OTHER PUBLICATIONS

Black, *Microbiology Principles and Applications*, 2d edition, Prentice Hall, New Jersey, (1993) p. 145–146.

Brock (ed.), *Thermophiles: General, Molecular and Applied Microbiology*, John Wiley & Sons, New York (1986), pp. 1–16.

Huber et al., "*Thermotoga maritima* sp. nov. Represents a New Genus of Unique Extremely Thermophilic Eubacteria Growing up to 90°C," *Arch. Microbiol.* 144:324–333 (1986).

Huber et al. "Validation of the Publication of New Names and New Combinations Previously Effectively Published Outside the IJSB," *Int. J. Syst. Bacteriol.*, 36:575 (1986).

Jannasch et al., "*Thermotoga neapolitana* sp. nov. of the Extremely Thermophilic, Eubacterial Genus Thermotoga," *Arch. Microbiol.*, 150:103–104 (1986).

Jannasch et al., "Validation of the Publication of New Names and New Combinations Previously Effectively Published Outside the IJSB,"*Int. J. Syst. Bacteriol.*, 39:93 (1989).

Windberger et al., *Thermotoga thermarum* sp. nov. and *Thermotoga neapolitana* Occurring in African Continental Solfataric Springs, *Arch. Microbiol.*, 151:506–512.

(List continued on next page.)

*Primary Examiner*—Kenneth R. Horlick
*Attorney, Agent, or Firm*—Melden & Carroll, LLP.

[57] ABSTRACT

The present invention relates to compositions of thermostable DNA polymerases derived from the hyperthermophilic eubacteria. In particular, the present invention comprises thermostable DNA polymerases from the hyperthermophilic eubacterium known as *Thermotoga neapolitana*. The present invention provides methods for utilizing naturally-occurring and non-naturally-occurring forms of *T. neopolitana* DNA polymerase. The *T. neopolitana* DNA polymerases of the present invention are used in combination with other compounds, including but not limited to pyrophosphatase and DNA polymerases from other thermophilic or hyperthermophilic organisms.

48 Claims, 6 Drawing Sheets

OTHER PUBLICATIONS

Windberger, et al., "Validation of the Publication of New Names and New Combinations Previously Effectively Published Outside the IJSB," *Int. J. Syst. Bacteriol.*, 42:327 (1992).

Holt et al. (eds.), *Bergey's Manual® of Determinative Bacteriology*, 9th ed., Williams & Wilkins, Baltimore, (1994), p. 333.

Ng and William R. Kenealy, "Industrial Applications of Thermostable Enzymes," in T.D. Brock (ed.), *Thermophiles: General, Molecular, and Applied Microbiology*, (1986), John Wiley & Sons, New York, pp. 197–215.

Bessman et al., "Enzymatic Synthesis of Deoxyribonucleic Acid," *J. Biol. Chem.* 223:171 (1957).

Buttin and Kornberg, "Enzymatic Synthesis of Deoxyribonucleic Acid," *J. Biol. Chem.* 241:5419 (1966).

Joyce and Steitz, "DNA Polymerase I: From Crystal Structure to Function Genetics," *Trends Biochem. Sci.*, 12:288–292 (1987).

Stenesh and McGowan, "DNA Polymerase from Mesophilic and Thermophilic Bacteria," *Biochim. Biophys. Acta* 475:32–44 (1977).

Stenesh and Roe, "DNA Polymerase From Mesophillic and Thermophilic Bacteria. I. Purfication and properties of DNA Polymerase from *Bacillus Licheniformis* and *Bacillus Stearothermophillus*," *Biochim. Biophys. Acta* 272:156–166 (1972).

Low et al., "Purification and Characterization of DNA Polymerase III from *Bacillus subtilis*," *J. Biol. Chem.*, 251:1311 (1976).

Ott et al."Cloning and Characterization of the polC Region of *Bacillus subtilis*," *J. Bacteriol.*, 165:951 (1986).

Harwood et al., "*Microcroccus luteus* Deoxyribonucleic Acid Polymerase,"*J. Biol. Chem.*, 245:5614 (1970).

Hamilton and Grossman, "Enzymatic Repair of Deoxribonucleic Acid: The Biochemical and Biological Repair Properties of a Deoxyribonucleic Acid Polymerase from *Micrococus luteus*," *Biochem.*, 13:1885 (1974).

Lopez et al., "Characterization of the polA Gene of *Streptococcus pneumoniae* and Comparison of the DNA Polymerase I It Encodes to Homologous Enzymes from *Escherichia coli* and Phage T7," *J. Biol. Chem.*, 264(7):4255–4263 (1989).

Engler and Bessman, "Characterization of a Mutator DNA Polymerase I from *Salmonella typhimurium*," Cold Spring Harbor Symp., 43:929 (1979).

Kaledin et al.,"Isolation and Properties of DNA Polymerase from Extremely Thermophilic Bacterium *Thermus aquaticus* YT1," *Biochem*, 45:494–501 (1980).

Chien et al., "Deoxyribonucleic Acid Polymerase from the Extreme Thermophile *Thermus aquaticus*," *J. Bacteriol.*, 127:1550–1557 (1976).

University of Cincinnati Master's thesis A. Chien, "Purification and Characterization of DNA Polymerase from *Thermus aquaticus*," (1976).

University of Cincinnati, Master's thesis by D. B. Edgar, "DNA Polymerase From an Extreme Thermophile: *Thermus aquaticus*," (1974.

Simpson et al., Biochem. "Purification and Some Properties of a Thermostable DNA Polymerase from a Thermotoga Species," *Biochem. Cell Biol.*, 68:1292–1296 (1990).

Myers and Gelfand, "Reverse Transcription and DNA Amplification by a *Thermus thermophilus* DNA Polymerase," *Biochem.*, 30(31):7661–7666 (1991).

Bechtereva et al., "DNA Sequencing with Thermostable Tet DNA Polymerase from *Thermus thermophilus*," *Nucleic Acids Res.*, 17(24):10507 (1989).

Glukhov et al., "Amplification of DNA Sequences of Epstein–Barr and Human Immunodeficiency Viruses Using DNA–Polymerase from *Thermus thermophilus*," *Mol. Cell. Probes* 4:435–443 (1990).

Carballeira et al., "Purification of a Thermostable DNA Polymerase from *Thermus thermophilus* HB8, Useful in the Polymerase Chain Reaction," *BioTech.*, 9:276–281 (1990).

Rüttiman et al., "DNA Polymerases from the Extremely Thermophilic Bacterium *Thermus thermophilus* HB–8," *Eur. J. Biochem.*, 149:41–46 (1985).

Oshima et al., "Physichemical Properties of Deoxyribnucleic Acid from an Extreme Thermophile," *J. Biochem.*, 75:179–183 (1974).

Sakaguchi and Yajima, "Thermophilic and Stable DNA Polymerase from *Thermus thermophilus*," *Fed. Proc.*, 33:1492 (1974).

Kaledin et al., "Isolation and Properties of DNA Polymerase from the Extremely Thermophilic Bacterium *Thermus flavus*," *Biochem.*, 46(9):1247–1254 (1981); Biokhimiya 46:1576–1584 (1981).

Kaledin et al., "Isolation and Properties of DNA Polymerase from the Extremely Thermophilic Bacterium *Thermus ruber*," *Biochem.*, 47(11):1515–1521 (1982); Biokhimiya 47:1785–1791 (1982).

Hamal et al., "Purification and Characterization of a DNA Polymerase from the Archaebacterium *Thermoplasma acidophilum*," *Eur. J. Biochem.*, 190:517–521 (1990).

Forterre et al., "Studies on DNA Polymerases and Topoisomerases in Archaebacteria," *Can. J. Microbiol.*, 35:228–233 (1989).

Salhi et al., "DNA Polymerase from *Sulfolobus acidocaldarius* Replication at Hight Temperature of Long Stretches of Single–Stranded DNA," *J. Mol. Biol.*, 209:635–644 (1989).

Salhi et al., "The DNA Polymerase from the Archaebacterium *Sulfolobus Acidocaldarius*: A Thermophilic and Thermoresistant Enzyme which can Perform Automated Polymerase Chain Reaction,"*Biochem. Biophys. Res. Comm.*, 167(3):1341–1347 (1990).

Rella et al., "Purification and Properties of a Thermophilic and Thermostable DNA Polymerase from the Archaebacterium *Sulfolobus Solfataricus*," *Ital. J. Biochem.*, 39:83–99 (1990).

Rossi et al., "Structure and Properties of a Thermophilic and Thermostable DNA Polymerase Isolated from *Sulfolobus solfataricus*," *System. Appl. Microbiol.*, 7:337–341 (1986).

Klimczak et al., "Purification and Characterization of DNA Polymerase from the Archaebacterium *Sulfolobus acidocaldarius*," *Nucleic Acids Res.*, 13(14):5269–5282 (1985).

Elie et al., "A DNA Polymerase from a Thermoacidophilic Archaebacterium: Evolutionary and Technological Interests," *Biochim. Biophys. Acta* 951:261–267 (1988).

Uenrori et al., "Cloning of the DNA Polymerase Gene of *Bacillus caldotenax* and Characterization of the Gene Product," *J. Biochem.*, 113:401–410 (1993).

Sellmann et al., "Purification and Characterization of DNA Polymerases from Bacillus Species," *J. Bacteriol.*, 174(13):4350–4355 (1992).

Kaboev et al., "Purification and Properties of Deoxyribonucleic Acid Polymerase from *Bacillus stearothermophilus*," *J. Bacteriol.*, 145(1):21–26 (1981).

Klimczak et al., "Purification and Characterization of DNA Polymerase from the Archaebacterium *Methanobacterium thermoautotrophicum,*" *Biochem.,* 25(17):4850–4855 (1986).

Kong et al., "Characterization of DNA Polymerase from the Hyperthermophile Archaea *Thermococcus litorali,*" *J. Biol. Chem.* 268:1965 (1993).

Lundberg et al., "High–fidelity Amplification Using a Thermostable DNA Polymerase Isolated From *Pyrococcus furiosus,*" *Gene* 108:1 (1991).

Bankier, "Dideoxy Sequencing Reactions Using Klenow Fragment DNA Polymerase I," in H. and A. Griffin (eds.), *Methods in Molecular Biology: DNA Sequencing Protocols,* Humana Press, Totowa, NJ, (1993), pp. 83–90.

Lawyer et al., "Isolation, Characterization, and Expression in *Escherichia coli* of the DNA Polymerase Gene from *Thermus aquaticus*," The *J.Bio. Chem.* 264(11):6427–6437 (1989).

Lawyer et al., "High–Level Expression, Purification, and Enzymatic Characterization of Full–length *Thermus aquaticus* DNA Polymerase and a Truncated Form Deficient in 5' to 3' Exonuclease Activity," *PCR Meth. Appl.,* 2:275–287 (1993).

Anderson and Young, Quantitative Filter Hybridization, in *Nucleic Acid Hybridization* (1985).

Kacian et al., "A Replicating RNA Molecule Suitable for a Detailed Analysis of Extracellular Evolution and Replication," *Proc. Natl. Acad. Sci USA* 69(10):3038–3042 (1972).

Chamberlin et al., "New RNA Polymerase from *Escherichia coli* Infected with Bacteriophage T7," *Nature* 228:227–231 (1970).

Wu and R. B. Wallace, "The Ligation Amplification Reaction (LAR)—Amplification of Specific DNA Sequences Using Sequential Rounds of Template–Dependent Ligation," *Genomics* 4:560–569 (1989).

Erlich (ed.) *PCR Technology* (Stockton Press 1989).

Maniatis, T. et al., "Regulation of Inducible and Tissue–Specific Gene Expression," *Science* 236:1237–1245 (1987).

Voss, S.D. et al., "The Role of Enhancers in the Regulation of Cell–Type–Specific Transcriptional Control," *Trends Biochem. Sci.,* 11:287–289 (1986).

Dijkema, R. et al., "Cloning and Expression of the Chromosomal Immune Interferon Gene of the Rat," *EMBO J.* 4(3):761–767 (1985).

Uetsuki, T. et al., "Isolation and Characterization of the Human Chromosomal Gene for Polypeptide Chain Elongation Factor–1α," *J. Biol. Chem.,* 264(10):5791–5798 (1989).

Kim, D.W. et al., "Use of the Human Elogation Factor 1α Promoter as a Versatile and Efficient Expression System," *Gene* 91:217–223 (1990).

Mizushima, S. and Nagata, S., "pEF–BOS, a Powerful Mammalian Expression Vector," *Nuc. Acids. Res.,* 18(17):5322 (1990).

Gorman, C.M. et al., "The Rous Sarcoma Virus Long Terminal Repeat is a Strong Promoter when Introduced into a Variety of Eukaryotic Cells by DNA–Mediated Transfection," *Proc. Natl. Acad. Sci. USA* 79:6777–6781 (1982).

Boshart, M. et al., "A Very Strong Enhancer is Located Upstream of an Immediate Early Gene of Human Cytomegalovirus," *Cell* 41:521–530 (1985).

Sambrook, J. et al., *Molecular Cloning: A Laboratory Manual,* 2nd ed., Cold Spring Harbor Laboratory Press, New York (1989) pp. 16.7–16.8.

Kornberg, *DNA Replication,* W.H. Freeman and Co., San Francisco, pp. 127–139 (1980).

Tindall and T.A. Kunkell, "Fidelity of DNA Synthesis by the *Thermus aquaticus* DNA Polymerase," *Biochem* 27:6008–6013 (1988).

Brutiag et al., "An Active Fragment of DNA Polymerase Produced by proteolytic Cleavage," *Biochem. Biophys. Res. Commun.* 37:982 (1969).

Erlich et al., "Recent Advances in the Polymerase Chain Reaction," *Science* 252:1643–1651 (1991).

Bebenek et al., "The Fidelity of DNA Synthesis Catalyzed by Derivatives of *Escherichia coli* DNA Polymerase I*," *J. Biol. Chem.* 265(23):13878–13887 (1990).

Barnes, "The Fidelity of Taq Polymerase Catalyzing PCR is Improved by an N–Terminal Deletion" *Gene* 112:29–35 (1992).

Bernad et al. "A Conserved 3'→5' Exonuclease Active Site in Prokaryotic and Eukaryotic DNA Polymerases," *Cell* 59:219–228 (1989).

Derbyshire et al., "The 3'–5' Exonuclease of DNA Polymerase I of *Escherichia coli*: Contribution of Each Amino Acid at the Active Site to the Reaction," *EMBO J.* 10(1):17–24 (1991).

Maxam and Gilbert, "A New Method for Sequencing DNA," *Proc. Natl. Acad. Sci. USA* 74:560 (1977).

Sanger et al., "DNA Sequencing with Chain Terminating Inhibitors," *Proc. Natl. Acad. Sci. USA* 74:5463 (1977).

Heiner et al., Applied Biosystems, Inc. DNA Sequencer Model 370 User Bulletin–Taq Polymerase: Increased Enzyme Versatility in DNA Sequencing (1988).

Mizusawa et al., "Improvement of the Dideoxy Chain Termination Method of DNA Sequencing by Use of Deoxy-7–deazaguanosine Triphosphate in Place of dGTP," *Nucl. Acids Res.* 14:1319 (1986).

Barr et al., "7–Deaza–2' –Deoxyguanosine–5' Triphosphate: Enhanced Resolution in M13 Dideoxy Sequencing," *Biotechniques* 4:428 (1986).

Innis et al., "DNA Sequencing with *Thermus aquaticus* DNA Polymerase and Direct Sequencing of Polymerase Chain Reaction–Amplified DNA," *Proc. Natl. Acad. Sci USA* 85:9436–9440 (1988).

Sambrook et al., Molecular Cloning: A Laboratory Manual, 2nd ed., Cold Spring Harbor Laboratory Press, NY (1989) pp. 6.30–6.31.

Ausubel et al. Eds, Short Protocols in Molecular Biology, 2nd ed. (1992) John Wiley & Sons, New York, pp.7–8 to 7–16 and 7–29 to 7–37.

Matthews, "Structural and genetic analysis of protein stability," *Ann. Rev. Biochem.* 62:139 (1993).

Frey and Suppmann, "Demonstration of the Expand™ PCR System's Greater Fidelity and Higher Yields with a lacl- –based PCR Fideltiy Assay," *Biochemica* 2:8 (1995).

Keohavong and Thilly, "Fidelity of DNA Polymerases in DNA Amplification," *Proc. Natl. Acad. Sci. USA* 86:9253–9257 (1989).

Provost et al. "Transgenic Systems for In Vivo Mutation Analysis,"*Mut. Research* 288:133 (1993).

Simpson et al, "Purification of a Thermostable DNA Polymerase from a Thermotoga Species," *Annals of New York Academy of Sciences* 613:426–428 (1990).

Tabor et al., "A single residue in DNA polymerases of the *Escherichia coli* DNA polymerase I family is critical for distinguishing between deoxy and dideoxynucleotides," *Proc. Natl. Acad. Sci* 92:6339–6343 (1995).

Reeve et al., "A novel thermostable polymerase for DNA sequencing," *Nature,* 376:796–797 (1995).

Brandis et al., "Slow Rate of Phosphodiester Bond Formation Accounts for the Strong Bias that Taq DNA Polymerase Shows against 2',3'-Dideoxynucleotide Terminators," *Biochemistry,* 35:2189–2200 (1996).

Kim et al., "Crystal Structure of *Thermus aquaticus* DNA polymerase," *Nature,* 376:612–616 (1995).

Lawyer et al., "The DNA Polymerase I Gene from the Extreme Thermophile, *Thermotoga maritima*: Identification, Cloning, and Expression of Full–Length and Truncated Forms in *Escherichia coli*," 92nd Gen.Mtg. of Am.Soc. for Microbiology, H–104:200 (1992).

Papanicolaou et al., "Polymerase–specific Differences in the DNA Intermediates of Frameshift Mutagenesis: In vitro Synthesis Errors of *Escherichia coli* DNA Polymerase I and its Large Fragment Derivative," *J. Mol. Biol,* 207:335–353 (1989).

Barnes, "PCR Amplification of up to 35–kb DNA with High Fidelity and High Yield from λ Bacteriophage Templates," Proc. Natl. Acad. *Science* 91:2216–2220 (1994).

FIGURE 2

|  |  | Exo I | | Exo II | | Exo III | |
|---|---|---|---|---|---|---|---|
| Bsu Pol III | 419 | ETYV--VFDVETTGLSAVY | 502 | LVAHN-A-SFDMGFLN | 552 | TLCKKF-DIELTQH |
| Eco Pol III ε | 6 | TRQL--VLDTETTGMNQIG | 95 | LVIHN-AA-FDIGFMD | 147 | ALCARY-EIDNSKR |
| ØT4 | 182 | RVIYMPFDNERDMMEYI | 210 | FTGWNI-EGFDVPYIM | 332 | DKIRGF--IDLVFS |
| ØT7 | 1 | ---MIVSDIEANALLESV | 57 | V-FHNGH-KYDVPALT | 165 | EEMMDYNVQDVVVT |
| Eco Pol I | 348 | KAPVFAFDTETDSLDNIS | 417 | V-GQNL--KYDRGILA | 492 | EEAGRVAAEDADVT |
| Tma | 316 | ESPSFAIDLETSSLDPFD | 382 | V-GQNL--KFDYKVLM | 459 | EKAANYSCEDADIT |
| Tne | 316 | EVPSFALDLETSSLDPFN | 382 | V-GQNL--KYDYKVLM | 459 | DKAANYSCEDADIT |

FIGURE 3

```
  1 MVQIPQNPLILVDGSSYLYRAYHAF-PPLTNSAGEPTSAMYGVLNMLRSILMQY---KPTHAAVVFDAKGKTFRDELFEH Eco
  1 MAR-----LFLFDGTALAYRAYYALDRSLSTSTGIPTNAIYGVARMLVRFIKDHIIVGKDYMAVAFDKKAATFRHKLLEI Tma
  1 MAR-----LFLFDGTALAYRAYYALDRSLSTSTGIPTNAVYGVARMLVKFIKEHIIPEKDYAAVAFDKKAATFRHKLLEA Tne

77 YKSHRPPMPDDLRAQIEPLHAMVKAMGLPLLAVSGVEADDVIGTLAREAEKAGRPVLISTGDKDMAQLVTPNITL---IN Eco
 76 YKAQRPKTPDLLIQQLPYIKKLMEALGMKVLEVEGYEADDIIATLAVKGLPLFDEIFIVTGDKDMLQLVNEKIKVWRIVK Tma
 76 YKAQRPKTPDLLVQQLPYIKRLIEALGFKVLELEGYEADDIIATLAVKGCTFFDEIFIITGDKDMLQLVNEKIKVWRIVK Tne

154 IMTNTIL-GPEEVWNKYGVPPELIIDFLALAGDSSDNIPGVEGVGEKTAQALLQGLGGLDTLYAEPEKIAGLSFRGAKTV Eco
156 GISDLELYDAQKVKEKYGVEPQQIPDLLALTGDEIDNIPGVTGIGEKTAVQLLPKYKDLEDII---NMVRELPQRVRKA- Tma
156 GISDLELYDSKKVKERYGVEPHQIPDLLALTGDEIDNIPGVTGIGEKTAVQLLGKYRNLEDIL---EHARELPQRVRKA- Tne

233 AAKLEONKEVAYLSYQLATIKIDVELELTCEQLEVQOPAAEELLGLEKKYEFKRWTADVEAGKWLQAKGAKPAAKPQETS Eco
232 ---LLRDRENAILSKKLAILETNVPIEIMWEELRYQGYDREKLLPILKELEF------------------ASIMKELQ Tma
232 ---LLRDREVAILSKKLATLVTNAPVEVDWEEMKYRGYDKRKLLPILKELEF------------------ASIMKELQ Tne

313 VADEAPEVTATVISYDNYVTILDEETLKAWIAKLEKAPVFAFDTIELDSLDNISANLVGLSFAIEPGVAAYIPVAHDYLDA Eco
289 LYEESEPVG---------YRIVKDLVEFEKLIEKIRESPSFAIDLETSSLDPFDCQIVGISVSFKPKEAYYIPLHHR---N Tma
289 LYEEAEPTG---------YEIVKDHKTFEDLIEKLKEVPSFALDLETSSLDPFNCEIVGISVSFKPKTAYYIPLHHR---N Tne

393 PDQISRERALELLKPLLEDEKALKVGQNLKYDRGILANYGIELRGIAFDTMLESYILNSVAGRHDMDSLAERWLKHKTIT Eco
358 AQNLDEKPVLKKLKEILEDFGAKIVGQNLKFDYKVLMVKGVEPVPFPFDTMIAAYLLEPNEKKFNLDDIALKFLGYKMTS Tma
358 AQNLDETLVLSKLKEILEDPSSKIVGQNLKYDYKVLMVKGISPVVPHFDTMIAAYLLEPNEKKFNLEDLSLKFLGYKMTS Tne

473 FEEIAGKGKN--OLTIFNOIALEEAGRYAAEDADVILQLHLKMWPDLQKHKGPLNVFENIEMPLVGVLSRIEFNGVKIDE Eco
438 YQELMSFSFPLFGFSFADVPVEKAANYSCEDADITYRLYKTIL--SLKLHEADLENVFYKIEMPLVNVLARMELNGVYVDT Tma
438 YQELMSFSSPLFGFSFADVPVDKAANYSCEDADITYRLYKTIL--SMKLHEAELENVFYRIEMPLVNVLARMELNGVYVDT Tne

550 KVLHNFSEEBLTLRLAEIEKKAHEIAGEDFNLSSIKQLOTILFEKQGIKPLKKIPGGAPSTSDEVLEEIALDYPLPKVIL Eco
516 EFLKKLSEEYGKKLEELABEIYRIAGEPFNINSPKQVSRILFEKLGIKPRGKTTKTGDYSTRIEVLEEIAGEHEIIPLIL Tma
516 EFLKKLSEEYGKKLEELAEKIYQIAGEPFNINSPKQVSKILFEKLGIKPRGKTTKTGAYSTRIEVLEEIANEHEIVPLIL Tne

629 EYRGLAKLKSTYIDKLPLMINPKTGRVHISYHQAVTATGRLSSIDPNLQNIFVRNEEGRRIRQAFIAPE-DYVIVSADYS Eco
596 EYRKIQKLKSTYIDALPKMVNPKTGRIHASFNQTGTATGRLSSSDPNLQNLPTKSEEGKEIRKAIVPQDENWWIVSADYS Tma
596 EYRKIQKLKSTYIDTLPKLVNPKTGRIHASFHQTGTATGRLSSSDPNLQNLPTKSEEGKEIRKAIVPQDPDWWIVSADYS Tne

708 QIELRIMAHLSRDKGLLTAFEEGKDIHRATAAEVFGLPLEIVTSEQRRSAKAINFGIIYGMSAFGLAROLNIPRKEACKY Eco
676 QIELRILAHLSGDENLLRAFEEGIDVHTLTASRIENVKPEEVIEEMRRAGKMVNFSIIYGVTPYGLSVRLGVPVKEAEKM Tma
676 QIELRILAHLSGDENLVKAFEEGIDVHTLTASRIYNVKPEEVNEEMRRVGKMVNFSIIYGVTPYGLSVRLGIPVKEAEKM Tne

788 VDLYFERYPEVLEYMERTRAQAKEQGYVETLDGRRLYLPDIKSSNGARRAAAERAAINAPMQGTAADIIKRAMIAVDAVL Eco
756 IWMYFVLYPKVRDYIQRVVSEAKEKGYVRTLFGRKRDIPQLMARDRNTQAEGERIAINTPIQGTAADIIKLAMIDIDREL Tma
756 IISYFTLYPKVRSYIQQVVAEAKEKGYVRTLFGRKRDIPQLMARDKNTQSEGERIAINTPIQGTAADIIKLAMIDIDEEL Tne

868 QAEQPRVRMIQVHDELVFEVHKDDVDAVAKQIHQLMENCTRLDVPLLVEVGSGENWDQAH. Eco
836 KERKMRSKMIIQVHDELVFEVPNEEKDALVELVKDRMTNVVKLSVPLEVDVIIGKIWS. Tma
836 RKRNMKSRMIIQVHDELVFEVPDEEKEELVDLVKNKMTNVVKLSVPLEVDISIGKSWS. Tne
```

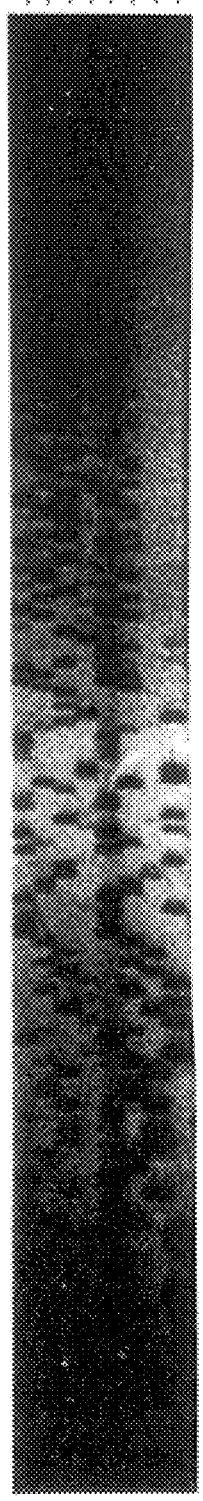
FIG. 5A
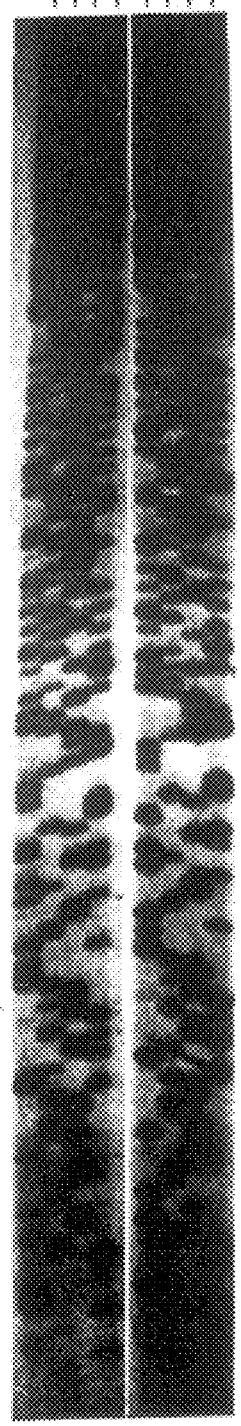
FIG. 5B

THERMOPHILIC DNA POLYMERASES FROM *THERMOTOGA NEAPOLITANA*

The present application is a Continuation-in-Part of U.S. patent application Ser. No. 08/484,661, filed Jun. 7, 1995, U.S. Pat. No. 6,001,645.

FIELD OF THE INVENTION

The present invention relates to thermostable DNA polymerases derived from the hyperthermophilic eubacteria *Thermotoga neapolitana* and means for isolating and producing the enzymes. Thermostable DNA polymerases are useful in many recombinant DNA techniques, especially thermal cycle sequencing and nucleic acid amplification.

BACKGROUND

Thermophilic bacteria are organisms which are capable of growth at elevated temperatures. Unlike the mesophiles, which grow best at temperatures in the range of 25–40° C., or psychrophiles, which grow best at temperatures in the range of 15–20° C., thermophiles grow best at temperatures greater than 50° C. Indeed, some thermophiles grow best at 65–75° C., and some of the hyperthermophiles grow at temperatures up to 130° C. (See e.g, J. G. Black, *Microbiology Principles and Applications,* 2d edition, Prentice Hall, N.J., [1993] p. 145–146).

The thermophilic bacteria encompass a wide variety of genera and species. There are thermophilic representatives included within the phototrophic bacteria (i.e., the purple bacteria, green bacteria, and cyanobacteria), eubacteria (i.e., Bacillus, Clostridium, Thiobacillus, Desulfotomaculum, Thermus, lactic acid bacteria, actinomycetes, spirochetes, and numerous other genera), and the archaebacteria (i.e., Pyrococcus, Thermococcus, Thermoplasma, Thermotoga, Sulfolobus, and the methanogens). There are aerobic, as well as anaerobic thermophilic organisms. Thus, the environments in which thermophiles may be isolated vary greatly, although all of these organisms are always isolated from areas associated with high temperatures. Natural geothermal habitats have a worldwide distribution and are primarily associated with tectonically active zones where major movements of the earth's crust occur. Thermophilic bacteria have been isolated from all of the various geothermal habitats, including boiling springs with neutral pH ranges, sulfur-rich acidic springs, and deep-sea vents. For all of these organisms, it appears that the organisms present in these geothermal habitats are optimally adapted to the temperatures at which they are living (T. D. Brock, "Introduction: An overview of the thermophiles," in T. D. Brock (ed.), *Thermophiles. General, Molecular and Applied Microbiology*, John Wiley & Sons, New York [1986], pp. 1–16). Basic as well as applied research on thermophiles has provided some insight into the physiology of these organisms, as well as promise for use of these organisms in industry and biotechnology.

I. The Genus Thermotoga

The Thermotoga is a recently described genus with three recognized species, which includes the most extremely thermophilic eubacteria known. The genus was first described in 1986, by Huber et al., (R. Huber et al. Arch. Microbiol. 144:324 [1986]; and Int. J. Syst. Bacteriol., 36:575 [1986]). At this time, there was only one species described, *T. maritima*. *T. neapolitana* was first described by Jannasch et al. in 1986 (Jannasch et al., Arch. Microbiol., 150:103–104 [1986]; and Int. J. Syst. Bacteriol., 39:93 [1989]). *T. thermarum* was described by Windberger et al. in 1989 (Windberger et al., Arch. Microbiol., 151:506–512; and Int. J. Syst. Bacteriol., 42:327 [1992]).

These organisms were originally isolated from geothermally heated marine sediments and hot springs. For example, *T. maritima* has been isolated from geothermally heated sea floors in Italy, the Azores, Indonesia, and Iceland as well as from continental, solfataric springs in Africa. *T. neapolitana* has been isolated from a submarine thermal vent near Naples and from continental, solfataric springs in Africa.

Members of the genus Thermotoga are considered to be hyperthermophilic, as they are capable of growth at temperatures up to 90° C., although growth will occur at temperatures between 55° C. and 90° C.; the optimum growth temperature is between 70–80° C. The Thermotoga are strictly anaerobic, non-sporing, Gram-negative rods, that ferment carbohydrates, and may be motile by polar, lateral or peritrichous flagella, although some strains are non-motile. The cells are surrounded by a sheath-like outer structure which usually balloons over the ends. In all species of Thermotoga, 1–4 cells may be enclosed within one sheath.

*T. maritima*, *T. neapolitana*, and *T. thermarum* are distinct species as judged by the numerous differences. For example, *T. maritima* possesses a single subpolar flagellum and is motile, while motile strains of *T. neapolitana* possess peritrichous flagella (some strains are non-motile), and *T. thermarum* possesses lateral flagella. In addition, *T. neapolitana* will grow in NaCl concentrations ranging from 0.25 to 6.0%, while *T. maritima* will grow in NaCl concentrations ranging from 0.25 to 3.75%, and *T. thermarum* will grow in NaCl concentrations ranging from 0.2–0.55% (J. G. Holt et al. (eds.), *Bergey's Manual® of Determinative Bacteriology,* 9th ed., Williams & Wilkins, Baltimore, [1994], p. 333). Also, there are differences in the susceptibility of these species to rifampicin, and differences in the inhibitory effects of hydrogen and sulfur on these species. Furthermore, the rate of growth at optimum growth temperature (80° C.) is a doubling time of about 45 min for *T. neapolitana* and about 75 min for *T. maritima*. The G+C content of the DNA of *T. maritima* and *T. neapolitana* is 46% and 41%, respectively. The DNA from *T. maritima* and *T. neapolitana* shows only about 25–30% homology by DNA-DNA hybridization studies.

A few of the enzymes of the Thermotoga and other thermophilic genera have been studied in varying degrees of detail. As discussed below, the use of thermophilic enzymes in industry has been viewed as providing advantages over the use of mesophilic enzymes.

II. Uses for Thermophilic Enzymes

Advances in molecular biology and industrial processes have led to an increased interest in thermophilic organisms such as Thermotoga. Of particular interest has been the development of thermophilic enzymes for use in industrial processes such as the detergent, flavor-enhancing, and starch industries. Indeed, the cost savings associated with the longer storage stability and higher activity at higher temperatures of thermophilic enzymes, as compared to mesophilic enzymes, provide good reason to select and develop thermophilic enzymes for industrial and biotechnology applications. Thus, there has been much research conducted to characterize enzymes from thermophilic organisms. However, some thermophilic enzymes have less activity than their mesophilic counterparts under similar conditions at the elevated temperatures used in industry (typically temperatures in the range of 50–100° C.) (T. K. Ng and William R. Kenealy, "Industrial Applications of Thermostable Enzymes," in T. D. Brock (ed.), *Thermophiles: General, Molecular, and Applied Microbiology,* [1986], John Wiley & Sons, New York, pp. 197–215). Thus, the choice of a thermostable enzyme over a mesophilic one may not be as beneficial as originally assumed. Nonetheless, of the $400 million worth of enzymes sold worldwide in 1984, 90% were thermostable enzymes used by the detergent and starch industries (Ng and Kenealy, at p. 206). However, much research remains to be done to characterize and compare thermophilic enzymes of importance in areas such as molecular biology (i.e., polymerases, ligases, topoisomerases, restriction endonucleases, etc.).

III. Thermophilic DNA Polymerases

Extensive research has been conducted on the isolation of DNA polymerases from mesophilic organisms such as *E. coli.* (See e.g., Bessman et al., J. Biol. Chem. 223:171 [1957]; Buttin and Kornberg, J. Biol. Chem. 241:5419 [1966]; and Joyce and Steitz, Trends Biochem. Sci., 12:288–292 [1987]). Other mesophilic polymerases have also been studied, such as those of *Bacillus licheniformis* (Stenesh and McGowan, Biochim. Biophys. Acta 475:32–44 [1977]; Stenesh and Roe, Biochim. Biophys. Acta 272:156–166 [1972]); *Bacillus subtilis* (Low et al., J. Biol. Chem., 251:1311 [1976]; and Ott et al., J. Bacteriol., 165:951 [1986]; *Salmonella typhimurium* (Harwood et al., J. Biol. Chem., 245:5614 [1970]; Hamilton and Grossman, Biochem., 13:1885 [1974]), *Streptococcus pneumoniae* (Lopez et al., J. Biol. Chem., 264:4255 [1989]), and *Micrococcus luteus* (Engler and Bessman, Cold Spring Harbor Symp., 43:929 [1979]), to name but a few.

Somewhat less investigation has been made on the isolation and purification of DNA polymerases from thermophilic organisms. However, native (i.e, non-recombinant) and/or recombinant thermostable DNA polymerases have been purified from various organisms, as shown in Table 1 below.

TABLE 1

Polymerases Isolation From Thermophilic Organisms

| Organism | Citation |
| --- | --- |
| *Thermus aquaticus* | Kaledin et al., Biochem., 45:494–501 (1980); Biokhimiya 45:644–651 (1980). |
| | Chien et al., J. Bacteriol., 127:1550 (1976). |
| | University of Cincinnati Master's thesis by A. Chien, "Purification and Characterization of DNA Polymerase from *Thermus aquaticus,*" (1976). |
| | University of Cincinnati, Master's thesis by D. B. Edgar, "DNA Polymerase From an Extreme Thermophile: *Thermus aquaticus,*" (1974). |
| | U.S. Pat. No. 4,889,818* |
| | U.S. Pat. No. 5,352,600* |
| | U.S. Pat. No. 5,079,352* |
| | European Patent Pub. No. 258,017* |
| | PCT Pub. No. WO 94/26766* |
| | PCT Pub. No. WO 92/06188* |
| | PCT Pub. No. WO 89/06691 * |
| *Thermotoga maritima* | PCT Pub. No. WO 92/03556* |
| Thermotoga strain FjSS3-B.1 | Simpson et al., Biochem. Cell Biol., 68:1292–1296 (1990). |
| *Thermosipho africanus* | PCT Pub. No. 92/06200* |
| *Thermus thermophilus* | Myers and Gelfand, Biochem., 30:7661 (1991) |
| | PCT Pub. No. WO 91/09950* |
| | PCT Pub. No. WO 91/09944* |
| | Bechtereva et al., Nucleic Acids Res., 17:10507 (1989). |
| | Glukhov et al., Mol. Cell. Probes 4:435–443 (1990). |
| *Thermus thermophilus* | Carballeira et al., BioTech., 9:276–281 (1990) |
| | Rüttiman et al., Eur. J. Biochem., 149:41–46 (1985). |
| | Oshima et al., J. Biochem., 75:179–183 (1974). |
| | Sakaguchi and Yajima, Fed. Proc., 33:1492 (1974) (abstract). |
| *Thermus flavus* | Kaledin et al., Biochem., 46:1247–1254 (1981); Biokhimiya 46:1576–1584 (1981). |
| | PCT Pub. No. WO 94/26766* |
| *Thermus ruber* | Kaledin et al., Biochem., 47:1515–1521 (1982); Biokhimiya 47:1785–1791 (1982) |
| *Thermoplasma acidophilum* | Hamal et al., Eur. J. Biochem., 190:517–521 (1990). |
| | Forterre et al., Can. J. Microbiol., 35:228–233 (1989). |
| *Sulfolobus acidocaldarius* | Salhi et al., J. Mol. Biol., 209:635–641 (1989). |
| | Salhi et al., Biochem. Biophys. Res. Comm., 167:1341–1347 (1990). |
| | Rella et al., Ital. J. Biochem., 39:83–99 (1990). |
| | Forterre et al., Can. J. Microbiol., 35:228–233 (1989). |
| | Rossi et al., System. Appl. Microbiol., 7:337–341 (1986). |
| | Klimczak et al., Nucleic Acids Res., 13:5269–5282 (1985). |
| | Elie et al., Biochim. Biophys. Acta 951:261–267 (1988). |
| *Bacillus caldotenax* | J. Biochem., 113:401–410 (1993). |

TABLE 1-continued

Polymerases Isolation From Thermophilic Organisms

| Organism | Citation |
| --- | --- |
| Bacillus stearothermophilus | Sellmann et al., J. Bacteriol., 174:4350–4355 (1992). |
| | Stenesh and McGowan, Biochim. Biophys. Acta 475:32–44 (1977). |
| | Stenesh and Roe, Biochim. Biophys. Acta 272:156–166 (1972). |
| | Kaboev et al., J. Bacteriol., 145:21–26 (1981). |
| Methanobacterium thermoautotropicum | Klimczak et al., Biochem., 25:4850–4855 (1986). |
| Thermococcus litoralis | Kong et al., J. Biol. Chem. 268:1965 (1993); U.S. Pat. No. 5,210,036*; U.S. Pat. No. 5,322,785* |
| Pyrococcus furiosus | Lundberg et al., Gene 108:1 (1991) PCT Pub. WO 92/09689 |

*Herein incorporated by reference.

Although the organisms listed in Table 1 are considered thermophiles, many are in the archaebacteria, a group that is evolutionarily distinct from the eubacterial genus Thermotoga.

In addition to native forms, modified forms of thermostable DNA polymerases having reduced or absent 5' to 3' exonuclease activity have been expressed and purified from *T. aquaticus*, *T. maritima*. Thermus species sps17, Thermus species Z05, *T. thermophilus* and *T. africanus* [PCT Publication No. 92/06200].

IV. Uses for Thermophilic DNA Polymerases

One application for thermostable DNA polymerases is the polymerase chain reaction (PCR). The PCR process is described in U.S. Pat. Nos. 4,683,195 and 4,683,202, the disclosures of which are incorporated herein by reference. Primers, template, nucleoside triphosphates, the appropriate buffer and reaction conditions, and polymerase are used in the PCR process, which involves denaturation of target DNA, hybridization of primers and synthesis of complementary strands. The extension product of each primer becomes a template for the production of the desired nucleic acid sequence. If the polymerase employed in the PCR is a thermostable enzyme, then polymerase need not be added after each denaturation step because heat will not destroy the polymerase activity. Use of such enzymes as Taq DNA polymerase allows repetitive heating/cooling cycles without the requirement of fresh enzyme at each cooling step. This represents a major advantage over the use of mesophilic enzymes such as Klenow, as fresh enzyme must be added to each individual reaction tube at every cooling step. The use of Taq in PCR is disclosed in U.S. Pat. No. 4,965,188, EP Publ. No. 258,017, and PCT Publ. No. 89/06691, herein incorporated by reference.

In addition to PCR, Taq DNA polymerase is widely used in other molecular biology techniques including recombinant DNA methods. For example, various forms of Taq have been used in a combination method which utilizes PCR and reverse transcription (see e.g., U.S. Pat. No. 5,322,770, herein incorporated by reference). DNA sequencing methods have also been described which utilize Taq. (See e.g., U.S. Pat. No. 5,075,216, herein incorporated by reference).

However, Taq DNA polymerase has certain characteristics which are undesirable in PCR and other applications including the presence of 5' to 3' exonuclease activity. When thermostable DNA polymerases which have 5' to 3' exonuclease activity (Taq, Tma, Tsps17, TZ05, Tth and Taf) are used in the PCR process and other methods, a variety of undesirable results have been observed, including a limitation of the amount of PCR product produced, an impaired ability to generate long PCR products or to amplify regions containing significant secondary structure, the production of shadow bands or the attenuation in signal strength of desired termination bands during DNA sequencing, the degradation of the 5' end of oligonucleotide primers in the context of double-stranded primer-template complex, nick-translation synthesis during oligonucleotide-directed mutagenesis and the degradation of the RNA component of RNA:DNA hybrids. When utilized in a PCR process with double-stranded primer-template complex, the 5' to 3' exonuclease activity of a DNA polymerase may result in the degradation of the 5' end of the oligonucleotide primers. This activity is not only undesirable in PCR, but also in second-strand cDNA synthesis and sequencing processes.

In the choice of enzyme for sequencing, various factors must be considered. For example, large quantities of the enzyme should be easy to prepare; the enzyme must be stable upon storage for considerable time periods; the enzyme should accept all deoxy and dideoxy nucleotides and analogues as substrates with equal affinities and high fidelity; the polymerase action should be highly processive over nucleotide extensions to 1 kb and beyond, even through regions of secondary structure within the template; the activity should remain high, even in suboptimal conditions; and it should be inexpensive (A. T. Bankier, "Dideoxy sequencing reactions using Klenow fragment DNA polymerase I," in H. and A. Griffin (eds.), *Methods in Molecular Biology: DNA Sequencing Protocols*, Humana Press, Totowa, N.J., [1993], pp. 83–90). Furthermore the enzyme should be able to function at elevated temperatures (i.e, greater than about 70° C.) so that non-specific priming reactions are minimized. However, there are no commercially available enzymes which fully meet all of these criteria. Thus, mutant forms of enzymes have been produced in order to address some of these needs.

For example, mutant forms of thermostable DNA polymerases which exhibit reduced or absent 5' to 3' exonuclease activity have been generated. The Stoffel fragment of Taq DNA polymerase lacks 5' to 3' exonuclease activity due to genetic manipulations which result in the production of a truncated protein lacking the N-terminal 289 amino acids. (See e.g., Lawyer et al., J. Biol. Chem., 264:6427–6437 [1989]; and Lawyer et al., PCR Meth. Appl., 2:275–287 [1993]). Analogous mutant polymerases have been generated for polymerases derived from *T. maritima*, Tsps17, TZ05, Tth and Taf. While the generation of thermostable polymerases lacking 5' to 3' exonuclease activity provides improved enzymes for certain applications, some of these mutant polymerases still have undesirable characteristics including the presence of 3' to 5' exonuclease activity.

The 3' to 5' exonuclease activity is commonly referred to as a proof-reading activity. The 3' to 5' exonuclease removes bases which are mismatched at the 3' end of a primer-template duplex. While the presence of 3' to 5' exonuclease activity may be advantageous as it leads to an increase in the fidelity of replication of nucleic acid strands it also has other undesirable characteristics. The 3' to 5' exonuclease activity found in thermostable DNA polymerases such as Tma (including mutant forms of Tma that lack 5' to 3' exonuclease activity) also degrades single-stranded DNA such as the primers used in the PCR, single-stranded templates and single-stranded PCR products. The integrity of the 3' end of an oligonucleotide primer used in a primer extension process (i.e., PCR, Sanger sequencing methods, etc.) is critical as it is from this terminus that extension of the nascent strand begins. Degradation of the 3' end leads to a shortened oligonucleotide which in turn results in a loss of specificity in the priming reaction (i.e., the shorter the primer the more likely it becomes that spurious or non-specific priming will occur).

The degradation of an oligonucleotide primer by a 3' exonuclease can be prevented by the use of modified nucleotides at the 3' terminus. For example, the use of dideoxynucleotides or deoxynucleotides having a phosphorothiolate linkage at the 3' terminus of an oligonucleotide would prevent degradation by 3' exonucleases. However, the need to use modified nucleotides to prevent degradation of oligonucleotides by 3' exonuclease increases the time and cost required to prepare oligonucleotide primers.

A few examples of a thermostable polymerase which lack both 5' to 3' exonuclease and 3' to 5' exonuclease are known. As discussed above, the Stoffel fragment of Taq DNA polymerase lacks the 5' to 3' exonuclease activity due to genetic manipulation and no 3' to 5' activity is present as Taq polymerase is naturally lacking in 3' to 5' exonuclease activity. Likewise the Tth polymerase naturally lacks 3' to 5' exonuclease activity and genetic deletion of N-terminal amino acids removes the 5' to 3' exonuclease activity.

Despite the development of recombinant enzymes such as Stoffel fragment, there remains a need for other thermostable polymerases having improved characteristics. For example, thermostable polymerases are used in Sanger dideoxynucleotide sequencing protocols. The most commonly used enzyme is Taq polymerase or a modified form of Taq polymerase. High concentrations of the expensive dideoxynucleotides must be used in the sequencing reaction when these enzymes are employed as they have a fairly low affinity for dideoxynucleotides. The art needs a thermostable polymerase which displays a higher affinity for dideoxynucleotides as this would result in considerable cost savings. In addition, the art needs additional thermostable polymerases having novel properties to improve the results obtained when using techniques such as DNA amplification, sequencing and nick-translation.

SUMMARY OF THE INVENTION

The present invention relates to purified thermostable DNA polymerases derived from the eubacteria *Thermotoga neapolitana* (Tne). Nucleic acid sequences encoding the full-length Tne DNA polymerase is provided. In addition, nucleic acid sequences encoding several modified forms of the Tne DNA polymerase are provided herein. The present invention provides methods for the isolation of purified preparations of Tne DNA polymerases. The Tne DNA polymerases may be isolated from *Thermotoga neapolitana* cells or from host cells containing nucleic sequences encoding a Tne DNA polymerase.

In one embodiment, the present invention contemplates a purified thermostable DNA polymerase derived from the eubacterium *Thermotoga neapolitana* which is capable of DNA synthetic activity. In another embodiment, the purified Tne DNA polymerase has 3' exonuclease activity. In yet another embodiment, the purified Tne DNA polymerase has 5' exonuclease activity. In one preferred embodiment, the purified Tne DNA polymerase comprises the amino acid sequence of SEQ ID NO:2. In a particularly preferred embodiment, the specific activity of the synthetic activity of the purified Tne DNA polymerase is approximately 100,000 units/mg.

In another embodiment, the purified thermostable Tne DNA polymerase is a non-naturally occurring or recombinant DNA polymerase. The recombinant Tne DNA polymerase may further contain 3' exonuclease activity and/or 5' exonuclease activity.

In a preferred embodiment, the non-naturally occurring Tne DNA polymerase has reduced levels of 3' exonuclease activity. In another embodiment, the non-naturally occurring Tne DNA polymerase lacks significant 5' exonuclease activity. In a particularly preferred embodiment, the non-naturally occurring Tne DNA polymerase comprises an amino acid sequence selected from the group consisting of SEQ ID NOS: 8, 16, 19, 23, 26, 29, 33 and 35.

The present invention provides nucleic acid sequences encoding thermostable DNA polymerases. In a preferred embodiment, an oligonucleotide comprising the nucleic acid sequence of SEQ ID NO: 1encodes the thermostable DNA polymerase. These nucleic acid sequences encoding thermostable DNA polymerases may be modified to encode a polymerase which lacks significant 5' exonuclease activity. In a preferred embodiment, the modified nucleic acid sequences encoding a thermostable DNA polymerase comprise the nucleotide sequence of SEQ ID NO:7. In one embodiment, the polymerase encoded by the modified nucleic acid sequences displays reduced levels of 3' exonuclease activity. In a particularly preferred embodiment, the modified nucleic acid sequences encoding a polymerase having reduced levels of 3' exonuclease activity are selected from the group consisting of SEQ ID NOS:7, 15, 18, 22, 25, 28, 32 and 34.

The present invention provides recombinant DNA vectors containing nucleic acid sequences which encode a thermostable DNA polymerase having DNA synthetic activity. In a preferred embodiment the polymerase-encoding nucleic acid sequences are set forth in SEQ ID NO:1. The recombinant DNA vector may contain a modified nucleic sequence encoding a thermostable DNA polymerase which lacks significant 5' exonuclease activity. In a preferred embodiment, the recombinant DNA vector contains a modified nucleic acid sequence which comprises SEQ ID NO:7.

In a preferred embodiment, the recombinant DNA vector contains modified nucleic acid sequences encoding a thermostable DNA polymerase which exhibits reduced levels 3' exonuclease activity. In a particularly preferred embodiment, the modified sequences encoding a thermostable DNA polymerase which exhibits reduced levels 3' exonuclease activity are selected from the group consisting of SEQ ID NOS:7, 15, 18, 22, 25, 28, 32 and 34.

The present invention further contemplates the transformation of host cells with the recombinant DNA vectors containing nucleic acid sequences encoding Tne DNA polymerases. The invention is not limited by the choice of host cell; host cells may comprise procaryotic or eucaryotic cells. In a preferred embodiment, the host cell is an *E. coli* host cell.

The invention further provides methods for determining the DNA sequence of a segment or portion of a DNA molecule using the Tne DNA polymerases of the invention. Dideoxynucleotide (ddNTP) chain termination sequencing protocols are used in conjunction with the polymerases of the invention. Traditional (i.e., Sanger) as well as other methods, including but not limited to, chain termination sequencing or thermal cycle sequencing protocols benefit from the use of the Tne DNA polymerases of the invention. The claimed Tne DNA polymerases have a high affinity for dideoxynucleotides; accordingly the following ratios of dNTPs and ddNTPs are contemplated for use in either thermal cycling or Sanger chain termination protocols when Tne DNA polymerases [e.g., Tne 284(D323A, D389A)] are employed: dATP:ddATP is 1:1.67±50%; dCTP:ddCTP is 1:0.83±50%; dGTP (or 7-deaza dGTP):ddGTP is 1:0.67±50% and TTP:ddTTP is 1:2.5±50% where each dNTP is present at a final concentration of about 1 $\mu$M to 120 $\mu$M. When the Tne Quad polymerase [Tne M284 (D323A, D389A, F730Y)] is used in enzymatic sequencing reactions (radioactive or fluorescent protocols) the following ratios of dNTPs:ddNTPs may be employed: 1:0.01 to 1:0.0005. In a prefered embodiment, the Tne Quad polymerase [Tne M284 (D323A, D389A, F730Y)] is used in radioactive sequencing reactions and the following ratios of dNTPs and ddNTPs are contemplated: dATP:ddATP is 1:0.01; dCTP:ddCTP is 1:0.0125; 7-deaza dGTP:ddGTP is 1:0.015 and TTP:ddTTP is 1:0.0125. In another preferred embodiment, the Tne Quad polymerase [Tne M284 (D323A, D389A, F730Y)] is used in fluorescent sequencing reactions and the following ratios of dNTPs and ddNTPs are contemplated: dATP:ddATP is 1:0.0025; dCTP:ddCTP is 1:0.005; 7-deaza dGTP:ddGTP is 1:0.0075 and TTP:ddTTP is 1:0.005.

In addition, the present invention provides purified full-length thermostable DNA polymerase capable of DNA synthetic activity, wherein the polymerase is derived from the eubacterium *Thermotoga neapolitana*. Both naturally-occurring and non-naturally-occurring *Thermotoga neapolitana* polymerases are encompassed by the present invention. In a preferred embodiment, the polymerase of *Thermotoga neapolitana* has the amino acid sequence set forth in SEQ ID NO:2.

The present invention further contemplates purified thermostable non-naturally occurring DNA polymerase derived from the eubacterium *Thermotoga neapolitana* comprising a portion of the amino acid sequence of SEQ ID NO:2, wherein the polymerase is capable of DNA synthetic activity. In one embodiment, the *Thermotoga neapolitana* polymerase lacks significant 5' exonuclease activity. In an alternative embodiment, the *Thermotoga neapolitana* has reduced 3' exonuclease activity. In another embodiment, the *Thermotoga neapolitana* polymerase lacks significant 5' exonuclease activity and has reduced 3' exonuclease activity. In yet another embodiment, the polymerase lacks both significant 5' exonuclease and 3' exonuclease activity. Another embodiment of the *Thermotoga neapolitana* polymerase has an increased affinity for a dideoxynucleotide, as compared to the affinity of naturally-occurring DNA polymerase. A preferred form of this embodiment of *Thermotoga neapolitana* polymerase has the amino acid sequence of SEQ ID NO:54.

In a particularly preferred embodiment, the *Thermotoga neapolitana* polymerase of the present invention comprises an amino acid sequence selected from the group consisting of SEQ ID NOS:8, 16, 19, 23, 26, 29, 33, 35 and 54.

The present invention also contemplates *Thermotoga neapolitana* polymerase with an increased affinity for a dideoxynucleotide as compared to sequencing grade *Thermus aquaticus* DNA polymerase (sTaq). In a preferred embodiment, the *Thermotoga neapolitana* polymerase with an increased affinity for a dideoxynucleotide is selected from the group consisting of SEQ ID NOS:8, 16, 19, 23, 26, 29, 33, 35 and 54.

The present invention further provides an oligonucleotide comprising the nucleic acid sequence of SEQ ID NO:53, wherein the nucleotide sequence encodes a thermostable DNA polymerase. One embodiment of this invention is a recombinant DNA vector comprising the oligonucleotide of Claim 15.

The present invention also includes methods for determining the nucleotide base sequence of a DNA molecule comprising step a) providing in any order: i) a reaction vessel (e.g., any suitable container such as microcentrifuge tubes or a microtiter plate); ii) at least one deoxynucleoside triphosphate; iii) a thermostable DNA polymerase derived from the eubacterium *Thermotoga neapolitana*; iv) at least one DNA synthesis terminating agent which terminates DNA synthesis at a specific nucleotide base; v) a first DNA molecule; and vi) a primer capable of hybridizing to the first DNA molecule; step b) adding to the reaction vessel, in any order, the deoxynucleoside triphosphate, DNA polymerase, DNA synthesis terminating agent, first DNA molecule, and the primer so as to form a reaction mixture, under conditions such that the primer hybridizes to the DNA molecule, and the DNA polymerase is capable of conducting primer extension to produce a population of DNA molecules complementary to the first DNA molecule; and step c) determining at least a part of the nucleotide base sequence of the first DNA molecule. The method of the present invention is not limited by the order in which the reaction components are added to the reaction vessel. Any order of addition which permits the primer to hybridize to the DNA molecule and the DNA polymerase to be capable of conducting primer extension is encompassed by the present invention. In a preferred embodiment, the DNA polymerase is added last. The conditions which permit the primer to hybridize to the DNA molecule, and allow the DNA polymerase to conduct primer extension may comprise the use of a buffer.

In one embodiment, the method uses a naturally-occurring DNA polymerase. In an alternative embodiment a non-naturally-occurring DNA polymerase is utilized. In a preferred embodiment, DNA the polymerase comprises an amino acid sequence selected from the group consisting of SEQ ID NOS:8, 16, 19, 23, 26, 29, 33, 35 and 54.

In an alternative embodiment, the conditions of the method comprise heating the mixture. In another embodiment, the method further comprises cooling the mixture to a temperature at which the thermostable DNA polymerase can conduct primer extension. In a particularly preferred embodiment, the method further comprises heating and cooling one or more times. In yet another embodiment of the method, the reaction mixture comprises 7-deaza dGTP, dATP, dTTP and dCTP.

It is contemplated that various DNA synthesis terminating agents will be useful in the present invention. In a preferred embodiment, the DNA synthesis terminating agent is a dideoxynucleoside triphosphate; in a preferred embodiment, the dideoxynucleoside triphosphate is selected from the group consisting of ddGTP, ddATP, ddTTP and ddCTP.

It is also contemplated that the primer used in the method of the present invention will be labelled. In a preferred embodiment, the primer is labelled with $^{32}$P, $^{33}$P, $^{35}$S, or a fluorescent molecule. It is also contemplated that reactants other than the primer used in the method of the present invention will be labelled. For example, in one embodiment, one deoxynucleoside triphosphate is labelled. In a preferred form of this embodiment, the deoxynucleoside triphosphate is labelled with $^{32}$P, $^{33}$P, $^{35}$S, or a fluorescent molecule.

It is further contemplated that additional steps or substeps will be incorporated into the method of the present invention. For example, in one embodiment, step b) further comprises adding a thermostable pyrophosphatase to the reaction mixture. In a preferred form of this embodiment, the thermostable pyrophosphatase is derived from *Thermus thermophilus*. In preferred embodiments, the method uses a mixture or blend comprising a Tne DNA polymerase and a thermostable pyrophosphatase. Particularly preferred ratios of Tne polymerase:pyrophosphatase present in the enzyme mixture are 1) a ratio of 9 parts Tne Quad polymerase (10 U/µl) and 1 part Tth pyrophosphatase (0.03 to 0.65 U/µl) and 2) a ratio of 15 parts Tne Quad polymerase (10 U/µl) and 1 part Tth pyrophosphatase (0.03 to 0.65 U/µl).

The present invention also provides kits for determining the nucleotide base sequence of a DNA molecule comprising: a) a thermostable DNA polymerase derived from the eubacterium *Thermotoga neapolitana*; and b) at least one nucleotide mixture comprising deoxynucleoside triphosphates and one dideoxynucleoside triphosphate. In a preferred embodiment, the polymerase of the kit is a non-naturally occurring DNA polymerase. It is also contemplated that the non-naturally occurring *Thermotoga neapolitana* DNA polymerase of the kit of the present invention exhibit such properties as the lack of significant 5' exonuclease activity. In another embodiment, the non-naturally occurring *Thermotoga neapolitana* DNA polymerase of the kit exhibits reduced 3' exonuclease activity. It is also contemplated that non-naturally occurring *Thermotoga neapolitana* DNA polymerase useful in this kit lacks significant 5' exonuclease activity and 3' exonuclease activity. In a particularly preferred embodiment of the kit, the polymerase comprises an amino acid sequence selected from the group consisting of SEQ ID NOS:2, 8, 16, 19, 23, 26, 29, 33, 35 and 54.

In an alternative embodiment, the kit of the present invention contains a first nucleotide mixture, a second nucleotide mixture, a third nucleotide mixture, and a fourth nucleotide mixture, with the first nucleotide mixture comprising ddGTP, 7-deaza dGTP, dATP, dTTP and dCTP, the second nucleotide mixture comprising ddATP, 7-deaza dGTP, dATP, dTTP and dCTP, the third nucleotide mixture comprising ddTTP, 7-deaza dGTP, dATP, dTTP and dCTP and the fourth nucleotide mixture ddCTP, 7-deaza dGTP, dATP, dTTP and dCTP. It is also contemplated that the kit of this embodiment further comprises a thermostable pyrophosphatase. In a particularly preferred embodiment, the thermostable pyrophosphatase is derived from *Thermus thermophilus*. In preferred embodiments, the kit contains a mixture or blend comprising a Tne DNA polymerase and a thermostable pyrophosphatase. Particularly preferred ratios of Tne polymerase:pyrophosphatase present in the enzyme mixture are 1) a ratio of 9 parts Tne Quad polymerase (10 U/µl) and 1 part Tth pyrophosphatase (0.03 to 0.65 U/µl) and 2) a ratio of 15 parts Tne Quad polymerase (10 U/µl) and 1 part Tth pyrophosphatase (0.03 to 0.65 U/µl).

The present invention also provides methods for amplifying a double stranded DNA molecule, comprising the steps of: a) providing: i) a first DNA molecule comprising a first strand and a second strand, wherein the first and second strands are complementary to one another; ii) a first primer and a second primer, wherein the first primer is complementary to the first DNA strand, and the second primer is complementary to the second DNA strand; and iii) a first thermostable DNA polymerase derived from the eubacterium *Thermotoga neapolitana*; and b) mixing the first DNA molecule, first primer, second primer, and polymerase to form a reaction mixture under conditions such that a second DNA molecule comprising a third strand and a fourth strand are synthesized, with the third strand having a region complementary to the first strand and the fourth strand having a region complementary to the second strand. The method of the present invention is not limited by the source of the first DNA molecule. In a preferred embodiment, the first DNA molecule is present in a genomic DNA mixture (i.e., in genomic DNA extracted from an organism, tissue or cell line). In alternative embodiments, the first DNA molecule is derived from an RNA molecule using reverse transcriptase-PCR (RT-PCR). The newly synthesized DNA molecule (cDNA) then serves as substrate in the subsequent amplification reaction. The conditions which permit the primer to hybridize to the DNA molecule, and allow the DNA polymerase to conduct primer extension may comprise the use of a buffer.

In one embodiment, the method conditions comprise heating the mixture. In an alternative embodiment, the method further comprises cooling the mixture to a temperature at which the thermostable DNA polymerase can conduct primer extension. In a particularly preferred embodiment, the method comprises repeating the heating and cooling one or more times.

It is also contemplated that the polymerase of the method will have various properties. It is therefore contemplated that in one embodiment of the method, the polymerase lacks significant 5' exonuclease activity. In an alternative embodiment, the polymerase has reduced 3' exonuclease activity. In yet another embodiment, the polymerase lacks significant 5' exonuclease activity and has reduced 3' exonuclease activity, while in yet another embodiment, the polymerase lacks significant 5' exonuclease activity and 3' exonuclease activity. In a particularly preferred embodiment, the polymerase comprises an amino acid sequence selected from the group consisting of SEQ ID NOS:8, 16, 19, 23, 26, 29, 33, 35 and 54.

In yet another embodiment, the method further comprises providing a second thermostable DNA polymerase, with the second polymerase comprising a high fidelity polymerase. In a preferred embodiment, the second polymerase is derived from a thermostable organism. In a particularly preferred embodiment, this second polymerase is derived from organisms selected from the group consisting of *Pyrococcus furiosus, Pyrococcus woesii* and *Thermococcus litoralis*.

DESCRIPTION OF THE DRAWINGS

FIG. 2 shows an alignment of amino acid residues from three regions within the 3' exonuclease domain of selected DNA polymerases.

FIG. 3 shows the alignment of the amino acid residues (using the one letter code for the amino acids) from *E. coli* DNA polymerase I, Tma DNA polymerase and Tne DNA polymerase.

FIG. 5A shows an autoradiograph of a sequencing gel.

FIG. 5B shows an autoradiograph of a sequencing gel.

DEFINITIONS

Figure 1:
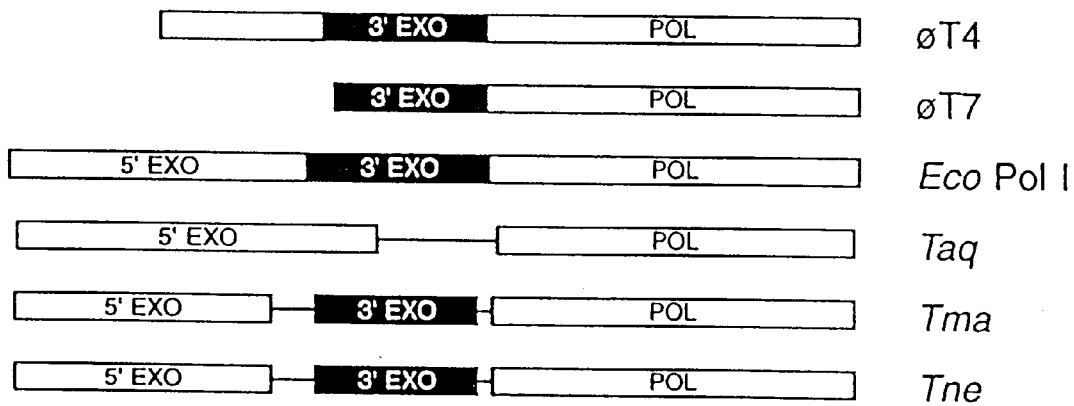
FIG. 1 provides a schematic representation of the 5' exonuclease, 3' exonuclease and polymerase domains in several DNA polymerases.

To facilitate understanding of the invention, a number of terms are defined below.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product. The wild-type form of the coding region for the Tne DNA polymerase is listed in SEQ ID NO:1; the wild-type form of the Tne DNA polymerase protein is listed in SEQ ID NO:2. The Tne DNA polymerase proteins encoded by "modified" or "mutant" genes are referred to as "non-naturally occurring" Tne DNA polymerases. The Tne DNA polymerase proteins encoded by the wild-type Tne DNA polymerase gene (i.e., SEQ ID NO:1) are referred to as "naturally occurring" Tne DNA polymerases.

A DNA polymerase is said to be "derived from the eubacterium *Thermotoga neapolitana*" if that polymerase comprises all or a portion of the amino acid sequence of the Tne DNA polymerase of SEQ ID NO:2. DNA polymerases derived from *Thermotoga neapolitana* include the native Tne DNA polymerase isolated from *Thermotoga neapolitana* cells as well as recombinant Tne DNA polymerases encoded by the wild-type Tne DNA polymerase gene (SEQ ID NO:1) or mutant Tne polymerase genes, including but not limited to, genes comprising the sequences listed in SEQ ID NOS:7, 15, 18, 22, 25, 28, 32, 34 and 53.

The term "full-length thermostable Tne DNA polymerase" refers to a DNA polymerase which encompasses essentially every amino acid encoded by the Tne DNA polymerase gene (SEQ ID NO:1). One skilled in the art knows there are subtle modifications of some proteins in living cells so that the protein is actually a group of closely related proteins with slight alterations. For example, some but not all proteins a) have amino acids removed from the amino-terminus and/or b) have chemical groups added which could increase molecular weight. Most bacterial proteins as encoded contain a methionine and an alanine residue at the amino-terminus of the protein; one or both of these residues are frequently removed from active forms of the protein in the bacterial cell. These types of modifications are typically heterogenous so not all modifications happen to every molecule. Thus, the natural "full-length" molecule is actually a family of molecules that start from the same amino acid sequence but have small differences in how they are modified. The term "full-length thermostable Tne DNA polymerase" encompasses such a family of molecules. The Tne DNA polymerase gene encodes a protein of 893 amino acids having a predicted molecular weight of 102,054; however as shown in the examples below, the full-length polymerase migrates with an apparent molecular weight of 97,000 on SDS-PAGE gels.

The term "recombinant DNA vector" as used herein refers to DNA sequences containing a desired coding sequence and appropriate DNA sequences necessary for the expression of the operably linked coding sequence in a particular host organism. DNA sequences necessary for expression in procaryotes include a promoter, optionally an operator sequence, a ribosome binding site and possibly other sequences. Eukaryotic cells are known to utilize promoters, polyadenlyation signals and enhancers.

As used herein, the terms "cell," "cell line," and cell culture" are used interchangeably and all such designations include progeny. The words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in procaryotes usually include a promoter, an operator (optional), and a ribosome binding site, often along with other sequences. Eucaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "transfection" as used herein refers to the introduction of foreign DNA into eucaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementary may be "partial," in which only some of the nucleic acids' bases are matched according to the base pairing rules. Or, there may be "complete" or "total" complementary between the nucleic acids. The degree of complementary between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementary. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5× SSPE (43.8 g/l NaCl, 6.9 g/l NaH$_2$PO$_4$.H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 μg/ml denatured salmon sperm DNA followed by washing in a solution comprising 5× SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl. (See e.g., Anderson and Young, Quantitative Filter Hybridization, in *Nucleic Acid Hybridization* (1985). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

A primer is said to be "capable of hybridizing to a DNA molecule" if that primer is capable of annealing to the DNA molecule; that is the primer shares a degree of complementarity with the DNA molecule. The degree of complementarity may be, but need not be, a complete degree of complementarity (i.e., the primer need not be 100% homologous to the DNA molecule). Indeed, when mutagenic PCR is to be conducted, the primer will contain at least one mismatched base which cannot hybridize to the DNA molecule. Any primer which can anneal to and support primer extension along a template DNA molecule under the reaction conditions employed is capable of hybridizing to a DNA molecule.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (i.e., ELISA, as well as enzyme-based histochemical assays), fluorescent, radioactive, and luminescent systems. It is not intended that the present invention be limited to any particular detection system or label. The terms "reporter molecule" and "label" as used herein interchangeably. Primers and deoxynuceoside triphosphates may contain labels; these labels may comprise, but are not limited to, $^{32}P$, $^{33}P$, $^{35}S$ or fluorescent molecules (e.g., fluorescent dyes).

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (i.e., hybridization with a labeled probe; incorporation of biotinylated primers followed by avidin-enzyme conjugate detection; incorporation of $^{32}P$-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase [D. L. Kacian et al., *Proc. Natl. Acad. Sci USA* 69:3038 (1972)]. Other nucleic acid will not be replicated by this amplification enzyme. Similarly, in the case of T7 RNA polymerase, this amplification enzyme has a stringent specificity for its own promoters [M. Chamberlin et al., *Nature* 228:227 (1970)]. In the case of T4 DNA ligase, the enzyme will not ligate the two oligonucleotides where there is a mismatch between the oligonucleotide substrate and the template at the ligation junction [D. Y. Wu and R. B. Wallace, *Genomics* 4:560 (1989)]. Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences [*PCR Technology*, H. A. Erlich (ed.) (Stockton Press 1989)].

As used herein, the terms "PCR product", "PCR fragment" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eucaryotes comprise "promoter" and "enhancer" elements. Promoters and enhancers consist of short arrays of DNA sequences that interact specifically with cellular proteins involved in transcription [Maniatis, T. et al., *Science* 236:1237 (1987)]. Promoter and enhancer elements have been isolated from a variety of eucaryotic sources including genes in yeast, insect and mammalian cells and viruses (analogous control elements, i.e., promoters, are also found in procaryotes). The selection of a particular promoter and enhancer depends on what cell type is to be used to express the protein of interest. Some eucaryotic promoters and enhancers have a broad host range while others are functional in a limited subset of cell types [for review see Voss, S. D. et al., *Trends Biochem. Sci.*, 11:287 (1986) and Maniatis, T. et al., supra (1987)]. For example, the SV40 early gene enhancer is very active in a wide variety of cell types from many mammalian species and has been widely used for the expression of proteins in mammalian cells [Dijkema, R. et al., *EMBO J.* 4:761 (1985)]. Two other examples of promoter/enhancer elements active in a broad range of mammalian cell types are those from the human elongation factor It gene [Uetsuki, T. et al., *J Biol. Chem.*, 264:5791 (1989), Kim, D. W. et al., *Gene* 91:217 (1990) and Mizushima, S. and Nagata, S., *Nuc. Acids. Res.*, 18:5322 (1990)] and the long terminal repeats of the Rous sarcoma virus [Gorman, C. M. et al., *Proc. Natl. Acad. Sci. USA* 79:6777 (1982)] and the human cytomegalovirus [Boshart, M. et al., *Cell* 41:521 (1985)].

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The presence of "splicing signals" on an expression vector often results in higher levels of expression of the recombinant transcript in eucaryotic host cells. Splicing signals mediate the removal of introns from the primary RNA transcript and consist of a splice donor and acceptor site [Sambrook, J. et al., *Molecular Cloning: A Laboratory Manual*, 2nd ed., Cold Spring Harbor Laboratory Press, New York (1989) pp. 16.7–16.8]. A commonly used splice donor and acceptor site is the splice junction from the 16S RNA of SV40.

Efficient expression of recombinant DNA sequences in eucaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation [J. Sambrook, supra, at 16.6–16.7].

Eucaryotic expression vectors may also contain "viral replicons " or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (~100 copies/cell).

The Tne polymerases may be expressed in either procaryotic or eucaryotic host cells. Nucleic acid encoding the Tne polymerase may be introduced into bacterial host cells by a number of means including transformation of bacterial cells made competent for transformation by treatment with calcium chloride or by electroporation. If the Tne polymerases are to be expressed in eucaryotic host cells, nucleic acid encoding the Tne polymerase may be introduced into eucaryotic host cells by a number of means including calcium phosphate co-precipitation, spheroplast fusion, electroporation and the like. When the eucaryotic host cell is a yeast cell, transformation may be affected by treatment of the host cells with lithium acetate or by electroporation.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a Tne polymerase includes, by way of example, such nucleic acid in cells ordinarily expressing a Tne polymerase where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

As used herein the term "coding region" when used in reference to structural gene refers to the nucleotide sequences which encode the amino acids found in the nascent polypeptide as a result of translation of a mRNA molecule. The coding region is bounded on the 5' side by the nucleotide triplet "ATG" which encodes the initiator methionine and on the 3' side by one of the three triplets which specify stop codons (i.e., TAA, TAG, TGA).

As used herein, the term "purified" or "to purify" refers to the removal of contaminants from a sample. For example, recombinant Tne DNA polymerases are expressed in bacterial host cells and the polymerases are purified by the removal of host cell proteins; the percent of recombinant Tne DNA polymerase is thereby increased in the sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" is used herein to indicate a protein isolated from a naturally occurring (i.e., a nonrecombinant) source. Molecular biological techniques may be used to produce a recombinant form of a protein which has identical properties when compared to the native form of the protein. The term "rTne" is used to designate a recombinant form of Tne polymerase. The terms "nTne" and "nTaq" are used to designate the native forms of Tne polymerase and Taq polymerase, respectively.

As used herein the term "portion" when in reference to an amino acid sequence or a protein (as in "a portion of an amino acid sequence") refers to fragments of that protein. The fragments may range in size from four amino acid residues to the entire amino acid sequence minus one amino acid. When used in relation to Tne polymerases, the fragments may range in size from greater than or equal to about 300 amino acid residues, more preferably greater than or equal to about 437 amino acid residues, most preferably greater to or equal to about 500 amino acids to the entire amino acid sequence minus one amino acid. Particularly preferred fragments of Tne polymerases retain one or more of the enzymatic activities associated with the wild-type Tne polymerase (i.e., 5' exonuclease, 3' exonuclease and polymerization activity)

As used herein, the term "fusion protein" refers to a chimeric protein containing the protein of interest (i.e., Tne DNA polymerases and fragments thereof) joined to an exogenous protein fragment (the fusion partner which consists of a non-Tne polymerase protein). The fusion partner may enhance solubility of the Tne polymerase protein as expressed in a host cell, may provide an affinity tag to allow purification of the recombinant fusion protein from the host cell or culture supernatant, or both. If desired, the fusion protein may be removed from the protein of interest (i.e., Tne DNA polymerase or fragments thereof) by a variety of enzymatic or chemical means known to the art.

The term "5' exonuclease activity" refers to the presence of an activity in a protein which is capable of removing nucleotides from the 5' end of an oligonucleotide. 5' exonuclease activity may be measured using any of the assays provided herein.

The term "3' exonuclease activity" refers to the presence of an activity in a protein which is capable of removing nucleotides from the 3' end of an oligonucleotide. 3' exonuclease activity may be measured using any of the assays provided herein.

The terms "DNA polymerase activity," "synthetic activity" and "polymerase activity" are used interchangeably and refer to the ability of an enzyme to synthesize new DNA strands by the incorporation of deoxynucleoside triphosphates. The examples below provide assays for the measurement of DNA polymerase activity. A protein which is can direct the synthesis of new DNA strands by the incorporation of deoxynucleoside triphosphates in a template-dependent manner is said to be "capable of DNA synthetic activity."

The term "reduced levels of 3' exonuclease" is used in reference to the level of 3' exonuclease activity displayed by the wild-type Tne DNA polymerase (i.e., the polymerase of SEQ ID NO:2) and indicates that the modified or "non-naturally occurring" polymerase exhibits lower levels of 3' exonuclease than does the full-length or unmodified enzyme. For example, the Tne M284 polymerase (SEQ ID NO:8) exhibits about 28% of the 3' exonuclease activity present in the wild-type Tne DNA polymerase. The Tne M284 polymerase thus has reduced levels of 3' exonuclease but does not lack significant 3' exonuclease activity.

The phrase "lacks significant 3' exonuclease activity" is used relative to the level of 3' exonuclease activity displayed by the wild-type Tne DNA polymerase (i.e., the polymerase of SEQ ID NO:2) and indicates that the modified or "non-naturally occurring" polymerase exhibits such low levels of 3' exonuclease that the measurement is at background levels in the assay. For example, the Tne M284(D323E), Tne M284(E325D), Tne M284 (D323A, D389A) and Tne M284 (D323A, D389A, F730Y) polymerases (SEQ ID NOS:16, 19, 35 and 54, respectively) lack significant 3' exonuclease activity. A polymerase which lacks significant 3' exonuclease activity is also a polymerase which has reduced levels of 3' exonuclease activity.

The phrase "lacks significant 5' exonuclease activity" is used relative to the level of 5' exonuclease activity displayed by the wild-type Tne DNA polymerase (i.e., the polymerase of SEQ ID NO:2) and indicates that the modified or "non-naturally occurring" polymerase exhibits such low levels of 5' exonuclease that the measurement is at background levels in the assay.

A polymerase which "lacks significant 5' exonuclease and 3' exonuclease activity" is a polymerase which exhibits such low levels of both 5' exonuclease and 3' exonuclease activity that the measurement of each activity is at background levels in the appropriate nuclease assay.

A polymerase is said to have an "increased affinity for a dideoxynucleotide" if that polymerase in comparison to a reference polymerase has either a lower $K_i$ for any one of the four dideoxynucleotides (ddATP, ddCTP, ddGTP, ddTTP) (as compared to the reference polymerase) or has an increased ability to incorporate a given dideoxynucleotide relative to the corresponding deoxynucleotide (as compared to the ability of the reference polymerase). A polymerase having an increased ability to incorporate a given dideoxynucleotide is a polymerase which discriminates to a lesser extent than a reference polymerase against a dideoxynucleotide compared to a deoxynucleotide. The $K_i$ or inhibition constant (also referred to as the dissociation constant of an enzyme-inhibitor complex) of a polymerase for a dideoxynucleotide can be measured using kinetic analysis well known to the art. The ability of a polymerase to incorporate a given dideoxynucleotide relative to the corresponding deoxynucleotide [or modified deoxynucleotide such as 7-deaza dGTP (see U.S. Pat. No. 4,804,748 the disclosure of which is herein incorporated by reference)] may be conveniently determined using dideoxynucleotide sequencing reactions (see, e.g., European Patent Application Publication No. 0 655 506, and Tabor and Richardson (1995) Proc. Natl. Acad. Sci. USA 92:6339, as well as, the examples below). For example, a polymerase which gives optimal sequencing ladders when the sequencing reaction is conducted using a ratio of dATP/ddATP of 100/1 has a higher affinity for a dideoxynucleotide than does a polymerase which requires a ratio of dATP/ddATP of 1/17.5. (See Example 16 below for a comparison of the ratio of dNTP/ddNTPs required to produce optimal sequencing ladders using the Tne Quad polymerase and sequencing grade Taq DNA polymerase). Methods for conducting enzymatic DNA sequencing (also referred to as dideoxy or chain-terminating sequencing) are well known to the art (see, e.g., U.S. Pat. Nos. 4,942,130 and 4,962,020, the disclosures of which are herein incorporated by reference).

A "DNA synthesis terminating agent which terminates DNA synthesis at a specific nucleotide base" refers to compounds, including but not limited to, dideoxynucleosides having a 2',3' dideoxy structure (e.g., ddATP, ddCTP, ddGTP and ddTTP). Any compound capable of specifically terminating a DNA sequencing reaction at a specific base may be employed as a DNA synthesis terminating agent.

The term "high fidelity polymerase" refers to DNA polymerases which have fidelity or error rate of $5 \times 10^{-6}$ per base pair or lower. Examples of high fidelity DNA polymerases include the Tli DNA polymerase derived from *Thermococcus litoralis* (Promega, NEB), Pfu DNA polymerase derived from *Pyrococcus furiosus* (Stratagene) and Pwo DNA polymerase derived from *Pyrococcus woesii* (BM). The fidelity or error rate of a DNA polymerase may be measured using assays known to the art, including the assays described in Examples 14 and 17 below.

DESCRIPTION OF THE INVENTION

The present invention provides purified thermostable DNA polymerase I enzymes derived from *Thermotoga neapolitana* (Tne). These thermostable enzymes comprise the wild-type form of the enzyme as well as mutant forms which posses altered characteristics relative to the wild-type enzyme. In particular, the present invention provides deletion mutants which lack 5' exonuclease activity. Further the present invention provides modified forms of Tne DNA polymerases which lack 5' exonuclease activity and have reduced or absent 3' exonuclease activity.

The present invention also relates to an improved method of determining the nucleic sequence of a DNA molecule using chain terminating dideoxynucleotides in conjunction with the modified Tne DNA polymerases. The novel properties of the polymerases of the invention provide improved enzymes for a variety of applications which utilize thermostable DNA polymerases.

The description of the invention is divided into: I. General Structural Features of Type A DNA Polymerases, II. Generation of Tne DNA Polymerases, III. Use of Tne DNA Polymerases in the PCR and IV. Use of Tne DNA Polymerases in DNA Sequencing Methods.

I. General Structural Features of DNA Polymerases

DNA polymerases (DNAPs), such as those isolated from *E. coli* or from thermophilic bacteria of the genera Thermus or Thermotoga, are enzymes that synthesize new DNA strands. Several of the known DNAPs contain associated nuclease activities in addition to the synthetic or polymerization activity of the enzyme.

Some DNAPs are known to remove nucleotides from the 5' and 3' ends of DNA chains [Kornberg, *DNA Replication*, W. H. Freeman and Co., San Francisco, pp. 127–139 (1980)]. These nuclease activities are usually referred to as 5' exonuclease and 3' exonuclease activities, respectively. For example, the 5' exonuclease activity located in the N-terminal domain of several DNAPs participates in the removal of RNA primers during lagging strand synthesis during DNA replication and the removal of damaged nucleotides during repair. Some DNAPs, such as the *E. coli* DNA polymerase, also have a 3' exonuclease activity responsible for proof-reading during DNA synthesis (Kornberg, supra).

DNAPs isolated from *Thermus aquaticus* (Taq), *Thermus flavus* (Tfl) and *Thermus thermophilus* (Tth) have a 5' exonuclease activity, but lack a functional 3' exonucleolytic domain [Tindall and Kunkell, *Biochem.* 27:6008 (1988)]. However, the lack of a 3' exonuclease domain is not a general feature of DNAPs derived from thermophilic bacteria as DNA polymerases from the thermophiles *Thermotoga maritima* (Tma), *Bacillus caldotenax*, *Thermococcus litoralis* (Tli) and *Pyrococcus furiosus* (Pfu) do contain 3' exonuclease activity.

The 5' nuclease activity associated with a number of eubacterial Type A DNA polymerases has been found to reside in the one-third N-terminal region of the protein as an independent functional domain. In these polymerase molecules, the C-terminal two-thirds of the molecule constitute the polymerization domain which is responsible for the synthesis of DNA. Some Type A DNA polymerases also have a 3' exonuclease activity associated with the two-third C-terminal region of the molecule. FIG. 1 provides a schematic showing the location of the 5' exonuclease, 3' exonuclease and polymerase domains of a number of eubacterial DNAPs. As noted above, not all DNAPs contain both 5' and 3' exonuclease domains.

FIG. 1 provides a schematic depicting the arrangement of the 5' exonuclease ("5' EXO"), 3' exonuclease ("3' EXO") and polymerase ("POL") domains in the DNA polymerases from phage T4 ("φT4"), phage T7 ("φT7"), *E. coli* (DNA polymerase I; "Eco Pol I"), *T. aquaticus* ("Taq"), *T. maritima* ("Tma") and *T. neapolitana* ("Tne"). The absence of a 3' exonuclease domain in Taq DNA polymerase is indicated by the use of the line between the boxed 5' exonuclease and polymerase domains; the absence of a 5' nuclease domain in phage T4 polymerase is indicated by the absence of the term "5' EXO" in the first boxed region of the molecule.

The 5' exonuclease activity and the polymerization activity of DNAPs have been separated by proteolytic cleavage or genetic manipulation of the polymerase molecule. The Klenow or large proteolytic cleavage fragment of *E. coli* DNA polymerase I contains the polymerase and 3' exonuclease activity but lacks the 5' nuclease activity [Brutlag et al., *Biochem. Biophys. Res. Commun.* 37:982 (1969)]. The Stoffel fragment of DNAP Taq lacks the 5' nuclease activity due to a genetic manipulation which deleted the N-terminal 289 amino acids of the polymerase molecule [Erlich et al., *Science* 252:1643 (1991)].

The removal of the 5' exonuclease domain from a DNAP may effect the activity of the remaining domains. For example, removal of the 5' exonuclease domain from the *E. coli* polymerase I protein to generate the Klenow fragment affects the fidelity of the remaining large polymerase domain. The fidelity of a DNA polymerase involves several functions including the ability to discriminate against errors when nucleotides are initially inserted, discriminate against extension from misaligned or mispaired primer termini and exonucleolytic removal of errors.

In comparison to the full-length enzyme, the Klenow fragment exhibits altered base substitution error specificity and is less accurate for minus one base frameshift errors at reiterated template nucleotides [Bebenek et al., J. Biol. Chem. 265:13878 (1990)]. Thus, the removal of the 5' exonuclease domain of *E. coli* DNA polymerase I adversely affects the fidelity of the remaining 3' exonuclease and synthetic domains.

Removal of a 5' exonuclease domain does not always adversely affect the fidelity of the resultant polymerase fragment. KlenTaq, a truncated version of Taq DNA polymerase lacks the first 235 N-terminal amino acids (which includes the 5' exonuclease domain) has been reported improved the fidelity of the polymerase two-fold [Barnes, Gene 112:29 (1992)].

Comparison of amino acid sequence in the 3' exonuclease domain of a number DNAPs has identified three domains, termed Exo I-III, which are highly conserved between a variety of mesophilic and thermophilic organisms [Bernad et al. Cell 59:219 (1989)]. FIG. 2 provides a schematic drawing which aligns the amino acid residues from a number of DNAPs over the 3' exonuclease domain. In FIG. 2, the one letter code is used for the amino acids; the numbers represent the amino acid residue in a given polymerase. In FIG. 2, residues which are highly conserved are indicated by the use of white letters within a black box. Portions of the 3' exonuclease domain of following polymerases are shown: *Bacillus subtilus* (Bsu) polymerase III; *E. coli* (Eco) polymerase IIII; phage T4, phage T7, *E. coli* polymerase I, *T. maritima* (Tma) polymerase and *T. neapolitana* (Tne) polymerase. The "∇" indicates amino acid residues involved in single strand DNA binding; the "Δ" indicates amino acid residues involved in metal binding and catalysis.

Site-directed mutagenesis experiments have identified a subset of these conserved residues as being critical for 3' exonuclease activity in *E. coli* polymerase I. The critical residues include D355, D424, D501 which are known to bind divalent metal ions and are essential for 3' exonuclease activity; mutation of these residues reduces 3' exonuclease activity several thousand fold. L361, F473 and Y497 are also important for 3' exonuclease activity and are believed to ensure correct positioning of the substrate in the active site. Mutation of L361 and Y497 reduces 3' exonuclease activity 12.5 to 25-fold; mutation of F473 reduces 3' exonuclease activity about 3000-fold.

PCT Publ. No. WO 92/03556 states that three characteristic domains are critical for 3' exonuclease activity in thermostable DNA polymerases; however, no site-directed mutagenesis is shown for any of the "critical" residues and no 3' exonuclease activity is reported for any of the mutant forms of Tma DNA polymerase (primarily deletion mutants) shown. The three domains identified in PCT Publ. No. WO 92/03556 are Domain A, which comprises D-X-E-X$^3$-L; Domain B, which comprises N-X$^3$-D-X$^3$-L and Domain C, which comprises Y-X$^3$-D where X$^N$ represents the number (N) of non-critical amino acids between the specified amino acids. As shown in FIG. 2, the location, sequence and spacing of these three domains found in polymerases derived from thermophilic organisms is consistent with the three domains identified in polymerases derived from mesophilic organisms.

While identification of residues which are highly conserved between a number of species provides a starting point for the design of site-directed mutagenesis experiments, it does not provide an absolute prediction of the effect of a given mutation in a particular protein. For example, the present invention shows that substitution of the aspartate at position 468 of the Tne DNA polymerase with a asparagine virtually eliminates the 3' exonuclease activity [Tne M284 (D468N)]. The analogous mutation in the Klenow fragment of DNA polymerase I (D501N) reduces 3' exonuclease activity only by 2-fold [Derbyshire et al., EMBO J. 10:17 (1991)]. These results underscore the fact that much remains to be learned about structure-function relationships and that one cannot predict, with certainty, the effect of a given mutation based on analogy to other proteins.

II. Generation of Tne DNA Polymerases

The present invention provides wild-type and modified forms of Tne DNA polymerases. The modified forms lack 5' exonuclease activity and some modified forms also display reduced or absent 3' exonuclease activity.

By the term "reduced or absent 3' exonuclease activity" it is meant that the modified enzyme has less than the level of 3' exonuclease activity found in the wild-type or unmodified enzyme whose protein sequence is listed in SEQ ID NO:2. The modified Tne polymerases of the present invention are advantageous in situations where the polymerization (i.e., synthetic) activity of the enzyme is desired but the presence of 5' exonuclease and/or 3' exonuclease activity is not.

The present invention is not intended to be limited by the nature of the alteration (e.g., deletion, insertion, substitution) necessary to render the Tne polymerase deficient in 5' exonuclease or 3' exonuclease activity. The present invention contemplates a variety of methods, including but not limited to proteolysis and genetic manipulation.

1. Reduction of Exonuclease Activity by Proteolysis

Tne DNA polymerases having a reduced level of either or both 5' exonuclease and 3' exonuclease activity are produced according to the present invention by physically cleaving the unmodified enzyme with proteolytic enzymes to produce fragments of the enzyme that are deficient in 5' and/or 3' exonuclease activity but retain synthetic activity. The proteolysis can remove the N-terminal one third of the protein (about residues 1 to 297 in SEQ ID NO:2) to remove 5' exonuclease activity. Proteolytic cleavage which removes all or a portion of the 3' exonuclease domain (about residues 298 to 482 in SEQ ID NO:2) will render the resulting enzyme deficient in 3' exonuclease activity. Following proteolytic digestion, the resulting fragments are separated by standard chromatographic techniques and assayed for the ability to synthesize DNA and to act as a 5' or 3' exonuclease. The assays to determine synthetic activity and 5' and 3' exonuclease activity are described in the experimental sections below.

2. Reduction of Exonuclease Activity by Genetic Manipulation

The examples below describe preferred methods for creating a construct (i.e., a vector) encoding a polymerase derived from Tne DNA polymerase I. The wild-type Tne polymerase is cloned by isolating genomic DNA using molecular biological methods from *T. neapolitana* cells. The genomic DNA is cleaved into fragments about 3 kb or larger using restriction enzymes and the fragments are inserted into a suitable cloning vector such as a plasmid or bacteriophage vector; the vectors containing fragments of *T. neapolitana* genomic DNA are then transformed into a suitable *E. coli* host. Clones containing DNA encoding the Tne polymerase may be isolated using functional assays (i.e., presence of thermostable polymerase in lysates of transformed cells) or by hybridization using a probe derived from a region of conservation among DNA polymerases derived from thermostable organisms. Alternatively, the *T. neapolitana* genomic DNA may be used as the target in a polymerase chain reaction (PCR) where the primers are selected from regions of high sequence conservation among the genes encoding thermostable DNA polymerases. Such a PCR may not amplify the entire coding region of the Tne polymerase I gene; in such a case, the full-length Tne gene could be isolated by using the amplified fragment as a probe to screen a genomic library containing *T. neapolitana* DNA.

Once the full-length Tne polymerase gene is obtained, regions encoding the 5' exonuclease and/or 3' exonuclease may be altered by a variety of means to reduce or eliminate these activities. Suitable deletion and site-directed mutagenesis procedures are described below in the examples.

Deletion of amino acids from the protein can be done either by deletion of the encoding genetic material, or by introduction of a translational stop codon by mutation or frame shift. In addition, proteolytic treatment of the protein molecule can be performed to remove segments of the protein.

In the examples below, specific alterations of the Tne polymerase gene were: a deletion between residues 1–849, a deletion between residues 1–945, a deletion between residues 1–966, deletion between residues 1–966, a deletion between residues 1–849 and residues 925–1272 and substitutions at residues 946, 947, 967, 968, 969, 975, 1166, 1167, 1391, 1402, 1407, 1410, 2184 and 2189. These modified sequences are described below in the examples and at SEQ ID NOS:7, 10, 15, 18, 22, 25, 28, 32, 34, 36, 38 and 53.

Those skilled in the art know that single base changes can be innocuous in terms of enzyme structure and function. Similarly small additions and deletions can be present without substantially changing the exonuclease or polymerase function of the wild-type or modified Tne DNA polymerases. To test whether a particular change is innocuous in terms of the effect upon enzymatic activity, the polymerase encoded by a given DNA sequence is tested for the presence of synthetic activity, 5' exonuclease activity and 3' exonuclease activity as in the assays described in the examples below. DNA sequences which contain alterations other than those listed in SEQ ID NOS:7, 10, 15, 18, 22, 25, 28, 32, 34, 36, 38 and 53 but which encode a polymerase molecule having the properties associated with the polymerases encoded by the above SEQ ID NOS are contained within the present invention.

Other deletions and substitutions are also suitable to create modified Tne DNA polymerases lacking 5' and/or 3' exonuclease activity. For example, given the degeneracy of the genetic code, several DNA sequences may be used to introduce substitutions which result in the expression of the same amino acid. It is preferable that the alteration decrease the 5' and/or 3' exonuclease activity to a level which is low enough to provide an improved enzyme for a variety of applications such as PCR and chain termination sequencing (including thermal cycle sequencing) as discussed below in the examples. These modifications will preferably not reduce the synthetic activity of the modified enzyme. Modified polymerases are tested for the presence of synthetic activity and 5' and 3' exonuclease activity as in assays described below. Thoughtful consideration of these assays allows for the screening of candidate enzymes whose structure is heretofore as yet unknown. In other words, construct "X" can be evaluated according to the protocol described below to determine whether it is a member of the genus of modified Tne polymerases of the present invention as defined functionally, rather than structurally.

The present invention contemplates that the nucleic acid construct of the present invention be capable of expression in a suitable host. In particular it is preferable that the expression system chosen utilize a tightly controlled promoter such that expression of the Tne polymerase is prevented until expression is induced. In this manner, potential problems of toxicity of the expressed polymerases to the host cells (and particularly to bacterial host cells) is avoided. Those in the art know methods for attaching various promoters and 3' sequences to a gene structure to achieve efficient and tightly controlled expression. The examples below disclose a number of suitable vectors and vector constructs. Of course, there are other promoter/vector combinations that would be suitable. The choice of a particular vector is also a function of the type of host cell to be employed (i.e., procaryotic or eucaryotic).

It is not necessary that a host organism be used for the expression of the nucleic acid constructs of the invention. For example, expression of the protein encoded by a nucleic acid construct may be achieved through the use of a cell-free in vitro transcription/translation system. An example of such a cell-free system is the commercially available TnT™ Coupled Reticulocyte Lysate System (Promega; this cell-free system is described in U.S. Pat. No. 5,324,637, the disclosure of which is herein incorporated by reference).

The nucleic acid construct containing DNA encoding the wild-type or a modified Tne polymerase may provide for the addition of exogenous sequences (i.e., sequences not encoded by the Tne polymerase coding region) to either the 5' or 3' end of the Tne polymerase coding region to allow for ease in purification of the resulting polymerase protein (the resulting protein containing such an affinity tag is termed a fusion protein). Several commercially available expression vectors are available which provide for the addition of affinity tags (an example of an exogenous sequence) to either the amino or carboxy-termini of a coding region; in general these affinity tags are short stretches of amino acids which do not alter the characteristics of the protein to be expressed (i.e., no change to enzymatic activities).

For example, the pET expression system (Novagen) utilizes a vector containing the T7 promoter which encodes the fusion protein containing a short stretch of histidine residues at either end of the protein and a host cell which can be induced to express the T7 DNA polymerase (i.e., a DE3 host strain). The production of fusion proteins containing a histidine tract is not limited to the use of a particular expression vector and host strain. Several commercially available expression vectors and host strains can be used to express protein sequences as a fusion protein containing a histidine tract (For example, the pQE series (pQE-8, 12, 16, 17, 18, 30, 31, 32, 40, 41, 42, 50, 51, 52, 60 and 70) of expression vectors (Qiagen) which are used with the host strains M15[pREP4] (Qiagen) and SG13009[pREP4] (Qiagen) can be used to express fusion proteins containing six histidine residues at the amino-terminus of the fusion protein). Additional expression systems which utilize other affinity tags are known to the art.

Once a suitable nucleic acid construct has been made, the Tne polymerase may be produced from the construct. The examples below and standard molecular biological teachings enable one to manipulate the construct by different suitable methods.

Once the desired Tne polymerase has been expressed, the polymerase is tested for both synthetic and exonuclease activity as described below.

III. Use of Tne DNA Polymerases in the PCR

The wild-type and modified Tne polymerases of the present invention provide suitable and in some cases superior enzymes for use in the PCR. As shown in the examples below, the wild-type and modified forms of Tne polymerase were found to require the use of fewer units of polymerase activity to produce a given amount of product DNA in PCRs as compared to wild-type Taq DNA polymerase (i.e., nTaq) or a modified form of Tma DNA polymerase (i.e., UlTma™). In addition, modified forms of Tne polymerase were found to tolerate a broader range of dNTP concentrations and a broader range of magnesium ion concentrations in the PCR. The ability to tolerate a broad range of dNTP is important as it allows flexibility in the range of dNTPs to be used in a reaction; additionally, the ability to tolerate a wide range of dNTP concentrations demonstrates that the enzymes of the invention provide for a robust PCR (i.e., the enzyme is not sensitive to small variations in dNTP concentration). The ability to produce only specific amplification products over a wide range of magnesium ion concentration is advantageous for use in multiplexing PCR reactions.

Several of the modified Tne polymerases provide enzymes having greater resistance to thermal inactivation as compared to nTaq or UlTma™ DNA polymerases. Greater thermal stability is important for PCR applications as the greater the thermal stability of the enzyme, the fewer units of enzyme must be used in the PCR.

In addition as described below, modified forms of Tne polymerases having reduced levels of 3' exonuclease activity have be used in combination with a high fidelity DNA polymerase (e.g., Tli, Pfu or Pwo DNA polymerase) to amplify long targets in a PCR.

IV. Use of Tne DNA Polymerases in DNA Sequencing Methods

The sequence of a deoxyribonucleic acid molecule can be elucidated using chemical [Maxam and Gilbert, Proc. Natl. Acad Sci. USA 74:560 (1977)] or enzymatic [Sanger et al., Proc. Natl. Acad Sci. USA 74:5463 (1977)] methods. The enzymatic method of sequencing is based on the ability of a DNA polymerase to extend a primer, hybridized to the template that is to be sequenced, until a chain-terminating nucleotide is incorporated (referred to as chain terminating sequencing). Each sequence determination is carried out as a set of four separate reactions, each of which contains all four deoxyribonucleoside triphosphates (dNTP) supplemented with a limiting amount of a different dideoxyribonucleoside triphosphate (ddNTP). Because ddNTPs lack the 3'-OH group necessary for chain elongation, the growing oligonucleotide is terminated selectively at G, A, T, or C, depending on the respective dideoxy analog in the reaction.

The relative concentrations of each of the dNTPs and ddNTPs can be adjusted to give a nested set of terminated chains over several hundred to a few thousand bases in length. The resulting fragments, each with a common origin but ending in a different nucleotide, are separated according to size by high-resolution denaturing gel electrophoresis.

Incorporation of a label (e.g., a radiolabel or a fluorescent label) into the oligonucleotide chain permits the visualization of the sequencing products by autoradiography or fluorescence detection. The end-labeled primer protocol, a modification of that described by Heiner et al. [(988) Applied Biosystems, Inc. DNA Sequencer Model 370 User Bulletin-Taq Polymerase: Increased Enzyme Versatility in DNA Sequencing], uses [$\gamma$-$^{32}$P]ATP, [$\gamma$-$^{33}$P]ATP or [$\gamma$-$^{35}$S] ATP to label the sequencing primer. Alternatively, primers containing a fluorescent dye at the 5' terminus may be employed. The DNA template and labeled primer are repeatedly annealed and enzymatically extended/terminated in thermal cycled sequencing. The end-labeled primer protocol is the most versatile sequencing method and is useful when working with lambda DNA [Kaledin et al., Biokhimiya 45:494 (1980)], PCR templates, and any template where false priming may be a problem. This protocol generates sequence data very close to the primer and is recommended when this is needed. The reaction also contains deaza nucleotide mixes that substitute 7-deaza dGTP for dGTP. The deaza mixes resolve band compressions associated with GC-rich regions [Mizusawa et al., Nucl. Acids Res. 14:1319 (1986) and Barr et al., Biotechniques 4:428 (1986)].

Thermal cycled sequencing is an alternative method for enzymatic sequence analysis which takes advantage of the intrinsic properties of thermophilic DNA polymerases, such as the one isolated from Thermus aquaticus (Taq DNA polymerase). Because the protocol utilizes a thermocycling apparatus, several advantages are realized over conventional sequencing strategies. First, the protocol yields a linear amplification of the template DNA, reducing the amount of template required to achieve a detectable sequence ladder.

Using a $^{32}$P end-labeled primer, greater than 500 bases of sequence can be obtained from as little as 4 fmol ($4 \times 10^{-15}$ moles) of template after an overnight exposure. Secondly, the high temperatures employed during each denaturation cycle eliminate the requirement for alkaline denaturation and ethanol precipitation of double-stranded DNA (dsDNA) templates. The denaturation cycles also help to circumvent the problems associated with rapid reannealing of linear dsDNA templates such as PCR reaction products. Third, high annealing temperatures increase the stringency of primer hybridization. Fourth, the high polymerization temperature decreases the secondary structure of DNA templates and thus permits polymerization through highly structured regions [Innis et al., Proc. Natl. Acad. Sci USA 85:9436 (1988)]. Thermal cycled sequencing is useful for sequencing a wide variety of templates such as recombinant DNA, amplified DNA, large double-stranded DNA templates such as lambda, GC-rich templates and palindrome-rich templates.

Existing thermostable polymerases which are used in chain termination methods of sequencing (both traditional and thermal cycling protocols) require fairly high concentrations of ddNTPs as the affinity of these polymerases for ddNTPs is somewhat low. For example, when Taq DNA polymerase is employed for chain termination sequencing protocols, the optimal concentrations of ddNTPs in the ddNTP termination mixtures (3× mixtures): 180 $\mu$M ddGTP, 1 mM ddATP, 1.5 mM ddTTP and 500 $\mu$M ddCTP [as described in U.S. Pat. No. 5,075,216, the disclosure of which is herein incorporated by reference]. When the polymerase employed is a modified form of Taq DNA polymerase, sTaq (sequencing grade Taq), the optimal concentrations of ddNTPs in the ddNTP termination mixtures: 30 $\mu$M ddGTP, 350 $\mu$M ddATP, 600 $\mu$M ddTTP and 200 $\mu$M ddCTP. In contrast, a modified form of Tne DNA polymerase (the Tne M284(D323A, D389A) polymerase) provided herein utilizes the following concentrations of ddNTPs in the termination mixtures (3× mixtures): 20 $\mu$M ddGTP, 50 $\mu$M ddATP, 75 $\mu$M ddTTP and 25 $\mu$M ddCTP. Another modified form of Tne DNA polymerase provided herein has a still further increased affinity for ddNTPs. The Tne Quad polymerase utilizes the following concentrations of ddNTPs in the termination mixtures (3× mixtures using a radioactive sequencing format): 0.3 $\mu$M ddGTP, 0.2 $\mu$M ddATP, 0.25 $\mu$M ddTTP and 0.25 $\mu$M ddCTP. Because ddNTPs are expensive, the use of a thermostable polymerase having a higher affinity for ddNTPs (i.e., the modified Tne polymerase of the invention) will result in considerable cost savings in DNA sequencing applications.

The Tne polymerases having an increased affinity for dideoxynucleotides provided herein may be employed in a variety of enzymatic sequencing formats including radioactive sequencing formats (using either end-labelled primers or incorporation of labelled deoxynucleotides) or fluorescent sequencing formats. The sequencing format may be a manual procedure or may be automated. Applied Biosystems (AB-Perkin-Elmer, Foster City, Calif.) produces an instrument in which four different primers are used, each labelled with a different fluorescent marker [Smith et al. (1985) Nuc. Acid. Res. 13:2399 and (1986) Nature 321:674 and U.S. Pat. No. 5,171,534 the disclosure of which is herein incorporated by reference]. Each primer is used in a separate reaction containing one of four dideoxynucleotides. After conducting the four reactions, the mixtures are combined and the DNA fragments are fractionated in a single lane on a gel. A laser at the bottom of the gel is used to detect the fluorescent products after they have been electrophoresed through the gel.

U.S. Pat. No. 4,707,235 (the disclosure of which is herein incorporated by reference) provides an automated system for the electrophoresis and analysis of radiolabelled products using a multichannel electrophoresis apparatus.

To determine the optimal ratio of dNTPs to ddNTPs to be used in any given sequencing protocol employing the Tne polymerases of the present invention, sequencing reactions are performed wherein the concentration of dNTPs remains constant and the concentration of the ddNTPs is varied. For example, the following ratios (dNTP:ddNTP) may be used initially to establish a rough estimate of the ratio to be employed: 1:001, 1:0.01, 1:0.1, 1:1, 1:10, 1:100 and 1:1000. Once a suitable ratio has been determined for a given Tne polymerase and a given dNTP:ddNTP mixture, the concentrations of dNTPs and ddNTP in a given mixture may be further refined to identify the optimal concentration and ratio. The optimal ratio of dNTP to ddNTP is that which produces uniform band intensities over the desired size range (e.g., 0 to 600 nucleotides). Examples of optimized ratios of dNTPs/ddNTPS using Tne polymerases in radioactive and fluorescent sequencing protocols are provided in the experimental sections below.

EXPERIMENTAL

The following examples serve to illustrate certain preferred embodiments and aspects of the present invention and are not to be construed as limiting the scope thereof.

In the disclosure which follows, the following abbreviations apply: ° C. (degrees Centigrade); g (gravitational field); vol (volume); w/v (weight to volume); v/v (volume to volume); BSA (bovine serum albumin); CTAB (cetyltrimethylammonium bromide); fmol (femtomole); HPLC (high pressure liquid chromatography); DTT (dithiothreitol); DMF (N, N dimethyl formamide); DNA (deoxyribonucleic acid); i.d. (internal diameter); p (plasmid); $\mu$l(microliters); ml (milliliters); $\mu$g (micrograms); pmoles (picomoles); mg (milligrams); MOPS (3-[N-Morpholino]propanesulfonic acid); M (molar); mM (milliMolar); $\mu$M (microMolar); nm (nanometers); kdal (kilodaltons); OD (optical density); EDTA (ethylene diamine tetra-acetic acid); FITC (fluorescein isothiocyanate); SDS (sodium dodecyl sulfate); NaPO$_4$ (sodium phosphate); Tris (tris(hydroxymethyl)-aminomethane); PMSF (phenylmethylsulfonylfluoride); TBE (Tris-Borate-EDTA, i.e., Tris buffer titrated with boric acid rather than HCl and containing EDTA) ; PBS (phosphate buffered saline); PPBS (phosphate buffered saline containing 1 mM PMSF); PAGE (polyacrylamide gel electrophoresis); Tween (polyoxyethylene-sorbitan); Boehringer Mannheim or BM (Boehringer Mannheim, Indianapolis, Ind.); Epicentre (Epicentre Technologies, Madison, Wis.); New England Biolabs or NEB (New England Biolabs, Beverly, Mass.); Novagen (Novagen, Inc., Madison, Wis.); Pharmacia (Pharmacia Biotech Inc., Piscataway, N.J.); Perkin Elmer (Perkin Elmer, Norwalk, Conn.); Promega (Promega Corp., Madison, Wis.); Qiagen (Qiagen Inc., Chatsworth, Calif.); Spectra (Spectra, Houston, Tex.); Stratagene (Stratagene Cloning Systems, La Jolla, Calif.); USB (U.S. Biochemical, Cleveland, Ohio).

EXAMPLE 1

Isolation of the Tne DNA Polymerase Gene a) Growth of *T. neapolitana* Cells

*T. neapolitana* cells (obtained from V. A. Svetlichny, The Institute of Microbiology, Russian Academy of Sciences, Moscow) were grown in a medium containing (per 100 ml): 0.1 ml K-phosphate solution [300 g/l $K_2HPO_4$ and 200 g/l $KH_2PO_4$]; 1 ml of Solution 1 [27 g/l $NH_4Cl$, 27 g/l $CaCl_2$ and 31 g/l $MgCl_2.6H_2O$]; 1 ml of a 10% solution of yeast extract (Difco); 2.5% natural sea salt; 0.1 ml of a 2% solution of resazurin; 1 ml of 5% $Na_2SO_3$; 150 mg $NaHCO_3$ and 0.5% glucose.

b) Isolation of Genomic DNA

Large scale cultures (10 liters) of *T. neapolitana* cells were grown in the above medium in a 10 l fermentation vessel under nitrogen (i.e., anaerobic conditions) at 75° C. for 28 hours (early stationary phase). The cells were then collected by centrifugation at 10,000×g and the cell pellet was washed once with a solution comprising 0.9% NaCl. The washed cell pellet was frozen at −70° C. DNA was isolated from the frozen cells as follows. The frozen cells (3 g) were thawed in 30 ml of a solution containing 100 mM Tris-HCl (pH 9.0), 50 mM EDTA and 2 mg/ml lysozyme. The mixture was incubated for 30 min at 0° C. and then SDS and proteinase K was added to a final concentration of 1% and 100 μg/ml, respectively. The mixture was incubated for 1.5 hours at 45° C. with light shaking. Following the incubation, the mixture was cooled to room temperature (about 25° C.) and NaCl was added to a concentration of 0.5 M. An equal volume of phenol/chloroform was added and the mixture was extracted and the aqueous and organic phases were separated by centrifugation for 10 min at 6,000×g at room temperature. The supernatant was transferred to a fresh tube using a wide-bore pipet. A total of six phenol/chloroform extractions were performed (until the interphase disappeared). The DNA was precipitated by the addition of ethanol and gently mixing the solution. The precipitated DNA was washed with 70% ethanol. The DNA was then centrifuged for 5 min at 10,000×g and the supernatant was discarded. The pellet was resuspended in a buffer containing 10 mM Tris-HCl (pH 7.4), 0.1 mM EDTA and stored at −20° C. until used.

c) Construction of a *T. neapolitana* Genomic DNA Library

The *T. neapolitana* DNA was then digested with Sau3A under conditions which promoted the generation of fragments 3–8 kb in length. Briefly, 10 μg of genomic DNA was digested with 1.6 units of Sau3A in a volume of 15 μl for 1 hour at 37° C. The reaction was stopped by the addition of 5 μl of sample buffer [70% glycerol, 50 mM EDTA] and the digested DNA was run on a low melting temperature agarose gel (BioRad). Fragments 3–8 kb in length were isolated from the gel using standard procedures [Sambrook et al., Molecular Cloning: A Laboratory Manual, 2nd ed., Cold Spring Harbor Laboratory Press, NY (1989) pp. 6.30–6.31]. The DNA recovered from the gel was precipitated with ethanol, dried and resuspended in 100 μl of 10 mM Tris-HCl (pH 7.5), 0.1 mM EDTA. Five microliters of the DNA mixture (about 0.1 μg) was ligated to 0.25 μg of the pTZ19R vector (Pharmacia) which had been digested with BamHI and treated with bacterial alkaline phosphatase. The ligation products were used to transform competent TG1 cells [TG1 cells are an EcoK[31] derivative of JM101 cells; a commercially available equivalents include NM522 cells (Pharmacia) and XL1-Blue cells (Stratagene)] and the cells were plated onto MacConkey agar plates (Difco).

White colonies (i.e., those containing plasmids having an insert) were picked onto 30 master plates (96 colonies/plate; a total of about 3,000 colonies were screened). Replica plates were generated to provide cells for DNA polymerase analysis. The library was screened by functional assay; the cells from each replica plate were removed and pooled by rinsing the plate with 2 ml of 0.9% NaCl. The cells were then collected by centrifugation (12,000 rpm for 3 min) in a microcentrifuge (Eppendorf). The pellets were then washed with 1.5 ml of 0.9% NaCl. The washed cell pellets were then lysed by sonication in 0.5 ml of a solution containing 50 mM Tris-HCl (pH 7.4), 1 mM EDTA and 5 mM PMSF. The lysates were then heated to 72° C.–75° C. in a water bath for 20 min. Following the incubation, the lysates were clarified by centrifugation in a microfuge at 12,000 rpm for 10 min. The supernatant was removed to a fresh tube. DNA polymerase activity was assayed using the supernatant as follows.

Denatured bovine thymus DNA was prepared as follows. A solution comprising 6 mM bovine thymus DNA (BioLAR, Olaine, Latvia; equivalent preparations of calf thymus DNA are available from Sigma, St. Louis, Mo.) in 1 mM NaOH was incubated for 15 min at 20° C. The solution was then neutralized by the addition of HCl to a final concentration of 100 mM and Tris-HCl, pH 8.0 to a final concentration of 50 mM.

The following components were mixed: 2.5 μl 0.5 M Tris-HCl (pH 7.6), 5 μl 100 mM $MgCl_2$, 2 μl denatured bovine thymus DNA (2 mg/ml), 0.2 μl of 12.5 mM of each of the dNTPs and 1.5 μCi of α-$^{32}$P-dTTP and $H_2O$ to a volume of 25 μl. Twenty-five microliters of supernatant from each of the pools of lysed cells were mixed with 25 μl of the above assay mixture in the well of a 96 well microtiter plate. The mixture was incubated for 1 hour at 75° C. The reaction was stopped by the addition of 5 μl of 200 mM EDTA (pH 8.0). Five microliters of the reaction mixture was then loaded onto a 1×1 inch square of DEAE paper (Whatman). The samples were dried at 80° C. and then washed with 0.5 M sodium phosphate (pH 7.2) (wash solution) using about 5 ml of wash solution per sample for 10 min with light shaking. Three washes were performed. The samples were then rinsed with water (10 ml/sample) for 1 min followed by an ethanol rinse. The ethanol rinsed samples were then dried at 80° C. and DEAE-absorbent radioactivity was counted using a liquid scintillation counter. The results of the initial DNA polymerase assays revealed that a single pool produced DNA polymerase activity.

To isolate clones containing Tne genomic DNA encoding the DNA polymerase activity, the colonies on the positive master plate were grown as smaller pools comprising either a single row or a single column of colonies. The smaller pools of colonies were grown, lysates were prepared and DNA polymerase activity was determined as described above. A single row and a single column contained DNA polymerase activity; the intersection of this row and column identified the single individual clone containing DNA encoding DNA polymerase activity. This single colony was grown and assayed for DNA polymerase activity to confirm the presence of thermostable DNA polymerase activity. This clone was called pTen.

DNA was prepared from the pTen clone using standard techniques of molecular biology; this clone was found to contain a insert of approximately 3.5 kb. Restriction enzyme digests were performed with a battery of enzymes to create a restriction map of the Tne genomic DNA insert. Subclones were generated from the positive clone and a series of nested deletions were generated using Exonuclease III and standard molecular biology techniques to facilitate DNA sequencing [Short Protocols in Molecular Biology, 2nd ed. (1992) Ausubel et al. Eds, John Wiley & Sons, New York, pp.7–8 to 7–16 and 7–29 to 7–37]. The DNA sequence of the insert was determined using the Sanger dideoxy sequencing method and Sequenase® (USB). The DNA sequence of the coding region for the full-length Tne DNA polymerase gene is listed in SEQ ID NO:1. The deduced amino acid sequence of the Tne DNA polymerase is listed in SEQ ID NO:2.

Analysis of the deduced amino acid sequence was performed using protein analysis software (DNAStar, Inc., Madison, Wis.). The open reading frame encodes a protein of 893 amino acids; the predicted molecular weight of the protein is 102,054 (however, as shown in Example below, the full-length protein migrates with an apparent molecular weight of 97,000 on SDS-PAGE gels). The predicted isolelectric point is 6.19 and the charge at pH 7.0 is −7.56.

The nucleotide and amino acid sequences of the Tne DNA polymerase were compared with the reported sequences for *E. coli* DNA polymerase I and the thermostable DNA polymerase from *T. maritima*. FIG. 3 provides an alignment of the amino acid residues of these three polymerases. In FIG. 3 the following abbreviations are used: Eco (*E. coli* DNA polymerase I); Tma (Tma DNA polymerase) and Tne (Tne DNA polymerase). Shading is used to indicate residues which differ from the amino acid sequence of Tne DNA polymerase.

In *E. coli* DNA polymerase I, the 5' exonuclease domain comprises approximately residues 1–323; the 3' exonuclease domain comprises approximately residues 324–517 and the synthetic or polymerization domain comprises approximately residues 521–928. Alignment of the amino acid sequences of *E. coli* DNA polymerase I with the sequence of the Tne DNA polymerase molecule of the present invention reveals that the 5' exonuclease domain of Tne DNA polymerase comprises approximately residues 1–297; the 3' exonuclease domain comprises approximately residues 298–482 and the polymerization domain comprises approximately residues 486–893.

Alignment of amino acid residues present in *E. coli* DNA polymerase I and Tne DNA polymerase shows that the two enzymes are 44% identical overall and 51% identical over the polymerase domain (residues 521–928 in *E. coli* and residues 486–893 in Tne). The alignment was performed using the Lipman-Pearson algorithm as provided by DNASTAR, Inc. (Madison, Wis.); gaps were introduced into the two sequences to provide for maximum alignment.

Comparison of the nucleotide and amino acid sequences of the Tne and Tma polymerases revealed that these two polymerases share 78% identity at the nucleotide level and 88% identity at the amino acid level.

EXAMPLE 2

Efficient Expression of Tne DNA Polymerase in *E. coli*

In order to express the Tne DNA polymerase in large amounts in host cells, the DNA sequences encoding the polymerase (i.e., the coding region) were removed from pTen (described in Example 1) and inserted into an expression vector.

Restriction enzyme analysis revealed that the Tne polymerase gene was present in the opposite transcriptional orientation relative to the T7 promoter present on the pTZ19R vector used to generate pTen. In order to produce Tne polymerase, sequences encoding the Tne polymerase gene were removed from pTen by digestion with SmaI and XbaI and an approximately 3.5 kb SmaI/XbaI fragment was isolated by electrophoresis of the digestion products on an agarose gel followed by excision of the desired band. DNA was recovered from the agarose block using the Wizard™ PCR Preps DNA Purification System (Promega). Briefly, 0.5 to 1.0 ml of Wizard™ PCR Preps DNA Purification Resin was added to the agarose block and the mixture was incubated at 42° C. for 5 minutes to melt the agarose. DNA was extracted using the protocol provided in the kit.

The 3.5 kb SmaI/XbaI fragment was ligated into the pGEM®-3Zf(+) vector (Promega) which had been digested with SmaI and XbaI to generate pGTne. This construction placed the 5' end (i.e., encodes the N terminal portion) of the Tne polymerase gene downstream of the T7 promoter in the same transcriptional orientation. The ligation mixture was used to transform competent JM109(DE3) cells (Promega). Recombinant clones were isolated, confirmed by restriction digestion using standard recombinant molecular biology techniques [Sambrook et al., Molecular Cloning, A Laboratory Manual (1989)].

Expression of the Tne DNA polymerase from the pGTne construct was next examined. JM109(DE3) cells containing pGTne were grown at 37° C. and induced with 1 mM IPTG. Parallel cultures of TG1 cells containing pTen were grown and induced. After a few hours (i.e, 1–3) of growth in the presence of IPTG, the cells were collected by centrifugation and crude lysates were prepared as follows. A 1 ml aliquot of each of the cultures containing the Tne constructs was centrifuged in a microcentrifuge at 14,000×g for 3 min at room temperature to pellet the cells. The cells were then resuspended in 200 µl of a solution comprising 50 mM Tris-HCl (pH 8.0), 50 mM glucose, 1 mM EDTA and the cells were pelleted again. The cells were next resuspended in 50 µl of the previous buffer containing 4 mg/ml lysozyme and the mixture was incubated at room temperature for 10 minutes. Following the incubation, 50 µl of a solution comprising 10 mM Tris-HCl (pH 8.0), 50 mM KCl, 1 mM EDTA, 1 mM PMSF, 0.5% Tween-20, 0.5% Nonidet P40 was added and the mixture was incubated at 75° C. for 10 minutes. The lysate was then clarified by centrifugation in a microcentrifuge at 14,000×g for 5 minutes. Eighty microliters of the supernatant was removed and stored in a separate tube at 4° C. The crude lysates were analyzed for polymerase activity at 74° C. as described in Example 5(b), below.

The following results were obtained. The pTen construct gave polymerase activity levels at or about 2 fold higher than the background level for the assay. The pGTne construct gave activity levels of about 50 times background levels. While the expression of Tne polymerase seen using pGTne was much improved relative to the level seen using pTen, this expression level was not sufficient to produce large amounts of the enzyme.

These above result suggested that the Tne polymerase promoter was non-functional in *E. coli* (very low level of activity present when pTen is used). Furthermore, the presence of the Tne polymerase promoter appeared to be detrimental to expression when transcription was initiated from the T7 promoter in the pGTne construct (perhaps due to transcriptional read-through interference). In order to remove the Tne polymerase gene promoter from the Tne polymerase coding region, the following experiments were conducted.

The DNA sequence of the 5' end of the Tne polymerase gene was sequenced using the M13 forward primer in conjunction with the fmole® DNA Sequencing System (Promega); sequencing was conducted according to the manufacturer's instructions. The sequence analysis revealed that a unique BglI site was found 43 bp into the coding region (i.e., 43 bp following the A of the initiator ATG codon). To remove the coding region of the Tne polymerase gene from pGTne, pGTne was digested with BglI and XbaI and the approximately 3.0 kb BglI/XbaI fragment was isolated (as described above). The 3.0 kb BglI[/XbaI fragment was ligated directly downstream of either the T7 promoter or the tac promoter present in pALTER®-Ex1 (Promega); pALTER®-Ex1 contains both the T7 and the tac promoters positioned in opposite transcriptional orientations relative to one another. These two ligations were performed as follows.

To insert the 3.0 kb BglI/XbaI fragment downstream of the T7 promoter, a 43 bp synthetic linker having a NcoI overhanging end at one end and a BglI overhanging end at the other end was ligated to the Tne polymerase coding region. This linker was formed by annealing of the following two oligonucleotides: JH64 which comprises 5'-CATGGCGAGACTATTTCTCTTTGATGGCACAG-CCCTGGC CTACA-3' (SEQ ID NO:3) and JH65 which comprises 5'-AGGCCAGGGCTGTGCCATCAAAGAGAA ATAGTCTCGC-3' (SEQ ID NO:4). This synthetic linker regenerates the native sequence of the Tne polymerase gene located upstream of the BglI site and allows insertion of the coding region into pALTER®-Ex1. pALTER®-Ex1 was digested with NcoI and XbaI and the coding region containing the synthetic linker was ligated to the digested vector to generate pATne2.

To insert the 3.0 kb BglI/XbaI fragment downstream of the tac promoter, a 43 bp synthetic linker having a NdeI overhanging end at one end and a BglI overhanging end at the other end was ligated to the Tne polymerase coding region. This linker is formed by annealing of the following two oligonucleotides: JH62 which comprises 5-AGGCCAGGGCTGTGCCATCAAAGAGAAATAGT-CTCGCCA (SEQ ID NO:5) and JH63 which comprises 5'-TATGGCGAGACTATTTCTCTTTGTGGCACAGCCCT GGCCTACA-3' (SEQ ID NO:6). This synthetic linker regenerates the native sequence of the Tne polymerase gene located upstream of the BglI site and allows insertion of the coding region into pALTER®-Ex1. pALTER®-Ex1 was digested with NdeI and XbaI and the coding region containing the synthetic linker was ligated to the digested vector to generate pATne1.

Competent *E. coli* cells were transformed with the above ligation mixtures corresponding to either pATne1 (JM109 cells; Promega) and pATne2 [JM109(DE3) cells; Promega]. Recombinant clones were isolated, confirmed by restriction digestion using standard recombinant molecular biology. Cells harboring either pATne1 or pATne2 were grown and induced as described above. Crude lysates were prepared and DNA polymerase assays were performed (as described above). The results of these polymerase assays showed that both pATne1 and pATne2 gave significantly better yields of Tne polymerase than pGTne (at least 2–3 fold higher).

EXAMPLE 3

Construction of Tne Deletion Mutants Lacking 5' to 3' Exonuclease Activity

As noted above, the presence of 5' to 3' exonuclease activity in a thermostable DNA polymerase is undesirable for certain applications. To construct mutant Tne polymerases lacking 5' to 3' exonuclease activity, two deletion mutants of the Tne polymerase gene were generated. Both mutants contain deletions which remove sequences encoding a large portion of the 5' to 3' exonuclease domain located at the N terminus of the Tne polymerase molecule.

a) Construction of a Vector Encoding Deletion Mutant Tne M284

Figure 4:
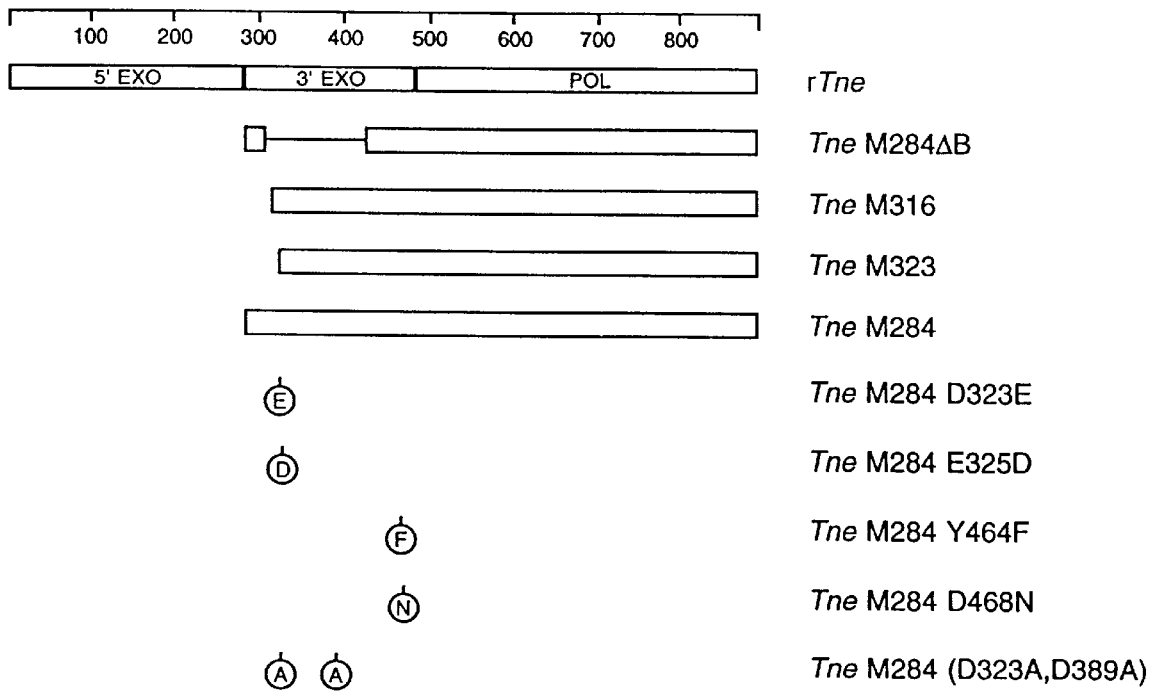
FIG. 4 provides a schematic depicting the full length and mutant Tne DNA polymerases of the present invention.

The deletion mutant Tne M284 is a truncated form of the Tne polymerase which uses the naturally occurring methionine at amino acid position 284 in the full-length protein (SEQ ID NO:2) as the initiating methionine for translation initiation. FIG. 4 provides a schematic representation of several modified Tne polymerases (constructed as described in Examples 3 and 4) along the map of the full-length Tne polymerase protein. The scale represents length in increments of 100 amino acid residues. The full length Tne polymerase (SEQ ID NO:2) contains 893 amino acids. The thick open boxes represent the presence of amino acid residues; thin lines between two regions of thick boxes indicates that amino acids were deleted between the two open boxes. Circles containing a single letter indicate the location of a mutated amino acid residue (the single letter code is used for the amino acid residues indicated).

To generate a construct containing the Tne M284 mutant, pGTne was digested with BspHI (generates ends compatible with NcoI ends) and KpnI and a 1.05 kb BspHI/KpnI fragment (containing the 5' portion of the coding region) was isolated as described in Example 2. A second aliquot of pGTne was digested with KpnI and XbaI and a 1.3 kb fragment containing the 3' portion of the Tne polymerase coding region was isolated. pALTER-Ex1 was digested with NcoI and XbaI. A three-way ligation was performed using the digested pALTEREx1 vector, 1.05 kb BspHI/KpnI fragment and the 1.3 kb KpnI/XbaI fragment. Competent JM109 (DE3) cells were transformed with the ligation mixture and recombinant clones were isolated, confirmed by restriction digestion using standard recombinant molecular biology. The resulting plasmid was called pM284. The nucleotide sequence of the region encoding the Tne M284 gene is listed in SEQ ID NO:7. The amino acid sequence of Tne M284 is listed in SEQ ID NO:8.

b) Construction of a Vector Encoding Deletion Mutant Tne M316

The deletion mutant Tne M316 is a truncated form of the Tne polymerase protein which uses an artificially created methionine at amino acid position 316 as the initiator methionine. Tne M316 was created by introducing a methionine residue at position 316 (and a corresponding NcoI site) via site-directed mutagenesis using the Altered Sites® II in vitro Mutagenesis System (Promega) in conjunction with mutagenesis oligonucleotide JH68 [5'-ATCGAAAAGCTGACCATGGTTCCATCTT TTG-3' (SEQ ID NO:9)] and pATne2. The manufacturer's protocol was followed exactly. Briefly, pATne2 was denatured using alkali and the JH68 mutagenic oligonucleotide was annealed to the denatured plasmid along with the ampicillin repair oligonucleotide (provided in the kit). The mutant strand was synthesized using T4 DNA polymerase and T4 DNA ligase. ES1301mutS cells (provided in the kit) were then cotransformed with the mutagenized pATne2 and R408 DNA (provided in the kit). Small scale DNA preparations were prepared from the transformed ES1301mutS cells and the DNA was used to transform JM109 cells. Mutants were selected by growth on ampicillin plates and the desired recombinant were confirmed by restriction enzyme analysis (i.e., presence of an additional NcoI site). The resulting plasmid containing the engineered NcoI site was then digested with NcoI which deleted the 5' to 3' exonuclease domain as a 948 bp fragment and the large fragment was isolated (as described above) and religated to itself to create the pM316 construct. The nucleotide sequence of the region encoding the Tne M316 gene is listed in SEQ ID NO:10. The amino acid sequence of Tne M316 is listed in SEQ ID NO:11.

c) Expression of Tne M284 and Tne M316 in *E. coli*

The pM284 and pM316 constructs (in JM109 cells) were grown, induced and crude lysates were prepared as described in Example 2. DNA polymerase activity was measured in crude lysates as described in Example 2.

The results of the polymerase assays showed that the Tne M284 mutant (pM284) contained 17 units per $\mu$l of polymerase activity from the crude lysate and the Tne M316 mutant (pM316) produced no detectable polymerase activity. No detectable polymerase activity was found when the Tne M316 polymerase was expressed from the trc promoter either (to express the Tne M316 coding region from the trc promoter, a 2.5 kb NcoI/PstI fragment was isolated from pM316 and ligated to pTrc 99 A (Pharmacia) digested with NcoI and PstI).

Aliquots (5 $\mu$l) of each crude lysate were electrophoresed on a pre-cast 4–20% denaturing gradient polyacrylamide gel (Novex, San Diego, Calif.); following electrophoresis, the gel was stained with Coomassie blue to visualize the separated proteins. A single, sharp protein band corresponding to the expected size was visible in lysates produced from cells containing the pATne1 (full-length Tne polymerase) and pM284 (Tne M284 deletion mutant) constructs. No protein band was observed for deletion mutant Tne M316 when expressed from either the T7 or trc promoters.

In order to increase the level of expression of Tne M284 protein in *E. coli*, the Tne M284 coding region was placed downstream of the strong tac promoter present in the JHEX3 vector to create pJM284. JHEX3 was created as follows. pALTER-1 (Promega) was digested with ClaI and StyI and the ends were made blunt by incubation with the Klenow fragment. The 1.345 kb ClaI/StyI fragment was isolated and ligated into pTrc 99 A (Pharmacia) which had been digested with BsaAI. This ligation inserted the tetracycline-resistance gene into the pTrc 99 A vector; the resulting vector was called JHEXa. The ampicillin-resistance gene was then removed from the JHEXa by digestion with SspI, DraI and PvuI; this digestion cut the ampicillin gene into four small fragments (483 bp, 227 bp, 209 bp and 19 bp). The large fragments (3.93 kp and 652 bp) were isolated and ligated together to create JHEXb. The Trc promoter was removed from JHEXb as an 89 bp SspII/NcoI fragment and replaced with the tac promoter. The tac promoter was inserted into the SspI/NcoI-digested JHEXb vector as a 141 bp BsrBI fragment from pALTER-Ex1 (Promega) together with a 30 bp linker formed by the oligonucleotide pair listed in SEQ ID NOS:45 and 46.

To generate pJM284 construct was made as follows. pGTne was digested with BspHI (generates ends compatible with NcoI ends) and KpnI and a 1.05 kb BspHI/KpnI fragment (containing the 5' portion of the coding region) was isolated as described in Example 2. A second aliquot of pGTne was digested with KpnI and XbaI and a 1.3 kb fragment containing the 3' portion of the Tne polymerase coding region was isolated. JHEX3 was digested with NcoI and XbaI. A three-way ligation was performed using the digested JHEX3 vector, 1.05 kb BspHI/KpnI fragment and the 1.3 kb KpnI/XbaI fragment. Competent JM109 cells were transformed with the ligation mixture and recombinant clones were isolated, confirmed by restriction digestion using standard recombinant molecular biology. The resulting plasmid was called pJM284.

Crude lysates were prepared from a small scale culture of JM109 cells containing the pJM284 construct or the pM284 construct. DNA polymerase assays were performed as described in Example 2. The level of Tne M284 polymerase produced by pJM284 was found to be about 50% greater than the level produced by expression from the pM284 construct.

EXAMPLE 4

Construction of Tne Polymerase Mutants having Altered 3' to 5' Exonuclease Activity In order to produce modified forms of Tne polymerase which possess varying amounts of 3' to 5' exonuclease activity, seven different point mutants and two deletion mutants were created using the pM284 construct as the starting material. FIG. 4 provides a schematic drawing of these mutant Tne polymerases.

All nine mutagenic changes also involved a change in the restriction digest pattern of the starting pM284 plasmid to allow for easy selection of the mutants. In all cases, a small portion of the mutagenized region was exchanged into an Tne M284 gene that did not undergo mutagenesis and the exchanged region was sequenced not only to confirm the mutation, but also to show that there were no second site mutations. DNA sequencing was performed using the fmol® DNA Sequencing System (Promega) in conjunction with using primers JH61 [5'-TGCCGTACACCTCC GAGAGC-3' (SEQ ID NO:12)] or JH66 [5'-CTCGTTTGGCTCCAGCAAATATGC-3' (SEQ ID NO:13)]. The mutants were constructed as follows.

a) Construction of pD323E pD323E produces a modified form of the Tne polymerase which lacks the first 283 amino acids from the N-terminus of the full-length protein and contains an amino acid substitution at residue 323 (number indicates position of the residue in the full length protein). At amino acid residue 323 the wild-type aspartic acid is replaced with glutamic acid. pM284 was used in conjunction with the mutagenic oligonucleotide JH74 [5'-TTTGCCCTGGAaCTTGAAACG-3' (SEQ ID NO:14)]; the mutagenic residues are indicated by the lower case letter] and the Altered Sites® II in vitro Mutagenesis System (Promega) to generate pD323E as described in Example 3. The desired mutants were confirmed by restriction analysis (absence of one of the SinI restriction sites present in pM284. The DNA sequence of pD323E was obtained as described above using the JH66 (SEQ ID NO:13) primer. The DNA sequence of the polymerase coding region present in pD323E is listed in SEQ ID NO:15. The corresponding amino acid sequence of the Tne M284(D323E) protein is listed in SEQ ID NO:16.

b) Construction of pE325D pE325D produces a modified form of the Tne polymerase which lacks the first 283 amino acids from the N-terminus of the full-length protein and contains an amino acid substitution at residue 325. At amino acid residue 325, the wild-type glutamic acid residue is replaced with aspartic acid. pM284 was used in conjunction with the mutagenesis oligonucleotide JH75 [5'-GACCTTGAcACGTCCTC (SEQ ID NO:17);the mutagenic residue is indicated by the lower case letter] and the Altered Sites® II in vitro Mutagenesis System (Promega) to generate pE325D as described in Example 3. The desired mutant was confirmed by restriction analysis (the presence of additional AflIII restriction site). The DNA sequence of pD323 was obtained as described above using the JH66 (SEQ ID NO:13) primer. The DNA sequence of the polymerase coding region present in pE325D is listed in SEQ ID NO:18. The corresponding amino acid sequence of the Tne M284(E325D) protein is listed in SEQ ID NO:19.

c) Construction of pY464F pY464F produces a modified form of the Tne polymerase which lacks the first 283 amino acids from the N-terminus of the full-length protein and contains an amino acid substitution at residue 464. At amino acid residue 464, the wild-type tyrosine residue is replaced with phenylalanine. pY464F was constructed by replacing a 39 bp FokI fragment present in pM284 with a 39 bp synthetic region. The 39 bp synthetic region was formed by the following two oligonucleotides: JH81 [5'-TAAGTGATATC TGCATCCTCGCAGGAGAAGTTCGCAGCC-3' (SEQ ID NO:20) and JH82 [5'-ACAAGGCTGCGAACTTCTCCTGCGAGGATGCAGAT ATCA-3' (SEQ ID NO:21)]. This synthetic 39 bp oligonucleotide contains the mutation. The desired mutant was confirmed by restriction analysis (the presence of additional EcoRV restriction site). The DNA sequence of pY464F was obtained as described above using the JH61 (SEQ ID NO:12) primer. The DNA sequence of the polymerase coding region present in pY464F is listed in SEQ ID NO:22. The corresponding amino acid sequence of the Tne M284 (Y464F) protein is listed in SEQ ID NO:23.

d) Construction of pD468N pD468N produces a modified form of the Tne polymerase which lacks the first 283 amino acids from the N-terminus of the full-length protein and contains an amino acid substitution at residue 468. At amino acid residue 468, the wild-type aspartic acid residue is replaced with asparagine. pM284 was used in conjunction with the mutagenesis oligonucleotide JH79 [5'-ACTCCTGCGAGaATGCtGACATCACTTAT AGG-3' (SEQ ID NO:24); the mutagenic residues are indicated by the use of lower case letters] and the Altered Sites® II in vitro Mutagenesis System (Promega) to generate pD468N as described in Example 3. The desired mutant was confirmed by restriction analysis (the presence of an additional BsmI restriction site). The DNA sequence of pD468N was obtained as described above using the JH61 (SEQ ID NO:12) primer. The DNA sequence of the polymerase coding region present in pD468N is listed in SEQ ID NO:25. The corresponding amino acid sequence of the Tne M284 (D468N) protein is listed in SEQ ID NO:26.

e) Construction of pD323A pD323A produces a modified form of the Tne polymerase which lacks the first 283 amino acids from the N-terminus of the full-length protein and contains an amino acid substitution at residue 323. At amino acid residue 323, the wild-type aspartic acid residue is replaced with alanine. pM284 was used in conjunction with the mutagenesis oligonucleotide JH70 [5'-TTTGCCCTGGcCCTTGAAACG-3' (SEQ ID NO:27); the mutagenic residue is indicated by the use of the lower case letter] and the Altered Sites® II in vitro Mutagenesis System (Promega) to generate pD323A as described in Example 3. The desired mutant was confirmed by restriction analysis (the absence of a SinI restriction site). The DNA sequence of pD323A was obtained as described above using the JH66 (SEQ ID NO: 13) primer. The DNA sequence of the polymerase coding region present in pD323A is listed in SEQ ID NO:28. The corresponding amino acid sequence of the Tne M284(D323A) protein is listed in SEQ ID NO:29.

f) Construction of pD389A pD389A produces a modified form of the Tne polymerase which lacks the first 283 amino acids from the N-terminus of the full-length protein and contains an amino acid substitution at residue 389. At amino acid residue 389, the wild-type aspartic acid residue is replaced with alanine.

To construct pD389A, the PCR was used to amplify two overlapping fragments independently; the PCR products were combined and the resulting large fragment was reamplified. Mutagenesis oligonucleotide JH80 [5'-CCTGAAGTACGcgTACAAGGT TCTTATGG-3' (SEQ ID NO:30); the mutagenic residues are indicated by the use of lower case letters] and sequencing primer JH61(SEQ ID NO:12) were used to prime a first PCR to create a 425 bp fragment which incorporates the desired mutation. The sequencing primers JH66 (SEQ ID NO:13) and M13 reverse (Promega Q5401; SEQ ID NO:31) were used to amplify a 564 bp fragment using pM284 as the template in a second PCR. When these two PCR products were combined using the M13 reverse and JH61 primers, a 889 bp fragment was made. A 348 bp BglII fragment was then removed from the 889 bp product and was exchanged with the analogous, but, non-mutagenic BglII fragment of pM284. The desired mutants was confirmed by the presence of an extra MluI restriction site. All PCR reactions were performed using a Perkin-Elmer 480 thermal cycler.

For generation of the 564 bp product, the PCR was conducted by performing 15 cycles comprising a denaturation step (95° C. for 15 sec) and an annealing/extension step (70° C. for 1 min). JM284 was used as the template in a reaction containing 1 μM of each of the primers (JH66 and M13 reverse), 1.5 mM MgCl$_2$ and 3 units Tli DNA polymerase (Promega).

For generation of the 425 bp product, the PCR was conducted by performing 20 cycles comprising a denaturation step (95° C. for 15 sec), an annealing step (55° C. for 30 sec; cycles 1–5) or an annealing step (70° C. for 15 sec; cycles 6–20) and an extension step (70° C. for 45 sec). JM284 was used as the template in a reaction containing 1 μM of each of the primers (JH80 and JH61), 1.5 mM MgCl$_2$ and 3 units Tli DNA polymerase (Promega).

For the generation of the 889 bp product, the 564 bp product and the 425 bp product were used as the template in a reaction containing 1.5 mM MgCl$_2$ and 3 units Tli DNA polymerase (Promega). The cycling conditions were: denaturation (95° C. for 15 sec) and annealing/extension at 70° C. for 1 min; no primers were present for cycles 1–5. One μM of the M13 reverse primer was present for cycles 5–10 and 1 μM of the M13 reverse and JH61 primers were present in cycles 11–25.

The DNA sequence of pD389A was obtained as described above using the JH61 and JH66 (SEQ ID NOS:12 and 13) primer. The DNA sequence of the polymerase coding region present in pD389A is listed in SEQ ID NO:32. The corresponding amino acid sequence of the Tne M284(D389A) protein is listed in SEQ ID NO:33.

g) Construction of pD323,389A pD323,389A produces a modified form of the Tne polymerase which lacks the first 283 amino acids from the N-terminus of the full-length protein and contains two amino acid substitutions at residues 323 and 389. At amino acid residue 323, the wild-type aspartic acid residue is replaced with alanine and at amino acid residue 389, the wild-type aspartic acid residue is replaced with alanine.

To create pD323,389A, the 215 bp Csp45I fragment of pD323A was exchanged with the analogous fragment in pD389A bringing the two single mutations into the same construct. The desired mutants were selected as having the two restriction site changes of the individual mutants (described above). The DNA sequence of pD323,389A was obtained as described above using the JH66 (SEQ ID NO:13) primer. The DNA sequence of the polymerase coding region present in pD323,389A is listed in SEQ ID NO:34. The corresponding amino acid sequence of the Tne M284(D323A,D389A) protein is listed in SEQ ID NO:35; this enzyme is referred to as the triple mutant Tne polymerase.

When all of the above point mutant constructs (sections a–g) were induced to express the modified Tne polymerases in an *E. coli* host, the crude extracts showed polymerase activity comparable with the activity observed using the original pM284 construct (cultures were grown, induced, lysates prepared and assayed for DNA polymerase activity as described in Example 2).

h) Construction of Deletion Mutants pM323 and pJM284ΔB

Two mutants were created which contained deletions into the putative 3' to 5' exonuclease domain of the Tne polymerase gene. It was predicted that these two deletion mutations would remove all 3' to 5' exonuclease activity. Surprisingly, when these two mutants were expressed in *E. coli* no polymerase activity was detected.

i) Construction of pM323 pM323 was constructed by digestion of pJM284 with SinI and EcoRV followed by removal of the 3' overhanging (i.e., sticky) ends with Mung Bean nuclease. The 1.9 kp SinI/EcoRV(polished ends) fragment was isolated as described in Example 2. JHEX3 (Example 3) was digested with NcoI and SmaI and the NcoI overhanging ends were made blunt by incubation with the Klenow fragment. The 1.9 kp SinI/EcoRV(polished ends) fragment was then blunt end ligated into the prepared JHEX3 vector. When the blunted SinI end ligates to the blunted NcoI end 39 amino acids are removed from the N terminus of the protein encoded by the pM284 construct; this junction also creates an initiating methionine at amino acid position 323 that is in-frame with the rest of the coding region. The polymerase coding region present in the pM323 construct was sequenced to confirm that no undesirable mutations were introduced (i.e., insertion of stop codons, frame-shift mutations). The DNA sequence of the polymerase coding region present in pM323 is listed in SEQ ID NO:36. The corresponding amino acid sequence of the Tne M323 protein is listed in SEQ ID NO:37.

ii) Construction of pJM284ΔB pJM284ΔB was constructed by digestion of the JM284 construct with BglII followed by religation of the large fragment (6.6 kb) back on itself. Digestion of JM284 with BglII created two fragments, the smaller being 348 bp which contains DNA sequences which encode a portion of the 3' to 5' exonuclease domain. The pJM284ΔB construct removed 116 amino acids of the 3' to 5' exonuclease domain which correspond to residues 309 through 424 in SEQ ID NO:2. pJM284ΔB contains the same 25 amino acids which encode the N terminus of the protein encoded by pM284. This deletion does not change the reading frame for the polymerase domain. Restriction digest analysis was conducted on the pJM284ΔB construct to confirm the proper construction was made. The DNA sequence of the polymerase coding region present in pJM284ΔB is listed in SEQ ID NO:38. The corresponding amino acid sequence of the Tne M284ΔB protein is listed in SEQ ID NO:39.

iii) Expression of pM323 and pJM284ΔB in *E. coli*

When both of these deletion mutants constructs were grown and induced to express the Tne polymerase in an *E. coli* host (JM109), no detectable polymerase activity was detected. As these two constructs were analyzed by restriction digestion or DNA sequencing to insure that no undesirable mutations were introduced, it appears, surprisingly, that deletion into the putative 3' exonuclease domain (approximately aa residues 291–484) is deleterious either for polymerase activity or alternatively for protein stability. These results, in conjunction with those obtained using the pM316 construct, show that deletions beyond about position 849 of SEQ ID NO:1 produce proteins which either are unstable (perhaps due to improper folding) or lack polymerase activity.

EXAMPLE 5

Purification of Tne DNA Polymerases

In order to produce purified preparations of the wild-type and modified Tne polymerases, cells harboring the Tne expression vectors described above were grown, induced and the Tne polymerases were isolated.

a) Growth of *E. coli* Cells Harboring Recombinant Tne (rTne) Constructs

*E. coli* strains containing a desired construct were streaked onto LB plates [10 g/l tryptone, 5 g/l yeast extract, 5 g/l NaCl, 1 ml/1N NaOH and 15 g/l agar] containing 10 μg/ml tetracycline to isolate single colonies and the plates were grown overnight at 37° C. A single colony was inoculated into 150 ml LB broth [10 g/l tryptone, 5 g/l yeast extract, 5 g/l NaCl and 1 ml/l 1N NaOH] containing 10 μg/ml tetracycline (divided into three flasks of 50 ml each); the three flasks were grown with shaking overnight at 37° C. The next day, 120 ml of the overnight culture was used to seed the fermentation of 6 liters of LB containing 10 μg/ml tetracycline prewarmed to 37° C. (divided into six flasks of 1 liter each). The large scale culture was grown for 5 hours at 37° C. and then IPTG was added to a final concentration of 1 mM and growth was continued for an additional 2 hours at 37° C. The induced cells were harvested by centrifugation at 9,000 rpm for 5 minutes in a Beckman JA10 rotor. Yields were typically 2 g cell paste per liter of fermented culture.

b) Purification of rTne DNA Polymerases

Ten grams of cell paste (prepared as described above) were resuspended in 100 ml of an ice-cold solution containing 0.25 M NaCl in TEDGT buffer [50 mM Tris-HCl (pH 7.3), 1 mM EDTA, 1 mM DTT, 10% glycerol and 0.1% Tween 20] containing 2.5 mM PMSF. The resuspended cells were lysed by sonication using a Vibracell sonicator (Model VCX600; Sonics and Materials, Inc., Danbury, Conn.). The solution was kept ice-cold during sonication by placement of the beaker containing the cell suspension in a salted ice bath. Sonication was repeated ten times at 40% output for 1 minute with a 2 minute rest between the 1 minute sonication bursts. The cell lysate was heat treated to denature the bulk of E. coli proteins by incubation of the lysate at 68° C. to 70° C. for 5 to 10 minutes; following heat treatment the lysate was placed on ice.

The following purification steps were performed at 4° C. The chilled lysate was centrifuged at 15,000 rpm for 15 minutes in a Beckman JA18 rotor to remove the heat-denatured proteins. The cleared lysate supernatant was removed and 4 ml of 5% polyethylenimine (PEI) was added to the supernatant to precipitate any DNA present in the lysate. The lysate was centrifuged at 15,000 rpm for 15 minutes in a Beckman JA18 rotor to remove the precipitated DNA. The supernatant was retrieved and solid ammonium sulfate was added to 60% saturation to precipitate the DNA polymerase. After dissolution of the ammonium sulfate, the sample was centrifuged at 15,000 rpm for 1 hour in a Beckman JA18 rotor. The supernatant was discarded and the precipitated proteins were gathered and dissolved in 10 ml TEDGT buffer. The resolubilized protein was then placed in a dialysis membrane tubing having a 12,000 to 14,000 mw cutoff (Spectra, Houston, Tex.) and then dialyzed against TEDGT buffer to remove the ammonium sulfate.

The dialyzed protein solution was then loaded onto a 15 ml Heparin Sepharose (Scientific Protein Laboratory, Waunakee, Wis.) column (1.7 cm i.d.×6.5 cm height). The column was washed with 150 ml 0.05 M NaCl in TEDGT buffer. A 100 ml salt (NaCl) gradient was run over the column to elute the DNA polymerase; the gradient started at 0.05 M NaCl and ended at 1 M NaCl (all in TEDGT buffer). Fractions (1.5 ml) were collected and assayed for DNA polymerase activity at 74° C. as described below.

Thermostable DNA polymerase activity was assayed by incorporation of radiolabeled dTTP into nicked and gapped (i.e., activated) calf thymus DNA (prepared as described below). One unit of thermostable DNA polymerase is defined as the amount of enzyme required to catalyze the incorporation of 10 nmol of dNTP into an acid-insoluble form in 30 minutes at 74° C. The reaction conditions comprised: 50 mM Tris-HCl (pH 9.0 at 25° C.), 50 mM NaCl, 10 mM $MgCl_2$, 200 $\mu$M dATP, 200 $\mu$M dCTP, 200 $\mu$M dGTP, 200 $\mu$M dTTP and 5 $\mu$Ci $^3$H-dTTP (Amersham) and 60 $\mu$g activated calf thymus DNA in a 250 $\mu$l final volume.

The reaction components were assembled at room temperature. Samples suspected of containing polymerase activity were added (5 $\mu$l containing 0.05 to 0.5 units) and the tube was incubated at 74° C.; aliquots (50 $\mu$l) were withdrawn at 6, 9, 12 and 15 minutes and placed immediately into 1.5 ml microcentrifuge tubes containing 0.5 ml of ice-cold 10% TCA on ice. After 10–30 minutes on ice, the entire TCA precipitation was filtered through a GF/A filter (Whatman). The reaction tubes were rinsed with 3 volumes of cold 5% TCA and the filters were washed twice with 10 ml of ice-cold 5% TCA followed by a rinse with 1 ml of acetone. The filters were dried and the radioactivity bound to filters was counted in a scintillation counter.

Total and background counts were determined as follows. For total cpm, 10 $\mu$l of the reaction mix (without any polymerase added) was spotted onto duplicate GF/A filters and counted. For background counts, 50 $\mu$l of the reaction mix (without any polymerase added) was added to duplicate tubes containing 0.5 ml cold 10% TCA and the samples were filtered through GF/A filters and washed as described above.

Activated calf thymus DNA was prepared by dissolving 1 g calf thymus DNA (#D-151, Sigma, St. Louis, Mo.) in 400 ml TM buffer [10 mM Tris-HCl (pH 7.3), 5 mM $MgCl_2$]. Four hundred microliters of a solution containing 40 units of RQ1-DNAse (Promega) in TM buffer was added to the DNA solution and incubated at 37° C. for 10 minutes. The DNAse digestion was stopped by heating the DNA solution at 68° C. for 30 minutes. The activated calf thymus DNA was stored at −20° C. until used. The activated calf thymus DNA was heated to 74° C. for 10 minutes and then cooled to room temperature before use.

As shown in Table 2 below, the Tne DNA polymerases generally eluted from the Heparin Sepharose column at a salt concentration of between 0.14 M and 0.29 M NaCl. Fractions containing the polymerase activity were pooled, placed into dialysis membrane tubing (as described above) and dialyzed against TEDGT buffer until the salt concentration was less than or equal to 0.05 M NaCl as measured by conductivity using a conductance meter (Yellow Spring Instrument Co., Yellow Springs, Ohio).

The dialyzed polymerase fraction was then loaded onto a 7 ml Cibracron Blue 3GA (Sigma, St. Louis, Mo.) column (1.25 cm i.d.×6 cm height). The Cibracron Blue 3GA column was washed with 70 ml of 0.05 M NaCl in TEDGT buffer. A 100 ml salt gradient was run over the column to elute the DNA polymerase; the gradient started at 0.05 M NaCl and ended at 1 M NaCl (all in TEDGT). Fractions (1.5 ml) were collected and assayed for DNA polymerase activity at 74° C. (as described above).

As shown in Table 2, the Tne DNA polymerases generally eluted from the Cibracron Blue 3GA column at a salt concentration of between 0.20 M and 0.46 M NaCl. Fractions containing the polymerase activity were pooled, placed in dialysis membrane (as described above) and dialyzed against storage buffer [20 mM Tris-HCl (pH 8.0), 100 mM KCl, 0.1 mM EDTA, 1 mM DTT, 50% glycerol and 0.5% Tween 20]. Aliquots of preparations of purified Tne polymerases were electrophoresed on SDS-PAGE gels and stained with Coomassie blue. The purified DNA polymerases produced by all of the recombinant Tne polymerase constructs were judged to be at least 95% pure based on visual inspection of the Coomassie-stained SDS PAGE gels.

TABLE 2

Salt Elution Characteristics For rTne DNA Polymerases

| DNA Polymerase | SEQ ID NO | Heparin Sepharose | Cibracron Blue |
|---|---|---|---|
| rTne DNA Polymerase full-length | 2 | 0.26 to 0.37 M NaCl | 0.5 to 0.8 M NaCl |
| Tne M284 | 8 | 0.13 to 0.3 M NaCl | 0.05 to 0.3 M NaCl |
| Tne M284 (E325D) | 19 | 0.15 to 0.28 M NaCl | 0.3 to 0.48 M NaCl |
| Tne M284 (D468N) | 26 | 0.11 to 0.23 M NaCl | 0.16 to 0.35 M NaCl |
| Tne M284 (D323E) | 16 | 0.05 to 0.32 M NaCl | 0.11 to 0.4 M NaCl |
| Tne M284 (Y464F) | 23 | 0.11 to 0.28 M NaCl | 0.24 to 0.4 M NaCl |

TABLE 2-continued

Salt Elution Characteristics For rTne DNA Polymerases

| DNA Polymerase | SEQ ID NO | Heparin Sepharose | Cibracron Blue |
|---|---|---|---|
| Tne M284 (D323A, D389A) | 35 | 0.14 to 0.27 M NaCl | 0.06 to 0.46 M NaCl |

The above results provide methods for the isolation of the full-length and modified forms of Tne DNA polymerase in a highly pure form at high yields.

EXAMPLE 6

Purification of Tne DNA Polymerase From *T. neapolitana* Cells

The preceding example described the isolation of recombinant Tne DNA polymerases from *E. coli* harboring plasmids which overexpress these enzymes. The full-length Tne DNA polymerase may also be isolated from *T. neapolitana* cells

*T. neapolitana* cells are obtained from the ATCC (ATCC 49049) and grown in anaerobic culture in MMS medium containing (per liter): 6.93 g NaCl; 1.75 g $MgSO_4.7H_2O$; 1.38 g $MgCl_2.6H_2O$; 0.16 g KCl; 25 mg NaBr; 7.5 mg $H_3BO_3$; 3.8 mg $SrCl_2.6 H_2O$; 0.025 mg KI; 0.38 g $CaCl_2$; 0.5 g $KH_2PO_4$; 0.5 g $Na_2S.9H_2O$; 2 mg $(NH_4)_2Ni(SO_4)_2$; 15 ml trace minerals [per liter: 3.0 g $MgSO_4.7H_2O$; 1.5 g nitriloacetic acid, 1.0 g NaCl; 0.5 g $MnSO_4.H_2O$; 0.1 g $FeSO_4.7H_2O$; 0.1 g $CoCl_2.6H_2O$; 0.1 g $CaCl_2$; 0.1 g $ZnSO_4.7H_2O$; 0.01 g $CuSO_4.5H_2O$; 0.01 g $AlK(SO_4)_2.12H_2O$; 0.01 g $H_3BO_3$ and 0.01 g $Na_2MoO_4.2H_2O$]; 1 mg resazurin and 5 g starch at a pH of 6.5 (adjusted with $H_2SO_4$). For growth on solid medium, 0.8% agar (Difco) was added to the above medium.

The cells are grown in a fermentation vessel maintained at 75–80° C. under anaerobic conditions (i.e., under nitrogen). The cells are grown for approximately 28 hours (early stationary phase). The cells are collected by centrifugation at 10,000×g. The cell pellet may be frozen at −70° C. until used. All of the subsequent operations should be carried out at 0 to 4° C. unless otherwise stated.

Resuspend about 50 g of frozen *Thermotoga neapolitana* cells in 100 ml of TEDGT [50 mM Tris-HCl (pH 7.3 at 25° C.), 1 mM EDTA, 1 mM DTT, 10% glycerol, 0.1% Tween 20] containing 2.5 mM PMSF (from 144 mM stock in DMF). The thawed and resuspended cells can be lysed in a Aminco French Pressure Cell (American Instrument Co., Silver Spring, Md., cat. no. FA-073) at 16,000 to 24,000 psi. This operation should be done twice to ensure adequate lysis. The lysate should be diluted by adding another 100 ml TEDGT containing 2.5 mM PMSF and stirring gently.

PEI (polyethyleneimine) is added to the lysate to precipitate the DNA. The exact amount of PEI is determined empirically, but in general 0.2% PEI should be adequate to precipitate most of the DNA (greater than 90%). Approximately 10 ml of 5% PEI is added to precipitate most of the DNA in the lysate. The lysate is centrifuged at 15,000 rpm for 15 minutes in a Beckman JA18 rotor to remove the precipitated DNA. The supernatant is retrieved and solid ammonium sulfate is added to 60% saturation to precipitate the DNA polymerase and other proteins. After the salt is dissolved, the sample is centrifuged at 15,000 rpm for 1 hour in a Beckmann JA18 rotor. The supernatant is discarded and the precipitated protein is gathered and dissolved in TEDGT buffer. The resolubilized protein is then placed in a dialysis membrane having a 12,000 to 14,000 mw cutoff (Spectra) and then dialyzed against TEDGT buffer to remove the ammonium sulfate.

The dialyzed protein solution is then loaded onto a 60 ml DEAE Sepharose (Sigma, St. Louis Mo.) column (2.5 cm i.d.×13 cm height). The column is washed with 300 ml 0 M NaCl in TEDGT buffer. A 300 ml salt gradient is run over the column to elute the DNA polymerase starting at 0 M NaCl and ending at 0.5 M NaCl (all in TEDGT buffer). Fractions (5.0 ml) are collected and assayed for DNA polymerase activity at 74° C. using the protocol described in Example 5. Fractions containing the polymerase activity are pooled, placed in dialysis membrane (12,000 to 14,000 mw cutoff; Spectra) and dialyzed against TEDGT buffer until the salt concentration is less than or equal to 0.05 M NaCl as measured by conductivity.

The pooled polymerase fraction is then loaded onto a 15 ml Heparin Sepharose (Scientific Protein Laboratory, Waunakee, Wis.) column (1.7 cm i.d.×6.5 cm height). The column is washed with 150 ml 0.05 M NaCl in TEDGT buffer. A 100 ml salt gradient is run over the column to elute the DNA polymerase starting at 0.05 M NaCl and ending at 1 M NaCl (all in TEDGT buffer). Fractions (1.5 ml) are collected and assayed for DNA polymerase activity at 74° C. using the assay described in Example 5. The Tne DNA polymerase should elute between 0.14 M and 0.29 M NaCl (in TEDGT buffer). Fractions containing the polymerase activity are pooled, placed in dialysis membrane (12,000 to 14,000 mw cutoff; Spectra) and dialyzed against TEDGT buffer until the salt concentration is less than or equal to 0.05 M NaCl as measured by conductivity.

The pooled polymerase fraction is then loaded onto a 15 ml DNA Agarose (Pharmacia) column (1.7 cm i.d.×6.5 cm height). The column is washed with 75 ml 0 M NaCl in TEDGT buffer. A 100 ml salt gradient is run over the column to elute the DNA polymerase starting at 0 M NaCl and ending at 0.5 M NaCl (all in TEDGT buffer). Fractions (1.5 ml) are collected and assayed for DNA polymerase activity at 74° C. using the assay described in Example 5. Fractions containing the polymerase activity are pooled, placed in dialysis membrane (12,000 to 14,000 mw cutoff, Spectra) and dialyzed against TEDGT buffer until the salt concentration is less than or equal to 0.05 M NaCl as measured by conductivity.

The pooled polymerase fraction is then loaded onto a 7 ml Cibracron Blue 3GA (Sigma, St. Louis, Mo.) column (1.25 cm i.d.×6 cm height). The column is washed with 70 ml of 0.05 M NaCl in TEDGT buffer. A 100 ml salt gradient is run over the column to elute the DNA polymerase starting at 0.05 M NaCl and ending at 1 M NaCl (all in TEDGT buffer). Fractions (1.5 ml) are collected and assayed for DNA polymerase activity at 74° C. using the assay described in Example 5. The Tne DNA polymerase should elute between 0.20 M and 0.46 M NaCl (in TEDGT buffer). Fractions containing the polymerase activity are pooled, placed in dialysis membrane (12,000 to 14,000 mw cutoff; Spectra) and dialyzed against storage buffer [20 mM Tris-HCl (pH 8.0), 100 mM KCl, 0.1 mM EDTA, 1 mM DTT, 50% glycerol, 0.5% Tween 20].

The purity and approximate molecular weight of the DNA polymerase can be assessed by SDS-PAGE gel electrophoresis using a 4–20% gradient Tris-Glycine SDS gel (Novex, San Diego, Calif.). An aliquot of the purified material is mixed with sample buffer [63 mM Tris-HCl pH 6.8, 10% glycerol, 2% SDS, 0.0025% Bromphenol Blue] and the gel is run using the following running buffer [25 mM Tris-Base, 192 mM glycine, 0.1% SDS, pH 8.3]. The gel can be run for 90 minutes at 125 V D.C. until the bromphenol blue band is just to the bottom of the gel. The apparent molecular weight for Tne DNA polymerase should be about 97,000. Using the activity assay described in Example 5 the number of units of DNA polymerase per microliter can be established. By visually assessing the quantity of DNA polymerase on the Coomassie stained SDS-PAGE gel compared to the protein standards run in the molecular weight marker lane, the specific activity of the DNA polymerase preparation may be estimated. The specific activity of the purified Tne DNA polymerase should be approximately 100,000 units/mg.

EXAMPLE 7

Characterization of The Full-Length and Modified Tne Polymerases

The full-length and modified Tne polymerases were assayed for 5' to 3' exonuclease activity and 3' to 5' exonuclease activity.

a) 5' to 3' Exonuclease Assay

A 5' to 3' exonuclease assay was performed on the Tne M284 DNA polymerase (SEQ ID NO:8) present in crude lysates of cells containing the pJM284 construct (prepared as described in Example 3c) to determine whether any residual 5' to 3' exonuclease activity remained in this molecule. A comparison was made of the amount of 5' to 3' exonuclease activity present in the following thermostable DNA polymerases: Tne M284 (SEQ ID NO:8), the full-length rTne polymerase (SEQ ID NO:2), nTaq (Promega) and UlTma (Perkin Elmer). The 5' to 3' exonuclease assay was performed as follows.

End-labeled substrate DNAs were prepared by digestion of pBR322 DNA with either EcoRI or EcoRV followed by incubation with $\gamma$-$^{32}$P-ATP and T4 polynucleotide kinase. The 5' to 3' exonuclease assay was performed in a final reaction volume of 25 µl and contained 1X Taq buffer (10 mM Tris-HCl (pH 9.0 at 25° C.), 50 mM KCl, 0.1% Triton X-100), 1.5 mM MgCl$_2$, 200 µM of each of the four dNTPs, 50 ng of labeled substrate DNA and 5 units of the DNA polymerase to be tested (a no enzyme control was also conducted; water was used in place of the enzyme). The reaction was incubated for 1 hour at 74° C. The reaction was terminated by the addition of 5 µl of 0.5 M EDTA. Ten microliters of this mixture were spotted onto 2.3 cm circular DE81 filters (Whatman). The filters were dried briefly under a heat lamp. The filters were washed in 50 ml of 0.5 M sodium phosphate (pH 6.8) twice for 5 minutes/wash to remove unincorporated counts. The no enzyme control was used to permit determination of the total cpm in the sample. The washed filters were dried under a heat lamp and then the incorporated cpm and total cpm (no enzyme control filter) were determined by liquid scintillation counting.

The results of this assay showed that nTaq and the full-length Tne (SEQ ID NO:2) polymerases contained considerable 5' to 3' exonuclease activity, while the UlTma and Tne M284 (SEQ ID NO:8) polymerases did not contain detectable levels of 5' to 3' exonuclease activity.

b) 3' to 5' Exonuclease Assay

3' to 5' exonuclease assays were performed in order to establish how mutations in the putative exonuclease domain of the Tne polymerase gene effected this activity. The assay was initially performed on crude lysates from E. coli cells containing a plasmid which produces the Tne M284 polymerase (SEQ ID NO:8). The assays were subsequently performed on purified preparations of Tne M284 polymerase (SEQ ID NO:8).

The assay was performed using either a single stranded or double stranded DNA substrate which contained a 3' end label. The substrate DNA were prepared as follows.

To create the double stranded substrate, Lambda DNA/ EcoRI Markers (Promega G1721) were 3' end labeled with [$\alpha$-$^{32}$P]dATP in a final reaction volume of 50 µl containing 10 µg of lambda DNA, 1× Buffer A [6 mM Tris-HCl (pH 7.5 at 37° C.), 6 mM MgCl$_2$, 6 mM NaCl and 1 mM DTT], 5 µl [$\alpha$-$^{32}$P]dATP (3000 Ci/mmol; Amersham), 5 units Klenow fragment (Promega) and 10 mM of each of the four dNTPs. The reaction was incubated for 20 minutes at 37° C. The Klenow enzyme was inactivated by heating the mixture at 65° C. for 15 min. Unincorporated counts were removed by chromatography of the reaction mixture on a Nick™ Column (Pharmacia) according to the manufacturer's instructions. The labeled DNA was eluted in a volume of 400 µl. A 10 µl aliquot of the eluted DNA was counted by liquid scintillation counting and the aliquot contained approximately 2×10$^5$ cpm.

To create the single stranded substrate, a synthetic 74 nucleotide oligonucleotide, PM3074 (SEQ ID NO:41) is 3' end labeled with [$\alpha$-$^{32}$P]dATP in a final reaction volume of 10 µl containing 10 pmoles of the PM3074 oligonucleotide, 1× TdT Buffer [50 mM Tris-HCl (pH 7.5), 10 mM MgCl$_2$, 5 mM DTT and 0.1 mM spermidine], 3 µl [$\alpha$-$^{32}$P]dATP (3000 Ci/mmol; Amersham) and 15 units terminal deoxynucleotidyl transferase (TdT) (Promega). The reaction was incubated for 60 minutes at 37° C. The TdT enzyme was inactivated by heating the mixture at 65° C. for 15 min. Unincorporated counts were removed by chromatography of the reaction mixture on a Nick™ Column (Pharmacia) according to the manufacturer's instructions. The labeled DNA was eluted in a volume of 400 µl. A 10 µl aliquot of the eluted DNA was counted by liquid scintillation counting and the aliquot contained approximately 1×10$^5$ cpm.

The 3' to 5' exonuclease assay was performed as follows. In a final volume of 50 µl, the following components were assembled, 1 or 2 units of the DNA polymerase to be assayed, 5 µl of 10×Toga buffer [10 mM Tris-HCl (pH 8.8 at 25° C.), 10 mM KCl, 0.002% Tween 20] and nuclease-free water (Promega). One tube was also set up which did not contain any polymerase (i.e., a no enzyme control). The reaction mixtures were prewarmed to the reaction temperature (reactions were performed at either 25° C. or 74° C.) and 10 µl of either the labeled single stranded or double stranded substrates were added to start the assay. Ten microliter fractions were removed at the following time points: 2, 4 or 6 minutes. The aliquots were spotted onto 2.3 cm circular DE81 filters and processed as described in section a) above.

The definition of one unit of 3' to 5' exonuclease activity is defined as the amount of enzyme required to remove 1 pmol of labeled 3' end from the substrate in 30 minutes.

In addition to assaying the polymerases for 3' exonuclease activity, all samples were also analyzed for DNA polymerase activity using the assay described in Example 5(b). In this manner, the ratio of 3' exonuclease activity to polymerase activity could be determined for each polymerase.

When the 3' to 5' exonuclease assay was performed using on crude lysates containing the Tne M284 enzyme, the assay was run using only the single stranded substrate at 25° C. Under these conditions, a comparison was made between purified UlTma (a modified form of Tma polymerase which lacks 5' to 3' exonuclease activity) and UlTma spiked into a lysate derived from *E. coli* cells shown to lack 3' to 5' exonuclease activity; the spiked sample showed a 22% lower 3' exonuclease: polymerase activity ratio (polymerase activity was measured using the assay described in Example). As *E. coli* lysate alone shows no 3' exonuclease activity, this result indicated that results obtained with crude lysates containing the Tne M284 protein (SEQ ID NO:8) should underestimate the 3' to 5' exonuclease levels that would be seen using purified Tne polymerase preparations.

When purified UlTma™ was compared with crude lysates containing the full-length (SEQ ID NO:2) or Tne M284 (SEQ ID NO:8) polymerases, the highest exonuclease:polymerase activity ratio was seen for the full-length Tne enzyme (1.37), then M284 Tne (0.83), then UlTma™ (0.45). These results were unexpected as it was not predictable that a deletion in the 5' to 3' exonuclease domain (Tne M284 polymerase) would result in a 39% decrease in 3' to 5' exonuclease activity.

Purified Tne M284 polymerase was used in 3' exonuclease assays in comparison to purified UlTma™ using both single stranded and double stranded substrates at 25° C. and 74° C. Surprisingly, both enzymes displayed the same level of 3' exonuclease activity on single stranded substrate at 25° C. Results obtained using crude lysates containing Tne M284 polymerase suggested that Tne M284 would have a higher activity. Both enzymes (purified Tne M284 and UlTma™) gave nearly identical results when the 3' exonuclease assay was performed using the double stranded substrate at 25° C. (and both showed very low activity under these conditions).

When the 3' exonuclease assay was performed using a single stranded substrate at 74° C., UlTma™ had no activity, whereas purified Tne M284 showed an exonuclease: polymerase ratio of 0.32.

These results demonstrate that purified Tne M284 polymerase and UlTma™ have significantly different 3' to 5' exonuclease activities.

EXAMPLE 8

Characterization of the Purified Tne Polymerases

In order to ascertain the characteristics of the full length and modified forms of the rTne polymerases, a number of determinations were made as described below.

a) Molecular Weight on SDS-PAGE Gels

The apparent molecular weight of the full length and modified rTne polymerases were determined by SDS-PAGE. An aliquot (10 units) of each purified polymerase was mixed with sample buffer [63 mM Tris-HCl pH 6.8, 10% glycerol, 2% SDS, 0.0025% bromophenol blue] and applied to a precast 4–20% gradient Tris-Glycine SDS gel (Novex, San Diego, Calif.). Molecular weight markers (Promega) were run on the same gel to allow calculation of the molecular weight of the Tne polymerases. The gel was run using the following running buffer [25 mM Tris-Base, 192 mM glycine, 0.1% SDS, pH 8.3] for 90 minutes at 125 V D.C. until the bromphenol blue band was just to the bottom of the gel.

Following electrophoresis, the gel was stained with Coomassie blue to visualize the proteins. The full-length rTne polymerase migrated with an apparent molecular weight of 97,000 daltons. Tne M284, Tne M284(D323E), Tne M284 (E325D), Tne M284(Y464F), Tne M284(D468N), and Tne M284(D323A, D389A) all migrated with an apparent molecular weight of 70,000 daltons.

b) Specific Activity of Purified Tne Polymerases

Preparations of purified full-length rTne and Tne M284, Tne M284(D323E), Tne M284(E325D), Tne M284(Y464F), Tne M284(D468N), and Tne M284(D323A, D389A) were all found to have a specific activity of 100,000 units/mg when the enzymes were purified and DNA polymerase assays were conducted as described in Example 5.

c) 3' to 5' Exonuclease Activity

Purified preparations of full-length rTne and Tne M284, Tne M284(D323E), Tne M284(E325D), Tne M284(Y464F), Tne M284(D468N) and Tne M284(D323A, D389A) were assayed for 3' to 5' exonuclease activity. In the same experiment, the 3' to 5' exonuclease activity of the UlTma™ (Perkin Elmer) and nTaq (Promega) polymerases were also measured for comparison to the Tne polymerases.

The 3' exonuclease assay involved the incubation of the above enzymes with a 3' end-labeled DNA substrate; the loss of radioactivity from the labeled substrate was measured after a 10 minute incubation period.

i) Preparation of the 3' End-labeled Substrate

Ten micrograms of lambda phage DNA was digested with 50 u of MluI (Promega) in a 50 µl reaction volume in 1× Buffer D [6 mM Tris-HCl (pH 7.9 at 37° C.), 6 mM $MgCl_2$, 150 mM NaCl and 1 mM DTT]. The reaction was incubated for 3 hours at 37° C. The 3' ends were then filled in using [$\alpha$-$^{32}$P]-dCTP and unlabelled dGTP in a reaction containing 5 u of Klenow Exo- (USB) and 1× Buffer D in a volume of 100 µl; the reaction mixture was incubated for 20 min at 25° C. The reaction was terminated by heating the sample to 74° C. for 15 min. The bulk of the unincorporated [$\alpha$-$^{32}$P]-dCTP was removed by passage of the sample over a Nick™ column (Pharmacia) and the labeled DNA was eluted in 400 µl TE [10 mM Tris-HCl (pH 7.4), 1 mM EDTA]. An aliquot (10 µl) of the eluted DNA was counted in a scintillation counter and the aliquot contained approximately $2 \times 10^5$ cpm.

ii) 3' to 5' Exonuclease Assay

The 3' to 5' exonuclease assay was performed as follows. In a final volume of 50 µl, the following components were assembled, 1 or 2 units of the DNA polymerase to be assayed, 5 µl of 10×Toga buffer [10 mM Tris-HCl (pH 8.8 at 25° C.), 10 mM KCl, 0.002% Tween 20] and nuclease-free water (Promega). One tube was also set up which did not contain any polymerase (i.e., a no enzyme control). The reaction mixtures were prewarmed to the reaction temperature (reactions were performed at either 25° C. or 74° C.) and 10 µl of the labeled double stranded substrates were added to start the assay. Ten microliter fractions were removed at the following time points: 2, 4, 6 and 10 minutes (In a subsequent experiment, aliquots were withdrawn at 30 and 60 minutes to permit the detection of activity for enzymes showing very low levels of activity). The aliquots were spotted onto 2.3 cm circular DE81 filters and processed as described in Example 7, section a) above.

The definition of one unit of 3' to 5' exonuclease activity is defined as the amount of enzyme required to remove 1 pmol of labeled 3' end from the substrate in 30 minutes.

In addition to assaying the polymerases for 3' exonuclease activity, all samples were also analyzed for DNA polymerase activity using the assay described in Example 5(b). In this manner, the ratio of 3' exonuclease activity to polymerase activity could be determined for each polymerase. The results are reported as the ratio of 3' exonuclease activity to polymerase activity. The value obtained for the full-length Tne polymerase was assigned a value of 100% and all other values are expressed relative to this value.

TABLE 3

3' Exonuclease Activity

| DNA Polymerase | Exo:Pol Ratio |
|---|---|
| rTne | 100 ± 9.0 |
| UlTma ™ | 23.3 ± 0.8 |
| Tne M284 | 28.0 ± 0.08 |
| Tne M284(Y464F) | 1.9 ± 0.2 |
| Tne M284(D468N) | 0.47 ± 0.02 |
| Tne M284(D323E) | 0.0 |
| Tne M284(E325D) | 0.0 |
| Tne M284(D323A, D389A) | 0.0 |
| nTaq | 0.0 |

The results shown in Table 3 demonstrate that deletions which remove 5' exonuclease activity (e.g., Tne M284) also affect 3' exonuclease activity in the Tne polymerases (compare rTne with Tne M284; activity of Tne M284 is roughly one third that seen in rTne). Mutation of amino acid residues suspected of being critical for 3' exonuclease activity (by analogy to similar residues in *E. coli* polymerase I) further reduces or eliminates 3' exonuclease. The virtual elimination of 3' exonuclease activity seen with the Tne M284(D468N) polymerase was unexpected. The analogous mutation in the Klenow fragment of DNA polymerase I (D501N) reduces 3' exonuclease activity only by 2-fold [Derbyshire et al., EMBO J. 10:17 (1991)]. These results underscore the fact that much remains to be learned about structure-function relationships and that one cannot predict, with certainty, the effect of a given mutation based on analogy to other proteins.

d) Thermostability of the Purified Tne Polymerases at 97.5° C.

Thermostability was measured by incubating a DNA polymerase at 97.5° C. for various amounts of time and measuring the remaining DNA polymerase activity at 74° C. Samples were withdrawn after 0, 5, 10, 30, 60, 90, and 120 minutes after exposure to 97.5° C. and DNA polymerase assays were conducted as described in Example 5b. The time necessary to reduce the activity by one-half the initial value was determined by plotting the remaining activity versus the time of incubation at 97.5° C.

The incubation buffer contained 10 mM Tris-HCl (pH 8.8 at 25° C.), 10 mM KCl, 0.002% Tween 20 and 1.5 mM $MgCl_2$ and 2–3 units of the enzyme to be tested. All enzymes, including commercially available enzymes (e.g., nTaq, UlTma™), were assayed using the DNA polymerase assay described in Example 5. The results of the thermostability assays are summarized in Table 4 below.

TABLE 4

Thermostability Of Tne Polymerases

| DNA Polymerase | SEQ ID NO: | Half-Life At 97.5° C. (min) |
|---|---|---|
| full-length rTne | 2 | 5 |
| Tne M284 (E325D) | 19 | 5 |
| native Taq | | 8 |
| UlTma ™ | | 12 |
| Tne M284(D323E) | 16 | 12.5 |
| Tne M284(Y464F) | 23 | 16 |
| Tne M284 | 8 | 18 |
| Tne M284(D323A, D389A) | 35 | 22 |
| Tne M284 (D468N) | 26 | 66 |

The results shown in Table 4 demonstrate that deletion of the amino terminal 5' to 3' exonuclease domain of Tne polymerase increases resistance to thermal degradation (2.5 to 13.2 fold). While amino-terminal deletions have been shown to increase thermostability (i.e., thermal tolerance) of certain modified forms of Taq DNA polymerase (e.g., the Stoffel fragment) and Tma DNA polymerase, the increase seen is generally about 2–3 fold. The increase in thermostability seen by the introduction of single or double point mutations into the Tne M284 deletion mutant was unexpected, especially the dramatic increase in thermostability caused by the single point mutation present in Tne M284(D468N) (SEQ ID NO:26).

The Tne M284(D468N) protein is identical to the Tne M284 protein with the exception that an asparagine is substituted for an aspartate at position 468; the carbon backbones of these two molecules should be identical, yet there is a greater than 5-fold resistance to thermal degradation seen when asparagine is present at position 468. The only difference between these two molecules should be a negatively charged carbonyl group (aspartate) and a neutral amide group (asparagine); both of these groups can participate in hydrogen-bonding. Substitutions of solvent-exposed amino acids (e.g., aspartate or asparagine) have been shown to have little effect on protein stability or structure [Matthews, *Ann. Rev. Biochem.* 62:139 (1993)], leading to the view that the rigid parts of proteins are critical for folding and stability. Based on analogy to the *E. coli* DNA polymerase I molecule at position 501, it is expected that position 468 in the Tne DNA polymerase is accessible to solvent Furthermore, since Tne M284(D468N) lacks the carbonyl group to coordinate a metal ion, it was predicted that a slight destabilization (in response to heat) would be seen rather than a dramatic stabilization. This data show that a subtle change in the 3' exonuclease active site can dramatically alter the thermostability (i.e., thermotolerance) of the Tne DNA polymerase.

The above results demonstrate that several of the modified Tne polymerases have superior thermostability; accordingly, when these enzymes are used in PCR and other reactions run at elevated temperature, less polymerase activity needs to be used as less enzyme is inactivated by exposure to elevated temperature.

g) Optimal Temperature for DNA Polymerase Activity

The DNA polymerase activity of several Tne polymerases and nTaq DNA polymerase was measured at various temperatures using the assay described in Example 5b (with the exception that the temperature of incubation was varied). The results are summarized in Table 5. The temperature which gave the highest activity for a given enzyme was assigned a value of 100% and all other values given are expressed relative to the 100% value.

The results shown in Table 5 demonstrate that for nTaq DNA polymerase, the maximal DNA polymerase activity was present when the reaction was run at 78° C. Optimal temperature for DNA polymerase activity for the full-length rTne DNA polymerase was 74° C. Optimal temperature for DNA polymerase activity for the Tne M284 and Tne M284 (D323A, D389A) DNA polymerases was 75° C.

TABLE 5

Optimal Temperature For Tne Polymerase Activity

| Temp. (° C.) | Tne M284 | Tne M284(D323A, D389A) | nTaq | rTne |
| --- | --- | --- | --- | --- |
| 40 | 12 | 15 | n.d. | n.d. |
| 45 | 15 | 17 | n.d. | n.d. |
| 50 | 18 | 20 | n.d. | n.d. |
| 55 | 24 | 26 | n.d. | n.d. |
| 60 | 33 | 36 | n.d. | n.d. |
| 65 | 53 | 52 | n.d. | n.d. |
| 70 | 71 | 80 | n.d. | 77 |
| 72 | n.d. | n.d. | n.d. | 86 |
| 74 | n.d. | n.d. | n.d. | 100 |
| 75 | 100 | 100 | n.d. | n.d. |
| 76 | n.d. | n.d. | 93 | 94 |
| 77 | n.d. | n.d. | 97 | n.d. |
| 78 | n.d. | n.d. | 100 | 96 |
| 79 | n.d. | n.d. | 97 | n.d. |
| 80 | 53 | 56 | 85 | 85 |
| 81 | n.d. | n.d. | 82 | n.d. |
| 82 | n.d. | n.d. | 68 | 68 |
| 85 | 16 | 16 | n.d. | n.d. |
| 90 | 8 | 8 | n.d. | n.d. |

EXAMPLE 9

The Tne DNA Polymerases Provide Improved Enzymes for use in the Polymerase Chain Reaction The use of the full-length and modified forms of Tne polymerase in the PCR was examined. The results of the following experiments show that the Tne polymerases provide improved enzymes for a variety of PCR applications.

a) The Modified Tne Polymerases Utilize a Broader Range of Optimal dNTP Concentrations in the PCR PCR reactions were conducted using a range of dNTP concentrations to determine the optimal range of dNTP concentrations utilized by either the UlTma™ DNA polymerase (Perkin Elmer) or the Tne M284 and Tne M284 (D323A, D389A) polymerases. The modified Tne polymerases were found to produce high yields of amplified product over a much broader range of nucleotide concentrations. The PCRs were conducted as follows.

The three enzyme preparations were assayed for DNA polymerase activity using the assay in Example 5b so that the same amount of enzyme was used in the PCRs. PCRs were performed in a buffer optimized for each type of enzyme; the UlTma™ and Tne enzymes were both found to give optimal results in the following buffer [10 mM Tris-HCl (pH 8.8 at 25° C.), 10 mM KCl, 0.002% Tween 20]. All reactions contained 1 ng of pGEM-luc (Promega) as the template, 20 pmol of each primer [the primers used were LME41(SEQ ID NO:42) and LME43(SEQ ID NO:43)], 1.5 mM MgCl$_2$ (this concentration was chosen as it was optimal for both the UlTma™ and the modified Tne enzymes as shown below in section b) and 2.5 units of each enzyme. The final reaction volume was 50 µl.

A dilution series was created for the mixture of all four dNTPs ranging from 20 to 200 µM (20, 40, 60, 80, 100, 120, 140, 160 and 200 µM). The PCRs were thermal cycled using the following conditions, an initial denaturation at 96° C. for 2 min, followed by 30 cycles comprising denaturation at 94° C. for 30 sec, annealing/extension at 65° C. for 2 min; following the last cycle the tubes were incubated at 65° C. for 10 min and then the tubes were incubated at 4° C. Thermal cycling was conducted on a Perkin Elmer Thermocycler Model 480. The PCR products were resolved on 1% agarose gels, stained with EtBr and quantitated by visual inspection of the stained gels. The experiment was repeated a second time and similar results were obtained.

The optimal dNTP concentration for UlTma™ was found to be 40 µM (the same value as reported to be optimal by Perkin Elmer in the UlTma™ product insert); slight levels of product could be detected using the UlTma™ enzyme at a concentration of 20 µM dNTPs but not at all at other concentrations tested. The optimal range of concentrations of dNTPs for Tne M284(D323A, D389A) was found to be from 60 µM to 200 µM with slight amounts of product being detected at both 20 and 40 µM dNTP. The optimal range of concentrations of dNTPS for Tne M284 was from 40 µM to 200 µM with slight amounts of product being detected at 20 µM dNTP.

The ability to use a wide range of dNTP concentrations is advantageous. The modified Tne polymerases allow PCR users wide flexibility in the design of the reaction conditions. Because the modified Tne polymerases are not sensitive to small variations in dNTP concentration, PCRs using these enzymes are more robust. Additionally the ability to use a higher concentration of dNTPs may also allow a higher yield of product to be generated in a PCR using the modified Tne polymerases as compared to the use of the UlTma™ polymerase.

b) The Tne Polymerases Tolerate a Broader Range of Mg++ Concentrations in PCR

In side-by-side tests with UlTma™ DNA polymerase and Tne M284 or Tne M284(D323A, D389A), the Tne variants were found to produce high yields of amplified product over a broader range of magnesium ion concentrations. A dilution series was created for magnesium (MgCl$_2$) ranging from 0.5 to 5 mM (0.5, 1.0, 1.5, 2.0, 2.5, 3.0, 4.0, and 5.0 mM). The other components of the PCR were as described above in section a) with the exception that a single dNTP concentration was used (40 µM dNTP was used for the UlTma™ enzyme and the modified Tne enzymes as this value was within the operable range for all three enzymes; it is noted that 40 µM dNTP is not optimal for the Tne M284(D323A, D389A enzyme and that even higher product yields would be expected if 60 µM dNTP were used for this enzyme) and the concentration of MgCl$_2$ was varied. Thermal cycling conditions were as described above in section a). The reaction products were treated as described above in section a).

The results of these assays showed that the UlTma™ enzyme (Perkin Elmer) had an optimal concentration of 1.5 mM MgCl$_2$ and a great deal of non-specific background products were seen on the gels (as a smear). The optimal concentration for Tne M284 enzyme was found to be from 1 to 3 mM MgCl$_2$ and some nonspecific background products were observed. The optimal concentration for M284 (D323A, D389A) was from 1 to 3 mM MgCl$_2$ and very little or no detectable non-specific background products were observed.

The ability of a thermostable enzyme to produce only specific PCR products over a wide range of Mg$^{++}$ concentrations is important for certain PCR applications. For example, multiplexing PCRs utilize several pairs of primers to amplify several different targets in the sample. As each primer pair and target combination will have a optimum $Mg^{++}$ concentration and this value may vary considerably from primer set to primer set, the availability of thermostable polymerases having a wide optimum for $Mg^{++}$ is advantageous. Therefore, the Tne M284 and Tne M284 (D323A, D389A) polymerases provide improved thermostable DNA polymerases.

c) Modified Tne Polymerases Produce High PCR Product Yields

A comparison was made between the yield of PCR product obtained using a consistent amount of polymerase activity when the following enzymes were used in the PCR: Tne M284, Tne M284(D323E), Tne M284(E325D), Tne M284(Y464F), Tne M284(D468N), Tne M284(D323A, D389A), AmpliTaq (Perkin Elmer), nTaq (Promega) and UlTma™ (Perkin Elmer). All enzymes were assayed using the DNA polymerase assay described in Example 5b so that the same number of units of enzyme were added to the PCRs.

PCRs which used UlTma™ polymerase contained 10 mM Tris-HCl (pH 8.8 at 25° C.), 10 mM KCl, 0.002% Tween 20 and 1.5 mM $MgCl_2$. This buffer gives optimal PCR results for the UlTma™ enzyme (as reported by Perkin Elmer). For the results shown in Table 6, PCRs which used the Tne DNA polymerases contained 10 mM Tris-HCl (pH 8.8 at 25° C.), 10 mM KCl, 0.002% Tween 20 and 1.5 mM $MgCl_2$. This buffer gives acceptable results for the Tne polymerases.

For the results shown in Table 7, PCRs which used the Tne DNA polymerases contained 10 mM Tris-HCl (pH 9.0 at 25° C.), 10 mM KCl, 0.01% Tween 20 and 1.5 mM $MgCl_2$ as it was found that the Tne DNA polymerases perform better when the pH of the buffer is raised to 9.0 and the amount of detergent (i.e., Tween 20) is increased to 0.01%.

PCRs which used the UlTma™ enzyme contained 40 µM dNTPs as this value was determined to be optimal for this enzyme. (See Section a, above). PCRs which used the modified Tne enzymes contained 140 µM dNTPs as this value was determined to be optimal for these enzymes. (See section a, above).

PCRs which used nTaq or AmpliTaq polymerase contained 10 mM Tris-HCl (pH 9.0 at 25° C.), 50 mM KCl, 1.5 mM $MgCl_2$, 0.1% Triton X-100; this buffer gives optimal PCR results for the nTaq and AmpliTaq polymerases. PCRs which used the nTaq and AmpliTaq enzymes contained 200 µM dNTPs as this value is reported to be optimal for these enzymes.

A single template, pGEM-luc was tested in conjunction with two different primer pairs. The primer pair comprising LME41 (SEQ ID NO:42) and LME45 (SEQ ID NO:44) amplifies a 500 bp target on the template. The primer pair comprising LME41 (SEQ ID NO:42) and LME43 (SEQ ID NO:43) amplifies a 1.5 kb target on the template.

All PCR reactions contained 3.0 units of the enzyme to be tested, 2 ng of pGEM-luc (Promega) as the template, 50 pmol of each primer pair, 1.5 mM $MgCl_2$ (this concentration was chosen as it was determined to be optimal for all three types of enzyme tested using this template and these primer pairs). The final reaction volume was 100 µl.

The PCRs which amplified the 500 bp target were thermal cycled using the following conditions, an initial denaturation at 96° C. for 2 min, followed by 25 cycles comprising denaturation at 95° C. for 30 sec, annealing at 65° C. for 30 sec and extension at 72° C. for 1 min; following the last cycle the tubes were incubated at 4° C.

The PCRs which amplified the 1500 bp target were thermal cycled using the following conditions, an initial denaturation at 94° C. for 2 min, followed by 30 cycles comprising denaturation at 94° C. for 1 min and annealing/extension at 65° C. for 2 min; following the last cycle, the tubes were incubated at 68° C. for 10 min and then the tubes were brought to 4° C.

Thermal cycling was conducted on a Perkin Elmer Thermocycler Model 480. Each reaction was run in duplicate. The PCR products were resolved by electrophoresis through 1% agarose gels, followed by staining with EtBr and quantitated by scanning the gels with a fluoroimager (Molecular Dynamics); product yields were quantitated using ImageQuant software (Molecular Dynamics). The results (average of the duplicates) are shown below in Tables 6 and 7. The enzyme which gave the highest yield was assigned a value of 100% and all other values are expressed as a percentage of the maximal yield.

The results shown above in Tables 6 and 7 demonstrate the following. Regardless of the target size, the modified Tne enzymes produced higher yields as compared to the UlTma™ enzyme (2.5 to 6.7 fold more product). The modified Tne enzymes also performed better than nTaq when the 500 bp target was used (about 2 fold more product) and better than the recombinant Taq polymerase (AmpliTaq) when the 1.5 kb target was used (about 30% more product).

Thus, to produce the same amount of PCR product, fewer units of modified Tne polymerases are required compared to the use of the UlTma™, nTaq and AmpliTaq enzymes. These modified Tne polymerases allow the user to use smaller amounts of enzyme in the PCR and therefore will provide significant cost savings in PCR applications.

TABLE 6

Product Yields For Amplification Of A 500 bp Target

| Enzyme | % Yield |
| --- | --- |
| nTaq | 59 |
| UlTma ™ | 16 |
| Tne M284 | 100 |
| Tne M284(D323E) | 89 |
| Tne M284(E325D) | 87 |
| Tne M284(Y464F) | 91 |
| Tne M284(D468N) | 89 |
| Tne M284(D323A, D389A) | 91 |

TABLE 7

Product Yields For Amplification Of A 1.5 kb Target

| Enzyme | % Yield |
| --- | --- |
| AmpliTaq | 67 |
| UlTma ™ | 40 |
| Tne M284 | 81 |
| Tne M284(D323E) | 70 |
| Tne M284(E325D) | 86 |
| Tne M284(Y464F) | 93 |
| Tne M284(D468N) | 100 |
| Tne M284(D323A, D389A) | 87 |

EXAMPLE 10

Thermal Cycle Sequencing using Modified Tne Polymerases

The modified Tne polymerases were further characterized by examining their ability to be used in thermal cycle sequencing reactions. Initial sequencing reactions were performed using with the Tne M284(D323E) and Tne M284 (E325D) mutants (SEQ ID NOS: 16 and 19, respectively) using the buffer and dideoxy mixes from the fmol® DNA Sequencing System kit (Promega) according to the manufacturer's instructions. The buffer and concentrations of dideoxy and deoxyribonucleotides in this kit were optimized for use with sTaq DNA polymerase (Promega; sTaq is a modified form of Taq DNA polymerase which has very low 5' to 3' exonuclease activity).

When the sequencing reactions were performed using purified preparations of either Tne M284(D323E) (SEQ ID NO: 16) or Tne M284(E325D) (SEQ ID NO: 19), the resulting reaction products were very short and uneven and created light bands on the sequencing gel in every position and in every lane. The light bands in every position were consistent with the presence of residual 3' to 5' exonuclease activity in the modified Tne polymerases.

Thermal cycle sequencing reactions were then performed using the triple mutant Tne M284(D323A, D389A) (SEQ ID NO:35). All thermal cycle sequencing was carried out using a Perkin-Elmer 9600 thermal cycler in conjunction with the fmol® DNA Sequencing System reagents (Promega). The template used in the sequencing reactions was the Tne clone pE325D (Example 4b) and the 5' labeled primer was the JH66 primer (SEQ ID NO:12). The reactions were run at 95° C. for 15 seconds and 70° C. for 60 seconds for 30 cycles.

The results of this experiment showed that the use of the triple mutant enzyme (SEQ ID NO:35) eliminated the light bands in every position which were seen with Tne M284 (D323E) and Tne M284(E325D); however the sequence ladders were still shifted toward short extension products. These short intense reads were indicative of a DNA polymerase having a higher affinity for the dideoxynucleotides than Taq DNA polymerase.

To examine if the triple mutant Tne enzyme (SEQ ID NO:35) had a higher affinity for dideoxynucleotides, the sequencing reactions were repeated using a lower ratio of dNTPs to ddNTPs in the sequencing reaction mixtures (all other conditions remained the same). Table 8 lists the 3× mixes used for sTaq and Tne M284(D323A, D389A) polymerases in this experiment. The use of lower concentration of dideoxynucleotides in the sequencing reaction run using the triple mutant Tne enzyme (SEQ ID NO:35) produced reads as long as those obtained using sTaq.

TABLE 8

|  | sTaq | | Tne M284, D323A, D389A | |
| --- | --- | --- | --- | --- |
|  | dNTPs | ddNTPs | dNTPs | ddNTPs |
| G mix | 20 μM | 30 μM | 20 μM | 30 μM |
| A mix | 20 μM | 350 μM | 20 μM | 75 μM |
| T mix | 20 μM | 600 μM | 40 μM | 40 μM |
| C mix | 20 μM | 200 μM | 40 μM | 20 μM |

EXAMPLE 11

Optimization of Nucleotide Mixtures for Thermal Cycle Sequencing using Tne M284(D323A, D389A) Polymerase The results discussed in Example 10 demonstrated that the Tne M284(D323A, D389A) polymerase (SEQ ID NO:35) has a higher affinity for dideoxynucleotides than does sTaq polymerase. Further testing with various concentrations of dideoxy- and deoxynucleotides, including modified dNTPs, in sequencing reactions was performed to ascertain the optimal concentration for these reagents. The optimized Tne dNTP/ddNTP mixes are detailed in Table 9 below. The values reported in Table 9 represent 3× mixtures; these mixtures are diluted 3-fold in the final reaction mixture as described below. To obtain the final concentration of dNTPs and ddNTPs in the reactions, the values in Table 9 are divided by 3.

TABLE 9

Optimized Nucleotide Mix Formulation For Tne Polymerase

| Component | G Nucleotide Mix | A Nucleotide Mix | T Nucleotide Mix | C Nucleotide Mix |
| --- | --- | --- | --- | --- |
| ddGTP | 20 μM | — | — | — |
| ddATP | — | 50 μM | — | — |
| ddTTP | — | — | 75 μM | — |
| ddCTP | — | — | — | 25 μM |
| 7-deaza dGTP | 30 μM | 30 μM | 30 μM | 30 μM |
| dATP | 30 μM | 30 μM | 30 μM | 30 μM |
| dTTP | 30 μM | 30 μM | 30 μM | 30 μM |
| dCTP | 30 μM | 30 μM | 30 μM | 30 μM |

To illustrate the fact that the Tne M284(D323A,D389A) enzyme has a higher affinity for ddNTPs as compared to sTaq, the following thermal cycle sequencing reactions were performed. The template used was pGEM-3Zf(+) (Promega) and the primer was the $\gamma$-$^{32}$P end labeled pUC/M13 Forward Primer (Promega; SEQ ID NO:40). Reactions using sTaq polymerase or the Tne M284(D323A, D389A) polymerase were performed using dNTP/ddNTP mixes optimized for sTaq as provided in the fmol® DNA Sequencing System.

The extension products of thermal cycle sequencing reactions performed using either sTaq or the Tne M284(D323A, D389A) polymerase were resolved by electrophoresis on a 6% denaturing polyacrylamide gel; following electrophoresis, the gel was exposed to X-ray film. The resulting autoradiograph is shown in FIG. 5, Panel A.

In FIG. 5, Panel A, lanes 1–4 contain reaction products generated using sTaq and lanes 5–8 contain reaction products generated using the Tne M284(D323A, D389A) polymerase. In each set of four lanes, reactions run in the presence of ddGTP, ddATP, ddTTP and ddCTP were loaded left to right.

The results shown in FIG. 5, Panel A show that the sequence ladders generated using the modified Tne polymerase were shifted toward short extension products. These short intense reads were indicative of a DNA polymerase having a higher affinity for the dideoxynucleotides than Taq DNA polymerase.

Sequencing reactions were then performed using sTaq in conjunction with dNTP/ddNTP mixes optimized for sTaq as provided in the fmol® DNA Sequencing System or the Tne M284(D323A, D389A) polymerase and the dNTP/ddNTP mixes shown in Table 9. The template used was pGEM-3Zf (+) (Promega) and the primer was the $\gamma$-$^{32}$P end labeled pUC/M13 Forward Primer (Promega; SEQ ID NO:40). An autoradiograph of reaction products is shown in FIG. 5, Panel B.

In FIG. 5, Panel B, lanes 1–4 contain reaction products generated using sTaq and sequencing mixes optimized for sTaq and lanes 5–8 contain reaction products generated using the Tne M284(D323A, D389A) polymerase and sequencing mixes shown in Table 9 for the Tne M284 (D323A, D389A) polymerase. In each set of four lanes, reactions run in the presence of ddGTP, ddATP, ddTTP and ddCTP were loaded left to right.

The results shown in FIG. 5, Panel B demonstrate that the Tne M284(D323A, D389A) polymerase has a higher affinity for ddNTPs than does sTaq polymerase and therefore lower concentrations of ddNTPs must be used in the sequencing reactions.

Using the optimized mixes shown in Table 9, the Tne M284(D323A,D389A) enzyme was compared with Sequencing Grade Taq (sTaq; Promega) for its ability to sequence three different templates. sTaq (Promega) was used in conjunction with the fmol DNA Sequencing System (Promega) and all protocols were followed as per the instructions. The Tne M284(D323A,D389A) polymerase was used in conjunction with the fmol® DNA Sequencing System kit (Promega), except that the dNTP's/ddNTP's mixes used were the Tne optimized mixes shown in Table 9.

The following three DNA templates used in the indicated amounts in the thermal cycle sequencing reactions. Forty femtomoles of pGEM-3Zf(+) (Promega) was sequenced using the $\gamma$-$^{32}$P end labeled pUC/M13 Forward Primer (Promega; SEQ ID NO:40). Four femtomoles of a 500 bp PCR fragment was sequenced using the gamma 32P end labeled LME-28 primer (5'-TAATACGACTCACTATAGGGCG AAT-3' (SEQ ID NO:47). Four femtomoles of λgt11 phage DNA (Promega) was sequenced using a $\gamma$-$^{32}$P end labeled λgt11 Forward Primer (Promega).

The 500 bp PCR product used as template was generated by amplification of the template pGEM-luc with primers LME41 (SEQ ID NO:42) and LME45 (SEQ ID NO:44) as described in Example 9.

The thermal profile of all sequencing reactions was 95° C. for 2 min, then 30 cycles of 95° C. for 30 sec, 70° C. for 60 sec; following the last cycle, the reactions were brought to 4° C. The thermal cycling was performed using a Perkin-Elmer 480 Thermal Cycler. The extension products were separated on a 6% denaturing polyacrylamide gel; following electrophoresis, the gel was exposed to X-ray film. The resulting autoradiographs are shown in FIG. 6.

Figure 6A:
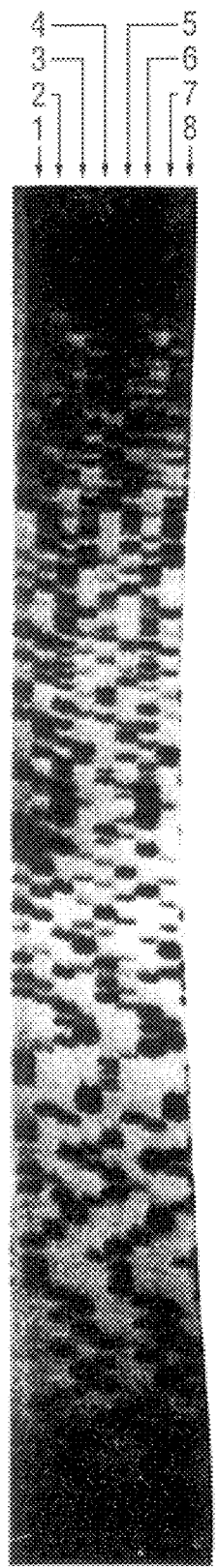
FIG. 6A shows an autoradiograph of a sequencing gel.
Figure 6B:
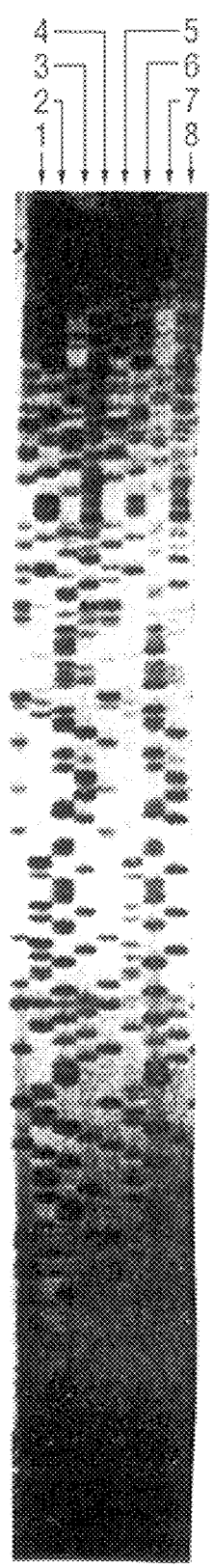
FIG. 6B shows an autoradiograph of a sequencing gel.
Figure 6C:
FIG. 6C shows an autoradiograph of a sequencing gel.

In FIG. 6, three panels are shown. Panel A contains the extension products generated using pGEM-3Zf(+) as the template; Panel B contains the extension products generated using the 500 bp PCR product as the template; Panel C contains the extension products generated using λgt11 phage DNA as the template. In all three panels, eight lanes are shown. The first four lanes correspond to extension products generated using sTaq polymerase; the last four lanes correspond to extension products generated using the Tne M284 (D323A, D389A) polymerase. In each set of four lanes, the termination mixes were used in the following order (left to right): G, A, T and C.

The results shown in FIG. 6 demonstrated that the Tne M284(D323A, D389A) polymerase produced sequencing ladders which were virtually identical in terms of quality and quantity to those produced using sTaq (Promega); both enzymes provided the correct DNA sequence for each template. While both enzymes produced similar results in thermal cycle sequencing reactions, the Tne M284(D323A, D389A) polymerase required lower concentrations of dideoxynucleotides. Thus, the use of the use of the Tne M284(D323A, D389A) polymerase will result in considerable cost savings for thermal cycle sequencing applications.

The optimal ddNTP concentrations shown in Table 9 for the Tne M284(D323A, D389A) polymerase (SEQ ID NO:35) as compared to the optimal concentrations for sTaq (Table 8) demonstrate that the modified Tne polymerase has a greater affinity four all four ddNTPs. In particular this modified Tne polymerase requires 8-fold less ddTTP or ddCTP, 7-fold less ddATP and 1.5-fold less ddGTP than does sTaq in thermal cycle sequencing reactions. As dideoxynucleotides are an expensive component of the sequencing reaction mixtures, the use of the Tne M284(D323A, D389A) polymerase (SEQ ID NO:35) in place of enzymes such as Taq polymerase which have lower affinities for ddNTPS will result in considerable cost savings. These results also demonstrate that the Tne M284(D323A, D389A) enzyme can utilize the nucleotide analog 7-deaza dGTP which is used to resolve band compression artifacts generated when sequencing G+C-rich regions of DNA.

EXAMPLE 12

Preferred Sequencing Protocol using Tne M284 (D323A, D389A) Polymerase

The preferred sequencing protocol uses a thermal cycling format. A detectable signal may be generated using either an end radiolabeled primer or a radiolabeled dNTP that is incorporated into the extension products.

a) Sequencing Protocol using an End-labeled Primer i) Primer Radiolabeling Reaction To generate a radiolabeled primer for use in the sequencing reaction, the following reaction components are assembled in a 0.5 ml microcentrifuge tube: 10 pmol of the desired sequencing primer; 10 pmol of $\gamma$-labeled ATP (see Table 10 for amount); 1 μl of 10× T4 polynucleotide kinase Buffer [500 mM Tris-HCl (pH 7.5); 100 mM MgCl$_2$; 50 mM DTT; 1.0 mM spermidine]; 5 units T4 polynucleotide kinase and sterile H$_2$O to a final volume of 10 μl. The reaction mixture is incubated at 37° C. for 10–30 min (if end-labeling is to be performed using [$\gamma$-$^{35}$S]ATP, 20 units of polynucleotide kinase are used and the reaction is incubated for 4 hours at 37° C.). The reaction is then terminated by inactivation of the kinase by incubation at 90° C. for 2 minutes. The tube is then briefly spun in a microcentrifuge to collect any condensation. The labeled primer may be used directly in the sequencing reaction without further purification.

TABLE 10

| Amount Of Radiolabeled Nucleotide Needed To Equal 10 pmol | | |
|---|---|---|
| [$\gamma$-$^{32}$P]ATP: | 3.0 μl of 3,000 Ci/mmol, | 10 μCi/μl |
| | 5.0 μl of 5,000 Ci/mmol, | 10 μCi/μl |
| | 0.5 μl of 6,000 Ci/mmol, | 135 μCi/μl |
| [$\gamma$-$^{35}$S]ATP: | 1.4 μl of 1,326 Ci/mmol, | 10 μCi/μl | ii) Extension/Termination Reactions

For each set of sequencing reactions, label four 0.5 ml microcentrifuge tubes (G, A, T, C). Add 2 μl of the appropriate 3× dNTP/ddNTP Mix to each tube (see Table 9 for components of the 3× mixes). Cap the tubes and store on ice or at 4° C. until needed. For each set of four sequencing reactions, mix the following reagents in a microcentrifuge tube: 4–40 fmol of template DNA (see Table 11 below for recommended amounts); 5μl fmol® Sequencing 5× Buffer [250 μM Tris-HCl (pH 9.0 at 25° C.), 10 mM MgCl$_2$]; 1.5 μl labeled primer (1.5pmol); sterile H$_2$O to a final volume of 16 μl (this comprises the primer/template mix).

Add 1.0 μl of Tne M284 (D323A,D389A) DNA Polymerase (5u/μl) to the primer/template mix. Mix briefly by pipetting up and down (this comprises the enzyme/primer/template mix). Add 4 μl of the enzyme/primer/template mix to the inside wall of each tube containing d/ddNTP mix. Add one drop (approximately 20 µl) of mineral oil to each tube and briefly spin in a microcentrifuge. Place the reaction tubes in a thermal cycler that has been preheated to 95° C. and start the cycling program.

TABLE 11

Recommended Amounts Of Template DNA (ng) For End-Labeled Primer Protocol

| Template Length | ng Of Template |
| --- | --- |
| 200 bp (PCR product) | 0.5 ng (4 fmol) |
| 3,000–5,000 bp (supercoiled plasmid DNA) | 100 ng (40 fmol) |
| 48,000 bp (lambda DNA) | 130 ng (4 fmol) |

When the primer used is less than 24 nucleotides in length or has a G+C-content less than 50%, the following cycling profile is used: 95° C. for 2 minutes followed by 30 cycles of 95° C. for 30 seconds (denaturation); 42° C. for 30 seconds (annealing); 70° C. for 1 minute (extension); the tubes are then brought to 4° C.

When the primer used is greater than or equal to 24 nucleotides in length or when shorter primers having a G+C-content greater than or equal to 50%, the following cycling profile is used: 95° C. for 2 minutes followed by 30 cycles of 95° C. for 30 seconds (denaturation); 70° C. for 30 seconds(annealing/extension); the tubes are then brought to 4° C.

After the thermocycling program has been completed, add 3 µl of fmol® Sequencing Stop Solution [10 mM NaOH; 95% formamide; 0.05% bromophenol blue; 0.05% xylene cyanol] to the inside wall of each tube. Briefly spin the tubes in a microcentrifuge to terminate the reactions. Heat the reactions at 70° C. for 2 minutes immediately before loading onto a sequencing gel. Load 2.5–3.0 µl of each reaction on the gel.

b) Sequencing Protocol using Direct Incorporation
i) Extension/Termination Reactions The following procedure requires about 500 fmol of plasmid templates and about 40 fmol of PCR product. The end-labeled primer protocol (section a) is recommended for PCR templates. This procedure is not recommended for the sequencing of lambda templates.

For each set of sequencing reactions, label four 0.5 ml microcentrifuge tubes (G, A, T, C). Add 2 µl of the appropriate d/ddNTP Mix to each tube. Cap the tubes and store on ice or at 4° C. until needed. For each set of four sequencing reactions, mix the following reagents in a microcentrifuge tube: 500 fmol template DNA (approx. 1 µg of a 3–5 kb template); 3.0 pmol primer (approx. 25 ng of a 24 mer); 0.5 µl [$\alpha$-$^{35}$S]dATP (>1,000 Ci/mmol, 10 µCi/µl) or [$\alpha$-$^{32}$P] dATP (800 Ci/mmol, 10 µCi/µl); 5 µl fmol® Sequencing 5× Buffer and sterile H$_2$O to final volume of 16 µl.

Add 1.0 µl of Tne M284 (D323A,D389A) DNA Polymerase (5 u/µl) to the primer/template mix. Mix briefly by pipetting up and down. Add 4µl of the enzyme/primer/template mix to the inside wall of each tube containing d/ddNTP Mix. Add one drop (approximately 20 µl) of mineral oil to each tube and briefly spin in a microcentrifuge. Place the reaction tubes in a thermal cycler that has been preheated to 95° C. and start the cycling program. The cycling profile chosen depends upon the characteristics of the primer used; see section a(i) above.

After the thermocycling program has been completed, add 3 µl of fmol® Sequencing Stop Solution to the inside wall of each tube. Briefly spin in a microcentrifuge to terminate the reactions. Heat the reactions at 70° C. for 2 minutes immediately before loading on a sequencing gel. Load 2.5–3.0 µl of each reaction on the gel.

EXAMPLE 13

Use of Tne M284(D323A, D389A) Polymerase in Sanger Sequencing Protocols

The above examples described the use of the Tne M284 (D323A, D389A) polymerase in thermal cycle sequencing protocols. The Tne M284(D323A, D389A) Polymerase may also be used in traditional Sanger sequencing protocols.

If a double stranded DNA template is used, the template is first denatured using alkali as follows. Four micrograms (approximately 2 pmol) of supercoiled plasmid DNA is added to a microcentrifuge tube and deionized H$_2$O is added to a final volume of 18 µl. Two microliters of 2 M NaOH, 2 mM EDTA is added and the mixture is incubated for 5 minutes at room temperature. To neutralize the reaction, add 8 µl of 5M ammonium acetate, pH 7.5, and vortex. Add 112 µl of 100% ethanol and vortex. Centrifuge the tube for 10 minutes at top speed in a microcentrifuge. Decant the supernatant. Wash the pellet with 1 ml of 70% ethanol and centrifuge for 1 minute. Remove the supernatant and dry the pellet. Resuspend the dried pellet in 18 µl of distilled water for sequencing. Proceed to either section i) or ii) depending on whether an end-labeled primer is employed or whether radiolabeled nucleotides are employed in the sequencing reaction.

a) Sequencing Protocol using an End-labeled Primer

The primer is end labeled using the protocol described in Example 11(a)(i). The template and primer are annealed as follows. When a single-stranded DNA template is employed the following reaction is used. For each set of four sequencing reactions, mix the following reagents in a microcentrifuge tube: 0.8 pmol ssDNA (approx. 2 µg of an M13 template); 5.0 µl of 5× Taq DNA Polymerase [250 mM Tris-HCL (pH 9.0 at 25° C.]; 50 mM MgCl$_2$]; 1.0 µl labeled primer (1 pmol); sterile dH$_2$O to a final volume of 25 µl. Incubate at 37° C. for 10 minutes. During the incubation, prepare the extension/termination reaction tubes as described in section c) below.

When a double-stranded plasmid is used as the template, the following reaction is used. For each set of four sequencing reactions, mix the following reagents in a microcentrifuge tube: 1.6 pmol denatured plasmid dsDNA (approx. 4 µg of a 3–5 kb template); 5.0 µl Taq DNA Polymerase 5× Buffer; 2.0 µl labeled primer (2 pmol) and sterile dH$_2$O to a final volume of 25 µl. Incubate at 37° C. for 10 minutes. During the incubation, prepare the extension/termination reaction tubes as described in section c) below.

b) Extension/Termination Reactions

For each set of sequencing reactions, label four microcentrifuge tubes (G,A,T and C) and add 1 µl of the 8× Tne optimized d/ddNTP Mix (see Table 12 for components of the 8× mixes) to each tube. Cap the tubes and store on ice or at 4° C. until needed. Add 1 µl of Tne M284 (D323A,D389A) DNA Polymerase (5 u/µl) to the annealed primer/template mix (prepared as described above) and mix briefly by pipetting up and down.

Add 6 µl of the enzyme/primer/template mix to each of the four tubes containing the d/ddNTP Mixes. Mix briefly by pipetting up and down. A brief spin may be needed to ensure that no liquid is left on the tube walls. Incubate at 70° C. for 15 minutes. Add 4 µl of Stop Solution to each tube and set at room temperature. Heat the reactions to ≧70° C. for 2–5 minutes before loading the sequencing gel. Load 2.5–3.0 µl of each reaction on the gel (6% denaturing polyacrylamide). Following electrophoresis of the sequencing gel, the gel is exposed to X-ray film to generate an autoradiograph.

If the extension products seen on the autoradiograph are too short, the ddNTP concentrations should be lowered and conversely if the extension products are all skewed to high molecular weight products, the ddNTP concentrations should be raised.

TABLE 12

8X Nucleotide Mix Formulation For Sanger Sequencing Using Tne M284(D323A, D389A) Polymerase

| Nucleotide Component | G Nucleotide Mix | A Nucleotide Mix | T Nucleotide Mix | C Nucleotide Mix |
|---|---|---|---|---|
| ddGTP | 20 µM | — | — | — |
| ddATP | — | 50 µM | — | — |
| ddTTP | — | — | 75 µM | — |
| ddCTP | — | — | — | 25 µM |
| 7-deaza dGTP | 30 µM | 250 µM | 250 µM | 250 µM |
| dATP | 250 µM | 30 µM | 250 µM | 250 µM |
| dTTP | 250 µM | 250 µM | 30 µM | 250 µM |
| dCTP | 250 µM | 250 µM | 250 µM | 30 µM | c) Sequencing Protocol using Direct Incorporation i) Annealing the Template and Primer When a single-stranded DNA template is employed the following reaction is used to anneal the template and primer. For each set of four sequencing reactions, mix the following reagents in a microcentrifuge tube: 0.8 pmol ssDNA (approx. 2 µg of an M13 template); 1.0 pmol primer (approx. 8 ng of a 24mer); 5.0 µl Taq DNA Polymerase 5× Buffer; 2.0 µl Extension/Labeling Mix [7.5 µM each of dGTP, dTTP and dCTP];sterile dH$_2$O to a final volume of 25 µl. Incubate at 37° C. for 10 minutes. During the incubation, prepare the nucleotide tubes for the termination reaction as described in section iii, below.

When a double-stranded DNA template is employed the following reaction is used to anneal the template and primer. For each set of four sequencing reactions, mix the following reagents in a microcentrifuge tube: 1.6 pmol denatured plasmid dsDNA (approx. 4 µg of a 3–5 kb template); 2 pmol primer (approx. 16 ng of a 24mer); 5.0 µl Taq DNA Polymerase 5× Buffer; 2.0 µl Extension/Labeling Mix; sterile dH$_2$O to a final volume of 25 µl. Incubate at 37° C. for 10 minutes. During the incubation, prepare the nucleotide tubes for the termination reaction as described in section iii, below.

ii) Extension/labeling Reaction

Add 0.5 µl of [α-$^{35}$S]dATP (1,000 Ci/mmol, approximately 10 µCi/µl) or 0.5 µl of [α-$^{32}$P]dATP (800 Ci/mmol, approximately 10 µCi/µl) to the annealed primer/template mixture. Add 1 µl of Tne M284 (D323A,D389A) DNA Polymerase (5 u/µl) and mix briefly by pipetting up and down. Incubate at 37° C. for 5 minutes.

iii) Termination Reaction

For each set of sequencing reactions, label four microcentrifuge tubes (G,A,T,C) and add 1 µl of the 8× Tne optimized d/ddNTP Mix to each tube (see Table 12 above). Store on ice or at 4° C. until just before completion of the extension/labeling reaction. When the extension/labeling reaction is complete, aliquot 6 µl to each tube (G,A,T,C) containing d/ddNTP Mix. Mix briefly by pipetting up and down. A brief spin may be needed to ensure that no liquid is left on the tube walls. Incubate at 70° C. for 15 minutes. Add 4 µl of Stop Solution to each tube and store at −20° C. Heat the reactions to ≧70° C. for 2–5 minutes immediately before loading on a sequencing gel. Load 2.5–3.0 µl of each reaction on the gel. Following electrophoresis of the sequencing gel, the gel is exposed to X-ray film to generate an autoradiograph.

If the extension products seen on the autoradiograph are too short, the ddNTP concentrations should be lowered and conversely if the extension products are all skewed to high molecular weight products, the ddNTP concentrations should be raised.

EXAMPLE 14

Fidelity of Tne DNA Polymerases

The fidelity of the Tne polymerases (full-length and modified forms) is measured using a PCR fidelity assay. This assay is based on the amplification, circularization, and transformation of the pUC19 derivative pLACIQ, which contains a functional lacI$^q$ allele [Frey and Suppmann, Biochemica 2:8 (1995)]. PCR-derived mutations in lacI result in a de-repression of the expression of lacZα and subsequent formation of a functional β-galactosidase enzyme, which can be easily detected on X-Gal indicator plates.

a) Construction of pLACIQ

The truncated lacI gene present in pUC19 is replaced by a functional copy of lacI$^q$. pUC19 (GibcoBRL) is digested with PvuII and AflIII and the 180 bp PvuII-AflIII fragment of pUC19 is replaced by a 1189 bp DNA fragment encoding lacI$^q$. The 1189 bp lacI$^q$ fragment is created by PCR amplification of residues 2972–4142 of pTrc 99 A (Pharmacia). The following primer pair is used in the PCR: 5'-CATGCCATGGCATGCATTTACGTTGACACCA3' (SEQ ID NO:48) and 5'-TCC CCCGGGTTGCGCTCACT-GCCCGCTTTCCAGT3' (SEQ ID NO:49). The oligonucleotide of SEQ ID NO:48 contains a NcoI recognition site and the oligonucleotide of SEQ ID NO:49 contains a SmaI recognition site. The PCR is performed using 18 cycles of denaturation at 94° C. for 30 sec; annealing at 57° C. for 30 sec and extension at 72° C. for 4 min. The PCR is performed using Pfu DNA polymerase (Stratagene) in the buffer recommended by the manufacturer. The PCR products are digested with NcoI and SmaI to generate a 1189 bp fragment having a blunt end (compatible with PvuII ends) and a 5' overhanging end compatible with the AflIII digested end of pUC19. The 1189 bp fragment is ligated into the digested pUC19 using standard techniques.

The ligation products are used to transform the α-complementing E. coli strain DH5α (GibcoBRL) and the desired plasmid, termed pLACIQ (3695 bp), is isolated using standard techniques. DH5α cells containing pLACIQ produce white (LAC1$^+$) colonies on LB plates containing ampicillin (100 µg/ml) and X-Gal (0.004% w/v).

b) The PCR Fidelity Assay

The template used in the PCR fidelity assay is prepared as follows. pLACIQ is linearized by digestion with Dra II. A typical PCR reaction contains 5 or 10 ng of linearized, gel-purified plasmid DNA.

The following primers are used in the PCR fidelity assay to amplify the lacI$^q$ sequences of pLACIQ; both PCR primers used have Cla I cleavage sites at their 5' ends: 5'-AGCTTATCGATGGCACTTTTCGGGGAAATGTGCG3' (SEQ ID NO:50) and 5'-AGCTT- ATCGATAAGCGATGC-CGGGAGCAGACAAGC3' (SEQ ID NO:51). The length of the resulting PCR product is 3,561 bp.

The PCRs which employ the Tne DNA polymerases or UlTma DNA polymerase are performed using the following buffer [10 mM Tris-HCl (pH 8.8 at 25° C.), 10 mM KCl, 0.002% Tween 20, 1.5 mM MgCl$_2$ and 40 µM all four dNTPs]. PCRs which employ nTaq DNA polymerase are performed using the following buffer [10 mM Tris-HCl (pH 9.0 at 25° C.), 50 mM KCl, 1.5 mM MgCl$_2$, 0.1% Triton X-100 and 140 µM all four dNTPs]. All reactions contain 5–10 ng of template, 20 pmol of each primer and 2.5 units of polymerase (all polymerases are assayed using the assay described in Example 5 to ensure the same amount of activity is used for each enzyme tested). The following cycling conditions are used: denaturation for 10 sec at 94° C.; annealing for 30 sec at 57° C. and extension for 4 min at 72° C. for 18 cycles.

Following the PCR, the amplification products are PEG-precipitated as follows. The PCR amplification mixtures are frozen at −20° C. and the mineral oil is removed by rinsing twice with cold chloroform. The mixtures are then thawed and 10 µg of glycogen and ½ volume of 30% PEG 3350/1.5 M NaCl is added. The mixture is allowed to stand for a minimum of 1 hr at 0–4° C. The mixture is then centrifuged in a microcentrifuge for 8 min and the supernatant is removed. The pellet is then rinsed with 75% ethanol and dried. The DNA is then digested with ClaI and the digested DNA is purified by gel electrophoresis. The purified DNA is then ligated to recircularize the plasmid in a reaction containing less than or equal to 30 ng DNA.

The resulting PCR-derived plasmids are transformed into competent *E. coli* DH5α and plated on LB Amp100 X-Gal plates [LB plates containing 100 µg/ml ampicillin and 0.004% X-Gal (w/v)]. After incubation overnight at 37° C., blue and white colonies are counted. The error rate (f) per bp is calculated using the rearranged equation published by Keohavong and Thilly [Proc. Natl. Acad. Sci. USA 86:9253 (1989): f=InF/dxb bp; where F is the fraction of white colonies: F=white (LACI$^+$)/total colony number; $2^d$ is the number of DNA duplications: $2^d$=output DNA/input DNA; and b is the effective target size of the (1080 bp) lacI gene, which is 349 bp according to Provost et al. [Mut. Research 288:133 (1993)]; there are 349 phenotypically identified (by color screening) single-based substitutions (nonsense and mis-sense) at 179 codons (approximately 50% of the coding region) within the lacI gene [Provost et al., supra]. Frame-shift errors, which may occur at every position in the 1080 bp open reading frame of lac, are not taken into account.

A religation control is prepared as follows. Fifty nano-grams of Dra II-linearized, gel-purified pLACIQ DNA is religated, and an aliquot of the ligation reaction is transformed into DH5α. After incubation overnight, the number of growing colonies (0.027%) showing a blue (LACI$^-$) phenotype on LB Amp X-Gal plates is measured to assess the rate of the formation of concatameric ligation products (with subsequent intramolecular recombination in *E. coli* that eliminates an additional origin of replication), which seems to be a very rare event. Restriction analysis of PCR-derived plasmids isolated from blue colonies is also performed to confirm that the LACI$^-$ phenotype originates in PCR-derived mutations of lacI, but not in deleterious recombination events after transformation of the ligated DNA in DH5α.

EXAMPLE 15

Generation of the Tne Quad Polymerase

In order to produce further modified forms of Tne DNA polymerase which could provide polymerases having improved characteristics for applications such as thermal cycle sequencing, PCR and long PCR, the following experiments were performed.

a) Construction of pD323,389A, F730Y pD323,389A, F730Y produces a modified form of the Tne DNA polymerase which lacks the first 283 amino acids from the N-terminus of the full-length protein and contains three amino acid substitutions at residues 323, 389 and 730. At amino acid residue 323, the wild-type aspartic acid residue is replaced with alanine; at amino acid residue 389, the wild-type aspartic acid residue is replaced with alanine and at amino acid residue 730, the wild-type phenylalanine residue is replaced with tyrosine.

pD323,389A, F730Y was created as follows. pD323, 389A (Example 4 g) was used in conjunction with a mutagenic oligonucleotide having the sequence: 5'-GGAA AGATGGTtAACTaCTCTATAATATACG3' (SEQ ID NO:52) and the Altered Sites® II in vitro Mutagenesis System (Promega) to generate pD323,389A, F730Y as described in Example 3. The mutagenic nucleotides are indicated by the lower case letters; the "t" residue changes only the nucleotide, but not the amino acid, sequence of the resulting polymerase (this change was made in order to introduce a diagnostic HpaI site).

The desired mutants were confirmed by restriction analysis (the addition of a HpaI site). This mutation was moved back into the pD323,389A, F730Y plasmid (which had not undergone the above mutagenesis) by substituting the 493 bp ClaI-SpeI fragment from the mutant (residues 1248 to 1740 of SEQ ID NO:53) into pD323,389A, F730Y. The DNA sequence of the 493 bp ClaI-SpeI fragment contained within pD323,389A, F730Y was determined to confirm that the desired mutations had been made. The DNA sequence of the polymerase coding region present in pD323,389A, F730Y is listed in SEQ ID NO:53. The corresponding amino acid sequence of the Tne M284(D323,389A, F730Y) protein is listed in SEQ ID NO:54. The Tne M284(D323,389A, F730Y) enzyme is referred to as the Tne Quad polymerase.

b) Expression and Purification of the Tne M284 (pD323,389A, F730Y) Polymerase i) Growth and Induction of *E. coli* Cells Containing the pD323,389A, F730Y Construct

*E. coli* strains containing the pD323,389A, F730Y construct were streaked onto LB plates containing 10 µg/ml tetracycline to isolate single colonies and the plates were grown overnight at 37° C. A single colony was resuspended in 1 liter of LB with 10 µg/ml of tetracycline and grown for 40 hours at 37° C. with shaking in a two liter Erlenmeyer flask. Two days later, 8 two liter flasks containing 1 liter of fresh LB with 10 µg/ml of tetracycline were each inoculated with 120 ml of this culture and grown for 2 hours at 37° C. with shaking. After the 2 hours growth, IPTG was added to 1 mM, and growth was continued for 3 hours at 37° C. Cells were harvested by centrifugation in a Beckman JA10 rotor 7K rpm for 7 minutes. The 8 liters yielded 19 grams of cell paste.

The Tne Quad polymerase was purified from 10 grams of cell paste prepared as described above. The cell paste was resuspended in 100 ml of an ice-cold solution containing 0.20 M NaCl in TEDGT buffer containing 2.5 mM PMSF. The resuspended cells were lysed by sonication using a Vibracell sonicator (Model VCX600; Sonics and Materials, Inc., Danbury, Conn.). The solution was kept ice-cold during sonication by placement of the beaker containing the cell suspension in a salted ice bath. Sonication was repeated seven times at 60% output for 1 minute with approximately a 2 minute rest between the 1 minute sonication bursts. The cell lysate was heat treated to denature the bulk of *E. coli* proteins by incubation of the lysate at 65° C. for 10 minutes; following heat treatment the lysate was placed on ice.

The following purification steps were performed at 4° C. The chilled lysate was centrifuged at 15,000 rpm for 15 minutes in a JA18 rotor (Beckman) to remove the heat-denatured proteins and other cell debris. The cleared supernatant was decanted and 1 ml was removed to determine the amount of polyethylenimine (PEI) to be added to precipitate the nucleic acids. The amount of PEI required to precipitate the nucleic acid was approximately 4% of the final volume.

Four milliliters of 5% PEI (w/v) was added to the supernatant to precipitate nucleic acid present in the remaining lysate. The lysate was centrifuged at 15,000 rpm for 15 minutes in a JA18 rotor (Beckman) to remove the precipitated nucleic acid. The supernatant was retrieved and solid ammonium sulfate was added to 60% saturation to precipitate the Tne Quad DNA polymerase. After dissolution of the ammonium sulfate, the sample was stirred for an additional 30 minutes and then was centrifuged at 15,000 rpm for 30 minutes in a JA18 (Beckman) rotor. The supernatant was discarded and the precipitated proteins were gathered and dissolved in 7.5 ml TEDGT buffer. The resolubilized protein was then placed in a dialysis membrane tubing having a 12,000 to 14,000 mw cutoff (Spectra, Houston, Tex.) and then dialyzed overnight against TEDGT buffer to remove the ammonium sulfate.

The dialyzed protein solution was then loaded onto a 15 ml Heparin Sepharose (Scientific Protein Laboratory) column (1.5 cm i.d.×9 cm height) which was equilibrated with TEDGT buffer (pH 7.4 at 25° C.) containing 0M NaCl. The dialyzate was then applied to the column. The column was then washed with 10 column volumes (150 ml) of TEDGT buffer (pH 7.4 at 25° C.) containing 0.05M NaCl. The polymerase activity was eluted using a 180 ml linear gradient of 0.05M NaCl to 0.75M NaCl in TEDGT buffer; the gradient was applied at a flow rate of approximately 1 ml/100 seconds. 2.7 ml fractions were assayed for DNA polymerase activity (as described in Example 5b) and those fractions containing polymerase activity were pooled. The fractions were also assayed for nicking activity (using a supercoiled DNA substrate), DNase activity and aliquots of the fractions were run on SDS-PAGE gels; however, pooling decisions were made based upon polymerase activity.

The Tne Quad polymerase eluted from the Heparin Sepharose column at a salt concentration of between 0.14 M and 0.28 M NaCl. The pooled fractions containing the polymerase activity were placed into dialysis membrane tubing (12,000 to 14,000 mw cutoff; Spectra, Houston, Tex.) and dialyzed against TEDGT buffer containing 0.0M NaCl until the salt concentration was less than or equal to 0.05 M NaCl as measured by conductivity using a conductance meter (Yellow Spring Instrument Co., Yellow Springs, Ohio).

The dialyzed polymerase fraction was then loaded (flow rate of 10 cm/hr) onto a 12 ml Affi-Gel blue (functional group: Cibacron blue F3GA; Bio-Rad, Hercules, Calif.) column (1 cm i.d.×12 cm height) which had been equilibrated with TEDGT buffer containing 0.0M NaCl. The Affi-Gel blue column was washed with 10 column volumes (120 ml) of TEDGT buffer containing 0.025 M NaCl. The DNA polymerase activity was eluted from the Affi-Gel blue column using a linear salt gradient (7 column volumes); the gradient started at 0.025 M NaCl and ended at 0.5 M NaCl (all in TEDGT) and was applied at a flow rate of 1 ml/100 seconds. Fractions (2.2 ml) were collected and assayed for DNA polymerase activity as described above (nicking activity DNase activity and SDS-PAGE analysis were also conducted).

The Tne Quad DNA polymerase eluted from the Affi-Gel blue column at a salt concentration of between 0.2 M and 0.35 M. The pooled fractions were placed in dialysis membrane (12,000 to 14,000 mw cutoff, Spectra, Houston, Tex.) and dialyzed against storage buffer [20 mM Tris-HCl (pH 8.0), 100 mM KCl, 0.1 mM EDTA, 1 mM DTT, 50% glycerol, 0.5% Nonidet-P40 and 0.5% Tween 20].

Aliquots of the purified Tne Quad polymerase (containing 5 to 50 units of activity) were electrophoresed on 4–20% Tris-glycine SDS PAGE gels (Novex, San Diego, Calif.) under denaturing, non-reducing conditions as described by the manufacturer. Following electrophoresis, the gels were stained with Coomassie blue. The purified polymerase was judged to be at least 95% pure based on visual inspection of the Coomassie-stained SDS PAGE gels.

The specific activity of the purified Tne Quad polymerase is determined using the assay described in Example 5. The absence of 3' to 5' exonuclease activity is confirmed using the assay described in Example 8c.

The purified Tne Quad polymerase preparation was examined for the presence of contaminating (i.e., nuclease activity not associated with the Tne polymerase itself) exonuclease and endonuclease activity. The following assays for nuclease activity were conducted.

Overdigest Assays

The absence of contaminating nucleases was demonstrated by incubating 1 µg of various DNAs with 0, 5, 10, 25, and 50 units of the purified Tne Quad polymerase for 21 hours at 70° C. in Toga buffer [10 mM Tris-HCl (pH 8.8 at 25° C.), 10 mM KCl, 0.002% Tween 20] including 10 mM $MgCl_2$. The total reaction volume was 50 µl and the reaction mixture was incubated under mineral oil (Sigma). Linear DNAs such as lambda DNA (Promega) or Phi X174 cut with HaeIII (Promega) were used to detect the presence of exonucleases and endonucleases. Circular DNAs such as pBR322 (Promega) were used detect endonucleases. Half (25 µl) of the samples were then run on a 2% agarose gel (a 1 to 2% agarose gel may be employed). Smearing of DNAs or conversion of covalently closed circular pBR322 to a nicked (relaxed or open circle conformation) or linear DNA indicates the presence of contaminating nucleases. A purified polymerase preparation is deemed free of contaminating nucleases if 5 units of the polymerase is incubated for 16 hours with any of the above DNAs and gives an normal sharp pattern on gel electrophoresis (i.e., there is no evidence of smearing or conversion of covalently closed plasmid DNA to relaxed or linear forms). No evidence of nuclease contamination was detected in the purified Tne Quad polymerase preparation.

Radioactive Nuclease Assay

The absence of contaminating nucleases was also demonstrated by incubating 2.5 to 50 units of the purified Tne Quad polymerase with 50 ng tritiated dsDNA (prepared as described below). Release of acid (5% TCA)-soluble radiolabeled nucleotides indicates the presence of a nuclease. The total volume of the reaction was 50 µl and Toga buffer including 10 m M $MgCl_2$ was employed. The reaction was incubated at 74° C. for 90 minutes under mineral oil (Sigma). Then 20 μl 1 mg/ml calf thymus DNA and 70 μl ice-cold 10% TCA was added to stop the reaction; the samples were then placed on ice for 10 minutes. The samples were spun in a microfuge at full speed for 10 minutes and 70 μl of the supernatant is removed. The amount of radiolabeled nucleotide in the supernatant was measured by scintillation counting (Beckman). A purified polymerase preparation is deemed free of contaminating nucleases if less than 3% of radiolabeled nucleotides are released. The purified Tne Quad polymerase showed 0% release of nucleotides, i.e., the level of released radiolabeled nucleotides was at or below background for the assay.

Preparation of $^3$H dsDNA Substrate

A 1000 bp double stranded DNA was generated using the PCR and $^3$H dTTP. The template used was pGEM-luc (Promega) and the primers were LME 41 (SEQ ID NO:42) and LME 44 (SEQ ID NO:57). The following components were added in order to 15 ml screw cap tube: 1991.2 μl nanopure water; 350 μl 10× Taq DNA pol buffer w/Mg (Promega); 3.5 μl 100 mM dATP; 3.5 μl 100 mM dGTP; 3.5 μl 100 mM dCTP; 3.3 μl 100 mM dTTP; 1 mCi $^3$H dTTP dried down and resuspended in 1 ml H$_2$O; 35 μl pGEM luc DNA at 10 ng/μl; 35 μl of each LME 41 and LME 44 (1 μg/μ); 40 μl Taq DNA polymerase (5U/μl; Promega). Aliquots (437.5 μl) were dispensed into 0.5 ml microfuge (or PCR) tubes and the tubes were placed into a thermal cycler (Perkin-Elmer) and the following program was run: Preheat—2 minutes 98° C.; followed by 25 cycles of denaturation for 1 minute, 97° C.; fast ramp to 64° C.; anneal for 2 minutes, 64° C.; fast ramp to 72° C.; extension for 2 minutes, 72° C. followed by an extension at 72° C. for 10 minutes and a 4° C. soak.

Following the thermal cycling, all reactions were pooled into a 15 ml tube. Unincorporated nucleotides and enzyme were then removed using standard techniques [i.e., precipitation with EtOH followed by chromatography over a NAP25 (Pharmacia) column]. The $^3$H dsDNA product was stored in TE buffer containing 50 mM NaCl.

c) Thermostability of the Tne Quad Polymerase

The thermostability of the purified Tne Quad polymerase was determined and compared with several thermostable DNA polymerases using the assay described in Example 8d. The following enzymes were compared to the Tne Quad polymerase in these studies: native Taq DNA polymerase (nTaq; Promega) and Sequencing Grade Taq DNA polymerase (sTaq; Promega). All enzymes were assayed using the DNA polymerase assay described in Example 5 so that equivalent amounts of polymerase activity were used in the thermostability assay. The results of the thermostability assays are summarized in Table 13 below.

TABLE 13

Thermostability Pf DNA Polymerases

| DNA Polymerase | Half-Life At 97.5° C. (min) |
| --- | --- |
| nTaq | 4.5 |
| sTaq | 21 |
| Tne Quad | 31 |

It is noted that half-life obtained for nTaq in this experiment was somewhat lower than that obtained in the experiment reported in Table 4 above (Ex. 8d). These two experiments were conducted using different lots of nTaq and the less than 2-fold difference observed in the half-life at 97.5° C. is presumed to be a result of lot to lot variation or minor experimental variations. The data obtained in these two experiments demonstrate that the Tne Quad polymerase is significantly more stable to heat than is nTaq.

The results shown in Table 13 demonstrate that the Tne Quad polymerase has a greatly enhanced thermostability relative to Taq DNA polymerase and represents a significant improvement in thermostability relative to sTaq. High thermostability is advantageous when the polymerase is to be used in thermal cycle sequencing reactions as less enzyme needs to added per reaction as less enzyme is denatured during incubation at the elevated temperatures used in the thermal cycle sequencing reaction.

d) The Tne Quad Polymerase Produces High PCR Product Yields

A comparison was made between the yield of PCR product obtained using a consistent amount of polymerase activity when the Tne Quad and nTaq enzymes were used in the PCR. Both enzymes were assayed using the DNA polymerase assay described in Example 5b so that the same number of units of enzyme were added to the PCRs. The PCRs were conducted as described in Example 9c using pGEM-luc as the template and the LME41/LME45 and LME41/LME43 primer pairs. The LME41/LME45 primer pair amplifies a 500 bp target on the template; the LME41/LME43 primer pair amplifies a 1.5 kb target on the template.

Each reaction was run in duplicate. The PCR products were resolved by electrophoresis through 1% agarose gels, followed by staining with EtBr and quantitation as described in Example 9c. The results (average of the duplicates) obtained for amplification of the 500 bp target were Tne Quad polymerase: 100% and nTaq polymerase: 59%. The results (average of the duplicates) obtained for amplification of the 1.5 kb target were Tne Quad polymerase: 92% and nTaq polymerase: 100%. The enzyme which gave the highest yield was assigned a value of 100% and all other values are expressed as a percentage of the maximal yield.

These results demonstrate the Tne Quad enzyme performed better than nTaq when the 500 bp target was used (about 2 fold more product) and produced essentially the same amount of product as did nTaq when the 1.5 kb target was used.

The above results demonstrate that the Tne Quad polymerase has improved characteristics relative to a number of other thermostable DNA polymerases, including a high degree of thermostability and the ability to produce high PCR product yields. As described in the examples below, the Tne Quad polymerase provides an improved enzyme for use in DNA sequencing protocols.

EXAMPLE 16

The Tne Quad Polymerase Provides a Superior Enzyme for Thermal Cycle Sequencing

To examine the usefulness of the Tne Quad polymerase in thermal cycle sequencing reactions, the following experiments were conducted.

a) Optimization of Nucleotide Mixtures of Thermal Cycle Sequencing Using the Tne Quad Mutant As described in Examples 10 and 11, the Tne M284 (D323A, D389A) polymerase, from which the Tne Quad polymerase was derived, had a higher affinity for dideoxynucleotides (ddNTPs) than does sTaq. The effect of the additional mutation introduced to generate the Tne Quad polymerase upon the affinity of the polymerase for ddNTPs was examined and the affinity of the Tne Quad polymerase for ddNTPs was compared with that of sTaq.

Various concentrations of dideoxy- and deoxynucleotides, including a modified dNTP, were tested in thermal cycle sequencing reactions to ascertain the optimal concentration for these reagents. The optimized Tne Quad polymerase dNTP/ddNTP mixes are detailed in Table 14 below. The values reported in Table 14 represent 3× mixtures; these mixtures are diluted 3-fold in the final reaction mixture as described below. To obtain the final concentration of dNTPs and ddNTPs in the reactions, the values in Table 14 are divided by 3. Thermal cycle sequencing reactions were carried as described in Example 11 with the exception that the polymerases tested were sTaq and the Tne Quad polymerase.

TABLE 14

Optimized Nucleotide Mix Formulation For Tne Quad Polymerase

| Component | G Nucleotide Mix | A Nucleotide Mix | T Nucleotide Mix | C Nucleotide Mix |
| --- | --- | --- | --- | --- |
| ddGTP | 0.3 µM | — | — | — |
| ddATP | — | 0.2 µM | — | — |
| ddTTP | — | — | 0.25 µM | — |
| ddCTP | — | — | — | 0.25 µM |
| 7-deaza dGTP | 20 µM | 20 µM | 20 µM | 20 µM |
| dATP | 20 µM | 20 µM | 20 µM | 20 µM |
| dTTP | 20 µM | 20 µM | 20 µM | 20 µM |
| dCTP | 20 µM | 20 µM | 20 µM | 20 µM |

In comparison, the optimal concentrations of dideoxynucleotides and deoxynucleotides when sTaq is used in thermal cycle sequencing reactions is listed in Table 15 (Table 15 lists the 3× mixes).

TABLE 15

Optimized Nucleotide Mix Formulation for sTaq Polymerase

| Component | G Nucleotide Mix | A Nucleotide Mix | T Nucleotide Mix | C Nucleotide Mix |
| --- | --- | --- | --- | --- |
| ddGTP | 30 µM | — | — | — |
| ddATP | — | 350 µM | — | — |
| ddTTP | — | — | 600 µM | — |
| ddCTP | — | — | — | 200 µM |
| 7-deaza dGTP | 20 µM | 20 µM | 20 µM | 20 µM |
| dATP | 20 µM | 20 µM | 20 µM | 20 µM |
| dTTP | 20 µM | 20 µM | 20 µM | 20 µM |
| dCTP | 20 µM | 20 µM | 20 µM | 20 µM |

A comparison between Table 14 and Table 15 shows that the Tne Quad polymerase has a 100 to 2400-fold greater affinity for ddNTPs than does sTaq. A higher affinity for ddNTPS is advantageous as smaller amounts of expensive ddNTPs are required in sequencing reactions when the Tne Quad polymerase is employed.

b) Preferred Radioactive Sequencing Protocol Using the Tne Quad Polymerase

The preferred radioactive sequencing protocol uses a thermal cycling format. The sequencing reactions may be carried out using either an end-labeled primer or direct incorporation of a labeled dNTP. The sequencing reactions are conducted as described in Example 12 with the exception that 1 µl of an enzyme mixture containing 15 parts Tne Quad polymerase [i.e., Tne M284(D323A, D389A, F730Y)] at 10 U/µl and 1 part Tth pyrophosphatase (described below) at 0.037 to 0.65 U/µl is added in place of the Tne M284 (D323A, D389A) polymerase and the d/ddNTP mixture (3× mixture) used is that shown in Table 14.

c) Preferred Fluorescent Sequencing Protocol Using the Tne Quad Polymerase

When using the Tne Quad polymerase, the preferred fluorescent radioactive sequencing protocol uses a thermal cycling format. In addition, a thermostable inorganic pyrophosphatase ($PP_i$ase) is included in the reaction mixture to eliminate pyrophosphate which accumulates during the sequencing reaction. The accumulation of pyrophosphate, which is a by-product of DNA synthesis, leads to pyrophosphorolysis (i.e., the reversal of polymerization). The use of pyrophosphatase, including thermostable pyrophosphatase, has been reported to be advantageous in DNA sequencing reactions [PCT International Publication WO 90/12111; PCT International Publication WO 94/05797 and U.S. Pat. No. 5,498,523, the disclosure of which is hereby incorporated by reference].

i) Fluorescent Sequencing Protocol

Four primers, each bearing a different fluorescent dye are utilized. Primers bearing the following dyes are frequently employed in fluorescent sequencing protocols: Tamara, Joe, Rox and Fam (available from AB/PE). When sequencing templates which contain the binding site for the -21M13 primer [e.g., pGEM-3Zf(+) (Promega)] the following -21M13 dye primers may be employed: G-Tamra-21 primer, A-Joe-21 primer, T-Rox-21 primer and C-Fam-21 primer (AB/PE). The d/ddNTP mixtures (3× mixtures) shown in Table 16 are used.

TABLE 16

Nucleotide Mix Formulation For Tne Quad Polymerase In Fluorescent Sequencing Reactions

| Component | G Nucleotide Mix | A Nucleotide Mix | T Nucleotide Mix | C Nucleotide Mix |
| --- | --- | --- | --- | --- |
| ddGTP | 0.3 µM | — | — | — |
| ddATP | — | 0.1 µM | — | — |
| ddTTP | — | — | 0.2 µM | — |
| ddCTP | — | — | — | 0.2 µM |
| 7-deaza dGTP | 40 µM | 40 µM | 40 µM | 40 µM |
| dATP | 40 µM | 40 µM | 40 µM | 40 µM |
| dTTP | 40 µM | 40 µM | 40 µM | 40 µM |
| dCTP | 40 µM | 40 µM | 40 µM | 40 µM |

The following reaction components are used. An enzyme mixture containing 9 µl of Tne Quad polymerase (10 U/µl) and 1 µl of Tth pyrophosphatase (0.037 to 0.65 U/µl) (purified as described below). A 5× buffer containing 250 mM Tris-HCl (pH 9.0 at 25° C.), 10 mM $MgCl_2$. Tracking dye which is a mixture of deionized formamide (5 volumes) and 25 mM EDTA containing 50 mg/ml Blue Dextran (1 volume). The template [e.g., pGEM-3Zf(+)] is brought to 200 ng/µl.

The extension/termination reactions are carried out as follows. For each set of sequencing reactions, label four 0.5 ml microcentrifuge tubes (G, A, T, C). The reactions are assembled as shown in Table 17.

TABLE 17

Reaction Setup

|  | G | A | T | C |
|---|---|---|---|---|
| Primer (0.4 pmole/μl) | 2 μl | 1 μl | 2 μl | 1 μl |
| Template (200 ng/μl) | 2 μl | 1 μl | 2 μl | 1 μl |
| 5X Buffer | 2 μl | 1 μl | 2 μl | 1 μl |
| d/ddNTP Mix | 4 μl | 2 μl | 4 μl | 2 μl |
| Enzyme Mix | 2 μl | 1 μl | 2 μl | 1 μl |

The reactions may be assembled on ice or at room temperature. The reaction components may be added in any order with the exception that the enzyme mix is added last Following assembly, one drop (approximately 20 μl) of mineral oil is added to each tube and the tubes are briefly spin in a microcentrifuge. The reaction tubes are placed in a thermal cycler that has been preheated to 95° C. and fifteen cycles comprising 95° C. for 30 sec; 55° C. for 30 sec; 70° C. for 60 sec are carried out followed by fifteen cycles comprising 95° C. for 30 sec; 70° C. for 60 sec followed by a 4° C. soak. Following the thermal cycling reaction, the reactions (G, A, T and C) are combined and 100 μl 95% EtOH is added. The tube is then centrifuged in a microfuge for 15 minutes at 16,000×g. The pellet is washed with 250 μl 70% EtOH and then dried in a vacuum desiccator for 5 minutes. The DNA is then resuspended in 6 μl of tracking dye and the mixture is heated to 70° for 2 minutes immediately before loading 1.5 to 6.0 μl/lane on a sequencing gel. Any suitable fluorescent DNA sequencer (e.g., ABI Model 373 or 377 Series DNA Sequencer) may be used to collect the data.

ii) Purification of Tth Pyrophosphatase

*Thermus thermophilus* 111 (Dr. T. Oshima, Tokyo Institute of Technology, Tokyo, Japan) and grown in anaerobic culture in medium containing (per liter): 3.0 g yeast extract, 3.0 g casein peptone, 5.0 g disodium succinic acid, 0.5 g calcium succinic acid, 0.7 g $NaNO_3$, 0.1 g $KNO_3$, 0.1 g $MgSO_4$, 0.1 g $CaCl_2$, and 1 ml trace elements [per liter: 2.9 g $H_3BO_3$, 1.8 g $MnCl_2.4H_2O$; 0.25 g $ZnSO_4.7H_2O$; 0.1 g $CuSO_4.5H_2O$, 0.1 g $CoCl_2.6H_2O$; and 0.4 g $Na_2MoO_4.2H_2O$]. For growth on solid medium, agar (Difco) was added to 1.5 g per 100 ml of the above medium.

Frozen seed vials of *Thermus thermophilus* 111 were removed from −70° C. and thawed at room temperature. The seeds were transferred to 5 flasks, each containing 1 liter of the above medium in a 2 liter Erlenmeyer flask. The flasks were placed in a New Brunswick incubator shaker 25D at 200 rpm for 20 hours. The cultures were then combined and used to inoculate a 450 liter fermenter. The cells were grown in a fermentation vessel (CHEMAP, Ltd, Männedorf, Switzerland) maintained at 70° C. Aeration was 2 standard cubic feet per minute and agitation was arbitrarily set at 4. The cells were grown for approximately 18 hours (early stationary). The fermenter contents were cooled to 20° C. and cells recovered by centrifugation using by two Sharples AS-16 tubular bowl centrifuges in parallel. The 2.5 kg cell pellet was frozen at −70° C. until used (alternatively, the cell pellet may be used without prior freezing). All of the subsequent operations were carried out at 0 to 8° C. unless otherwise stated.

Approximately 2 kg of frozen *Thermus thermophilus* 111 cells were resuspended in 4 volumes of TEDG [50 mM Tris-HCl (pH 7.3 at 25° C.), 1 mM EDTA, 1 mM DTT, 10% glycerol] containing 0.35M NaCl and 1 mM PMSF (from 144 mM stock in DMF). The thawed and resuspended cells were lysed using a Homogenizer (APV Gaulin 15MR-8TBA) at 9,000 psi. Cells were passed through the Homogenizer 3 to 5 times and the $A_{660}$ was monitored to determine the efficiency of cell breakage. A decrease in the $A_{660}$ of >60% indicated acceptable cell lysis.

PEI [35 μl/ml of a 5% (w/v) stock] was added to the lysate to precipitate the nucleic acids. The lysate was centrifuged at 9,000 rpm at 4° C. for 1 hour in a Beckman JA10 rotor (14,300×g) to remove the precipitated nucleic acids and cell debris. The supernatant was decanted and to it solid ammonium sulfate was added to 55% saturation. After the salt was completely dissolved, the sample was centrifuged at 9,000 rpm for 1 hour in a Beckman JA10 rotor (14,3000×g). The supernatant was discarded and the precipitate was gathered and dissolved in 250 ml (TEDG+0.05 M NaCl) buffer. The resolubilized pellet was then dialyzed (12,000 mw cutoff; Spectra) against 60 volumes of TEDG buffer containing 0.05M NaCl to remove the ammonium sulfate. The buffer was changed twice.

The dialyzate was then loaded onto a BioRex 70 (Bio-Rad) column (2.5×45 cm; 221 ml bed volume) equilibrated with TEDG pH 7.4 buffer containing 0.05M NaCl. The column was washed with 1 liter of TEDG buffer containing 0.05M NaCl. The inorganic pyrophosphatase was eluted from the column with TEDG buffer containing 0.25M NaCl (0.6 liter) was applied and 20 ml fractions were collected. Pyrophosphatase activity was measured using the following assay.

The inorganic pyrophosphatase assay measures the production of inorganic phosphate. The assay conditions are 50 mM Tris-HCl (pH 8.8), 50 mM NaCl, 1 mM $MgCl_2$, and 1 to 2 mM pyrophosphate (substrate) in a total reaction volume of 50 μl at 74° C. for 5 minutes. After incubation, the reactions are stopped with 450 μl of 0.01 M HCl, and 100 μl of Acid Molybdate (Sigma) solution and 25 μl Fiske & Subbarow Reducer (Sigma) [1.0 g in 6.3 ml deionized water], mixed at room temperature for 10 minutes, and absorbance measured at 660 nm. The amount of phosphate produced is measured by comparing the results to that of a standard curve of reactions containing known amounts of phosphate and pyrophosphate. One unit of pyrophosphatase activity is defined as that producing 1 μmole of inorganic phosphate per minute at 74° C.

Fractions containing pyrophosphatase activity were pooled and dialyzed against 60 volumes of 20 mM Tris-HCl (pH 8.5) at 4° C. The sample was then loaded onto a DEAE-Sepharose (Pharmacia) column (2.5×26 cm; 128 ml bed volume) which was equilibrated with 20 mM Tris-HCl (pH 8.5). The DEAE-Sepharose column was then washed with 500 ml of 20 mM Tris-HCl (pH 8.5). A 500 ml linear salt gradient was run over the column to elute the pyrophosphatase activity starting at 0M KCl and ending at 0.3M KCl (all in 20 mM Tris-HCl, pH 8.5). Fractions (11 ml) were collected and assayed for pyrophosphatase activity. Fractions containing the pyrophosphatase activity were pooled (~110 ml), placed in dialysis membrane (12,000 MW cutoff; Spectra) and dialyzed against 20 mM Tris-HCl (pH 7.5) containing 1.36M ammonium sulfate.

The pooled pyrophosphatase fraction was then loaded onto a 88 ml Butyl-Toyopearl (Tosohaas) column (2.5 cm i.d.×18 cm height). The column was washed with 300 ml 20 mM Tris-HCl (pH 7.5) containing 1.36M ammonium sulfate. A 400 ml linear salt gradient was applied to elute the pyrophosphatase starting at 1.36M ammonium sulfate and ending at 0M ammonium sulfate (all in 20 mM Tris-HCl, pH 7.5). Fractions (8.3 ml) were collected and assayed for pyrophosphatase activity. The Tth pyrophosphatase eluted between 0.5 M and 0.35 M ammonium sulfate. Fractions containing the pyrophosphatase activity were pooled (~34 ml), placed in dialysis membrane (12,000 mw cutoff, Spectra) and dialyzed against storage buffer [20 mM Tris-HCl (pH 7.5), 50% glycerol] and stored at −20° C.

The purity and approximate molecular weight of the pyrophosphatase was assessed by SDS-PAGE gel electrophoresis using a 4–20% gradient Tris-Glycine SDS gel (Novex, San Diego, Calif.). An aliquot of the purified material was mixed with sample buffer [63 mM Tris-HCl pH 6.8, 10% glycerol, 2% SDS, 0.0025% Bromphenol Blue] and the gel was run using the following running buffer [25 mM Tris-Base, 192 mM glycine, 0.1% SDS, pH 8.3]. The gel was run for 90 minutes at 125 V DC until the bromphenol blue band reached the bottom of the gel; the gel was then stained with Coomassie blue. The apparent monomer molecular weight of the Tth pyrophosphatase was approximately 24 kD and the pyrophosphatase represented greater than 95% of the protein visible on the gel.

Using the activity assay described above, the number of units of pyrophosphatase per microliter was established (0.65 units/$\mu$l). By visually assessing the quantity of Tth pyrophosphatase on the Coomassie stained SDS-PAGE gel compared to the protein standards run in the molecular weight marker lane, the specific activity of the pyrophosphatase preparation was estimated to be approximately 1760 units/mg.

EXAMPLE 17

Fidelity of Tne DNA Polymerases Alone and in Combination with Tli DNA Polymerase The fidelity of the Tne polymerases (full-length and modified forms) was measured using a PCR fidelity assay similar to the assay described in Example 14; other thermostable DNA polymerases were run in the fidelity assay to permit a comparison between the Tne polymerases and other polymerases. In addition the fidelity of the Tne M284 polymerase was compared using Tne M284 polymerase alone and in combination with various amounts of the *Thermococcus litoralis* (Tli) DNA polymerase. The Tli polymerase has a strong 3' exonuclease or "proof-reading" activity while the Tne M284 polymerase has reduced levels of 3' exonuclease activity (about 28% that of the wild-type Tne polymerase level).

The fidelity assay is based on the amplification, circularization, and transformation of the pUC19 derivative pFIDO2 (described below) which contains a functional lacI allele and a kanamycin resistance gene (Kan$^r$) [Frey and Suppmann, Biochemica 2:8 (1995)]. PCR-derived mutations in lacI result in a de-repression of the expression of lacZ$\alpha$ and subsequent formation of a functional β-galactosidase enzyme, which can be easily detected on X-Gal indicator plates. pFIDO2 differs from pLACIQ (used in Example 14) in that pFIDO2 contains the lacI gene and contains the Kan$^r$ gene.

pFIDO2 was constructed by combining the ampicillin resistance gene and the origin of replication from pTrc99A (a pUCI 8-based plasmid available from Pharmacia P-L Biochemicals), the lacZ$\alpha$ peptide gene from M13mp2 (T. Kunkel, NIEHS, Research Triangle, North Carolina), and the lacI gene and the Kan$^r$ gene from pREP4 (Qiagen). The construction was performed as follows: the 807 bp VspI fragment of M13mp2 carrying the lacZ$\alpha$ peptide gene was ligated into the unique NdeI site of pTrc99A to yield the plasmid pFIDO. The 3454 bp NsiI-HindIII fragment of pFIDO was ligated to the 2700 bp NsiI-HindIII fragment of pREP4 containing the lacI gene and Kan$^r$ to yield pFIDO2.

The template used in the PCR fidelity assay was prepared as follows. pFIDO2 was digested with DraI and the 3875 bp fragment containing the lacI gene and the KanR gene was isolated on an agarose gel. This destroys the ability of templates made from pFIDO2 to circularize and replicate the lacI gene as digestion with DraI and subsequent gel purification removes the origin of replication. PCR reactions contained 4.3 ng of linearized, gel-purified pFIDO2 DNA.

The following primers were used in the PCR fidelity assay to amplify a 1802 bp region of pFIDO2 containing the lacI sequences and the carboxy terminus portion of the KanR gene. The 5' primer contains a NcoI site at the 5' end and the 3' primer contains a NsiI site at the 5' end: 5' primer: 5'-GTGACCCATGGCGATGCCTG-3' (SEQ ID NO:55) and 3' primer: 5'-GGCGAAGCGGCATGCATTTA3' (SEQ ID NO:56). The results of the fidelity assays are summarized in Tables 18–21. The following abbreviation is used in Table 18–21: Duplns (Duplications).

The results shown in Table 18 were generated using the following PCR conditions: for UlTma (Perkin-Elmer) and all variants of Tne M284, the buffer was 10 mM Tris-HCl (pH 9.0 at 25° C.), 10 mM KCl, 0.002% Tween 20; for nTaq, Tli (Promega), and rTne, the buffer was 10 mM Tris-HCl (pH 9.0 at 25° C.), 50 mM KCl, 0.1% Triton X-100; all reactions contained 1.5 mM MgCl$_2$ and 200 $\mu$M all four dNTPs; 4.3 ng of template; 100 pmol of each primer and 2 to 3 units of each polymerase with the exception of the full length rTne DNA polymerase which was used at 0.3 units/100 $\mu$l reaction (all polymerases were assayed using the assay described in Example 5 to ensure the same amount of activity is used for each enzyme tested). The following cycling conditions are used: 96° C. for 1 minute followed by 20 cycles of denaturation for 10 sec at 94° C.; annealing for 30 sec at 67° C. and extension for 2 min at 72° C.

TABLE 18

| Polymerase | Trial | DNA Duplns (d) | White Colonies LacI+ | Total Number Of Colonies | % LacI- | Error Rate (× 10$^{-6}$) | Average Error Rate (× 10$^{-6}$) | Standard Deviation (× 10$^{-6}$) |
|---|---|---|---|---|---|---|---|---|
| Taq | 1 | 11.7 | 822 | 1162 | 29 | 85 | 90 | 4 |
|  | 2 | 11.5 | 709 | 989 | 28 | 83 |  |  |
|  | 3 | 11.5 | 576 | 832 | 31 | 92 |  |  |
| Tli | 1 | 12.0 | 2762 | 2785 | 0.8 | 2.0 | 2 | 0.2 |
|  | 2 | 12.1 | 1948 | 1963 | 0.8 | 1.8 |  |  |
|  | 3 | 12.0 | 2364 | 2379 | 0.6 | 1.5 |  |  |
| UlTma | 1 | 10.4 | 654 | 881 | 26 | 82 | 90 | 4 |
|  | 2 | 10.3 | 522 | 723 | 28 | 91 |  |  |
|  | 3 | 10.4 | 560 | 778 | 2& | 90 |  |  |

TABLE 18-continued

| Polymerase | Trial | DNA Duplns (d) | White Colonies LacI+ | Total Number Of Colonies | % LacI- | Error Rate (× 10$^{-6}$) | Average Error Rate (× 10$^{-6}$) | Standard Deviation (× 10$^{-6}$) |
|---|---|---|---|---|---|---|---|---|
| rTne | 1 | 9.6 | 1164 | 1394 | 16 | 54 | 50 | 0.7 |
|  | 2 | 7.2 | 1005 | 1148 | 12 | 53 |  |  |
| Tne M284 | 1 | 11.9 | 396 | 672 | 41 | 130 | 100 | 7 |
|  | 2 | 12.0 | 630 | 1089 | 42 | 130 |  |  |
|  | 3 | 11.3 | 293 | 516 | 43 | 140 |  |  |
| Tne M284 D323E | 1 | 12.1 | 529 | 871 | 61 | 220 | 200 | 10 |
|  | 2 | 12.0 | 497 | 827 | 60 | 220 |  |  |
|  | 3 | 11.9 | 603 | 929 | 65 | 250 |  |  |
| Tne M284 E325D | 1 | 12.1 | 875 | 1382 | 63 | 240 | 200 | 10 |
|  | 2 | 12.1 | 393 | 679 | 58 | 210 |  |  |
|  | 3 | 12.1 | 721 | 1205 | 60 | 220 |  |  |
| Tne M284 Y464F | 1 | 11.7 | 102 | 198 | 52 | 180 | 200 | 20 |
|  | 2 | 11.5 | 471 | 787 | 60 | 230 |  |  |
|  | 3 | 11.6 | 855 | 1466 | 58 | 220 |  |  |
| Tne M284 D468N | 1 | 12.0 | 1075 | 1699 | 63 | 240 | 200 | 8 |
|  | 2 | 12.0 | 451 | 745 | 61 | 220 |  |  |
| Tne M284 D323A, D389A | 1 | 11.3 | 691 | 1096 | 63 | 250 | 200 | 20 |
|  | 2 | 11.4 | 538 | 850 | 63 | 250 |  |  |
|  | 3 | 11.9 | 560 | 938 | 60 | 220 |  |  |

TABLE 19

| Polymerase | Trial | DNA Duplns (d) | White Colonies LacI+ | Total Number Of Colonies | % LacI- | Error Rate (× 10$^{-6}$) |
|---|---|---|---|---|---|---|
| nTaq | 1 | 8.8 | 1345 | 1459 | 8 | 26 |
|  | 2 | 9.3 | 1125 | 1338 | 16 | 54 |
|  | 3 | 8.7 | 1147 | 1256 | 9 | 30 |
|  | 4 | 9.2 | 908 | 1066 | 15 | 50 |

TABLE 20

| Polymerase | Trial | DNA Duplns (d) | White Colonies LacI+ | Total Number Of Colonies | % LacI- | Error Rate (× 10$^{-6}$) |
|---|---|---|---|---|---|---|
| Tne M284 | 1 | 6.7 | 470 | 523 | 10 | 46 |
| Blend 1:100 | 2 | 6.8 | 61 | 62 | 2 | 68 |
| Blend 12100 | 3 | 6.8 | 61 | 66 | 8 | 33 |
| Blend 1::500 | 4 | 6.8 | 1312 | 1504 | 13 | 58 |

TABLE 21

| Polymerase | Trail | Blue Colonies LacI- | White Colonies LacI+ | Total Number Of Colonies | % LacI- | Error Rate (× 10$^{-6}$) | Average Error Rate (× 10$^{-6}$) | Standard Deviation (× 10$^{-6}$) |
|---|---|---|---|---|---|---|---|---|
| Taq | 1 | 350 | 1314 | 1664 | 21 | 59 | 60 | 2 |
|  | 2 | 438 | 1519 | 1957 | 22 | 62 |  |  |
|  | 3 | 402 | 1443 | 1845 | 22 | 61 |  |  |
| Tne Quad | 1 | 854 | 944 | 1798 | 47 | 170 | 200 | 2 |
|  | 2 | 587 | 658 | 1245 | 47 | 160 |  |  |
|  | 3 | 513 | 562 | 1075 | 48 | 170 |  |  |

The results shown in Table 19 were generated using four different PCR conditions: buffer [10 mM Tris-HCl (pH 9.0 at 25° C.), 50 mM KCl, 1.0 or 1.5 mM MgCl$_2$ (see below), 0.1% Triton X-100 and 50 µM all four dNTPs]; 4.3 ng of template; 100 pmol of each primer and 2.5 units of nTaq DNA polymerase. Thermal cycling was conducted in each case by first heating the reaction at 94° C. for 20 sec. followed by 18 cycles of 94° C. for 10 sec; 67° C. for 30 sec and an extension step at either 68° C. or 72° C. for 2 min. Condition I comprised the use of 1.0 mM MgCl$_2$ and a 68° C. extension step. Condition 2 comprised the use of 1.5 mM MgCl$_2$ and a 68° C. extension step. Condition 3 comprised the use of 1.0 mM MgCl$_2$ and a 72° C. extension step. Condition 4 comprised the use of 1.5 mM MgCl$_2$ and a 72° C. extension step. The results shown in Table 19 demonstrate that the fidelity assay employed in this example gives results for the fidelity of Taq DNA polymerase which are consistent with published values [Tindall and Kunkel (1988) Biochem. 27:6008].

Blends comprising mixtures of Tne M284 DNA polymerase with Tli DNA polymerase were also assayed for replication fidelity during PCR. These results are shown in Table 20. The Tli DNA polymerase has a very active 3' to 5' exonuclease and provides very high fidelity, whereas the Tne M284 DNA polymerase showed fidelity lower than nTaq due to the uncoupling of the proofreading function. This is also displayed in the lower 3' exonuclease activity of Tne M284 compared to rTne (see Example 8cii and Table 3).

By combining small amounts of the high fidelity Tli DNA polymerase and Tne M284 DNA polymerase, the fidelity of the overall reaction was greatly improved (relative to reactions containing only Tne M284). The results shown in Table 20 were generated using the following PCR conditions: buffer [10 mM Tris-HCl (pH 9.0), 10 mM KCl, 0.002% Tween-20], 1.0 mM $MgCl_2$, 50 μM dNTPs, 4.3 ng template DNA, 100 pmol of each primer and 2.5 units of M284 DNA polymerase. The PCRs also contained 0, 0.25, 0.125, or 0.05 units of Tli DNA polymerase. The cycling conditions were denaturation at 94° C. for 20 seconds followed by 18 cycles of 94° C. for 10 seconds, 67° C. for 30 seconds, and 72° C. for 1 minute.

The fidelity of Tne Quad polymerase was compared to nTaq DNA polymerase (Table 21). The following buffers were used: for Tne Quad polymerase, the buffer was 10 mM Tris-HCl (pH 9.0 at 25° C.), 10 mM KCl, 0.002% Tween 20; for nTaq, the buffer was 10 mM Tris-HCl (pH 9.0 at 25° C.), 50 mM KCl, 0.1% Triton X-100; all reactions contained 1.5 mM $MgCl_2$ and 200 μM all four dNTPs; 4.3 ng of template; 100 pmol of each primer and 2.5 units of polymerase. The cycling conditions were denaturation at 94° C. for 20 seconds followed by 20 cycles of 94° C. for 10 seconds, 67° C. for 30 seconds, and 72° C. for 2 minutes.

Following the PCR, 1/10 of each reaction was run on an agarose gel and the 1802 bp amplifer was quantitated by staining with ethidium bromide and measuring the fluorescence with a fluoroimager (Molecular Dynamics). The amplifer was then excised from the gel and purified using the Wizard PCR Preps DNA Purification Resin (Promega) according to the manufacturer's instructions. The purified DNA was then digested with NcoI and NsiI. The resulting 1776 bp NcoI-NsiI fragment was purified using the Wizard PCR Preps DNA Purification Resin (Promega). The purified DNA was then ligated into the gel-purified 4343 bp ori-containing vector backbone of pFIDO2 digested NcoI and NsiI.

The resulting PCR-derived plasmids were transformed into competent *E. coli* DH5α and plated on LB Kan X-Gal plates [LB plates containing 50 μg/ml kanamycin and 0.004% X-Gal (w/v)]. After incubation overnight at 37° C., blue and white colonies were counted. The error rate (f) per bp was calculated as described in Example 14. As a control to measure background levels of colonies, the gel-purified 4343 bp ori-containing vector backbone of pFIDO2 digested with NcoI and NsiI was ligated and used to transform competent DHα and plated on LB Kan X-Gal plates; no colonies were detected.

The above results demonstrate that a reduction in 3' exonuclease activity results in a lowered fidelity for the modified Tne polymerases (Table 18). The use of these lower fidelity Tne polymerases is advantageous when mutagenic PCR is to be performed. Mutagenic PCR is a technique well known to the art in which primers containing the mutation(s) to be introduced are employed in the PCR; these primers therefore contain mismatches relative to the sequence of the complementary target DNA [see for example, Tao and Lee in PCR Technology: Current Innovations (1994), Griffin and Griffin, Eds., CRC Press, Boca Raton, Fla., pp. 69–83].

The above results show that the addition of a small amount of the high fidelity Tli DNA polymerase to the Tne M284 DNA, a modified Tne polymerase which has reduced levels of 3' exonuclease activity, greatly improves the fidelity of the overall reaction. In addition, the above results shown that the unmodified rTne polymerase has a higher level of fidelity than does either the nTaq or UlTma® DNA polymerase.

EXAMPLE 18

Tne DNA Polymerases may be Used to Amplify Long Amplifers in the PCR

The PCR amplification of DNA targets longer than a few kilobases is difficult using Taq DNA polymerase (and derivatives such as Klentaq1, AmpliTaq) or other enzymes lacking significant 3' exonuclease activity. It is thought that the inability of these polymerases to amplify long targets is due, at least in part, to the accumulation of mismatched 3' ends during the PCR [Barnes (1994) Proc. Natl. Acad. Sci. USA 91:2216, PCT WO/9426,766 and U.S. Pat. No. 5,436, 149 the disclsoure of which is herein incorporated by reference]. The presence of mismatched 3' ends results in inefficient primer extension. The mismatched 3' ends which accumulate in long PCRs can be removed by polymerases which have 3' exonuclease or "proof-reading" activity. Because polymerases having 3' exonuclease activity can also degrade the oligonucleotide primers used in the PCR, a blend of a low fidelity enzyme (such as Taq DNA polymerase which lacks 3' exonuclease activity) and a high fidelity enzyme such as Pfu or Tli DNA polymerases is used in long PCRs. The final reaction mixture should contain just enough 3' exonuclease activity to remove mismatched 3' ends but not so much 3' exonuclease activity that excessive degradation of the primers occurs.

In this experiment, Tne DNA polymerases which have been modified to reduce 3' exonuclease activity are used in combination with a high fidelity thermostable DNA polymerase, Tli DNA polymerase, in PCRs in which long targets are to be amplified.

The optimal ratio of Tne polymerase to Tli polymerase is determined as follows. A blend comprising a modified Tne polymerase (e.g., Tne M284 or any other 3' exonuclease reduced Tne polymerase) as the majority component and a high fidelity thermostable DNA polymerase [e.g., Tli polymerase (Promega)] is generated. The ratio of the modified Tne polymerase to the high fidelity polymerase varies between 5:1 (e.g., Tne M284:Tli) to 2000:1.

The total amount of polymerase activity present in the reaction mixture may vary between 1.25 U to 100 U per 10 to 100 μl reaction. The concentration of primers can vary between 0.1 to 1.0 μM and the number of template molecules present may vary between 1 and 100,000 molecules per reaction.

The reaction conditions are optimized to allow high fidelity long amplifer polymerization; that is sufficient proof-reading activity is present to permit high fidelity amplification of the target but this activity does not significantly degrade the primers prior to extension. The reaction conditions include a buffer capable of buffering the reaction at a pH of 8.0 to 9.5 (e.g., 10 to 50 mM tricine, Tris-HCl or Tris-Acetate, salts (e.g., 5 to 100 mM NaCl, KCl or K-Acetate), a source of magnesium ions (e.g., $MgCl_2$, Mg-Acetate or $MgSO_4$) at a concentration of 1 to 5mM, a source of ammonium ions [e.g., $NH_4Cl$, $NH_4C_2H_3O_2$, $(NH_4)_2SO_4$] at a concentration of 1 to 30 mM and all four dNTPs (100 to 500 μM). The reaction mixture may also contain cosolvents (1 to 5% final concentration) including, but not limited to water excluders such as formamide, DMSO, glycerol, dextran, polyethylene glycol or sugars (e.g., glucose, sucrose, fructose, sorbitol, hexoses and pentoses) and/or stabilizers such as BSA, DNA binding proteins, gelatin, or detergents.

Cycling parameters are optimized for each template/primer pair combination to 1) allow for the shortest denaturation time and lowest denaturation temperature, 2) provide the optimal accurate annealing time and annealing temperature, and 3) provide the optimal extension time and temperature.

Using the above considerations, a 4 Kb or 1.3 Kb target within the β-globin gene was amplified from human genomic DNA using a blend of Tne M284(Y464F) polymerase and Tli polymerase. For amplification of the 4 Kb target, a ratio of 250:1 (Tne:Tli) was used; for amplification of the 1.3 Kb target, a ratio of 75:1 was used.

The reactions were performed as follows. In a 50 μl final reaction volume, the following components were assembled: human genomic DNA ($1\times10^5$ molecules for the 4 Kb target and $1\times10^3$ molecules for the 1.3 Kb target); 5U of Tne:Tli blended in a 250:1 ratio for the 4 Kb target and a 75:1 ratio for the 1.3 Kb target; 10 mM Tricine pH 9.0; 10 mM KCl; 0.01% Tween 20; 1.5mM $MgCl_2$; 200 μM each of all 4 dNTPs; and 1 μM each primer (primer pairs which specifically amplify either a 4 or 1.3 Kb human beta globin gene sequence were employed). For amplification of the 4 Kb target, the thermal cycling conditions comprised: heating at 96° C. for 2 min prior to the addition of the enzymes (i.e., a hot start was conducted) followed by 35 cycles of 95° C. for 30 sec, 60° C. for 30 sec, 68° C. for 5 min followed by a 10 min incubation 72° C. followed by a 4° C. soak overnight. For amplification of the 1.3 Kb target, the thermal cycling conditions comprised: heating at 96° C. for 2 min prior to the addition of the enzymes (i.e., a hot start was conducted) followed by 35 cycles of 95° C. for 30 sec, 60° C. for 30 sec, 68° C. for 1 min followed by a 5 min incubation at 72° C. followed by a 4° C. soak overnight.

Following the thermal cycling, an aliquot of each of the reaction mixtures (10–20 μl for the 4 Kb target and 5 μl for the 1.3 Kb target) was electrophoresed on a 1.4% agarose, 1× TAE, 0.5 μg/ml EtBr gel. The gel was analyzed by UV transillumination and also by laser scan and revealed the presence of both 4 Kb and 1.3 Kb products.

These results demonstrate that a modified Tne polymerase lacking 5' exonuclease activity and having reduced 3' exonuclease activity (e.g., Tne M284 polymerase) can be used in conjunction with a high fidelity polymerase (e.g., Tli DNA polymerase) for the amplification of long PCR targets.

From the above, it is clear that the enzymes of the present invention provide thermostable DNA polymerase having novel features. In particular, these enzymes provide superior polymerases for use in DNA sequencing applications.

Other modifications of the embodiments of the invention described above that are obvious to those of ordinary skill in the areas of molecular biology, biochemistry and related disciplines are intended to be within the scope of the accompanying claims.

What is claimed is:

1. A purified full-length thermostable DNA polymerase capable of DNA synthetic activity, said polymerase derived from the eubacterium *Thermotoga neapolitana*, wherein said polymerase comprises an amino acid sequence selected from the group consisting of SEQ ID NOS:2, 8, 16, 19, 23, 26, 29, 33, 35 and 54.

2. The polymerase of claim 1, wherein said polymerase is a naturally-occurring polymerase.

3. The polymerase of claim 1, wherein said polymerase is a non-naturally-occurring polymerase.

4. A purified thermostable non-naturally occurring DNA polymerase derived from the eubacterium *Thermotoga neapolitana* comprising a portion of the amino acid sequence of SEQ ID NO:2, said polymerase being capable of DNA synthetic activity.

5. The polymerase of claim 4, wherein said polymerase lacks significant 5' exonuclease activity.

6. The polymerase of claim 4, wherein said polymerase has reduced 3' exonuclease activity.

7. The polymerase of claim 4, wherein said polymerase lacks significant 5' exonuclease activity and has reduced 3' exonuclease activity.

8. The polymerase of claim 4, wherein said polymerase lacks significant 5' exonuclease and 3' exonuclease activity.

9. The polymerase of claim 4, wherein said polymerase has an increased affinity for a dideoxynucleotide compared to naturally-occurring DNA polymerase derived from the eubacterium *Thermotoga neapolitana*.

10. The polymerase of claim 9 having the amino acid sequence of SEQ ID NO:54.

11. The polymerase of claim 4 wherein said polymerase has an increased affinity for a dideoxynucleotide compared to sequencing grade *Thermus aquaticus* DNA polymerase.

12. The polymerase of claim 13, wherein said polymerase comprises SEQ ID NO:54.

13. An oligonucleotide comprising the nucleic acid sequence of SEQ ID NO:53, said nucleotide sequence encoding a thermostable DNA polymerase.

14. A recombinant DNA vector comprising the oligonucleotide of claim 13.

15. A method for determining the nucleotide base sequence of a DNA molecule comprising the steps of:
  a) providing in any order:
    i) a reaction vessel;
    ii) at least one deoxynucleoside triphosphate;
    iii) a thermostable DNA polymerase derived from the eubacterium *Thermotoga neapolitana*, wherein said polymerase comprises an amino acid sequence selected from the group consisting of SEQ ID NOS:2, 8, 16, 19, 23, 26, 29, 33, 35 and 54;
    iv) at least one DNA synthesis terminating agent which terminates DNA synthesis at a specific nucleotide base;
    v) a first DNA molecule; and
    vi) a primer capable of hybridizing to said first DNA molecule;
  b) adding, in any order, said deoxynucleoside triphosphate, said DNA polymerase, said DNA synthesis terminating agent, said first DNA molecule and said primer to said reaction vessel to form a reaction mixture, under conditions such that said primer hybridizes to said DNA molecule and said DNA polymerase is capable of conducting primer extension to produce a population of DNA molecules complementary to said first DNA molecule; and c) determining at least a part of the nucleotide base sequence of said first DNA molecule.

16. The method of claim 15 wherein said polymerase is a naturally-occurring DNA polymerase.

17. The method of claim 15 wherein said polymerase is a non-naturally-occurring DNA polymerase.

18. The method of claim 15, wherein said conditions comprise heating said mixture.

19. The method of claim 18, wherein said method further comprises cooling said mixture to a temperature at which said thermostable DNA polymerase can conduct primer extension.

20. The method of claim 19 further comprising repeating said heating and said cooling one or more times.

21. The method of claim 15 wherein said reaction mixture comprises 7-deaza dGTP, dATP, dTTP and dCTP.

22. The method of claim 15 wherein said DNA synthesis terminating agent is a dideoxynucleoside triphosphate.

23. The method of claim 22 wherein said dideoxynucleoside triphosphate is selected from the group consisting of ddGTP, ddATP, ddTTP and ddCTP.

24. The method of claim 15 wherein said primer molecule is labelled.

25. The method of claim 24 wherein said primer is labelled with $^{32}P$, $^{35}S$ or a fluorescent molecule.

26. The method of claim 15 wherein one deoxynucleoside triphosphate is labelled.

27. The method of claim 26 wherein said deoxynucleoside triphosphate is labelled with $^{32}P$, $^{32}P$, $^{35}S$ or a fluorescent molecule.

28. The method of claim 15 further comprising, adding at step b), a thermostable pyrophosphatase.

29. The method of claim 28 wherein said thermostable pyrophosphatase is derived from *Thermus thermophilus*.

30. A kit for determining the nucleotide base sequence of a DNA molecule comprising:

a) a thermostable DNA polymerase derived from the eubacterium *Thermotoga neapolitana*, wherein said polymerase comprises an amino acid sequence selected from the group consisting of SEQ ID NOS:2, 8, 16, 19, 23, 26, 29, 33, 35 and 54; and b) at least one nucleotide mixture comprising deoxynucleoside triphosphates and one dideoxynucleoside triphosphate.

31. The kit of claim 30, wherein said polymerase is a non-naturally occurring DNA polymerase.

32. The kit of claim 31, wherein said polymerase lacks significant 5' exonuclease activity.

33. The kit of claim 31, wherein said polymerase has reduced 3' exonuclease activity.

34. The kit of claim 31, wherein said polymerase lacks significant 5' exonuclease activity and has reduced 3' exonuclease activity.

35. The kit of claim 31, wherein said polymerase lacks significant 5' exonuclease activity and 3' exonuclease activity.

36. The kit of claim 30, wherein said kit contains a first nucleotide mixture, a second nucleotide mixture, a third nucleotide mixture, and a fourth nucleotide mixture, said first nucleotide mixture comprising ddGTP, 7-deaza dGTP, dATP, dTTP and dCTP, said second nucleotide mixture comprising ddATP, 7-deaza dGTP, dATP, dTTP and dCTP, said third nucleotide mixture comprising ddTTP, 7-deaza dGTP, dATP, dTTP and dCTP and said fourth nucleotide mixture ddCTP, 7-deaza dGTP, dATP, dTTP and dCTP.

37. The kit of claim 30 further comprising a thermostable pyrophosphatase.

38. The kit of claim 37 wherein said thermostable pyrophosphatase is derived from *Thermus thermophilus*.

39. A method for amplifying a double stranded DNA molecule, comprising the steps of:

a) providing:

i) a first DNA molecule comprising a first strand and a second strand, said first and second strands being complementary to one another;

ii) a first primer and a second primer, wherein said first primer is complementary to said first DNA strand and said second primer is complementary to said second DNA strand; and iii) a first thermostable DNA polymerase derived from the eubacterium *Thermotoga neapolitana*, wherein said polymerase comprises an amino acid sequence selected from the group consisting of SEQ ID NOS:2, 8 16, 19, 23, 26, 29, 33, 35 and 54; and b) mixing said first DNA molecule, said first primer, said second primer and said polymerase to form a reaction mixture under conditions such that a second DNA molecule comprising a third strand and a fourth strand are synthesized, said third strand having a region complementary to said first strand and said fourth strand having a region complementary to said second strand.

40. The method of claim 39 wherein said conditions comprise heating said mixture.

41. The method of claim 40 further comprising cooling said mixture to a temperature at which said thermostable DNA polymerase can conduct primer extension.

42. The method of claim 41 further comprising repeating said heating and said cooling one or more times.

43. The method of claim 39 wherein said polymerase lacks significant 5' exonuclease activity.

44. The method of claim 39, wherein said polymerase has reduced 3' exonuclease activity.

45. The method of claim 39, wherein said polymerase lacks significant 5' exonuclease activity and has reduced 3' exonuclease activity.

46. The method of claim 39, wherein said polymerase lacks significant 5' exonuclease activity and 3' exonuclease activity.

47. The method of claim 37 further comprising providing a second thermostable DNA polymerase, said second polymerase comprising a high fidelity polymerase.

48. The method of claim 47, wherein said second polymerase is derived from a thermostable organism selected from the group consisting of *Pyrococcus furiosus, Pyrococcus woesii* and *Thermococcus litoralis*.

* * * * *

SEQUENCE LISTING (1) GENERAL INFORMATION:

(iii) NUMBER OF SEQUENCES: 57

(2) INFORMATION FOR SEQ ID NO:1:

(i) SEQUENCE CHARACTERISTICS:
        (A) LENGTH: 2682 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..2679

(xi) SEQUENCE DESCRIPTION: SEQ ID NO:1:

```
ATG GCG AGA CTA TTT CTC TTT GAT GGC ACA GCC CTG GCC TAC AGG GCA        48
Met Ala Arg Leu Phe Leu Phe Asp Gly Thr Ala Leu Ala Tyr Arg Ala
 1               5                  10                  15

TAT TAC GCC CTC GAC AGA TCC CTT TCC ACA TCC ACA GGA ATT CCA ACG        96
Tyr Tyr Ala Leu Asp Arg Ser Leu Ser Thr Ser Thr Gly Ile Pro Thr
                20                  25                  30

AAC GCC GTC TAT GGC GTT GCC AGG ATG CTC GTT AAA TTC ATA AAG GAA       144
Asn Ala Val Tyr Gly Val Ala Arg Met Leu Val Lys Phe Ile Lys Glu
            35                  40                  45

CAC ATT ATA CCC GAA AAG GAC TAC GCG GCT GTG GCC TTC GAC AAG AAG       192
His Ile Ile Pro Glu Lys Asp Tyr Ala Ala Val Ala Phe Asp Lys Lys
        50                  55                  60

GCA GCG ACG TTC AGA CAC AAA CTG CTC GAA GCG TAC AAG GCG CAA AGG       240
```

-continued

```
Ala Ala Thr Phe Arg His Lys Leu Leu Glu Ala Tyr Lys Ala Gln Arg
 65                  70                  75                  80

CCA AAG ACG CCG GAT CTT CTA GTT CAG CAG CTA CCT TAC ATC AAG CGG      288
Pro Lys Thr Pro Asp Leu Leu Val Gln Gln Leu Pro Tyr Ile Lys Arg
                 85                  90                  95

CTG ATA GAA GCT CTT GGT TTC AAA GTG CTG GAG CTG GAA GGA TAC GAA      336
Leu Ile Glu Ala Leu Gly Phe Lys Val Leu Glu Leu Glu Gly Tyr Glu
            100                 105                 110

GCA GAC GAT ATC ATC GCC ACG CTT GCA GTC AAG GGC TGC ACG TTT TTT      384
Ala Asp Asp Ile Ile Ala Thr Leu Ala Val Lys Gly Cys Thr Phe Phe
                115                 120                 125

GAT GAG ATT TTC ATA ATA ACC GGT GAC AAG GAT ATG CTT CAA CTT GTA      432
Asp Glu Ile Phe Ile Ile Thr Gly Asp Lys Asp Met Leu Gln Leu Val
130                 135                 140

AAC GAG AAG ATA AAG GTC TGG AGA ATC GTC AAG GGG ATA TCG GAT CTT      480
Asn Glu Lys Ile Lys Val Trp Arg Ile Val Lys Gly Ile Ser Asp Leu
145                 150                 155                 160

GAG CTT TAC GAT TCG AAA AAG GTG AAA GAA AGA TAC GGT GTG GAA CCA      528
Glu Leu Tyr Asp Ser Lys Lys Val Lys Glu Arg Tyr Gly Val Glu Pro
                165                 170                 175

CAT CAG ATA CCG GAT CTT CTA GCA CTG ACG GGA GAC GAG ATA GAC AAC      576
His Gln Ile Pro Asp Leu Leu Ala Leu Thr Gly Asp Glu Ile Asp Asn
                180                 185                 190

ATT CCC GGT GTA ACG GGA ATA GGT GAA AAG ACC GCT GTA CAG CTT CTC      624
Ile Pro Gly Val Thr Gly Ile Gly Glu Lys Thr Ala Val Gln Leu Leu
            195                 200                 205

GGC AAG TAC AGA AAT CTT GAA GAC ATT CTG GAG CAT GCC CGT GAA CTC      672
Gly Lys Tyr Arg Asn Leu Glu Asp Ile Leu Glu His Ala Arg Glu Leu
        210                 215                 220

CCC CAG AGA GTG AGA AAG GCT CTC TTG AGA GAC AGG GAA GTT GCC ATC      720
Pro Gln Arg Val Arg Lys Ala Leu Leu Arg Asp Arg Glu Val Ala Ile
225                 230                 235                 240

CTC AGT AAA AAA CTT GCA ACT CTG GTG ACG AAC GCA CCT GTT GAA GTG      768
Leu Ser Lys Lys Leu Ala Thr Leu Val Thr Asn Ala Pro Val Glu Val
                245                 250                 255

GAC TGG GAA GAG ATG AAA TAC AGA GGA TAC GAC AAG AGA AAA CTA CTT      816
Asp Trp Glu Glu Met Lys Tyr Arg Gly Tyr Asp Lys Arg Lys Leu Leu
            260                 265                 270

CCG ATA TTG AAA GAA CTG GAG TTT GCT TCC ATC ATG AAG GAA CTT CAA      864
Pro Ile Leu Lys Glu Leu Glu Phe Ala Ser Ile Met Lys Glu Leu Gln
        275                 280                 285

CTG TAC GAA GAA GCA GAA CCC ACC GGA TAC GAA ATC GTG AAG GAT CAT      912
Leu Tyr Glu Glu Ala Glu Pro Thr Gly Tyr Glu Ile Val Lys Asp His
    290                 295                 300

AAG ACC TTC GAA GAT CTC ATC GAA AAG CTG AAG GAG GTT CCA TCT TTT      960
Lys Thr Phe Glu Asp Leu Ile Glu Lys Leu Lys Glu Val Pro Ser Phe
305                 310                 315                 320

GCC CTG GAC CTT GAA ACG TCC TCC CTT GAC CCG TTC AAC TGT GAG ATA     1008
Ala Leu Asp Leu Glu Thr Ser Ser Leu Asp Pro Phe Asn Cys Glu Ile
                325                 330                 335

GTC GGC ATC TCC GTG TCG TTC AAA CCG AAA ACA GCT TAT TAC ATT CCA     1056
Val Gly Ile Ser Val Ser Phe Lys Pro Lys Thr Ala Tyr Tyr Ile Pro
            340                 345                 350

CTT CAT CAC AGA AAC GCC CAG AAT CTT GAT GAA ACA CTG GTG CTG TCG     1104
Leu His His Arg Asn Ala Gln Asn Leu Asp Glu Thr Leu Val Leu Ser
        355                 360                 365

AAG TTG AAA GAG ATC CTC GAA GAC CCG TCT TCG AAG ATT GTG GGT CAG     1152
Lys Leu Lys Glu Ile Leu Glu Asp Pro Ser Ser Lys Ile Val Gly Gln
    370                 375                 380
```

-continued

```
AAC CTG AAG TAC GAC TAC AAG GTT CTT ATG GTA AAG GGT ATA TCG CCA        1200
Asn Leu Lys Tyr Asp Tyr Lys Val Leu Met Val Lys Gly Ile Ser Pro
385                 390                 395                 400

GTT TAT CCG CAT TTT GAC ACG ATG ATA GCT GCA TAT TTG CTG GAG CCA        1248
Val Tyr Pro His Phe Asp Thr Met Ile Ala Ala Tyr Leu Leu Glu Pro
                405                 410                 415

AAC GAG AAA AAA TTC AAT CTC GAA GAT CTG TCT TTG AAA TTT CTC GGA        1296
Asn Glu Lys Lys Phe Asn Leu Glu Asp Leu Ser Leu Lys Phe Leu Gly
            420                 425                 430

TAC AAA ATG ACG TCT TAT CAG GAA CTG ATG TCG TTT TCC TCA CCA CTT        1344
Tyr Lys Met Thr Ser Tyr Gln Glu Leu Met Ser Phe Ser Ser Pro Leu
        435                 440                 445

TTT GGT TTC AGC TTT GCG GAT GTT CCG GTA GAC AAG GCT GCG AAC TAC        1392
Phe Gly Phe Ser Phe Ala Asp Val Pro Val Asp Lys Ala Ala Asn Tyr
    450                 455                 460

TCC TGC GAG GAT GCA GAC ATC ACT TAT AGG CTC TAC AAG ATA CTC AGC        1440
Ser Cys Glu Asp Ala Asp Ile Thr Tyr Arg Leu Tyr Lys Ile Leu Ser
465                 470                 475                 480

ATG AAG CTC CAT GAA GCG GAA CTT GAG AAC GTC TTC TAC AGG ATA GAG        1488
Met Lys Leu His Glu Ala Glu Leu Glu Asn Val Phe Tyr Arg Ile Glu
                485                 490                 495

ATG CCG CTT GTG AAC GTT CTT GCA CGC ATG GAA TTG AAC GGG GTG TAT        1536
Met Pro Leu Val Asn Val Leu Ala Arg Met Glu Leu Asn Gly Val Tyr
                500                 505                 510

GTG GAC ACA GAA TTC CTG AAA AAG CTC TCG GAG GAG TAC GGC AAA AAG        1584
Val Asp Thr Glu Phe Leu Lys Lys Leu Ser Glu Glu Tyr Gly Lys Lys
            515                 520                 525

CTC GAG GAA CTG GCC GAA AAA ATC TAC CAG ATA GCA GGA GAG CCC TTC        1632
Leu Glu Glu Leu Ala Glu Lys Ile Tyr Gln Ile Ala Gly Glu Pro Phe
530                 535                 540

AAC ATC AAT TCT CCA AAA CAG GTT TCA AAG ATC CTT TTT GAG AAG CTG        1680
Asn Ile Asn Ser Pro Lys Gln Val Ser Lys Ile Leu Phe Glu Lys Leu
545                 550                 555                 560

GGA ATA AAA CCC CGT GGA AAA ACG ACA AAA ACA GGA GCG TAC TCT ACC        1728
Gly Ile Lys Pro Arg Gly Lys Thr Thr Lys Thr Gly Ala Tyr Ser Thr
                565                 570                 575

AGG ATA GAG GTG TTG GAA GAG ATA GCG AAT GAG CAC GAG ATA GTA CCC        1776
Arg Ile Glu Val Leu Glu Glu Ile Ala Asn Glu His Glu Ile Val Pro
                580                 585                 590

CTC ATT CTC GAG TAC AGA AAG ATC CAG AAA CTG AAA TCG ACC TAC ATA        1824
Leu Ile Leu Glu Tyr Arg Lys Ile Gln Lys Leu Lys Ser Thr Tyr Ile
            595                 600                 605

GAC ACC CTT CCG AAA CTT GTG AAC CCG AAA ACC GGA AGA ATT CAT GCA        1872
Asp Thr Leu Pro Lys Leu Val Asn Pro Lys Thr Gly Arg Ile His Ala
610                 615                 620

TCT TTC CAC CAG ACG GGT ACC GCC ACT GGC AGG TTG AGT AGC AGT GAT        1920
Ser Phe His Gln Thr Gly Thr Ala Thr Gly Arg Leu Ser Ser Ser Asp
625                 630                 635                 640

CCA AAT CTT CAG AAT CTT CCG ACA AAG AGC GAA GAG GGA AAA GAA ATT        1968
Pro Asn Leu Gln Asn Leu Pro Thr Lys Ser Glu Glu Gly Lys Glu Ile
                645                 650                 655

AGA AAA GCG ATT GTG CCC CAG GAT CCA GAC TGG TGG ATC GTC AGT GCG        2016
Arg Lys Ala Ile Val Pro Gln Asp Pro Asp Trp Trp Ile Val Ser Ala
                660                 665                 670

GAT TAT TCC CAA ATA GAA CTC AGA ATC CTC GCT CAT CTC AGT GGT GAT        2064
Asp Tyr Ser Gln Ile Glu Leu Arg Ile Leu Ala His Leu Ser Gly Asp
            675                 680                 685

GAG AAC CTT GTG AAG GCC TTC GAG GAG GGC ATC GAT GTG CAC ACC TTG        2112
Glu Asn Leu Val Lys Ala Phe Glu Glu Gly Ile Asp Val His Thr Leu
        690                 695                 700
```

```
ACT GCC TCC AGG ATC TAC AAC GTA AAG CCA GAA GAA GTG AAC GAA GAA      2160
Thr Ala Ser Arg Ile Tyr Asn Val Lys Pro Glu Glu Val Asn Glu Glu
705                 710                 715                 720

ATG CGA CGG GTT GGA AAG ATG GTG AAC TTC TCT ATA ATA TAC GGT GTC      2208
Met Arg Arg Val Gly Lys Met Val Asn Phe Ser Ile Ile Tyr Gly Val
                725                 730                 735

ACA CCG TAC GGT CTT TCT GTG AGA CTT GGA ATA CCG GTT AAA GAA GCA      2256
Thr Pro Tyr Gly Leu Ser Val Arg Leu Gly Ile Pro Val Lys Glu Ala
            740                 745                 750

GAA AAG ATG ATT ATC AGC TAT TTC ACA CTG TAT CCA AAG GTG CGA AGC      2304
Glu Lys Met Ile Ile Ser Tyr Phe Thr Leu Tyr Pro Lys Val Arg Ser
        755                 760                 765

TAC ATC CAG CAG GTT GTT GCA GAG GCA AAA GAG AAG GGC TAC GTC AGG      2352
Tyr Ile Gln Gln Val Val Ala Glu Ala Lys Glu Lys Gly Tyr Val Arg
    770                 775                 780

ACT CTC TTT GGA AGA AAA AGA GAT ATT CCC CAG CTC ATG GCA AGG GAC      2400
Thr Leu Phe Gly Arg Lys Arg Asp Ile Pro Gln Leu Met Ala Arg Asp
785                 790                 795                 800

AAG AAC ACC CAG TCC GAA GGC GAA AGA ATC GCA ATA AAC ACC CCC ATT      2448
Lys Asn Thr Gln Ser Glu Gly Glu Arg Ile Ala Ile Asn Thr Pro Ile
                805                 810                 815

CAG GGA ACG GCG GCA GAT ATA ATA AAA TTG GCT ATG ATA GAT ATA GAC      2496
Gln Gly Thr Ala Ala Asp Ile Ile Lys Leu Ala Met Ile Asp Ile Asp
            820                 825                 830

GAG GAG CTG AGA AAA AGA AAC ATG AAA TCC AGA ATG ATC ATT CAG GTT      2544
Glu Glu Leu Arg Lys Arg Asn Met Lys Ser Arg Met Ile Ile Gln Val
        835                 840                 845

CAT GAC GAA CTG GTC TTC GAG GTT CCC GAT GAG GAA AAA GAA GAA CTA      2592
His Asp Glu Leu Val Phe Glu Val Pro Asp Glu Glu Lys Glu Glu Leu
    850                 855                 860

GTT GAT CTG GTG AAG AAC AAA ATG ACA AAT GTG GTG AAA CTC TCT GTG      2640
Val Asp Leu Val Lys Asn Lys Met Thr Asn Val Val Lys Leu Ser Val
865                 870                 875                 880

CCT CTT GAG GTT GAC ATA AGC ATC GGA AAA AGC TGG TCT TGA              2682
Pro Leu Glu Val Asp Ile Ser Ile Gly Lys Ser Trp Ser
                885                 890

(2) INFORMATION FOR SEQ ID NO:2:

(i) SEQUENCE CHARACTERISTICS:
        (A) LENGTH: 893 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Arg Leu Phe Leu Phe Asp Gly Thr Ala Leu Ala Tyr Arg Ala
 1               5                  10                  15

Tyr Tyr Ala Leu Asp Arg Ser Leu Ser Thr Ser Thr Gly Ile Pro Thr
                20                  25                  30

Asn Ala Val Tyr Gly Val Ala Arg Met Leu Val Lys Phe Ile Lys Glu
            35                  40                  45

His Ile Ile Pro Glu Lys Asp Tyr Ala Ala Val Ala Phe Asp Lys Lys
        50                  55                  60

Ala Ala Thr Phe Arg His Lys Leu Leu Glu Ala Tyr Lys Ala Gln Arg
65                  70                  75                  80

Pro Lys Thr Pro Asp Leu Leu Val Gln Gln Leu Pro Tyr Ile Lys Arg
                85                  90                  95
```

-continued

```
Leu Ile Glu Ala Leu Gly Phe Lys Val Leu Glu Leu Glu Gly Tyr Glu
            100                 105                 110

Ala Asp Asp Ile Ile Ala Thr Leu Ala Val Lys Gly Cys Thr Phe Phe
            115                 120                 125

Asp Glu Ile Phe Ile Ile Thr Gly Asp Lys Asp Met Leu Gln Leu Val
            130                 135                 140

Asn Glu Lys Ile Lys Val Trp Arg Ile Val Lys Gly Ile Ser Asp Leu
145                 150                 155                 160

Glu Leu Tyr Asp Ser Lys Lys Val Lys Glu Arg Tyr Gly Val Glu Pro
                165                 170                 175

His Gln Ile Pro Asp Leu Leu Ala Leu Thr Gly Asp Glu Ile Asp Asn
            180                 185                 190

Ile Pro Gly Val Thr Gly Ile Gly Glu Lys Thr Ala Val Gln Leu Leu
            195                 200                 205

Gly Lys Tyr Arg Asn Leu Glu Asp Ile Leu Glu His Ala Arg Glu Leu
            210                 215                 220

Pro Gln Arg Val Arg Lys Ala Leu Leu Arg Asp Arg Glu Val Ala Ile
225                 230                 235                 240

Leu Ser Lys Lys Leu Ala Thr Leu Val Thr Asn Ala Pro Val Glu Val
                245                 250                 255

Asp Trp Glu Glu Met Lys Tyr Arg Gly Tyr Asp Lys Arg Lys Leu Leu
            260                 265                 270

Pro Ile Leu Lys Glu Leu Glu Phe Ala Ser Ile Met Lys Glu Leu Gln
            275                 280                 285

Leu Tyr Glu Glu Ala Glu Pro Thr Gly Tyr Glu Ile Val Lys Asp His
            290                 295                 300

Lys Thr Phe Glu Asp Leu Ile Glu Lys Leu Lys Glu Val Pro Ser Phe
305                 310                 315                 320

Ala Leu Asp Leu Glu Thr Ser Ser Leu Asp Pro Phe Asn Cys Glu Ile
                325                 330                 335

Val Gly Ile Ser Val Ser Phe Lys Pro Lys Thr Ala Tyr Tyr Ile Pro
            340                 345                 350

Leu His His Arg Asn Ala Gln Asn Leu Asp Glu Thr Leu Val Leu Ser
            355                 360                 365

Lys Leu Lys Glu Ile Leu Glu Asp Pro Ser Ser Lys Ile Val Gly Gln
            370                 375                 380

Asn Leu Lys Tyr Asp Tyr Lys Val Leu Met Val Lys Gly Ile Ser Pro
385                 390                 395                 400

Val Tyr Pro His Phe Asp Thr Met Ile Ala Ala Tyr Leu Leu Glu Pro
                405                 410                 415

Asn Glu Lys Lys Phe Asn Leu Glu Asp Leu Ser Leu Lys Phe Leu Gly
            420                 425                 430

Tyr Lys Met Thr Ser Tyr Gln Glu Leu Met Ser Phe Ser Ser Pro Leu
            435                 440                 445

Phe Gly Phe Ser Phe Ala Asp Val Pro Val Asp Lys Ala Ala Asn Tyr
            450                 455                 460

Ser Cys Glu Asp Ala Asp Ile Thr Tyr Arg Leu Tyr Lys Ile Leu Ser
465                 470                 475                 480

Met Lys Leu His Glu Ala Glu Leu Glu Asn Val Phe Tyr Arg Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
```

```
                515                 520                 525
Leu Glu Glu Leu Ala Glu Lys Ile Tyr Gln Ile Ala Gly Glu Pro Phe
        530                 535                 540
Asn Ile Asn Ser Pro Lys Gln Val Ser Lys Ile Leu Phe Glu Lys Leu
545                 550                 555                 560
Gly Ile Lys Pro Arg Gly Lys Thr Thr Lys Thr Gly Ala Tyr Ser Thr
                565                 570                 575
Arg Ile Glu Val Leu Glu Glu Ile Ala Asn Glu His Glu Ile Val Pro
        580                 585                 590
Leu Ile Leu Glu Tyr Arg Lys Ile Gln Lys Leu Lys Ser Thr Tyr Ile
        595                 600                 605
Asp Thr Leu Pro Lys Leu Val Asn Pro Lys Thr Gly Arg Ile His Ala
        610                 615                 620
Ser Phe His Gln Thr Gly Thr Ala Thr Gly Arg Leu Ser Ser Ser Asp
625                 630                 635                 640
Pro Asn Leu Gln Asn Leu Pro Thr Lys Ser Glu Gly Lys Glu Ile
                645                 650                 655
Arg Lys Ala Ile Val Pro Gln Asp Pro Asp Trp Trp Ile Val Ser Ala
                660                 665                 670
Asp Tyr Ser Gln Ile Glu Leu Arg Ile Leu Ala His Leu Ser Gly Asp
                675                 680                 685
Glu Asn Leu Val Lys Ala Phe Glu Glu Gly Ile Asp Val His Thr Leu
    690                 695                 700
Thr Ala Ser Arg Ile Tyr Asn Val Lys Pro Glu Val Asn Glu Glu
705                 710                 715                 720
Met Arg Arg Val Gly Lys Met Val Asn Phe Ser Ile Ile Tyr Gly Val
                725                 730                 735
Thr Pro Tyr Gly Leu Ser Val Arg Leu Gly Ile Pro Val Lys Glu Ala
                740                 745                 750
Glu Lys Met Ile Ile Ser Tyr Phe Thr Leu Tyr Pro Lys Val Arg Ser
                755                 760                 765
Tyr Ile Gln Gln Val Val Ala Glu Ala Lys Glu Lys Gly Tyr Val Arg
        770                 775                 780
Thr Leu Phe Gly Arg Lys Arg Asp Ile Pro Gln Leu Met Ala Arg Asp
785                 790                 795                 800
Lys Asn Thr Gln Ser Glu Gly Glu Arg Ile Ala Ile Asn Thr Pro Ile
                805                 810                 815
Gln Gly Thr Ala Ala Asp Ile Ile Lys Leu Ala Met Ile Asp Ile Asp
                820                 825                 830
Glu Glu Leu Arg Lys Arg Asn Met Lys Ser Arg Met Ile Ile Gln Val
        835                 840                 845
His Asp Glu Leu Val Phe Glu Val Pro Asp Glu Glu Lys Glu Glu Leu
        850                 855                 860
Val Asp Leu Val Lys Asn Lys Met Thr Asn Val Val Lys Leu Ser Val
865                 870                 875                 880
Pro Leu Glu Val Asp Ile Ser Ile Gly Lys Ser Trp Ser
                885                 890

(2) INFORMATION FOR SEQ ID NO:3:

(i) SEQUENCE CHARACTERISTICS:
        (A) LENGTH: 44 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:3:

CATGGCGAGA CTATTTCTCT TTGATGGCAC AGCCCTGGCC TACA                    44

(2) INFORMATION FOR SEQ ID NO:4:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AGGCCAGGGC TGTGCCATCA AAGAGAAATA GTCTCGC                            37

(2) INFORMATION FOR SEQ ID NO:5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AGGCCAGGGC TGTGCCATCA AAGAGAAATA GTCTCGCCA                          39

(2) INFORMATION FOR SEQ ID NO:6:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TATGGCGAGA CTATTTCTCT TTGATGGCAC AGCCCTGGCC TACA                    44

(2) INFORMATION FOR SEQ ID NO:7:

(i) SEQUENCE CHARACTERISTICS:
        (A) LENGTH: 1833 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1830

(xi) SEQUENCE DESCRIPTION: SEQ ID NO:7:

ATG AAG GAA CTT CAA CTG TAC GAA GAA GCA GAA CCC ACC GGA TAC GAA    48
Met Lys Glu Leu Gln Leu Tyr Glu Glu Ala Glu Pro Thr Gly Tyr Glu
 1               5                  10                  15

ATC GTG AAG GAT CAT AAG ACC TTC GAA GAT CTC ATC GAA AAG CTG AAG    96
Ile Val Lys Asp His Lys Thr Phe Glu Asp Leu Ile Glu Lys Leu Lys
             20                  25                  30

GAG GTT CCA TCT TTT GCC CTG GAC CTT GAA ACG TCC TCC CTT GAC CCG   144
Glu Val Pro Ser Phe Ala Leu Asp Leu Glu Thr Ser Ser Leu Asp Pro

```
                35                  40                  45
TTC AAC TGT GAG ATA GTC GGC ATC TCC GTG TCG TTC AAA CCG AAA ACA    192
Phe Asn Cys Glu Ile Val Gly Ile Ser Val Ser Phe Lys Pro Lys Thr
         50                  55                  60

GCT TAT TAC ATT CCA CTT CAT CAC AGA AAC GCC CAG AAT CTT GAT GAA    240
Ala Tyr Tyr Ile Pro Leu His His Arg Asn Ala Gln Asn Leu Asp Glu
 65              70                  75                  80

ACA CTG GTG CTG TCG AAG TTG AAA GAG ATC CTC GAA GAC CCG TCT TCG    288
Thr Leu Val Leu Ser Lys Leu Lys Glu Ile Leu Glu Asp Pro Ser Ser
                 85                  90                  95

AAG ATT GTG GGT CAG AAC CTG AAG TAC GAC TAC AAG GTT CTT ATG GTA    336
Lys Ile Val Gly Gln Asn Leu Lys Tyr Asp Tyr Lys Val Leu Met Val
                100                 105                 110

AAG GGT ATA TCG CCA GTT TAT CCG CAT TTT GAC ACG ATG ATA GCT GCA    384
Lys Gly Ile Ser Pro Val Tyr Pro His Phe Asp Thr Met Ile Ala Ala
            115                 120                 125

TAT TTG CTG GAG CCA AAC GAG AAA AAA TTC AAT CTC GAA GAT CTG TCT    432
Tyr Leu Leu Glu Pro Asn Glu Lys Lys Phe Asn Leu Glu Asp Leu Ser
130                 135                 140

TTG AAA TTT CTC GGA TAC AAA ATG ACG TCT TAT CAG GAA CTG ATG TCG    480
Leu Lys Phe Leu Gly Tyr Lys Met Thr Ser Tyr Gln Glu Leu Met Ser
145                 150                 155                 160

TTT TCC TCA CCA CTT TTT GGT TTC AGC TTT GCG GAT GTT CCG GTA GAC    528
Phe Ser Ser Pro Leu Phe Gly Phe Ser Phe Ala Asp Val Pro Val Asp
                165                 170                 175

AAG GCT GCG AAC TAC TCC TGC GAG GAT GCA GAC ATC ACT TAT AGG CTC    576
Lys Ala Ala Asn Tyr Ser Cys Glu Asp Ala Asp Ile Thr Tyr Arg Leu
                180                 185                 190

TAC AAG ATA CTC AGC ATG AAG CTC CAT GAA GCG GAA CTT GAG AAC GTC    624
Tyr Lys Ile Leu Ser Met Lys Leu His Glu Ala Glu Leu Glu Asn Val
            195                 200                 205

TTC TAC AGG ATA GAG ATG CCG CTT GTG AAC GTT CTT GCA CGC ATG GAA    672
Phe Tyr Arg Ile Glu Met Pro Leu Val Asn Val Leu Ala Arg Met Glu
        210                 215                 220

TTG AAC GGG GTG TAT GTG GAC ACA GAA TTC CTG AAA AAG CTC TCG GAG    720
Leu Asn Gly Val Tyr Val Asp Thr Glu Phe Leu Lys Lys Leu Ser Glu
225                 230                 235                 240

GAG TAC GGC AAA AAG CTC GAG GAA CTG GCC GAA AAA ATC TAC CAG ATA    768
Glu Tyr Gly Lys Lys Leu Glu Glu Leu Ala Glu Lys Ile Tyr Gln Ile
                245                 250                 255

GCA GGA GAG CCC TTC AAC ATC AAT TCT CCA AAA CAG GTT TCA AAG ATC    816
Ala Gly Glu Pro Phe Asn Ile Asn Ser Pro Lys Gln Val Ser Lys Ile
                260                 265                 270

CTT TTT GAG AAG CTG GGA ATA AAA CCC CGT GGA AAA ACG ACA AAA ACA    864
Leu Phe Glu Lys Leu Gly Ile Lys Pro Arg Gly Lys Thr Thr Lys Thr
            275                 280                 285

GGA GCG TAC TCT ACC AGG ATA GAG GTG TTG GAA GAG ATA GCG AAT GAG    912
Gly Ala Tyr Ser Thr Arg Ile Glu Val Leu Glu Glu Ile Ala Asn Glu
        290                 295                 300

CAC GAG ATA GTA CCC CTC ATT CTC GAG TAC AGA AAG ATC CAG AAA CTG    960
His Glu Ile Val Pro Leu Ile Leu Glu Tyr Arg Lys Ile Gln Lys Leu
305                 310                 315                 320

AAA TCG ACC TAC ATA GAC ACC CTT CCG AAA CTT GTG AAC CCG AAA ACC    1008
Lys Ser Thr Tyr Ile Asp Thr Leu Pro Lys Leu Val Asn Pro Lys Thr
                325                 330                 335

GGA AGA ATT CAT GCA TCT TTC CAC CAG ACG GGT ACC GCC ACT GGC AGG    1056
Gly Arg Ile His Ala Ser Phe His Gln Thr Gly Thr Ala Thr Gly Arg
                340                 345                 350

TTG AGT AGC AGT GAT CCA AAT CTT CAG AAT CTT CCG ACA AAG AGC GAA    1104
```

```
Leu Ser Ser Ser Asp Pro Asn Leu Gln Asn Leu Pro Thr Lys Ser Glu
        355                 360                 365

GAG GGA AAA GAA ATT AGA AAA GCG ATT GTG CCC CAG GAT CCA GAC TGG      1152
Glu Gly Lys Glu Ile Arg Lys Ala Ile Val Pro Gln Asp Pro Asp Trp
370                 375                 380

TGG ATC GTC AGT GCG GAT TAT TCC CAA ATA GAA CTC AGA ATC CTC GCT      1200
Trp Ile Val Ser Ala Asp Tyr Ser Gln Ile Glu Leu Arg Ile Leu Ala
385                 390                 395                 400

CAT CTC AGT GGT GAT GAG AAC CTT GTG AAG GCC TTC GAG GAG GGC ATC      1248
His Leu Ser Gly Asp Glu Asn Leu Val Lys Ala Phe Glu Glu Gly Ile
                405                 410                 415

GAT GTG CAC ACC TTG ACT GCC TCC AGG ATC TAC AAC GTA AAG CCA GAA      1296
Asp Val His Thr Leu Thr Ala Ser Arg Ile Tyr Asn Val Lys Pro Glu
        420                 425                 430

GAA GTG AAC GAA GAA ATG CGA CGG GTT GGA AAG ATG GTG AAC TTC TCT      1344
Glu Val Asn Glu Glu Met Arg Arg Val Gly Lys Met Val Asn Phe Ser
            435                 440                 445

ATA ATA TAC GGT GTC ACA CCG TAC GGT CTT TCT GTG AGA CTT GGA ATA      1392
Ile Ile Tyr Gly Val Thr Pro Tyr Gly Leu Ser Val Arg Leu Gly Ile
450                 455                 460

CCG GTT AAA GAA GCA GAA AAG ATG ATT ATC AGC TAT TTC ACA CTG TAT      1440
Pro Val Lys Glu Ala Glu Lys Met Ile Ile Ser Tyr Phe Thr Leu Tyr
465                 470                 475                 480

CCA AAG GTG CGA AGC TAC ATC CAG CAG GTT GTT GCA GAG GCA AAA GAG      1488
Pro Lys Val Arg Ser Tyr Ile Gln Gln Val Val Ala Glu Ala Lys Glu
                485                 490                 495

AAG GGC TAC GTC AGG ACT CTC TTT GGA AGA AAA AGA GAT ATT CCC CAG      1536
Lys Gly Tyr Val Arg Thr Leu Phe Gly Arg Lys Arg Asp Ile Pro Gln
                500                 505                 510

CTC ATG GCA AGG GAC AAG AAC ACC CAG TCC GAA GGC GAA AGA ATC GCA      1584
Leu Met Ala Arg Asp Lys Asn Thr Gln Ser Glu Gly Glu Arg Ile Ala
        515                 520                 525

ATA AAC ACC CCC ATT CAG GGA ACG GCG GCA GAT ATA ATA AAA TTG GCT      1632
Ile Asn Thr Pro Ile Gln Gly Thr Ala Ala Asp Ile Ile Lys Leu Ala
    530                 535                 540

ATG ATA GAT ATA GAC GAG GAG CTG AGA AAA AGA AAC ATG AAA TCC AGA      1680
Met Ile Asp Ile Asp Glu Glu Leu Arg Lys Arg Asn Met Lys Ser Arg
545                 550                 555                 560

ATG ATC ATT CAG GTT CAT GAC GAA CTG GTC TTC GAG GTT CCC GAT GAG      1728
Met Ile Ile Gln Val His Asp Glu Leu Val Phe Glu Val Pro Asp Glu
                565                 570                 575

GAA AAA GAA GAA CTA GTT GAT CTG GTG AAG AAC AAA ATG ACA AAT GTG      1776
Glu Lys Glu Glu Leu Val Asp Leu Val Lys Asn Lys Met Thr Asn Val
                580                 585                 590

GTG AAA CTC TCT GTG CCT CTT GAG GTT GAC ATA AGC ATC GGA AAA AGC      1824
Val Lys Leu Ser Val Pro Leu Glu Val Asp Ile Ser Ile Gly Lys Ser
            595                 600                 605

TGG TCT TGA                                                          1833
Trp Ser
    610

(2) INFORMATION FOR SEQ ID NO:8:

(i) SEQUENCE CHARACTERISTICS:
        (A) LENGTH: 610 amino acids
        (B) TYPE: amino acid
        (D) TOPOLOGY: linear (ii) MOLECULE TYPE: protein (xi) SEQUENCE DESCRIPTION: SEQ ID NO:8:
```

```
Met Lys Glu Leu Gln Leu Tyr Glu Ala Glu Pro Thr Gly Tyr Glu
 1               5                  10                 15

Ile Val Lys Asp His Lys Thr Phe Glu Asp Leu Ile Glu Lys Leu Lys
                 20                  25                 30

Glu Val Pro Ser Phe Ala Leu Asp Leu Glu Thr Ser Ser Leu Asp Pro
         35                  40                  45

Phe Asn Cys Glu Ile Val Gly Ile Ser Val Ser Phe Lys Pro Lys Thr
         50                  55                  60

Ala Tyr Tyr Ile Pro Leu His His Arg Asn Ala Gln Asn Leu Asp Glu
 65                  70                  75                  80

Thr Leu Val Leu Ser Lys Leu Lys Glu Ile Leu Glu Asp Pro Ser Ser
                 85                  90                  95

Lys Ile Val Gly Gln Asn Leu Lys Tyr Asp Tyr Lys Val Leu Met Val
                100                 105                 110

Lys Gly Ile Ser Pro Val Tyr Pro His Phe Asp Thr Met Ile Ala Ala
                115                 120                 125

Tyr Leu Leu Glu Pro Asn Glu Lys Lys Phe Asn Leu Glu Asp Leu Ser
130                 135                 140

Leu Lys Phe Leu Gly Tyr Lys Met Thr Ser Tyr Gln Glu Leu Met Ser
145                 150                 155                 160

Phe Ser Ser Pro Leu Phe Gly Phe Ser Phe Ala Asp Val Pro Val Asp
                165                 170                 175

Lys Ala Ala Asn Tyr Ser Cys Glu Asp Ala Asp Ile Thr Tyr Arg Leu
                180                 185                 190

Tyr Lys Ile Leu Ser Met Lys Leu His Glu Ala Glu Leu Glu Asn Val
                195                 200                 205

Phe Tyr Arg Ile Glu Met Pro Leu Val Asn Val Leu Ala Arg Met Glu
210                 215                 220

Leu Asn Gly Val Tyr Val Asp Thr Glu Phe Leu Lys Lys Leu Ser Glu
225                 230                 235                 240

Glu Tyr Gly Lys Lys Leu Glu Glu Leu Ala Glu Lys Ile Tyr Gln Ile
                245                 250                 255

Ala Gly Glu Pro Phe Asn Ile Asn Ser Pro Lys Gln Val Ser Lys Ile
                260                 265                 270

Leu Phe Glu Lys Leu Gly Ile Lys Pro Arg Gly Lys Thr Thr Lys Thr
                275                 280                 285

Gly Ala Tyr Ser Thr Arg Ile Glu Val Leu Glu Glu Ile Ala Asn Glu
290                 295                 300

His Glu Ile Val Pro Leu Ile Leu Glu Tyr Arg Lys Ile Gln Lys Leu
305                 310                 315                 320

Lys Ser Thr Tyr Ile Asp Thr Leu Pro Lys Leu Val Asn Pro Lys Thr
                325                 330                 335

Gly Arg Ile His Ala Ser Phe His Gln Thr Gly Thr Ala Thr Gly Arg
                340                 345                 350

Leu Ser Ser Ser Asp Pro Asn Leu Gln Asn Leu Pro Thr Lys Ser Glu
                355                 360                 365

Glu Gly Lys Glu Ile Arg Lys Ala Ile Val Pro Gln Asp Pro Asp Trp
                370                 375                 380

Trp Ile Val Ser Ala Asp Tyr Ser Gln Ile Glu Leu Arg Ile Leu Ala
385                 390                 395                 400

His Leu Ser Gly Asp Glu Asn Leu Val Lys Ala Phe Glu Glu Gly Ile
                405                 410                 415

Asp Val His Thr Leu Thr Ala Ser Arg Ile Tyr Asn Val Lys Pro Glu
```

```
                    420                 425                 430
Glu Val Asn Glu Glu Met Arg Arg Val Gly Lys Met Val Asn Phe Ser
            435                 440                 445

Ile Ile Tyr Gly Val Thr Pro Tyr Gly Leu Ser Val Arg Leu Gly Ile
450                 455                 460

Pro Val Lys Glu Ala Glu Lys Met Ile Ile Ser Tyr Phe Thr Leu Tyr
465                 470                 475                 480

Pro Lys Val Arg Ser Tyr Ile Gln Gln Val Val Ala Glu Ala Lys Glu
            485                 490                 495

Lys Gly Tyr Val Arg Thr Leu Phe Gly Arg Lys Arg Asp Ile Pro Gln
            500                 505                 510

Leu Met Ala Arg Asp Lys Asn Thr Gln Ser Glu Gly Glu Arg Ile Ala
            515                 520                 525

Ile Asn Thr Pro Ile Gln Gly Thr Ala Ala Asp Ile Ile Lys Leu Ala
            530                 535                 540

Met Ile Asp Ile Asp Glu Glu Leu Arg Lys Arg Asn Met Lys Ser Arg
545                 550                 555                 560

Met Ile Ile Gln Val His Asp Glu Leu Val Phe Glu Val Pro Asp Glu
            565                 570                 575

Glu Lys Glu Glu Leu Val Asp Leu Val Lys Asn Lys Met Thr Asn Val
            580                 585                 590

Val Lys Leu Ser Val Pro Leu Glu Val Asp Ile Ser Ile Gly Lys Ser
            595                 600                 605

Trp Ser
    610

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ATCGAAAAGC TGACCATGGT TCCATCTTTT G                                     31

(2) INFORMATION FOR SEQ ID NO:10:

(i) SEQUENCE CHARACTERISTICS:
        (A) LENGTH: 1737 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1734

(xi) SEQUENCE DESCRIPTION: SEQ ID NO:10:

ATG GTT CCA TCT TTT GCC CTG GAC CTT GAA ACG TCC TCC CTT GAC CCG        48
Met Val Pro Ser Phe Ala Leu Asp Leu Glu Thr Ser Ser Leu Asp Pro
1               5                   10                  15

TTC AAC TGT GAG ATA GTC GGC ATC TCC GTG TCG TTC AAA CCG AAA ACA        96
Phe Asn Cys Glu Ile Val Gly Ile Ser Val Ser Phe Lys Pro Lys Thr
                20                  25                  30

GCT TAT TAC ATT CCA CTT CAT CAC AGA AAC GCC CAG AAT CTT GAT GAA        144
```

```
                    Ala Tyr Tyr Ile Pro Leu His His Arg Asn Ala Gln Asn Leu Asp Glu
                                35                  40                  45

ACA CTG GTG CTG TCG AAG TTG AAA GAG ATC CTC GAA GAC CCG TCT TCG              192
Thr Leu Val Leu Ser Lys Leu Lys Glu Ile Leu Glu Asp Pro Ser Ser
 50                  55                  60

AAG ATT GTG GGT CAG AAC CTG AAG TAC GAC TAC AAG GTT CTT ATG GTA              240
Lys Ile Val Gly Gln Asn Leu Lys Tyr Asp Tyr Lys Val Leu Met Val
 65                  70                  75                  80

AAG GGT ATA TCG CCA GTT TAT CCG CAT TTT GAC ACG ATG ATA GCT GCA              288
Lys Gly Ile Ser Pro Val Tyr Pro His Phe Asp Thr Met Ile Ala Ala
                 85                  90                  95

TAT TTG CTG GAG CCA AAC GAG AAA AAA TTC AAT CTC GAA GAT CTG TCT              336
Tyr Leu Leu Glu Pro Asn Glu Lys Lys Phe Asn Leu Glu Asp Leu Ser
            100                 105                 110

TTG AAA TTT CTC GGA TAC AAA ATG ACG TCT TAT CAG GAA CTG ATG TCG              384
Leu Lys Phe Leu Gly Tyr Lys Met Thr Ser Tyr Gln Glu Leu Met Ser
            115                 120                 125

TTT TCC TCA CCA CTT TTT GGT TTC AGC TTT GCG GAT GTT CCG GTA GAC              432
Phe Ser Ser Pro Leu Phe Gly Phe Ser Phe Ala Asp Val Pro Val Asp
        130                 135                 140

AAG GCT GCG AAC TAC TCC TGC GAG GAT GCA GAC ATC ACT TAT AGG CTC              480
Lys Ala Ala Asn Tyr Ser Cys Glu Asp Ala Asp Ile Thr Tyr Arg Leu
145                 150                 155                 160

TAC AAG ATA CTC AGC ATG AAG CTC CAT GAA GCG GAA CTT GAG AAC GTC              528
Tyr Lys Ile Leu Ser Met Lys Leu His Glu Ala Glu Leu Glu Asn Val
                165                 170                 175

TTC TAC AGG ATA GAG ATG CCG CTT GTG AAC GTT CTT GCA CGC ATG GAA              576
Phe Tyr Arg Ile Glu Met Pro Leu Val Asn Val Leu Ala Arg Met Glu
            180                 185                 190

TTG AAC GGG GTG TAT GTG GAC ACA GAA TTC CTG AAA AAG CTC TCG GAG              624
Leu Asn Gly Val Tyr Val Asp Thr Glu Phe Leu Lys Lys Leu Ser Glu
            195                 200                 205

GAG TAC GGC AAA AAG CTC GAG GAA CTG GCC GAA AAA ATC TAC CAG ATA              672
Glu Tyr Gly Lys Lys Leu Glu Glu Leu Ala Glu Lys Ile Tyr Gln Ile
       210                 215                 220

GCA GGA GAG CCC TTC AAC ATC AAT TCT CCA AAA CAG GTT TCA AAG ATC              720
Ala Gly Glu Pro Phe Asn Ile Asn Ser Pro Lys Gln Val Ser Lys Ile
225                 230                 235                 240

CTT TTT GAG AAG CTG GGA ATA AAA CCC CGT GGA AAA ACG ACA AAA ACA              768
Leu Phe Glu Lys Leu Gly Ile Lys Pro Arg Gly Lys Thr Thr Lys Thr
                245                 250                 255

GGA GCG TAC TCT ACC AGG ATA GAG GTG TTG GAA GAG ATA GCG AAT GAG              816
Gly Ala Tyr Ser Thr Arg Ile Glu Val Leu Glu Glu Ile Ala Asn Glu
            260                 265                 270

CAC GAG ATA GTA CCC CTC ATT CTC GAG TAC AGA AAG ATC CAG AAA CTG              864
His Glu Ile Val Pro Leu Ile Leu Glu Tyr Arg Lys Ile Gln Lys Leu
            275                 280                 285

AAA TCG ACC TAC ATA GAC ACC CTT CCG AAA CTT GTG AAC CCG AAA ACC              912
Lys Ser Thr Tyr Ile Asp Thr Leu Pro Lys Leu Val Asn Pro Lys Thr
        290                 295                 300

GGA AGA ATT CAT GCA TCT TTC CAC CAG ACG GGT ACC GCC ACT GGC AGG              960
Gly Arg Ile His Ala Ser Phe His Gln Thr Gly Thr Ala Thr Gly Arg
305                 310                 315                 320

TTG AGT AGC AGT GAT CCA AAT CTT CAG AAT CTT CCG ACA AAG AGC GAA             1008
Leu Ser Ser Ser Asp Pro Asn Leu Gln Asn Leu Pro Thr Lys Ser Glu
                325                 330                 335

GAG GGA AAA GAA ATT AGA AAA GCG ATT GTG CCC CAG GAT CCA GAC TGG             1056
Glu Gly Lys Glu Ile Arg Lys Ala Ile Val Pro Gln Asp Pro Asp Trp
            340                 345                 350
```

```
TGG ATC GTC AGT GCG GAT TAT TCC CAA ATA GAA CTC AGA ATC CTC GCT      1104
Trp Ile Val Ser Ala Asp Tyr Ser Gln Ile Glu Leu Arg Ile Leu Ala
        355                 360                 365

CAT CTC AGT GGT GAT GAG AAC CTT GTG AAG GCC TTC GAG GAG GGC ATC      1152
His Leu Ser Gly Asp Glu Asn Leu Val Lys Ala Phe Glu Glu Gly Ile
370                 375                 380

GAT GTG CAC ACC TTG ACT GCC TCC AGG ATC TAC AAC GTA AAG CCA GAA      1200
Asp Val His Thr Leu Thr Ala Ser Arg Ile Tyr Asn Val Lys Pro Glu
385                 390                 395                 400

GAA GTG AAC GAA GAA ATG CGA CGG GTT GGA AAG ATG GTG AAC TTC TCT      1248
Glu Val Asn Glu Glu Met Arg Arg Val Gly Lys Met Val Asn Phe Ser
                405                 410                 415

ATA ATA TAC GGT GTC ACA CCG TAC GGT CTT TCT GTG AGA CTT GGA ATA      1296
Ile Ile Tyr Gly Val Thr Pro Tyr Gly Leu Ser Val Arg Leu Gly Ile
            420                 425                 430

CCG GTT AAA GAA GCA GAA AAG ATG ATT ATC AGC TAT TTC ACA CTG TAT      1344
Pro Val Lys Glu Ala Glu Lys Met Ile Ile Ser Tyr Phe Thr Leu Tyr
                435                 440                 445

CCA AAG GTG CGA AGC TAC ATC CAG CAG GTT GTT GCA GAG GCA AAA GAG      1392
Pro Lys Val Arg Ser Tyr Ile Gln Gln Val Val Ala Glu Ala Lys Glu
        450                 455                 460

AAG GGC TAC GTC AGG ACT CTC TTT GGA AGA AAA AGA GAT ATT CCC CAG      1440
Lys Gly Tyr Val Arg Thr Leu Phe Gly Arg Lys Arg Asp Ile Pro Gln
465                 470                 475                 480

CTC ATG GCA AGG GAC AAG AAC ACC CAG TCC GAA GGC GAA AGA ATC GCA      1488
Leu Met Ala Arg Asp Lys Asn Thr Gln Ser Glu Gly Glu Arg Ile Ala
                485                 490                 495

ATA AAC ACC CCC ATT CAG GGA ACG GCG GCA GAT ATA ATA AAA TTG GCT      1536
Ile Asn Thr Pro Ile Gln Gly Thr Ala Ala Asp Ile Ile Lys Leu Ala
            500                 505                 510

ATG ATA GAT ATA GAC GAG GAG CTG AGA AAA AGA AAC ATG AAA TCC AGA      1584
Met Ile Asp Ile Asp Glu Glu Leu Arg Lys Arg Asn Met Lys Ser Arg
            515                 520                 525

ATG ATC ATT CAG GTT CAT GAC GAA CTG GTC TTC GAG GTT CCC GAT GAG      1632
Met Ile Ile Gln Val His Asp Glu Leu Val Phe Glu Val Pro Asp Glu
        530                 535                 540

GAA AAA GAA GAA CTA GTT GAT CTG GTG AAG AAC AAA ATG ACA AAT GTG      1680
Glu Lys Glu Glu Leu Val Asp Leu Val Lys Asn Lys Met Thr Asn Val
545                 550                 555                 560

GTG AAA CTC TCT GTG CCT CTT GAG GTT GAC ATA AGC ATC GGA AAA AGC      1728
Val Lys Leu Ser Val Pro Leu Glu Val Asp Ile Ser Ile Gly Lys Ser
                565                 570                 575

TGG TCT TGA                                                          1737
Trp Ser (2) INFORMATION FOR SEQ ID NO:11:

(i) SEQUENCE CHARACTERISTICS:
        (A) LENGTH: 578 amino acids
        (B) TYPE: amino acid
        (D) TOPOLOGY: linear (ii) MOLECULE TYPE: protein (xi) SEQUENCE DESCRIPTION: SEQ ID NO:11:

Met Val Pro Ser Phe Ala Leu Asp Leu Glu Thr Ser Ser Leu Asp Pro
 1               5                  10                  15

Phe Asn Cys Glu Ile Val Gly Ile Ser Val Ser Phe Lys Pro Lys Thr
                20                  25                  30

Ala Tyr Tyr Ile Pro Leu His His Arg Asn Ala Gln Asn Leu Asp Glu
            35                  40                  45
```

-continued

```
Thr Leu Val Leu Ser Lys Leu Lys Glu Ile Leu Glu Asp Pro Ser Ser
 50                  55                  60

Lys Ile Val Gly Gln Asn Leu Lys Tyr Asp Tyr Lys Val Leu Met Val
 65                  70                  75                  80

Lys Gly Ile Ser Pro Val Tyr Pro His Phe Asp Thr Met Ile Ala Ala
                 85                  90                  95

Tyr Leu Leu Glu Pro Asn Glu Lys Lys Phe Asn Leu Glu Asp Leu Ser
                100                 105                 110

Leu Lys Phe Leu Gly Tyr Lys Met Thr Ser Tyr Gln Glu Leu Met Ser
            115                 120                 125

Phe Ser Ser Pro Leu Phe Gly Phe Ser Phe Ala Asp Val Pro Val Asp
            130                 135                 140

Lys Ala Ala Asn Tyr Ser Cys Glu Asp Ala Asp Ile Thr Tyr Arg Leu
145                 150                 155                 160

Tyr Lys Ile Leu Ser Met Lys Leu His Glu Ala Glu Leu Glu Asn Val
                165                 170                 175

Phe Tyr Arg Ile Glu Met Pro Leu Val Asn Val Leu Ala Arg Met Glu
                180                 185                 190

Leu Asn Gly Val Tyr Val Asp Thr Glu Phe Leu Lys Lys Leu Ser Glu
            195                 200                 205

Glu Tyr Gly Lys Lys Leu Glu Glu Leu Ala Glu Lys Ile Tyr Gln Ile
210                 215                 220

Ala Gly Glu Pro Phe Asn Ile Asn Ser Pro Lys Gln Val Ser Lys Ile
225                 230                 235                 240

Leu Phe Glu Lys Leu Gly Ile Lys Pro Arg Gly Lys Thr Thr Lys Thr
                245                 250                 255

Gly Ala Tyr Ser Thr Arg Ile Glu Val Leu Glu Glu Ile Ala Asn Glu
                260                 265                 270

His Glu Ile Val Pro Leu Ile Leu Glu Tyr Arg Lys Ile Gln Lys Leu
            275                 280                 285

Lys Ser Thr Tyr Ile Asp Thr Leu Pro Lys Leu Val Asn Pro Lys Thr
290                 295                 300

Gly Arg Ile His Ala Ser Phe His Gln Thr Gly Thr Ala Thr Gly Arg
305                 310                 315                 320

Leu Ser Ser Ser Asp Pro Asn Leu Gln Asn Leu Pro Thr Lys Ser Glu
                325                 330                 335

Glu Gly Lys Glu Ile Arg Lys Ala Ile Val Pro Gln Asp Pro Asp Trp
                340                 345                 350

Trp Ile Val Ser Ala Asp Tyr Ser Gln Ile Glu Leu Arg Ile Leu Ala
            355                 360                 365

His Leu Ser Gly Asp Glu Asn Leu Val Lys Ala Phe Glu Glu Gly Ile
            370                 375                 380

Asp Val His Thr Leu Thr Ala Ser Arg Ile Tyr Asn Val Lys Pro Glu
385                 390                 395                 400

Glu Val Asn Glu Glu Met Arg Arg Val Gly Lys Met Val Asn Phe Ser
                405                 410                 415

Ile Ile Tyr Gly Val Thr Pro Tyr Gly Leu Ser Val Arg Leu Gly Ile
                420                 425                 430

Pro Val Lys Glu Ala Glu Lys Met Ile Ile Ser Tyr Phe Thr Leu Tyr
            435                 440                 445

Pro Lys Val Arg Ser Tyr Ile Gln Gln Val Val Ala Glu Ala Lys Glu
            450                 455                 460
```

```
Lys Gly Tyr Val Arg Thr Leu Phe Gly Arg Lys Arg Asp Ile Pro Gln
465                 470                 475                 480

Leu Met Ala Arg Asp Lys Asn Thr Gln Ser Glu Gly Glu Arg Ile Ala
                485                 490                 495

Ile Asn Thr Pro Ile Gln Gly Thr Ala Ala Asp Ile Ile Lys Leu Ala
                500                 505                 510

Met Ile Asp Ile Asp Glu Glu Leu Arg Lys Arg Asn Met Lys Ser Arg
            515                 520                 525

Met Ile Ile Gln Val His Asp Glu Leu Val Phe Glu Val Pro Asp Glu
            530                 535                 540

Glu Lys Glu Glu Leu Val Asp Leu Val Lys Asn Lys Met Thr Asn Val
545                 550                 555                 560

Val Lys Leu Ser Val Pro Leu Glu Val Asp Ile Ser Ile Gly Lys Ser
                565                 570                 575

Trp Ser
```

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TGCCGTACAC CTCCGAGAGC                                             20

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CTCGTTTGGC TCCAGCAAAT ATGC                                    24

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

TTTGCCCTGG AACTTGAAAC G                                         21

(2) INFORMATION FOR SEQ ID NO:15:

(i) SEQUENCE CHARACTERISTICS:
        (A) LENGTH: 1833 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1830

(xi) SEQUENCE DESCRIPTION: SEQ ID NO:15:

| | | | | | | | | | | | | | | | | |
|---|---|---|---|---|---|---|---|---|---|---|---|---|---|---|---|---|
| ATG | AAG | GAA | CTT | CAA | CTG | TAC | GAA | GAA | GCA | GAA | CCC | ACC | GGA | TAC | GAA | 48 |
| Met | Lys | Glu | Leu | Gln | Leu | Tyr | Glu | Glu | Ala | Glu | Pro | Thr | Gly | Tyr | Glu | |
| 1 | | | | 5 | | | | | 10 | | | | | 15 | | |
| ATC | GTG | AAG | GAT | CAT | AAG | ACC | TTC | GAA | GAT | CTC | ATC | GAA | AAG | CTG | AAG | 96 |
| Ile | Val | Lys | Asp | His | Lys | Thr | Phe | Glu | Asp | Leu | Ile | Glu | Lys | Leu | Lys | |
| | | | 20 | | | | | 25 | | | | | 30 | | | |
| GAG | GTT | CCA | TCT | TTT | GCC | CTG | GAA | CTT | GAA | ACG | TCC | TCC | CTT | GAC | CCG | 144 |
| Glu | Val | Pro | Ser | Phe | Ala | Leu | Glu | Leu | Glu | Thr | Ser | Ser | Leu | Asp | Pro | |
| | | | 35 | | | | | 40 | | | | | 45 | | | |
| TTC | AAC | TGT | GAG | ATA | GTC | GGC | ATC | TCC | GTG | TCG | TTC | AAA | CCG | AAA | ACA | 192 |
| Phe | Asn | Cys | Glu | Ile | Val | Gly | Ile | Ser | Val | Ser | Phe | Lys | Pro | Lys | Thr | |
| | 50 | | | | | 55 | | | | | 60 | | | | | |
| GCT | TAT | TAC | ATT | CCA | CTT | CAT | CAC | AGA | AAC | GCC | CAG | AAT | CTT | GAT | GAA | 240 |
| Ala | Tyr | Tyr | Ile | Pro | Leu | His | His | Arg | Asn | Ala | Gln | Asn | Leu | Asp | Glu | |
| 65 | | | | | 70 | | | | | 75 | | | | | 80 | |
| ACA | CTG | GTG | CTG | TCG | AAG | TTG | AAA | GAG | ATC | CTC | GAA | GAC | CCG | TCT | TCG | 288 |
| Thr | Leu | Val | Leu | Ser | Lys | Leu | Lys | Glu | Ile | Leu | Glu | Asp | Pro | Ser | Ser | |
| | | | | 85 | | | | | 90 | | | | | 95 | | |
| AAG | ATT | GTG | GGT | CAG | AAC | CTG | AAG | TAC | GAC | TAC | AAG | GTT | CTT | ATG | GTA | 336 |
| Lys | Ile | Val | Gly | Gln | Asn | Leu | Lys | Tyr | Asp | Tyr | Lys | Val | Leu | Met | Val | |
| | | | 100 | | | | | 105 | | | | | 110 | | | |
| AAG | GGT | ATA | TCG | CCA | GTT | TAT | CCG | CAT | TTT | GAC | ACG | ATG | ATA | GCT | GCA | 384 |
| Lys | Gly | Ile | Ser | Pro | Val | Tyr | Pro | His | Phe | Asp | Thr | Met | Ile | Ala | Ala | |
| | | 115 | | | | | 120 | | | | | 125 | | | | |
| TAT | TTG | CTG | GAG | CCA | AAC | GAG | AAA | AAA | TTC | AAT | CTC | GAA | GAT | CTG | TCT | 432 |
| Tyr | Leu | Leu | Glu | Pro | Asn | Glu | Lys | Lys | Phe | Asn | Leu | Glu | Asp | Leu | Ser | |
| | 130 | | | | | 135 | | | | | 140 | | | | | |
| TTG | AAA | TTT | CTC | GGA | TAC | AAA | ATG | ACG | TCT | TAT | CAG | GAA | CTG | ATG | TCG | 480 |
| Leu | Lys | Phe | Leu | Gly | Tyr | Lys | Met | Thr | Ser | Tyr | Gln | Glu | Leu | Met | Ser | |
| 145 | | | | | 150 | | | | | 155 | | | | | 160 | |
| TTT | TCC | TCA | CCA | CTT | TTT | GGT | TTC | AGC | TTT | GCG | GAT | GTT | CCG | GTA | GAC | 528 |
| Phe | Ser | Ser | Pro | Leu | Phe | Gly | Phe | Ser | Phe | Ala | Asp | Val | Pro | Val | Asp | |
| | | | | 165 | | | | | 170 | | | | | 175 | | |
| AAG | GCT | GCG | AAC | TAC | TCC | TGC | GAG | GAT | GCA | GAC | ATC | ACT | TAT | AGG | CTC | 576 |
| Lys | Ala | Ala | Asn | Tyr | Ser | Cys | Glu | Asp | Ala | Asp | Ile | Thr | Tyr | Arg | Leu | |
| | | | 180 | | | | | 185 | | | | | 190 | | | |
| TAC | AAG | ATA | CTC | AGC | ATG | AAG | CTC | CAT | GAA | GCG | GAA | CTT | GAG | AAC | GTC | 624 |
| Tyr | Lys | Ile | Leu | Ser | Met | Lys | Leu | His | Glu | Ala | Glu | Leu | Glu | Asn | Val | |
| | | 195 | | | | | 200 | | | | | 205 | | | | |
| TTC | TAC | AGG | ATA | GAG | ATG | CCG | CTT | GTG | AAC | GTT | CTT | GCA | CGC | ATG | GAA | 672 |
| Phe | Tyr | Arg | Ile | Glu | Met | Pro | Leu | Val | Asn | Val | Leu | Ala | Arg | Met | Glu | |
| | 210 | | | | | 215 | | | | | 220 | | | | | |
| TTG | AAC | GGG | GTG | TAT | GTG | GAC | ACA | GAA | TTC | CTG | AAA | AAG | CTC | TCG | GAG | 720 |
| Leu | Asn | Gly | Val | Tyr | Val | Asp | Thr | Glu | Phe | Leu | Lys | Lys | Leu | Ser | Glu | |
| 225 | | | | | 230 | | | | | 235 | | | | | 240 | |
| GAG | TAC | GGC | AAA | AAG | CTC | GAG | GAA | CTG | GCC | GAA | AAA | ATC | TAC | CAG | ATA | 768 |
| Glu | Tyr | Gly | Lys | Lys | Leu | Glu | Glu | Leu | Ala | Glu | Lys | Ile | Tyr | Gln | Ile | |
| | | | | 245 | | | | | 250 | | | | | 255 | | |
| GCA | GGA | GAG | CCC | TTC | AAC | ATC | AAT | TCT | CCA | AAA | CAG | GTT | TCA | AAG | ATC | 816 |
| Ala | Gly | Glu | Pro | Phe | Asn | Ile | Asn | Ser | Pro | Lys | Gln | Val | Ser | Lys | Ile | |
| | | | 260 | | | | | 265 | | | | | 270 | | | |
| CTT | TTT | GAG | AAG | CTG | GGA | ATA | AAA | CCC | CGT | GGA | AAA | ACG | ACA | AAA | ACA | 864 |
| Leu | Phe | Glu | Lys | Leu | Gly | Ile | Lys | Pro | Arg | Gly | Lys | Thr | Thr | Lys | Thr | |
| | | 275 | | | | | 280 | | | | | 285 | | | | |
| GGA | GCG | TAC | TCT | ACC | AGG | ATA | GAG | GTG | TTG | GAA | GAG | ATA | GCG | AAT | GAG | 912 |

```
Gly Ala Tyr Ser Thr Arg Ile Glu Val Leu Glu Glu Ile Ala Asn Glu
            290                 295                 300

CAC GAG ATA GTA CCC CTC ATT CTC GAG TAC AGA AAG ATC CAG AAA CTG        960
His Glu Ile Val Pro Leu Ile Leu Glu Tyr Arg Lys Ile Gln Lys Leu
305                 310                 315                 320

AAA TCG ACC TAC ATA GAC ACC CTT CCG AAA CTT GTG AAC CCG AAA ACC       1008
Lys Ser Thr Tyr Ile Asp Thr Leu Pro Lys Leu Val Asn Pro Lys Thr
                    325                 330                 335

GGA AGA ATT CAT GCA TCT TTC CAC CAG ACG GGT ACC GCC ACT GGC AGG       1056
Gly Arg Ile His Ala Ser Phe His Gln Thr Gly Thr Ala Thr Gly Arg
                340                 345                 350

TTG AGT AGC AGT GAT CCA AAT CTT CAG AAT CTT CCG ACA AAG AGC GAA       1104
Leu Ser Ser Ser Asp Pro Asn Leu Gln Asn Leu Pro Thr Lys Ser Glu
            355                 360                 365

GAG GGA AAA GAA ATT AGA AAA GCG ATT GTG CCC CAG GAT CCA GAC TGG       1152
Glu Gly Lys Glu Ile Arg Lys Ala Ile Val Pro Gln Asp Pro Asp Trp
370                 375                 380

TGG ATC GTC AGT GCG GAT TAT TCC CAA ATA GAA CTC AGA ATC CTC GCT       1200
Trp Ile Val Ser Ala Asp Tyr Ser Gln Ile Glu Leu Arg Ile Leu Ala
385                 390                 395                 400

CAT CTC AGT GGT GAT GAG AAC CTT GTG AAG GCC TTC GAG GAG GGC ATC       1248
His Leu Ser Gly Asp Glu Asn Leu Val Lys Ala Phe Glu Glu Gly Ile
                405                 410                 415

GAT GTG CAC ACC TTG ACT GCC TCC AGG ATC TAC AAC GTA AAG CCA GAA       1296
Asp Val His Thr Leu Thr Ala Ser Arg Ile Tyr Asn Val Lys Pro Glu
            420                 425                 430

GAA GTG AAC GAA GAA ATG CGA CGG GTT GGA AAG ATG GTG AAC TTC TCT       1344
Glu Val Asn Glu Glu Met Arg Arg Val Gly Lys Met Val Asn Phe Ser
            435                 440                 445

ATA ATA TAC GGT GTC ACA CCG TAC GGT CTT TCT GTG AGA CTT GGA ATA       1392
Ile Ile Tyr Gly Val Thr Pro Tyr Gly Leu Ser Val Arg Leu Gly Ile
450                 455                 460

CCG GTT AAA GAA GCA GAA AAG ATG ATT ATC AGC TAT TTC ACA CTG TAT       1440
Pro Val Lys Glu Ala Glu Lys Met Ile Ile Ser Tyr Phe Thr Leu Tyr
465                 470                 475                 480

CCA AAG GTG CGA AGC TAC ATC CAG CAG GTT GTT GCA GAG GCA AAA GAG       1488
Pro Lys Val Arg Ser Tyr Ile Gln Gln Val Val Ala Glu Ala Lys Glu
                485                 490                 495

AAG GGC TAC GTC AGG ACT CTC TTT GGA AGA AAA AGA GAT ATT CCC CAG       1536
Lys Gly Tyr Val Arg Thr Leu Phe Gly Arg Lys Arg Asp Ile Pro Gln
                500                 505                 510

CTC ATG GCA AGG GAC AAG AAC ACC CAG TCC GAA GGC GAA AGA ATC GCA       1584
Leu Met Ala Arg Asp Lys Asn Thr Gln Ser Glu Gly Glu Arg Ile Ala
            515                 520                 525

ATA AAC ACC CCC ATT CAG GGA ACG GCG GCA GAT ATA ATA AAA TTG GCT       1632
Ile Asn Thr Pro Ile Gln Gly Thr Ala Ala Asp Ile Ile Lys Leu Ala
530                 535                 540

ATG ATA GAT ATA GAC GAG GAG CTG AGA AAA AGA AAC ATG AAA TCC AGA       1680
Met Ile Asp Ile Asp Glu Glu Leu Arg Lys Arg Asn Met Lys Ser Arg
545                 550                 555                 560

ATG ATC ATT CAG GTT CAT GAC GAA CTG GTC TTC GAG GTT CCC GAT GAG       1728
Met Ile Ile Gln Val His Asp Glu Leu Val Phe Glu Val Pro Asp Glu
                565                 570                 575

GAA AAA GAA GAA CTA GTT GAT CTG GTG AAG AAC AAA ATG ACA AAT GTG       1776
Glu Lys Glu Glu Leu Val Asp Leu Val Lys Asn Lys Met Thr Asn Val
                580                 585                 590

GTG AAA CTC TCT GTG CCT CTT GAG GTT GAC ATA AGC ATC GGA AAA AGC       1824
Val Lys Leu Ser Val Pro Leu Glu Val Asp Ile Ser Ile Gly Lys Ser
            595                 600                 605
```

```
TGG TCT TGA                                                    1833
Trp Ser
    610
```

(2) INFORMATION FOR SEQ ID NO:16:

(i) SEQUENCE CHARACTERISTICS:
      (A) LENGTH: 610 amino acids
      (B) TYPE: amino acid
      (D) TOPOLOGY: linear (ii) MOLECULE TYPE: protein (xi) SEQUENCE DESCRIPTION: SEQ ID NO:16:

```
Met Lys Glu Leu Gln Leu Tyr Glu Glu Ala Glu Pro Thr Gly Tyr Glu
 1               5                  10                  15

Ile Val Lys Asp His Lys Thr Phe Glu Asp Leu Ile Glu Lys Leu Lys
                20                  25                  30

Glu Val Pro Ser Phe Ala Leu Glu Leu Glu Thr Ser Ser Leu Asp Pro
            35                  40                  45

Phe Asn Cys Glu Ile Val Gly Ile Ser Val Ser Phe Lys Pro Lys Thr
        50                  55                  60

Ala Tyr Tyr Ile Pro Leu His His Arg Asn Ala Gln Asn Leu Asp Glu
 65                  70                  75                  80

Thr Leu Val Leu Ser Lys Leu Lys Glu Ile Leu Glu Asp Pro Ser Ser
                85                  90                  95

Lys Ile Val Gly Gln Asn Leu Lys Tyr Asp Tyr Lys Val Leu Met Val
            100                 105                 110

Lys Gly Ile Ser Pro Val Tyr Pro His Phe Asp Thr Met Ile Ala Ala
        115                 120                 125

Tyr Leu Leu Glu Pro Asn Glu Lys Lys Phe Asn Leu Glu Asp Leu Ser
130                 135                 140

Leu Lys Phe Leu Gly Tyr Lys Met Thr Ser Tyr Gln Glu Leu Met Ser
145                 150                 155                 160

Phe Ser Ser Pro Leu Phe Gly Phe Ser Phe Ala Asp Val Pro Val Asp
                165                 170                 175

Lys Ala Ala Asn Tyr Ser Cys Glu Asp Ala Asp Ile Thr Tyr Arg Leu
            180                 185                 190

Tyr Lys Ile Leu Ser Met Lys Leu His Glu Ala Glu Leu Glu Asn Val
        195                 200                 205

Phe Tyr Arg Ile Glu Met Pro Leu Val Asn Val Leu Ala Arg Met Glu
210                 215                 220

Leu Asn Gly Val Tyr Val Asp Thr Glu Phe Leu Lys Lys Leu Ser Glu
225                 230                 235                 240

Glu Tyr Gly Lys Lys Leu Glu Glu Leu Ala Glu Lys Ile Tyr Gln Ile
                245                 250                 255

Ala Gly Glu Pro Phe Asn Ile Asn Ser Pro Lys Gln Val Ser Lys Ile
            260                 265                 270

Leu Phe Glu Lys Leu Gly Ile Lys Pro Arg Gly Lys Thr Thr Lys Thr
        275                 280                 285

Gly Ala Tyr Ser Thr Arg Ile Glu Val Leu Glu Glu Ile Ala Asn Glu
290                 295                 300

His Glu Ile Val Pro Leu Ile Leu Glu Tyr Arg Lys Ile Gln Lys Leu
305                 310                 315                 320

Lys Ser Thr Tyr Ile Asp Thr Leu Pro Lys Leu Val Asn Pro Lys Thr
                325                 330                 335
```

```
Gly Arg Ile His Ala Ser Phe His Gln Thr Gly Thr Ala Thr Gly Arg
                340                 345                 350

Leu Ser Ser Ser Asp Pro Asn Leu Gln Asn Leu Pro Thr Lys Ser Glu
        355                 360                 365

Glu Gly Lys Glu Ile Arg Lys Ala Ile Val Pro Gln Asp Pro Asp Trp
    370                 375                 380

Trp Ile Val Ser Ala Asp Tyr Ser Gln Ile Glu Leu Arg Ile Leu Ala
385                 390                 395                 400

His Leu Ser Gly Asp Glu Asn Leu Val Lys Ala Phe Glu Gly Ile
                405                 410                 415

Asp Val His Thr Leu Thr Ala Ser Arg Ile Tyr Asn Val Lys Pro Glu
                420                 425                 430

Glu Val Asn Glu Glu Met Arg Arg Val Gly Lys Met Val Asn Phe Ser
            435                 440                 445

Ile Ile Tyr Gly Val Thr Pro Tyr Gly Leu Ser Val Arg Leu Gly Ile
        450                 455                 460

Pro Val Lys Glu Ala Glu Lys Met Ile Ile Ser Tyr Phe Thr Leu Tyr
465                 470                 475                 480

Pro Lys Val Arg Ser Tyr Ile Gln Gln Val Val Ala Glu Ala Lys Glu
                485                 490                 495

Lys Gly Tyr Val Arg Thr Leu Phe Gly Arg Lys Arg Asp Ile Pro Gln
            500                 505                 510

Leu Met Ala Arg Asp Lys Asn Thr Gln Ser Glu Gly Glu Arg Ile Ala
        515                 520                 525

Ile Asn Thr Pro Ile Gln Gly Thr Ala Ala Asp Ile Ile Lys Leu Ala
    530                 535                 540

Met Ile Asp Ile Asp Glu Leu Arg Lys Arg Asn Met Lys Ser Arg
545                 550                 555                 560

Met Ile Ile Gln Val His Asp Glu Leu Val Phe Glu Val Pro Asp Glu
                565                 570                 575

Glu Lys Glu Glu Leu Val Asp Leu Val Lys Asn Lys Met Thr Asn Val
            580                 585                 590

Val Lys Leu Ser Val Pro Leu Glu Val Asp Ile Ser Ile Gly Lys Ser
        595                 600                 605

Trp Ser
    610

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GACCTTGACA CGTCCTC                                                    17

(2) INFORMATION FOR SEQ ID NO:18:

(i) SEQUENCE CHARACTERISTICS:
        (A) LENGTH: 1833 base pairs
        (B) TYPE: nucleic acid
        (C) STRANDEDNESS: double
        (D) TOPOLOGY: linear (ii) MOLECULE TYPE: DNA (genomic)
```

(ix) FEATURE:
    (A) NAME/KEY: CDS
    (B) LOCATION: 1..1830

(xi) SEQUENCE DESCRIPTION: SEQ ID NO:18:

| | | | | | | | | | | | | | | | | |
|---|---|---|---|---|---|---|---|---|---|---|---|---|---|---|---|---|
| ATG | AAG | GAA | CTT | CAA | CTG | TAC | GAA | GAA | GCA | GAA | CCC | ACC | GGA | TAC | GAA | 48 |
| Met | Lys | Glu | Leu | Gln | Leu | Tyr | Glu | Glu | Ala | Glu | Pro | Thr | Gly | Tyr | Glu | |
| 1 | | | | 5 | | | | | 10 | | | | | 15 | | |
| ATC | GTG | AAG | GAT | CAT | AAG | ACC | TTC | GAA | GAT | CTC | ATC | GAA | AAG | CTG | AAG | 96 |
| Ile | Val | Lys | Asp | His | Lys | Thr | Phe | Glu | Asp | Leu | Ile | Glu | Lys | Leu | Lys | |
| | | | 20 | | | | | 25 | | | | | 30 | | | |
| GAG | GTT | CCA | TCT | TTT | GCC | CTG | GAC | CTT | GAC | ACG | TCC | TCC | CTT | GAC | CCG | 144 |
| Glu | Val | Pro | Ser | Phe | Ala | Leu | Asp | Leu | Asp | Thr | Ser | Ser | Leu | Asp | Pro | |
| | | | 35 | | | | | 40 | | | | | 45 | | | |
| TTC | AAC | TGT | GAG | ATA | GTC | GGC | ATC | TCC | GTG | TCG | TTC | AAA | CCG | AAA | ACA | 192 |
| Phe | Asn | Cys | Glu | Ile | Val | Gly | Ile | Ser | Val | Ser | Phe | Lys | Pro | Lys | Thr | |
| | 50 | | | | | 55 | | | | | 60 | | | | | |
| GCT | TAT | TAC | ATT | CCA | CTT | CAT | CAC | AGA | AAC | GCC | CAG | AAT | CTT | GAT | GAA | 240 |
| Ala | Tyr | Tyr | Ile | Pro | Leu | His | His | Arg | Asn | Ala | Gln | Asn | Leu | Asp | Glu | |
| 65 | | | | | 70 | | | | | 75 | | | | | 80 | |
| ACA | CTG | GTG | CTG | TCG | AAG | TTG | AAA | GAG | ATC | CTC | GAA | GAC | CCG | TCT | TCG | 288 |
| Thr | Leu | Val | Leu | Ser | Lys | Leu | Lys | Glu | Ile | Leu | Glu | Asp | Pro | Ser | Ser | |
| | | | | 85 | | | | | 90 | | | | | 95 | | |
| AAG | ATT | GTG | GGT | CAG | AAC | CTG | AAG | TAC | GAC | TAC | AAG | GTT | CTT | ATG | GTA | 336 |
| Lys | Ile | Val | Gly | Gln | Asn | Leu | Lys | Tyr | Asp | Tyr | Lys | Val | Leu | Met | Val | |
| | | | 100 | | | | | 105 | | | | | 110 | | | |
| AAG | GGT | ATA | TCG | CCA | GTT | TAT | CCG | CAT | TTT | GAC | ACG | ATG | ATA | GCT | GCA | 384 |
| Lys | Gly | Ile | Ser | Pro | Val | Tyr | Pro | His | Phe | Asp | Thr | Met | Ile | Ala | Ala | |
| | | | 115 | | | | | 120 | | | | | 125 | | | |
| TAT | TTG | CTG | GAG | CCA | AAC | GAG | AAA | AAA | TTC | AAT | CTC | GAA | GAT | CTG | TCT | 432 |
| Tyr | Leu | Leu | Glu | Pro | Asn | Glu | Lys | Lys | Phe | Asn | Leu | Glu | Asp | Leu | Ser | |
| | 130 | | | | | 135 | | | | | 140 | | | | | |
| TTG | AAA | TTT | CTC | GGA | TAC | AAA | ATG | ACG | TCT | TAT | CAG | GAA | CTG | ATG | TCG | 480 |
| Leu | Lys | Phe | Leu | Gly | Tyr | Lys | Met | Thr | Ser | Tyr | Gln | Glu | Leu | Met | Ser | |
| 145 | | | | | 150 | | | | | 155 | | | | | 160 | |
| TTT | TCC | TCA | CCA | CTT | TTT | GGT | TTC | AGC | TTT | GCG | GAT | GTT | CCG | GTA | GAC | 528 |
| Phe | Ser | Ser | Pro | Leu | Phe | Gly | Phe | Ser | Phe | Ala | Asp | Val | Pro | Val | Asp | |
| | | | | 165 | | | | | 170 | | | | | 175 | | |
| AAG | GCT | GCG | AAC | TAC | TCC | TGC | GAG | GAT | GCA | GAC | ATC | ACT | TAT | AGG | CTC | 576 |
| Lys | Ala | Ala | Asn | Tyr | Ser | Cys | Glu | Asp | Ala | Asp | Ile | Thr | Tyr | Arg | Leu | |
| | | | 180 | | | | | 185 | | | | | 190 | | | |
| TAC | AAG | ATA | CTC | AGC | ATG | AAG | CTC | CAT | GAA | GCG | GAA | CTT | GAG | AAC | GTC | 624 |
| Tyr | Lys | Ile | Leu | Ser | Met | Lys | Leu | His | Glu | Ala | Glu | Leu | Glu | Asn | Val | |
| | | | 195 | | | | | 200 | | | | | 205 | | | |
| TTC | TAC | AGG | ATA | GAG | ATG | CCG | CTT | GTG | AAC | GTT | CTT | GCA | CGC | ATG | GAA | 672 |
| Phe | Tyr | Arg | Ile | Glu | Met | Pro | Leu | Val | Asn | Val | Leu | Ala | Arg | Met | Glu | |
| | 210 | | | | | 215 | | | | | 220 | | | | | |
| TTG | AAC | GGG | GTG | TAT | GTG | GAC | ACA | GAA | TTC | CTG | AAA | AAG | CTC | TCG | GAG | 720 |
| Leu | Asn | Gly | Val | Tyr | Val | Asp | Thr | Glu | Phe | Leu | Lys | Lys | Leu | Ser | Glu | |
| 225 | | | | | 230 | | | | | 235 | | | | | 240 | |
| GAG | TAC | GGC | AAA | AAG | CTC | GAG | GAA | CTG | GCC | GAA | AAA | ATC | TAC | CAG | ATA | 768 |
| Glu | Tyr | Gly | Lys | Lys | Leu | Glu | Glu | Leu | Ala | Glu | Lys | Ile | Tyr | Gln | Ile | |
| | | | | 245 | | | | | 250 | | | | | 255 | | |
| GCA | GGA | GAG | CCC | TTC | AAC | ATC | AAT | TCT | CCA | AAA | CAG | GTT | TCA | AAG | ATC | 816 |
| Ala | Gly | Glu | Pro | Phe | Asn | Ile | Asn | Ser | Pro | Lys | Gln | Val | Ser | Lys | Ile | |
| | | | 260 | | | | | 265 | | | | | 270 | | | |
| CTT | TTT | GAG | AAG | CTG | GGA | ATA | AAA | CCC | CGT | GGA | AAA | ACG | ACA | AAA | ACA | 864 |
| Leu | Phe | Glu | Lys | Leu | Gly | Ile | Lys | Pro | Arg | Gly | Lys | Thr | Thr | Lys | Thr | |
| | | | 275 | | | | | 280 | | | | | 285 | | | |

```
                                                       -continued

GGA GCG TAC TCT ACC AGG ATA GAG GTG TTG GAA GAG ATA GCG AAT GAG      912
Gly Ala Tyr Ser Thr Arg Ile Glu Val Leu Glu Glu Ile Ala Asn Glu
        290                 295                 300

CAC GAG ATA GTA CCC CTC ATT CTC GAG TAC AGA AAG ATC CAG AAA CTG      960
His Glu Ile Val Pro Leu Ile Leu Glu Tyr Arg Lys Ile Gln Lys Leu
305                 310                 315                 320

AAA TCG ACC TAC ATA GAC ACC CTT CCG AAA CTT GTG AAC CCG AAA ACC     1008
Lys Ser Thr Tyr Ile Asp Thr Leu Pro Lys Leu Val Asn Pro Lys Thr
                325                 330                 335

GGA AGA ATT CAT GCA TCT TTC CAC CAG ACG GGT ACC GCC ACT GGC AGG     1056
Gly Arg Ile His Ala Ser Phe His Gln Thr Gly Thr Ala Thr Gly Arg
            340                 345                 350

TTG AGT AGC AGT GAT CCA AAT CTT CAG AAT CTT CCG ACA AAG AGC GAA     1104
Leu Ser Ser Ser Asp Pro Asn Leu Gln Asn Leu Pro Thr Lys Ser Glu
        355                 360                 365

GAG GGA AAA GAA ATT AGA AAA GCG ATT GTG CCC CAG GAT CCA GAC TGG     1152
Glu Gly Lys Glu Ile Arg Lys Ala Ile Val Pro Gln Asp Pro Asp Trp
370                 375                 380

TGG ATC GTC AGT GCG GAT TAT TCC CAA ATA GAA CTC AGA ATC CTC GCT     1200
Trp Ile Val Ser Ala Asp Tyr Ser Gln Ile Glu Leu Arg Ile Leu Ala
385                 390                 395                 400

CAT CTC AGT GGT GAT GAG AAC CTT GTG AAG GCC TTC GAG GAG GGC ATC     1248
His Leu Ser Gly Asp Glu Asn Leu Val Lys Ala Phe Glu Glu Gly Ile
                405                 410                 415

GAT GTG CAC ACC TTG ACT GCC TCC AGG ATC TAC AAC GTA AAG CCA GAA     1296
Asp Val His Thr Leu Thr Ala Ser Arg Ile Tyr Asn Val Lys Pro Glu
            420                 425                 430

GAA GTG AAC GAA GAA ATG CGA CGG GTT GGA AAG ATG GTG AAC TTC TCT     1344
Glu Val Asn Glu Glu Met Arg Arg Val Gly Lys Met Val Asn Phe Ser
        435                 440                 445

ATA ATA TAC GGT GTC ACA CCG TAC GGT CTT TCT GTG AGA CTT GGA ATA     1392
Ile Ile Tyr Gly Val Thr Pro Tyr Gly Leu Ser Val Arg Leu Gly Ile
450                 455                 460

CCG GTT AAA GAA GCA GAA AAG ATG ATT ATC AGC TAT TTC ACA CTG TAT     1440
Pro Val Lys Glu Ala Glu Lys Met Ile Ile Ser Tyr Phe Thr Leu Tyr
465                 470                 475                 480

CCA AAG GTG CGA AGC TAC ATC CAG CAG GTT GTT GCA GAG GCA AAA GAG     1488
Pro Lys Val Arg Ser Tyr Ile Gln Gln Val Val Ala Glu Ala Lys Glu
                485                 490                 495

AAG GGC TAC GTC AGG ACT CTC TTT GGA AGA AAA AGA GAT ATT CCC CAG     1536
Lys Gly Tyr Val Arg Thr Leu Phe Gly Arg Lys Arg Asp Ile Pro Gln
            500                 505                 510

CTC ATG GCA AGG GAC AAG AAC ACC CAG TCC GAA GGC GAA AGA ATC GCA     1584
Leu Met Ala Arg Asp Lys Asn Thr Gln Ser Glu Gly Glu Arg Ile Ala
        515                 520                 525

ATA AAC ACC CCC ATT CAG GGA ACG GCG GCA GAT ATA ATA AAA TTG GCT     1632
Ile Asn Thr Pro Ile Gln Gly Thr Ala Ala Asp Ile Ile Lys Leu Ala
530                 535                 540

ATG ATA GAT ATA GAC GAG GAG CTG AGA AAA AGA AAC ATG AAA TCC AGA     1680
Met Ile Asp Ile Asp Glu Glu Leu Arg Lys Arg Asn Met Lys Ser Arg
545                 550                 555                 560

ATG ATC ATT CAG GTT CAT GAC GAA CTG GTC TTC GAG GTT CCC GAT GAG     1728
Met Ile Ile Gln Val His Asp Glu Leu Val Phe Glu Val Pro Asp Glu
                565                 570                 575

GAA AAA GAA GAA CTA GTT GAT CTG GTG AAG AAC AAA ATG ACA AAT GTG     1776
Glu Lys Glu Glu Leu Val Asp Leu Val Lys Asn Lys Met Thr Asn Val
            580                 585                 590

GTG AAA CTC TCT GTG CCT CTT GAG GTT GAC ATA AGC ATC GGA AAA AGC     1824
Val Lys Leu Ser Val Pro Leu Glu Val Asp Ile Ser Ile Gly Lys Ser
        595                 600                 605
```

```
TGG TCT TGA                                                             1833
Trp Ser
    610
```

(2) INFORMATION FOR SEQ ID NO:19:

(i) SEQUENCE CHARACTERISTICS:
       (A) LENGTH: 610 amino acids
       (B) TYPE: amino acid
       (D) TOPOLOGY: linear (ii) MOLECULE TYPE: protein (xi) SEQUENCE DESCRIPTION: SEQ ID NO:19:

```
Met Lys Glu Leu Gln Leu Tyr Glu Glu Ala Glu Pro Thr Gly Tyr Glu
 1               5                  10                  15

Ile Val Lys Asp His Lys Thr Phe Glu Asp Leu Ile Glu Lys Leu Lys
                20                  25                  30

Glu Val Pro Ser Phe Ala Leu Asp Leu Asp Thr Ser Ser Leu Asp Pro
            35                  40                  45

Phe Asn Cys Glu Ile Val Gly Ile Ser Val Ser Phe Lys Pro Lys Thr
        50                  55                  60

Ala Tyr Tyr Ile Pro Leu His His Arg Asn Ala Gln Asn Leu Asp Glu
65                  70                  75                  80

Thr Leu Val Leu Ser Lys Leu Lys Glu Ile Leu Glu Asp Pro Ser Ser
                85                  90                  95

Lys Ile Val Gly Gln Asn Leu Lys Tyr Asp Tyr Lys Val Leu Met Val
            100                 105                 110

Lys Gly Ile Ser Pro Val Tyr Pro His Phe Asp Thr Met Ile Ala Ala
        115                 120                 125

Tyr Leu Leu Glu Pro Asn Glu Lys Lys Phe Asn Leu Glu Asp Leu Ser
130                 135                 140

Leu Lys Phe Leu Gly Tyr Lys Met Thr Ser Tyr Gln Glu Leu Met Ser
145                 150                 155                 160

Phe Ser Ser Pro Leu Phe Gly Phe Ser Phe Ala Asp Val Pro Val Asp
                165                 170                 175

Lys Ala Ala Asn Tyr Ser Cys Glu Asp Ala Asp Ile Thr Tyr Arg Leu
            180                 185                 190

Tyr Lys Ile Leu Ser Met Lys Leu His Glu Ala Glu Leu Glu Asn Val
        195                 200                 205

Phe Tyr Arg Ile Glu Met Pro Leu Val Asn Val Leu Ala Arg Met Glu
    210                 215                 220

Leu Asn Gly Val Tyr Val Asp Thr Glu Phe Leu Lys Lys Leu Ser Glu
225                 230                 235                 240

Glu Tyr Gly Lys Lys Leu Glu Glu Leu Ala Glu Lys Ile Tyr Gln Ile
                245                 250                 255

Ala Gly Glu Pro Phe Asn Ile Asn Ser Pro Lys Gln Val Ser Lys Ile
            260                 265                 270

Leu Phe Glu Lys Leu Gly Ile Lys Pro Arg Gly Lys Thr Thr Lys Thr
        275                 280                 285

Gly Ala Tyr Ser Thr Arg Ile Glu Val Leu Glu Glu Ile Ala Asn Glu
    290                 295                 300

His Glu Ile Val Pro Leu Ile Leu Glu Tyr Arg Lys Ile Gln Lys Leu
305                 310                 315                 320

Lys Ser Thr Tyr Ile Asp Thr Leu Pro Lys Leu Val Asn Pro Lys Thr
                325                 330                 335
```

```
Gly Arg Ile His Ala Ser Phe His Gln Thr Gly Thr Ala Thr Gly Arg
            340                 345                 350

Leu Ser Ser Ser Asp Pro Asn Leu Gln Asn Leu Pro Thr Lys Ser Glu
            355                 360                 365

Glu Gly Lys Glu Ile Arg Lys Ala Ile Val Pro Gln Asp Pro Asp Trp
            370                 375                 380

Trp Ile Val Ser Ala Asp Tyr Ser Gln Ile Glu Leu Arg Ile Leu Ala
385                 390                 395                 400

His Leu Ser Gly Asp Glu Asn Leu Val Lys Ala Phe Glu Glu Gly Ile
                405                 410                 415

Asp Val His Thr Leu Thr Ala Ser Arg Ile Tyr Asn Val Lys Pro Glu
            420                 425                 430

Glu Val Asn Glu Glu Met Arg Arg Val Gly Lys Met Val Asn Phe Ser
            435                 440                 445

Ile Ile Tyr Gly Val Thr Pro Tyr Gly Leu Ser Val Arg Leu Gly Ile
            450                 455                 460

Pro Val Lys Glu Ala Glu Lys Met Ile Ile Ser Tyr Phe Thr Leu Tyr
465                 470                 475                 480

Pro Lys Val Arg Ser Tyr Ile Gln Gln Val Val Ala Glu Ala Lys Glu
                485                 490                 495

Lys Gly Tyr Val Arg Thr Leu Phe Gly Arg Lys Arg Asp Ile Pro Gln
            500                 505                 510

Leu Met Ala Arg Asp Lys Asn Thr Gln Ser Glu Gly Glu Arg Ile Ala
            515                 520                 525

Ile Asn Thr Pro Ile Gln Gly Thr Ala Ala Asp Ile Ile Lys Leu Ala
            530                 535                 540

Met Ile Asp Ile Asp Glu Glu Leu Arg Lys Arg Asn Met Lys Ser Arg
545                 550                 555                 560

Met Ile Ile Gln Val His Asp Glu Leu Val Phe Glu Val Pro Asp Glu
                565                 570                 575

Glu Lys Glu Glu Leu Val Asp Leu Val Lys Asn Lys Met Thr Asn Val
            580                 585                 590

Val Lys Leu Ser Val Pro Leu Glu Val Asp Ile Ser Ile Gly Lys Ser
            595                 600                 605

Trp Ser
    610

(2) INFORMATION FOR SEQ ID NO:20:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TAAGTGATAT CTGCATCCTC GCAGGAGAAG TTCGCAGCC                              39

(2) INFORMATION FOR SEQ ID NO:21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear
```

-continued (ii) MOLECULE TYPE: DNA (genomic)

(xi) SEQUENCE DESCRIPTION: SEQ ID NO:21:

ACAAGGCTGC GAACTTCTCC TGCGAGGATG CAGATATCA          39

(2) INFORMATION FOR SEQ ID NO:22:

(i) SEQUENCE CHARACTERISTICS:
      (A) LENGTH: 1833 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 1..1830

(xi) SEQUENCE DESCRIPTION: SEQ ID NO:22:

```
ATG AAG GAA CTT CAA CTG TAC GAA GAA GCA GAA CCC ACC GGA TAC GAA         48
Met Lys Glu Leu Gln Leu Tyr Glu Glu Ala Glu Pro Thr Gly Tyr Glu
 1               5                  10                  15

ATC GTG AAG GAT CAT AAG ACC TTC GAA GAT CTC ATC GAA AAG CTG AAG         96
Ile Val Lys Asp His Lys Thr Phe Glu Asp Leu Ile Glu Lys Leu Lys
                20                  25                  30

GAG GTT CCA TCT TTT GCC CTG GAC CTT GAA ACG TCC TCC CTT GAC CCG        144
Glu Val Pro Ser Phe Ala Leu Asp Leu Glu Thr Ser Ser Leu Asp Pro
            35                  40                  45

TTC AAC TGT GAG ATA GTC GGC ATC TCC GTG TCG TTC AAA CCG AAA ACA        192
Phe Asn Cys Glu Ile Val Gly Ile Ser Val Ser Phe Lys Pro Lys Thr
        50                  55                  60

GCT TAT TAC ATT CCA CTT CAT CAC AGA AAC GCC CAG AAT CTT GAT GAA        240
Ala Tyr Tyr Ile Pro Leu His His Arg Asn Ala Gln Asn Leu Asp Glu
 65                  70                  75                  80

ACA CTG GTG CTG TCG AAG TTG AAA GAG ATC CTC GAA GAC CCG TCT TCG        288
Thr Leu Val Leu Ser Lys Leu Lys Glu Ile Leu Glu Asp Pro Ser Ser
                85                  90                  95

AAG ATT GTG GGT CAG AAC CTG AAG TAC GAC TAC AAG GTT CTT ATG GTA        336
Lys Ile Val Gly Gln Asn Leu Lys Tyr Asp Tyr Lys Val Leu Met Val
                100                 105                 110

AAG GGT ATA TCG CCA GTT TAT CCG CAT TTT GAC ACG ATG ATA GCT GCA        384
Lys Gly Ile Ser Pro Val Tyr Pro His Phe Asp Thr Met Ile Ala Ala
            115                 120                 125

TAT TTG CTG GAG CCA AAC GAG AAA AAA TTC AAT CTC GAA GAT CTG TCT        432
Tyr Leu Leu Glu Pro Asn Glu Lys Lys Phe Asn Leu Glu Asp Leu Ser
        130                 135                 140

TTG AAA TTT CTC GGA TAC AAA ATG ACG TCT TAT CAG GAA CTG ATG TCG        480
Leu Lys Phe Leu Gly Tyr Lys Met Thr Ser Tyr Gln Glu Leu Met Ser
145                 150                 155                 160

TTT TCC TCA CCA CTT TTT GGT TTC AGC TTT GCG GAT GTT CCG GTA GAC        528
Phe Ser Ser Pro Leu Phe Gly Phe Ser Phe Ala Asp Val Pro Val Asp
                165                 170                 175

AAG GCT GCG AAC TTC TCC TGC GAG GAT GCA GAT ATC ACT TAT AGG CTC        576
Lys Ala Ala Asn Phe Ser Cys Glu Asp Ala Asp Ile Thr Tyr Arg Leu
                180                 185                 190

TAC AAG ATA CTC AGC ATG AAG CTC CAT GAA GCG GAA CTT GAG AAC GTC        624
Tyr Lys Ile Leu Ser Met Lys Leu His Glu Ala Glu Leu Glu Asn Val
            195                 200                 205

TTC TAC AGG ATA GAG ATG CCG CTT GTG AAC GTT CTT GCA CGC ATG GAA        672
Phe Tyr Arg Ile Glu Met Pro Leu Val Asn Val Leu Ala Arg Met Glu
        210                 215                 220
```

```
TTG AAC GGG GTG TAT GTG GAC ACA GAA TTC CTG AAA AAG CTC TCG GAG      720
Leu Asn Gly Val Tyr Val Asp Thr Glu Phe Leu Lys Lys Leu Ser Glu
225                 230                 235                 240

GAG TAC GGC AAA AAG CTC GAG GAA CTG GCC GAA AAA ATC TAC CAG ATA      768
Glu Tyr Gly Lys Lys Leu Glu Glu Leu Ala Glu Lys Ile Tyr Gln Ile
                245                 250                 255

GCA GGA GAG CCC TTC AAC ATC AAT TCT CCA AAA CAG GTT TCA AAG ATC      816
Ala Gly Glu Pro Phe Asn Ile Asn Ser Pro Lys Gln Val Ser Lys Ile
            260                 265                 270

CTT TTT GAG AAG CTG GGA ATA AAA CCC CGT GGA AAA ACG ACA AAA ACA      864
Leu Phe Glu Lys Leu Gly Ile Lys Pro Arg Gly Lys Thr Thr Lys Thr
        275                 280                 285

GGA GCG TAC TCT ACC AGG ATA GAG GTG TTG GAA GAG ATA GCG AAT GAG      912
Gly Ala Tyr Ser Thr Arg Ile Glu Val Leu Glu Glu Ile Ala Asn Glu
290                 295                 300

CAC GAG ATA GTA CCC CTC ATT CTC GAG TAC AGA AAG ATC CAG AAA CTG      960
His Glu Ile Val Pro Leu Ile Leu Glu Tyr Arg Lys Ile Gln Lys Leu
305                 310                 315                 320

AAA TCG ACC TAC ATA GAC ACC CTT CCG AAA CTT GTG AAC CCG AAA ACC     1008
Lys Ser Thr Tyr Ile Asp Thr Leu Pro Lys Leu Val Asn Pro Lys Thr
                325                 330                 335

GGA AGA ATT CAT GCA TCT TTC CAC CAG ACG GGT ACC GCC ACT GGC AGG     1056
Gly Arg Ile His Ala Ser Phe His Gln Thr Gly Thr Ala Thr Gly Arg
            340                 345                 350

TTG AGT AGC AGT GAT CCA AAT CTT CAG AAT CTT CCG ACA AAG AGC GAA     1104
Leu Ser Ser Ser Asp Pro Asn Leu Gln Asn Leu Pro Thr Lys Ser Glu
        355                 360                 365

GAG GGA AAA GAA ATT AGA AAA GCG ATT GTG CCC CAG GAT CCA GAC TGG     1152
Glu Gly Lys Glu Ile Arg Lys Ala Ile Val Pro Gln Asp Pro Asp Trp
370                 375                 380

TGG ATC GTC AGT GCG GAT TAT TCC CAA ATA GAA CTC AGA ATC CTC GCT     1200
Trp Ile Val Ser Ala Asp Tyr Ser Gln Ile Glu Leu Arg Ile Leu Ala
385                 390                 395                 400

CAT CTC AGT GGT GAT GAG AAC CTT GTG AAG GCC TTC GAG GAG GGC ATC     1248
His Leu Ser Gly Asp Glu Asn Leu Val Lys Ala Phe Glu Glu Gly Ile
                405                 410                 415

GAT GTG CAC ACC TTG ACT GCC TCC AGG ATC TAC AAC GTA AAG CCA GAA     1296
Asp Val His Thr Leu Thr Ala Ser Arg Ile Tyr Asn Val Lys Pro Glu
            420                 425                 430

GAA GTG AAC GAA GAA ATG CGA CGG GTT GGA AAG ATG GTG AAC TTC TCT     1344
Glu Val Asn Glu Glu Met Arg Arg Val Gly Lys Met Val Asn Phe Ser
        435                 440                 445

ATA ATA TAC GGT GTC ACA CCG TAC GGT CTT TCT GTG AGA CTT GGA ATA     1392
Ile Ile Tyr Gly Val Thr Pro Tyr Gly Leu Ser Val Arg Leu Gly Ile
450                 455                 460

CCG GTT AAA GAA GCA GAA AAG ATG ATT ATC AGC TAT TTC ACA CTG TAT     1440
Pro Val Lys Glu Ala Glu Lys Met Ile Ile Ser Tyr Phe Thr Leu Tyr
465                 470                 475                 480

CCA AAG GTG CGA AGC TAC ATC CAG CAG GTT GTT GCA GAG GCA AAA GAG     1488
Pro Lys Val Arg Ser Tyr Ile Gln Gln Val Val Ala Glu Ala Lys Glu
                485                 490                 495

AAG GGC TAC GTC AGG ACT CTC TTT GGA AGA AAA AGA GAT ATT CCC CAG     1536
Lys Gly Tyr Val Arg Thr Leu Phe Gly Arg Lys Arg Asp Ile Pro Gln
            500                 505                 510

CTC ATG GCA AGG GAC AAG AAC ACC CAG TCC GAA GGC GAA AGA ATC GCA     1584
Leu Met Ala Arg Asp Lys Asn Thr Gln Ser Glu Gly Glu Arg Ile Ala
        515                 520                 525

ATA AAC ACC CCC ATT CAG GGA ACG GCG GCA GAT ATA ATA AAA TTG GCT     1632
Ile Asn Thr Pro Ile Gln Gly Thr Ala Ala Asp Ile Ile Lys Leu Ala
530                 535                 540
```

```
ATG ATA GAT ATA GAC GAG GAG CTG AGA AAA AGA AAC ATG AAA TCC AGA      1680
Met Ile Asp Ile Asp Glu Glu Leu Arg Lys Arg Asn Met Lys Ser Arg
545                 550                 555                 560

ATG ATC ATT CAG GTT CAT GAC GAA CTG GTC TTC GAG GTT CCC GAT GAG      1728
Met Ile Ile Gln Val His Asp Glu Leu Val Phe Glu Val Pro Asp Glu
                565                 570                 575

GAA AAA GAA GAA CTA GTT GAT CTG GTG AAG AAC AAA ATG ACA AAT GTG      1776
Glu Lys Glu Glu Leu Val Asp Leu Val Lys Asn Lys Met Thr Asn Val
            580                 585                 590

GTG AAA CTC TCT GTG CCT CTT GAG GTT GAC ATA AGC ATC GGA AAA AGC      1824
Val Lys Leu Ser Val Pro Leu Glu Val Asp Ile Ser Ile Gly Lys Ser
        595                 600                 605

TGG TCT TGA                                                          1833
Trp Ser
    610

(2) INFORMATION FOR SEQ ID NO:23:

(i) SEQUENCE CHARACTERISTICS:
        (A) LENGTH: 610 amino acids
        (B) TYPE: amino acid
        (D) TOPOLOGY: linear (ii) MOLECULE TYPE: protein (xi) SEQUENCE DESCRIPTION: SEQ ID NO:23:

Met Lys Glu Leu Gln Leu Tyr Glu Glu Ala Glu Pro Thr Gly Tyr Glu
1               5                   10                  15

Ile Val Lys Asp His Lys Thr Phe Glu Asp Leu Ile Glu Lys Leu Lys
            20                  25                  30

Glu Val Pro Ser Phe Ala Leu Asp Leu Glu Thr Ser Ser Leu Asp Pro
        35                  40                  45

Phe Asn Cys Glu Ile Val Gly Ile Ser Val Ser Phe Lys Pro Lys Thr
    50                  55                  60

Ala Tyr Tyr Ile Pro Leu His His Arg Asn Ala Gln Asn Leu Asp Glu
65                  70                  75                  80

Thr Leu Val Leu Ser Lys Leu Lys Glu Ile Leu Glu Asp Pro Ser Ser
                85                  90                  95

Lys Ile Val Gly Gln Asn Leu Lys Tyr Asp Tyr Lys Val Leu Met Val
            100                 105                 110

Lys Gly Ile Ser Pro Val Tyr Pro His Phe Asp Thr Met Ile Ala Ala
        115                 120                 125

Tyr Leu Leu Glu Pro Asn Glu Lys Lys Phe Asn Leu Glu Asp Leu Ser
    130                 135                 140

Leu Lys Phe Leu Gly Tyr Lys Met Thr Ser Tyr Gln Glu Leu Met Ser
145                 150                 155                 160

Phe Ser Ser Pro Leu Phe Gly Phe Ser Phe Ala Asp Val Pro Val Asp
                165                 170                 175

Lys Ala Ala Asn Phe Ser Cys Glu Asp Ala Asp Ile Thr Tyr Arg Leu
            180                 185                 190

Tyr Lys Ile Leu Ser Met Lys Leu His Glu Ala Glu Leu Glu Asn Val
        195                 200                 205

Phe Tyr Arg Ile Glu Met Pro Leu Val Asn Val Leu Ala Arg Met Glu
    210                 215                 220

Leu Asn Gly Val Tyr Val Asp Thr Glu Phe Leu Lys Lys Leu Ser Glu
225                 230                 235                 240

Glu Tyr Gly Lys Lys Leu Glu Glu Leu Ala Glu Lys Ile Tyr Gln Ile
```

```
                    245                 250                 255
Ala Gly Glu Pro Phe Asn Ile Asn Ser Pro Lys Gln Val Ser Lys Ile
                260                 265                 270

Leu Phe Glu Lys Leu Gly Ile Lys Pro Arg Gly Lys Thr Thr Lys Thr
            275                 280                 285

Gly Ala Tyr Ser Thr Arg Ile Glu Val Leu Glu Ile Ala Asn Glu
        290                 295                 300

His Glu Ile Val Pro Leu Ile Leu Glu Tyr Arg Lys Ile Gln Lys Leu
305                 310                 315                 320

Lys Ser Thr Tyr Ile Asp Thr Leu Pro Lys Leu Val Asn Pro Lys Thr
                325                 330                 335

Gly Arg Ile His Ala Ser Phe His Gln Thr Gly Thr Ala Thr Gly Arg
            340                 345                 350

Leu Ser Ser Ser Asp Pro Asn Leu Gln Asn Leu Pro Thr Lys Ser Glu
        355                 360                 365

Glu Gly Lys Glu Ile Arg Lys Ala Ile Val Pro Gln Asp Pro Asp Trp
    370                 375                 380

Trp Ile Val Ser Ala Asp Tyr Ser Gln Ile Glu Leu Arg Ile Leu Ala
385                 390                 395                 400

His Leu Ser Gly Asp Glu Asn Leu Val Lys Ala Phe Glu Gly Ile
                405                 410                 415

Asp Val His Thr Leu Thr Ala Ser Arg Ile Tyr Asn Val Lys Pro Glu
            420                 425                 430

Glu Val Asn Glu Glu Met Arg Arg Val Gly Lys Met Val Asn Phe Ser
        435                 440                 445

Ile Ile Tyr Gly Val Thr Pro Tyr Gly Leu Ser Val Arg Leu Gly Ile
    450                 455                 460

Pro Val Lys Glu Ala Glu Lys Met Ile Ile Ser Tyr Phe Thr Leu Tyr
465                 470                 475                 480

Pro Lys Val Arg Ser Tyr Ile Gln Gln Val Val Ala Glu Ala Lys Glu
                485                 490                 495

Lys Gly Tyr Val Arg Thr Leu Phe Gly Arg Lys Arg Asp Ile Pro Gln
            500                 505                 510

Leu Met Ala Arg Asp Lys Asn Thr Gln Ser Glu Gly Glu Arg Ile Ala
        515                 520                 525

Ile Asn Thr Pro Ile Gln Gly Thr Ala Ala Asp Ile Ile Lys Leu Ala
    530                 535                 540

Met Ile Asp Ile Asp Glu Leu Arg Lys Arg Asn Met Lys Ser Arg
545                 550                 555                 560

Met Ile Ile Gln Val His Asp Glu Leu Val Phe Glu Val Pro Asp Glu
                565                 570                 575

Glu Lys Glu Glu Leu Val Asp Leu Val Lys Asn Lys Met Thr Asn Val
            580                 585                 590

Val Lys Leu Ser Val Pro Leu Glu Val Asp Ile Ser Ile Gly Lys Ser
        595                 600                 605

Trp Ser
    610
```

(2) INFORMATION FOR SEQ ID NO:24:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

ACTCCTGCGA GAATGCTGAC ATCACTTATA GG                                  32

(2) INFORMATION FOR SEQ ID NO:25:

(i) SEQUENCE CHARACTERISTICS:
         (A) LENGTH: 1833 base pairs
         (B) TYPE: nucleic acid
         (C) STRANDEDNESS: double
         (D) TOPOLOGY: linear (ii) MOLECULE TYPE: DNA (genomic)

(ix) FEATURE:
         (A) NAME/KEY: CDS
         (B) LOCATION: 1..1830

(xi) SEQUENCE DESCRIPTION: SEQ ID NO:25:

```
ATG AAG GAA CTT CAA CTG TAC GAA GAA GCA GAA CCC ACC GGA TAC GAA         48
Met Lys Glu Leu Gln Leu Tyr Glu Glu Ala Glu Pro Thr Gly Tyr Glu
  1               5                  10                  15

ATC GTG AAG GAT CAT AAG ACC TTC GAA GAT CTC ATC GAA AAG CTG AAG         96
Ile Val Lys Asp His Lys Thr Phe Glu Asp Leu Ile Glu Lys Leu Lys
             20                  25                  30

GAG GTT CCA TCT TTT GCC CTG GAC CTT GAA ACG TCC TCC CTT GAC CCG        144
Glu Val Pro Ser Phe Ala Leu Asp Leu Glu Thr Ser Ser Leu Asp Pro
         35                  40                  45

TTC AAC TGT GAG ATA GTC GGC ATC TCC GTG TCG TTC AAA CCG AAA ACA        192
Phe Asn Cys Glu Ile Val Gly Ile Ser Val Ser Phe Lys Pro Lys Thr
     50                  55                  60

GCT TAT TAC ATT CCA CTT CAT CAC AGA AAC GCC CAG AAT CTT GAT GAA        240
Ala Tyr Tyr Ile Pro Leu His His Arg Asn Ala Gln Asn Leu Asp Glu
 65                  70                  75                  80

ACA CTG GTG CTG TCG AAG TTG AAA GAG ATC CTC GAA GAC CCG TCT TCG        288
Thr Leu Val Leu Ser Lys Leu Lys Glu Ile Leu Glu Asp Pro Ser Ser
                 85                  90                  95

AAG ATT GTG GGT CAG AAC CTG AAG TAC GAC TAC AAG GTT CTT ATG GTA        336
Lys Ile Val Gly Gln Asn Leu Lys Tyr Asp Tyr Lys Val Leu Met Val
            100                 105                 110

AAG GGT ATA TCG CCA GTT TAT CCG CAT TTT GAC ACG ATG ATA GCT GCA        384
Lys Gly Ile Ser Pro Val Tyr Pro His Phe Asp Thr Met Ile Ala Ala
        115                 120                 125

TAT TTG CTG GAG CCA AAC GAG AAA AAA TTC AAT CTC GAA GAT CTG TCT        432
Tyr Leu Leu Glu Pro Asn Glu Lys Lys Phe Asn Leu Glu Asp Leu Ser
    130                 135                 140

TTG AAA TTT CTC GGA TAC AAA ATG ACG TCT TAT CAG GAA CTG ATG TCG        480
Leu Lys Phe Leu Gly Tyr Lys Met Thr Ser Tyr Gln Glu Leu Met Ser
145                 150                 155                 160

TTT TCC TCA CCA CTT TTT GGT TTC AGC TTT GCG GAT GTT CCG GTA GAC        528
Phe Ser Ser Pro Leu Phe Gly Phe Ser Phe Ala Asp Val Pro Val Asp
                165                 170                 175

AAG GCT GCG AAC TAC TCC TGC GAG AAT GCT GAC ATC ACT TAT AGG CTC        576
Lys Ala Ala Asn Tyr Ser Cys Glu Asn Ala Asp Ile Thr Tyr Arg Leu
            180                 185                 190

TAC AAG ATA CTC AGC ATG AAG CTC CAT GAA GCG GAA CTT GAG AAC GTC        624
Tyr Lys Ile Leu Ser Met Lys Leu His Glu Ala Glu Leu Glu Asn Val
        195                 200                 205

TTC TAC AGG ATA GAG ATG CCG CTT GTG AAC GTT CTT GCA CGC ATG GAA        672
Phe Tyr Arg Ile Glu Met Pro Leu Val Asn Val Leu Ala Arg Met Glu
    210                 215                 220
```

-continued

| | |
|---|---|
| TTG AAC GGG GTG TAT GTG GAC ACA GAA TTC CTG AAA AAG CTC TCG GAG<br>Leu Asn Gly Val Tyr Val Asp Thr Glu Phe Leu Lys Lys Leu Ser Glu<br>225                                230                              235                             240 | 720 |
| GAG TAC GGC AAA AAG CTC GAG GAA CTG GCC GAA AAA ATC TAC CAG ATA<br>Glu Tyr Gly Lys Lys Leu Glu Glu Leu Ala Glu Lys Ile Tyr Gln Ile<br>                          245                              250                              255 | 768 |
| GCA GGA GAG CCC TTC AAC ATC AAT TCT CCA AAA CAG GTT TCA AAG ATC<br>Ala Gly Glu Pro Phe Asn Ile Asn Ser Pro Lys Gln Val Ser Lys Ile<br>                    260                              265                              270 | 816 |
| CTT TTT GAG AAG CTG GGA ATA AAA CCC CGT GGA AAA ACG ACA AAA ACA<br>Leu Phe Glu Lys Leu Gly Ile Lys Pro Arg Gly Lys Thr Thr Lys Thr<br>         275                              280                              285 | 864 |
| GGA GCG TAC TCT ACC AGG ATA GAG GTG TTG GAA GAG ATA GCG AAT GAG<br>Gly Ala Tyr Ser Thr Arg Ile Glu Val Leu Glu Glu Ile Ala Asn Glu<br>290                                295                              300 | 912 |
| CAC GAG ATA GTA CCC CTC ATT CTC GAG TAC AGA AAG ATC CAG AAA CTG<br>His Glu Ile Val Pro Leu Ile Leu Glu Tyr Arg Lys Ile Gln Lys Leu<br>305                              310                              315                             320 | 960 |
| AAA TCG ACC TAC ATA GAC ACC CTT CCG AAA CTT GTG AAC CCG AAA ACC<br>Lys Ser Thr Tyr Ile Asp Thr Leu Pro Lys Leu Val Asn Pro Lys Thr<br>                          325                              330                             335 | 1008 |
| GGA AGA ATT CAT GCA TCT TTC CAC CAG ACG GGT ACC GCC ACT GGC AGG<br>Gly Arg Ile His Ala Ser Phe His Gln Thr Gly Thr Ala Thr Gly Arg<br>         340                              345                              350 | 1056 |
| TTG AGT AGC AGT GAT CCA AAT CTT CAG AAT CTT CCG ACA AAG AGC GAA<br>Leu Ser Ser Ser Asp Pro Asn Leu Gln Asn Leu Pro Thr Lys Ser Glu<br>355                                360                              365 | 1104 |
| GAG GGA AAA GAA ATT AGA AAA GCG ATT GTG CCC CAG GAT CCA GAC TGG<br>Glu Gly Lys Glu Ile Arg Lys Ala Ile Val Pro Gln Asp Pro Asp Trp<br>                    370                              375                              380 | 1152 |
| TGG ATC GTC AGT GCG GAT TAT TCC CAA ATA GAA CTC AGA ATC CTC GCT<br>Trp Ile Val Ser Ala Asp Tyr Ser Gln Ile Glu Leu Arg Ile Leu Ala<br>385                                390                              395                             400 | 1200 |
| CAT CTC AGT GGT GAT GAG AAC CTT GTG AAG GCC TTC GAG GAG GGC ATC<br>His Leu Ser Gly Asp Glu Asn Leu Val Lys Ala Phe Glu Glu Gly Ile<br>                          405                              410                             415 | 1248 |
| GAT GTG CAC ACC TTG ACT GCC TCC AGG ATC TAC AAC GTA AAG CCA GAA<br>Asp Val His Thr Leu Thr Ala Ser Arg Ile Tyr Asn Val Lys Pro Glu<br>         420                              425                              430 | 1296 |
| GAA GTG AAC GAA GAA ATG CGA CGG GTT GGA AAG ATG GTG AAC TTC TCT<br>Glu Val Asn Glu Glu Met Arg Arg Val Gly Lys Met Val Asn Phe Ser<br>435                                440                              445 | 1344 |
| ATA ATA TAC GGT GTC ACA CCG TAC GGT CTT TCT GTG AGA CTT GGA ATA<br>Ile Ile Tyr Gly Val Thr Pro Tyr Gly Leu Ser Val Arg Leu Gly Ile<br>                    450                              455                              460 | 1392 |
| CCG GTT AAA GAA GCA GAA AAG ATG ATT ATC AGC TAT TTC ACA CTG TAT<br>Pro Val Lys Glu Ala Glu Lys Met Ile Ile Ser Tyr Phe Thr Leu Tyr<br>465                                470                              475                             480 | 1440 |
| CCA AAG GTG CGA AGC TAC ATC CAG CAG GTT GTT GCA GAG GCA AAA GAG<br>Pro Lys Val Arg Ser Tyr Ile Gln Gln Val Val Ala Glu Ala Lys Glu<br>                          485                              490                             495 | 1488 |
| AAG GGC TAC GTC AGG ACT CTC TTT GGA AGA AAA AGA GAT ATT CCC CAG<br>Lys Gly Tyr Val Arg Thr Leu Phe Gly Arg Lys Arg Asp Ile Pro Gln<br>         500                              505                              510 | 1536 |
| CTC ATG GCA AGG GAC AAG AAC ACC CAG TCC GAA GGC GAA AGA ATC GCA<br>Leu Met Ala Arg Asp Lys Asn Thr Gln Ser Glu Gly Glu Arg Ile Ala<br>515                                520                              525 | 1584 |
| ATA AAC ACC CCC ATT CAG GGA ACG GCG GCA GAT ATA ATA AAA TTG GCT<br>Ile Asn Thr Pro Ile Gln Gly Thr Ala Ala Asp Ile Ile Lys Leu Ala | 1632 |

```
              530                 535                 540
ATG ATA GAT ATA GAC GAG GAG CTG AGA AAA AGA AAC ATG AAA TCC AGA      1680
Met Ile Asp Ile Asp Glu Glu Leu Arg Lys Arg Asn Met Lys Ser Arg
545                 550                 555                 560

ATG ATC ATT CAG GTT CAT GAC GAA CTG GTC TTC GAG GTT CCC GAT GAG      1728
Met Ile Ile Gln Val His Asp Glu Leu Val Phe Glu Val Pro Asp Glu
                    565                 570                 575

GAA AAA GAA GAA CTA GTT GAT CTG GTG AAG AAC AAA ATG ACA AAT GTG      1776
Glu Lys Glu Glu Leu Val Asp Leu Val Lys Asn Lys Met Thr Asn Val
                580                 585                 590

GTG AAA CTC TCT GTG CCT CTT GAG GTT GAC ATA AGC ATC GGA AAA AGC      1824
Val Lys Leu Ser Val Pro Leu Glu Val Asp Ile Ser Ile Gly Lys Ser
            595                 600                 605

TGG TCT TGA                                                          1833
Trp Ser
    610
```

(2) INFORMATION FOR SEQ ID NO:26:

(i) SEQUENCE CHARACTERISTICS:
        (A) LENGTH: 610 amino acids
        (B) TYPE: amino acid
        (D) TOPOLOGY: linear (ii) MOLECULE TYPE: protein (xi) SEQUENCE DESCRIPTION: SEQ ID NO:26:

```
Met Lys Glu Leu Gln Leu Tyr Glu Glu Ala Glu Pro Thr Gly Tyr Glu
 1               5                  10                  15

Ile Val Lys Asp His Lys Thr Phe Glu Asp Leu Ile Glu Lys Leu Lys
                20                  25                  30

Glu Val Pro Ser Phe Ala Leu Asp Leu Glu Thr Ser Ser Leu Asp Pro
            35                  40                  45

Phe Asn Cys Glu Ile Val Gly Ile Ser Val Ser Phe Lys Pro Lys Thr
        50                  55                  60

Ala Tyr Tyr Ile Pro Leu His His Arg Asn Ala Gln Asn Leu Asp Glu
 65                  70                  75                  80

Thr Leu Val Leu Ser Lys Leu Lys Glu Ile Leu Glu Asp Pro Ser Ser
                85                  90                  95

Lys Ile Val Gly Gln Asn Leu Lys Tyr Asp Tyr Lys Val Leu Met Val
            100                 105                 110

Lys Gly Ile Ser Pro Val Tyr Pro His Phe Asp Thr Met Ile Ala Ala
        115                 120                 125

Tyr Leu Leu Glu Pro Asn Glu Lys Phe Asn Leu Glu Asp Leu Ser
130                 135                 140

Leu Lys Phe Leu Gly Tyr Lys Met Thr Ser Tyr Gln Glu Leu Met Ser
145                 150                 155                 160

Phe Ser Ser Pro Leu Phe Gly Phe Ser Phe Ala Asp Val Pro Val Asp
                165                 170                 175

Lys Ala Ala Asn Tyr Ser Cys Glu Asn Ala Asp Ile Thr Tyr Arg Leu
            180                 185                 190

Tyr Lys Ile Leu Ser Met Lys Leu His Glu Ala Glu Leu Glu Asn Val
        195                 200                 205

Phe Tyr Arg Ile Glu Met Pro Leu Val Asn Val Leu Ala Arg Met Glu
    210                 215                 220

Leu Asn Gly Val Tyr Val Asp Thr Glu Phe Leu Lys Lys Leu Ser Glu
225                 230                 235                 240
```

```
Glu Tyr Gly Lys Lys Leu Glu Glu Leu Ala Glu Lys Ile Tyr Gln Ile
                245                 250                 255

Ala Gly Glu Pro Phe Asn Ile Asn Ser Pro Lys Gln Val Ser Lys Ile
            260                 265                 270

Leu Phe Glu Lys Leu Gly Ile Lys Pro Arg Gly Lys Thr Thr Lys Thr
        275                 280                 285

Gly Ala Tyr Ser Thr Arg Ile Glu Val Leu Glu Glu Ile Ala Asn Glu
    290                 295                 300

His Glu Ile Val Pro Leu Ile Leu Glu Tyr Arg Lys Ile Gln Lys Leu
305                 310                 315                 320

Lys Ser Thr Tyr Ile Asp Thr Leu Pro Lys Leu Val Asn Pro Lys Thr
                325                 330                 335

Gly Arg Ile His Ala Ser Phe His Gln Thr Gly Thr Ala Thr Gly Arg
            340                 345                 350

Leu Ser Ser Ser Asp Pro Asn Leu Gln Asn Leu Pro Thr Lys Ser Glu
        355                 360                 365

Glu Gly Lys Glu Ile Arg Lys Ala Ile Val Pro Gln Asp Pro Asp Trp
    370                 375                 380

Trp Ile Val Ser Ala Asp Tyr Ser Gln Ile Glu Leu Arg Ile Leu Ala
385                 390                 395                 400

His Leu Ser Gly Asp Glu Asn Leu Val Lys Ala Phe Glu Glu Gly Ile
                405                 410                 415

Asp Val His Thr Leu Thr Ala Ser Arg Ile Tyr Asn Val Lys Pro Glu
            420                 425                 430

Glu Val Asn Glu Glu Met Arg Arg Val Gly Lys Met Val Asn Phe Ser
        435                 440                 445

Ile Ile Tyr Gly Val Thr Pro Tyr Gly Leu Ser Val Arg Leu Gly Ile
    450                 455                 460

Pro Val Lys Glu Ala Glu Lys Met Ile Ile Ser Tyr Phe Thr Leu Tyr
465                 470                 475                 480

Pro Lys Val Arg Ser Tyr Ile Gln Gln Val Val Ala Glu Ala Lys Glu
                485                 490                 495

Lys Gly Tyr Val Arg Thr Leu Phe Gly Arg Lys Arg Asp Ile Pro Gln
            500                 505                 510

Leu Met Ala Arg Asp Lys Asn Thr Gln Ser Glu Gly Arg Ile Ala
        515                 520                 525

Ile Asn Thr Pro Ile Gln Gly Thr Ala Ala Asp Ile Ile Lys Leu Ala
    530                 535                 540

Met Ile Asp Ile Asp Glu Glu Leu Arg Lys Arg Asn Met Lys Ser Arg
545                 550                 555                 560

Met Ile Ile Gln Val His Asp Glu Leu Val Phe Glu Val Pro Asp Glu
                565                 570                 575

Glu Lys Glu Glu Leu Val Asp Leu Val Lys Asn Lys Met Thr Asn Val
            580                 585                 590

Val Lys Leu Ser Val Pro Leu Glu Val Asp Ile Ser Ile Gly Lys Ser
        595                 600                 605

Trp Ser
    610

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO:27:

TTTGCCCTGG CCCTTGAAAC G                                                   21

(2) INFORMATION FOR SEQ ID NO:28:

(i) SEQUENCE CHARACTERISTICS:
        (A) LENGTH: 1833 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1830

(xi) SEQUENCE DESCRIPTION: SEQ ID NO:28:

```
ATG AAG GAA CTT CAA CTG TAC GAA GAA GCA GAA CCC ACC GGA TAC GAA          48
Met Lys Glu Leu Gln Leu Tyr Glu Glu Ala Glu Pro Thr Gly Tyr Glu
 1               5                  10                  15

ATC GTG AAG GAT CAT AAG ACC TTC GAA GAT CTC ATC GAA AAG CTG AAG          96
Ile Val Lys Asp His Lys Thr Phe Glu Asp Leu Ile Glu Lys Leu Lys
                20                  25                  30

GAG GTT CCA TCT TTT GCC CTG GCC CTT GAA ACG TCC TCC CTT GAC CCG         144
Glu Val Pro Ser Phe Ala Leu Ala Leu Glu Thr Ser Ser Leu Asp Pro
            35                  40                  45

TTC AAC TGT GAG ATA GTC GGC ATC TCC GTG TCG TTC AAA CCG AAA ACA         192
Phe Asn Cys Glu Ile Val Gly Ile Ser Val Ser Phe Lys Pro Lys Thr
 50                  55                  60

GCT TAT TAC ATT CCA CTT CAT CAC AGA AAC GCC CAG AAT CTT GAT GAA         240
Ala Tyr Tyr Ile Pro Leu His His Arg Asn Ala Gln Asn Leu Asp Glu
 65                  70                  75                  80

ACA CTG GTG CTG TCG AAG TTG AAA GAG ATC CTC GAA GAC CCG TCT TCG         288
Thr Leu Val Leu Ser Lys Leu Lys Glu Ile Leu Glu Asp Pro Ser Ser
                85                  90                  95

AAG ATT GTG GGT CAG AAC CTG AAG TAC GAC TAC AAG GTT CTT ATG GTA         336
Lys Ile Val Gly Gln Asn Leu Lys Tyr Asp Tyr Lys Val Leu Met Val
            100                 105                 110

AAG GGT ATA TCG CCA GTT TAT CCG CAT TTT GAC ACG ATG ATA GCT GCA         384
Lys Gly Ile Ser Pro Val Tyr Pro His Phe Asp Thr Met Ile Ala Ala
        115                 120                 125

TAT TTG CTG GAG CCA AAC GAG AAA AAA TTC AAT CTC GAA GAT CTG TCT         432
Tyr Leu Leu Glu Pro Asn Glu Lys Lys Phe Asn Leu Glu Asp Leu Ser
130                 135                 140

TTG AAA TTT CTC GGA TAC AAA ATG ACG TCT TAT CAG GAA CTG ATG TCG         480
Leu Lys Phe Leu Gly Tyr Lys Met Thr Ser Tyr Gln Glu Leu Met Ser
145                 150                 155                 160

TTT TCC TCA CCA CTT TTT GGT TTC AGC TTT GCG GAT GTT CCG GTA GAC         528
Phe Ser Ser Pro Leu Phe Gly Phe Ser Phe Ala Asp Val Pro Val Asp
                165                 170                 175

AAG GCT GCG AAC TAC TCC TGC GAG GAT GCA GAC ATC ACT TAT AGG CTC         576
Lys Ala Ala Asn Tyr Ser Cys Glu Asp Ala Asp Ile Thr Tyr Arg Leu
            180                 185                 190

TAC AAG ATA CTC AGC ATG AAG CTC CAT GAA GCG GAA CTT GAG AAC GTC         624
Tyr Lys Ile Leu Ser Met Lys Leu His Glu Ala Glu Leu Glu Asn Val
        195                 200                 205

TTC TAC AGG ATA GAG ATG CCG CTT GTG AAC GTT CTT GCA CGC ATG GAA         672
Phe Tyr Arg Ile Glu Met Pro Leu Val Asn Val Leu Ala Arg Met Glu
```

-continued

```
            210                 215                 220
TTG AAC GGG GTG TAT GTG GAC ACA GAA TTC CTG AAA AAG CTC TCG GAG      720
Leu Asn Gly Val Tyr Val Asp Thr Glu Phe Leu Lys Lys Leu Ser Glu
225                 230                 235                 240

GAG TAC GGC AAA AAG CTC GAG GAA CTG GCC GAA AAA ATC TAC CAG ATA      768
Glu Tyr Gly Lys Lys Leu Glu Glu Leu Ala Glu Lys Ile Tyr Gln Ile
                245                 250                 255

GCA GGA GAG CCC TTC AAC ATC AAT TCT CCA AAA CAG GTT TCA AAG ATC      816
Ala Gly Glu Pro Phe Asn Ile Asn Ser Pro Lys Gln Val Ser Lys Ile
            260                 265                 270

CTT TTT GAG AAG CTG GGA ATA AAA CCC CGT GGA AAA ACG ACA AAA ACA      864
Leu Phe Glu Lys Leu Gly Ile Lys Pro Arg Gly Lys Thr Thr Lys Thr
        275                 280                 285

GGA GCG TAC TCT ACC AGG ATA GAG GTG TTG GAA GAG ATA GCG AAT GAG      912
Gly Ala Tyr Ser Thr Arg Ile Glu Val Leu Glu Glu Ile Ala Asn Glu
290                 295                 300

CAC GAG ATA GTA CCC CTC ATT CTC GAG TAC AGA AAG ATC CAG AAA CTG      960
His Glu Ile Val Pro Leu Ile Leu Glu Tyr Arg Lys Ile Gln Lys Leu
305                 310                 315                 320

AAA TCG ACC TAC ATA GAC ACC CTT CCG AAA CTT GTG AAC CCG AAA ACC     1008
Lys Ser Thr Tyr Ile Asp Thr Leu Pro Lys Leu Val Asn Pro Lys Thr
                325                 330                 335

GGA AGA ATT CAT GCA TCT TTC CAC CAG ACG GGT ACC GCC ACT GGC AGG     1056
Gly Arg Ile His Ala Ser Phe His Gln Thr Gly Thr Ala Thr Gly Arg
            340                 345                 350

TTG AGT AGC AGT GAT CCA AAT CTT CAG AAT CTT CCG ACA AAG AGC GAA     1104
Leu Ser Ser Ser Asp Pro Asn Leu Gln Asn Leu Pro Thr Lys Ser Glu
        355                 360                 365

GAG GGA AAA GAA ATT AGA AAA GCG ATT GTG CCC CAG GAT CCA GAC TGG     1152
Glu Gly Lys Glu Ile Arg Lys Ala Ile Val Pro Gln Asp Pro Asp Trp
370                 375                 380

TGG ATC GTC AGT GCG GAT TAT TCC CAA ATA GAA CTC AGA ATC CTC GCT     1200
Trp Ile Val Ser Ala Asp Tyr Ser Gln Ile Glu Leu Arg Ile Leu Ala
385                 390                 395                 400

CAT CTC AGT GGT GAT GAG AAC CTT GTG AAG GCC TTC GAG GAG GGC ATC     1248
His Leu Ser Gly Asp Glu Asn Leu Val Lys Ala Phe Glu Glu Gly Ile
                405                 410                 415

GAT GTG CAC ACC TTG ACT GCC TCC AGG ATC TAC AAC GTA AAG CCA GAA     1296
Asp Val His Thr Leu Thr Ala Ser Arg Ile Tyr Asn Val Lys Pro Glu
            420                 425                 430

GAA GTG AAC GAA GAA ATG CGA CGG GTT GGA AAG ATG GTG AAC TTC TCT     1344
Glu Val Asn Glu Glu Met Arg Arg Val Gly Lys Met Val Asn Phe Ser
        435                 440                 445

ATA ATA TAC GGT GTC ACA CCG TAC GGT CTT TCT GTG AGA CTT GGA ATA     1392
Ile Ile Tyr Gly Val Thr Pro Tyr Gly Leu Ser Val Arg Leu Gly Ile
450                 455                 460

CCG GTT AAA GAA GCA GAA AAG ATG ATT ATC AGC TAT TTC ACA CTG TAT     1440
Pro Val Lys Glu Ala Glu Lys Met Ile Ile Ser Tyr Phe Thr Leu Tyr
465                 470                 475                 480

CCA AAG GTG CGA AGC TAC ATC CAG CAG GTT GTT GCA GAG GCA AAA GAG     1488
Pro Lys Val Arg Ser Tyr Ile Gln Gln Val Val Ala Glu Ala Lys Glu
                485                 490                 495

AAG GGC TAC GTC AGG ACT CTC TTT GGA AGA AAA AGA GAT ATT CCC CAG     1536
Lys Gly Tyr Val Arg Thr Leu Phe Gly Arg Lys Arg Asp Ile Pro Gln
            500                 505                 510

CTC ATG GCA AGG GAC AAG AAC ACC CAG TCC GAA GGC GAA AGA ATC GCA     1584
Leu Met Ala Arg Asp Lys Asn Thr Gln Ser Glu Gly Glu Arg Ile Ala
        515                 520                 525

ATA AAC ACC CCC ATT CAG GGA ACG GCG GCA GAT ATA ATA AAA TTG GCT     1632
```

-continued

```
Ile Asn Thr Pro Ile Gln Gly Thr Ala Ala Asp Ile Ile Lys Leu Ala
                530                 535                 540

ATG ATA GAT ATA GAC GAG GAG CTG AGA AAA AGA AAC ATG AAA TCC AGA       1680
Met Ile Asp Ile Asp Glu Glu Leu Arg Lys Arg Asn Met Lys Ser Arg
545                 550                 555                 560

ATG ATC ATT CAG GTT CAT GAC GAA CTG GTC TTC GAG GTT CCC GAT GAG       1728
Met Ile Ile Gln Val His Asp Glu Leu Val Phe Glu Val Pro Asp Glu
                565                 570                 575

GAA AAA GAA GAA CTA GTT GAT CTG GTG AAG AAC AAA ATG ACA AAT GTG       1776
Glu Lys Glu Glu Leu Val Asp Leu Val Lys Asn Lys Met Thr Asn Val
                580                 585                 590

GTG AAA CTC TCT GTG CCT CTT GAG GTT GAC ATA AGC ATC GGA AAA AGC       1824
Val Lys Leu Ser Val Pro Leu Glu Val Asp Ile Ser Ile Gly Lys Ser
                595                 600                 605

TGG TCT TGA                                                           1833
Trp Ser
610
```

(2) INFORMATION FOR SEQ ID NO:29:

(i) SEQUENCE CHARACTERISTICS:
        (A) LENGTH: 610 amino acids
        (B) TYPE: amino acid
        (D) TOPOLOGY: linear (ii) MOLECULE TYPE: protein (xi) SEQUENCE DESCRIPTION: SEQ ID NO:29:

```
Met Lys Glu Leu Gln Leu Tyr Glu Glu Ala Glu Pro Thr Gly Tyr Glu
1               5                   10                  15

Ile Val Lys Asp His Lys Thr Phe Glu Asp Leu Ile Glu Lys Leu Lys
                20                  25                  30

Glu Val Pro Ser Phe Ala Leu Ala Leu Glu Thr Ser Ser Leu Asp Pro
            35                  40                  45

Phe Asn Cys Glu Ile Val Gly Ile Ser Val Ser Phe Lys Pro Lys Thr
        50                  55                  60

Ala Tyr Tyr Ile Pro Leu His His Arg Asn Ala Gln Asn Leu Asp Glu
65                  70                  75                  80

Thr Leu Val Leu Ser Lys Leu Lys Glu Ile Leu Glu Asp Pro Ser Ser
                85                  90                  95

Lys Ile Val Gly Gln Asn Leu Lys Tyr Asp Tyr Lys Val Leu Met Val
            100                 105                 110

Lys Gly Ile Ser Pro Val Tyr Pro His Phe Asp Thr Met Ile Ala Ala
        115                 120                 125

Tyr Leu Leu Glu Pro Asn Glu Lys Lys Phe Asn Leu Glu Asp Leu Ser
130                 135                 140

Leu Lys Phe Leu Gly Tyr Lys Met Thr Ser Tyr Gln Glu Leu Met Ser
145                 150                 155                 160

Phe Ser Ser Pro Leu Phe Gly Phe Ser Phe Ala Asp Val Pro Val Asp
                165                 170                 175

Lys Ala Ala Asn Tyr Ser Cys Glu Asp Ala Asp Ile Thr Tyr Arg Leu
            180                 185                 190

Tyr Lys Ile Leu Ser Met Lys Leu His Glu Ala Glu Leu Glu Asn Val
        195                 200                 205

Phe Tyr Arg Ile Glu Met Pro Leu Val Asn Val Leu Ala Arg Met Glu
    210                 215                 220

Leu Asn Gly Val Tyr Val Asp Thr Glu Phe Leu Lys Lys Leu Ser Glu
225                 230                 235                 240
```

Glu Tyr Gly Lys Lys Leu Glu Leu Ala Lys Ile Tyr Gln Ile
              245                 250                 255

Ala Gly Glu Pro Phe Asn Ile Asn Ser Pro Lys Gln Val Ser Lys Ile
          260                 265                 270

Leu Phe Glu Lys Leu Gly Ile Lys Pro Arg Gly Lys Thr Thr Lys Thr
          275                 280                 285

Gly Ala Tyr Ser Thr Arg Ile Glu Val Leu Glu Glu Ile Ala Asn Glu
          290                 295                 300

His Glu Ile Val Pro Leu Ile Leu Glu Tyr Arg Lys Ile Gln Lys Leu
305                 310                 315                 320

Lys Ser Thr Tyr Ile Asp Thr Leu Pro Lys Leu Val Asn Pro Lys Thr
                325                 330                 335

Gly Arg Ile His Ala Ser Phe His Gln Thr Gly Thr Ala Thr Gly Arg
                340                 345                 350

Leu Ser Ser Ser Asp Pro Asn Leu Gln Asn Leu Pro Thr Lys Ser Glu
              355                 360                 365

Glu Gly Lys Glu Ile Arg Lys Ala Ile Val Pro Gln Asp Pro Asp Trp
          370                 375                 380

Trp Ile Val Ser Ala Asp Tyr Ser Gln Ile Glu Leu Arg Ile Leu Ala
385                 390                 395                 400

His Leu Ser Gly Asp Glu Asn Leu Val Lys Ala Phe Glu Glu Gly Ile
              405                 410                 415

Asp Val His Thr Leu Thr Ala Ser Arg Ile Tyr Asn Val Lys Pro Glu
              420                 425                 430

Glu Val Asn Glu Glu Met Arg Arg Val Gly Lys Met Val Asn Phe Ser
          435                 440                 445

Ile Ile Tyr Gly Val Thr Pro Tyr Gly Leu Ser Val Arg Leu Gly Ile
450                 455                 460

Pro Val Lys Glu Ala Glu Lys Met Ile Ile Ser Tyr Phe Thr Leu Tyr
465                 470                 475                 480

Pro Lys Val Arg Ser Tyr Ile Gln Gln Val Val Ala Glu Ala Lys Glu
              485                 490                 495

Lys Gly Tyr Val Arg Thr Leu Phe Gly Arg Lys Arg Asp Ile Pro Gln
          500                 505                 510

Leu Met Ala Arg Asp Lys Asn Thr Gln Ser Glu Gly Glu Arg Ile Ala
          515                 520                 525

Ile Asn Thr Pro Ile Gln Gly Thr Ala Ala Asp Ile Ile Lys Leu Ala
          530                 535                 540

Met Ile Asp Ile Asp Glu Glu Leu Arg Lys Arg Asn Met Lys Ser Arg
545                 550                 555                 560

Met Ile Ile Gln Val His Asp Glu Leu Val Phe Glu Val Pro Asp Glu
                565                 570                 575

Glu Lys Glu Glu Leu Val Asp Leu Val Lys Asn Lys Met Thr Asn Val
              580                 585                 590

Val Lys Leu Ser Val Pro Leu Glu Val Asp Ile Ser Ile Gly Lys Ser
              595                 600                 605

Trp Ser
    610

(2) INFORMATION FOR SEQ ID NO:30:

(i) SEQUENCE CHARACTERISTICS:
       (A) LENGTH: 29 base pairs
       (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:30:

CCTGAAGTAC GCGTACAAGG TTCTTATGG                                         29

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

TCACACAGGA AACAGCTATG AC                                                22

(2) INFORMATION FOR SEQ ID NO:32:

(i) SEQUENCE CHARACTERISTICS:
        (A) LENGTH: 1833 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1830

(xi) SEQUENCE DESCRIPTION: SEQ ID NO:32:

```
ATG AAG GAA CTT CAA CTG TAC GAA GAA GCA GAA CCC ACC GGA TAC GAA         48
Met Lys Glu Leu Gln Leu Tyr Glu Glu Ala Glu Pro Thr Gly Tyr Glu
 1               5                  10                  15

ATC GTG AAG GAT CAT AAG ACC TTC GAA GAT CTC ATC GAA AAG CTG AAG         96
Ile Val Lys Asp His Lys Thr Phe Glu Asp Leu Ile Glu Lys Leu Lys
             20                  25                  30

GAG GTT CCA TCT TTT GCC CTG GAC CTT GAA ACG TCC TCC CTT GAC CCG        144
Glu Val Pro Ser Phe Ala Leu Asp Leu Glu Thr Ser Ser Leu Asp Pro
         35                  40                  45

TTC AAC TGT GAG ATA GTC GGC ATC TCC GTG TCG TTC AAA CCG AAA ACA        192
Phe Asn Cys Glu Ile Val Gly Ile Ser Val Ser Phe Lys Pro Lys Thr
     50                  55                  60

GCT TAT TAC ATT CCA CTT CAT CAC AGA AAC GCC CAG AAT CTT GAT GAA        240
Ala Tyr Tyr Ile Pro Leu His His Arg Asn Ala Gln Asn Leu Asp Glu
 65                  70                  75                  80

ACA CTG GTG CTG TCG AAG TTG AAA GAG ATC CTC GAA GAC CCG TCT TCG        288
Thr Leu Val Leu Ser Lys Leu Lys Glu Ile Leu Glu Asp Pro Ser Ser
                 85                  90                  95

AAG ATT GTG GGT CAG AAC CTG AAG TAC GCG TAC AAG GTT CTT ATG GTA        336
Lys Ile Val Gly Gln Asn Leu Lys Tyr Ala Tyr Lys Val Leu Met Val
            100                 105                 110

AAG GGT ATA TCG CCA GTT TAT CCG CAT TTT GAC ACG ATG ATA GCT GCA        384
Lys Gly Ile Ser Pro Val Tyr Pro His Phe Asp Thr Met Ile Ala Ala
        115                 120                 125

TAT TTG CTG GAG CCA AAC GAG AAA AAA TTC AAT CTC GAA GAT CTG TCT        432
Tyr Leu Leu Glu Pro Asn Glu Lys Lys Phe Asn Leu Glu Asp Leu Ser
    130                 135                 140

TTG AAA TTT CTC GGA TAC AAA ATG ACG TCT TAT CAG GAA CTG ATG TCG        480
Leu Lys Phe Leu Gly Tyr Lys Met Thr Ser Tyr Gln Glu Leu Met Ser
```

-continued

```
        145                 150                 155                 160
TTT TCC TCA CCA CTT TTT GGT TTC AGC TTT GCG GAT GTT CCG GTA GAC              528
Phe Ser Ser Pro Leu Phe Gly Phe Ser Phe Ala Asp Val Pro Val Asp
                165                 170                 175

AAG GCT GCG AAC TAC TCC TGC GAG GAT GCA GAC ATC ACT TAT AGG CTC              576
Lys Ala Ala Asn Tyr Ser Cys Glu Asp Ala Asp Ile Thr Tyr Arg Leu
                180                 185                 190

TAC AAG ATA CTC AGC ATG AAG CTC CAT GAA GCG GAA CTT GAG AAC GTC              624
Tyr Lys Ile Leu Ser Met Lys Leu His Glu Ala Glu Leu Glu Asn Val
                195                 200                 205

TTC TAC AGG ATA GAG ATG CCG CTT GTG AAC GTT CTT GCA CGC ATG GAA              672
Phe Tyr Arg Ile Glu Met Pro Leu Val Asn Val Leu Ala Arg Met Glu
                210                 215                 220

TTG AAC GGG GTG TAT GTG GAC ACA GAA TTC CTG AAA AAG CTC TCG GAG              720
Leu Asn Gly Val Tyr Val Asp Thr Glu Phe Leu Lys Lys Leu Ser Glu
225                 230                 235                 240

GAG TAC GGC AAA AAG CTC GAG GAA CTG GCC GAA AAA ATC TAC CAG ATA              768
Glu Tyr Gly Lys Lys Leu Glu Glu Leu Ala Glu Lys Ile Tyr Gln Ile
                245                 250                 255

GCA GGA GAG CCC TTC AAC ATC AAT TCT CCA AAA CAG GTT TCA AAG ATC              816
Ala Gly Glu Pro Phe Asn Ile Asn Ser Pro Lys Gln Val Ser Lys Ile
                260                 265                 270

CTT TTT GAG AAG CTG GGA ATA AAA CCC CGT GGA AAA ACG ACA AAA ACA              864
Leu Phe Glu Lys Leu Gly Ile Lys Pro Arg Gly Lys Thr Thr Lys Thr
                275                 280                 285

GGA GCG TAC TCT ACC AGG ATA GAG GTG TTG GAA GAG ATA GCG AAT GAG              912
Gly Ala Tyr Ser Thr Arg Ile Glu Val Leu Glu Glu Ile Ala Asn Glu
                290                 295                 300

CAC GAG ATA GTA CCC CTC ATT CTC GAG TAC AGA AAG ATC CAG AAA CTG              960
His Glu Ile Val Pro Leu Ile Leu Glu Tyr Arg Lys Ile Gln Lys Leu
305                 310                 315                 320

AAA TCG ACC TAC ATA GAC ACC CTT CCG AAA CTT GTG AAC CCG AAA ACC             1008
Lys Ser Thr Tyr Ile Asp Thr Leu Pro Lys Leu Val Asn Pro Lys Thr
                325                 330                 335

GGA AGA ATT CAT GCA TCT TTC CAC CAG ACG GGT ACC GCC ACT GGC AGG             1056
Gly Arg Ile His Ala Ser Phe His Gln Thr Gly Thr Ala Thr Gly Arg
                340                 345                 350

TTG AGT AGC AGT GAT CCA AAT CTT CAG AAT CTT CCG ACA AAG AGC GAA             1104
Leu Ser Ser Ser Asp Pro Asn Leu Gln Asn Leu Pro Thr Lys Ser Glu
                355                 360                 365

GAG GGA AAA GAA ATT AGA AAA GCG ATT GTG CCC CAG GAT CCA GAC TGG             1152
Glu Gly Lys Glu Ile Arg Lys Ala Ile Val Pro Gln Asp Pro Asp Trp
                370                 375                 380

TGG ATC GTC AGT GCG GAT TAT TCC CAA ATA GAA CTC AGA ATC CTC GCT             1200
Trp Ile Val Ser Ala Asp Tyr Ser Gln Ile Glu Leu Arg Ile Leu Ala
385                 390                 395                 400

CAT CTC AGT GGT GAT GAG AAC CTT GTG AAG GCC TTC GAG GAG GGC ATC             1248
His Leu Ser Gly Asp Glu Asn Leu Val Lys Ala Phe Glu Glu Gly Ile
                405                 410                 415

GAT GTG CAC ACC TTG ACT GCC TCC AGG ATC TAC AAC GTA AAG CCA GAA             1296
Asp Val His Thr Leu Thr Ala Ser Arg Ile Tyr Asn Val Lys Pro Glu
                420                 425                 430

GAA GTG AAC GAA GAA ATG CGA CGG GTT GGA AAG ATG GTG AAC TTC TCT             1344
Glu Val Asn Glu Glu Met Arg Arg Val Gly Lys Met Val Asn Phe Ser
                435                 440                 445

ATA ATA TAC GGT GTC ACA CCG TAC GGT CTT TCT GTG AGA CTT GGA ATA             1392
Ile Ile Tyr Gly Val Thr Pro Tyr Gly Leu Ser Val Arg Leu Gly Ile
                450                 455                 460

CCG GTT AAA GAA GCA GAA AAG ATG ATT ATC AGC TAT TTC ACA CTG TAT             1440
```

```
Pro Val Lys Glu Ala Glu Lys Met Ile Ile Ser Tyr Phe Thr Leu Tyr
465                 470                 475                 480

CCA AAG GTG CGA AGC TAC ATC CAG CAG GTT GTT GCA GAG GCA AAA GAG     1488
Pro Lys Val Arg Ser Tyr Ile Gln Gln Val Val Ala Glu Ala Lys Glu
                    485                 490                 495

AAG GGC TAC GTC AGG ACT CTC TTT GGA AGA AAA AGA GAT ATT CCC CAG     1536
Lys Gly Tyr Val Arg Thr Leu Phe Gly Arg Lys Arg Asp Ile Pro Gln
                500                 505                 510

CTC ATG GCA AGG GAC AAG AAC ACC CAG TCC GAA GGC GAA AGA ATC GCA     1584
Leu Met Ala Arg Asp Lys Asn Thr Gln Ser Glu Gly Glu Arg Ile Ala
            515                 520                 525

ATA AAC ACC CCC ATT CAG GGA ACG GCG GCA GAT ATA ATA AAA TTG GCT     1632
Ile Asn Thr Pro Ile Gln Gly Thr Ala Ala Asp Ile Ile Lys Leu Ala
        530                 535                 540

ATG ATA GAT ATA GAC GAG GAG CTG AGA AAA AGA AAC ATG AAA TCC AGA     1680
Met Ile Asp Ile Asp Glu Glu Leu Arg Lys Arg Asn Met Lys Ser Arg
545                 550                 555                 560

ATG ATC ATT CAG GTT CAT GAC GAA CTG GTC TTC GAG GTT CCC GAT GAG     1728
Met Ile Ile Gln Val His Asp Glu Leu Val Phe Glu Val Pro Asp Glu
                    565                 570                 575

GAA AAA GAA GAA CTA GTT GAT CTG GTG AAG AAC AAA ATG ACA AAT GTG     1776
Glu Lys Glu Glu Leu Val Asp Leu Val Lys Asn Lys Met Thr Asn Val
                580                 585                 590

GTG AAA CTC TCT GTG CCT CTT GAG GTT GAC ATA AGC ATC GGA AAA AGC     1824
Val Lys Leu Ser Val Pro Leu Glu Val Asp Ile Ser Ile Gly Lys Ser
            595                 600                 605

TGG TCT TGA                                                          1833
Trp Ser
610
```

(2) INFORMATION FOR SEQ ID NO:33:

(i) SEQUENCE CHARACTERISTICS:
        (A) LENGTH: 610 amino acids
        (B) TYPE: amino acid
        (D) TOPOLOGY: linear (ii) MOLECULE TYPE: protein (xi) SEQUENCE DESCRIPTION: SEQ ID NO:33:

```
Met Lys Glu Leu Gln Leu Tyr Glu Glu Ala Pro Thr Gly Tyr Glu
 1               5                  10                  15

Ile Val Lys Asp His Lys Thr Phe Glu Asp Leu Ile Glu Lys Leu Lys
                20                  25                  30

Glu Val Pro Ser Phe Ala Leu Asp Leu Glu Thr Ser Ser Leu Asp Pro
            35                  40                  45

Phe Asn Cys Glu Ile Val Gly Ile Ser Val Ser Phe Lys Pro Lys Thr
       50                  55                  60

Ala Tyr Tyr Ile Pro Leu His His Arg Asn Ala Gln Asn Leu Asp Glu
65                  70                  75                  80

Thr Leu Val Leu Ser Lys Leu Lys Glu Ile Leu Glu Asp Pro Ser Ser
                85                  90                  95

Lys Ile Val Gly Gln Asn Leu Lys Tyr Ala Tyr Lys Val Leu Met Val
            100                 105                 110

Lys Gly Ile Ser Pro Val Tyr Pro His Phe Asp Thr Met Ile Ala Ala
        115                 120                 125

Tyr Leu Leu Glu Pro Asn Glu Lys Lys Phe Asn Leu Glu Asp Leu Ser
       130                 135                 140

Leu Lys Phe Leu Gly Tyr Lys Met Thr Ser Tyr Gln Glu Leu Met Ser
```

```
145                 150                 155                 160
Phe Ser Ser Pro Leu Phe Gly Phe Ser Phe Ala Asp Val Pro Val Asp
                165                 170                 175

Lys Ala Ala Asn Tyr Ser Cys Glu Asp Ala Asp Ile Thr Tyr Arg Leu
            180                 185                 190

Tyr Lys Ile Leu Ser Met Lys Leu His Glu Ala Glu Leu Glu Asn Val
        195                 200                 205

Phe Tyr Arg Ile Glu Met Pro Leu Val Asn Val Leu Ala Arg Met Glu
    210                 215                 220

Leu Asn Gly Val Tyr Val Asp Thr Glu Phe Leu Lys Lys Leu Ser Glu
225                 230                 235                 240

Glu Tyr Gly Lys Lys Leu Glu Glu Leu Ala Glu Lys Ile Tyr Gln Ile
                245                 250                 255

Ala Gly Glu Pro Phe Asn Ile Asn Ser Pro Lys Gln Val Ser Lys Ile
            260                 265                 270

Leu Phe Glu Lys Leu Gly Ile Lys Pro Arg Gly Lys Thr Thr Lys Thr
        275                 280                 285

Gly Ala Tyr Ser Thr Arg Ile Glu Val Leu Glu Glu Ile Ala Asn Glu
    290                 295                 300

His Glu Ile Val Pro Leu Ile Leu Glu Tyr Arg Lys Ile Gln Lys Leu
305                 310                 315                 320

Lys Ser Thr Tyr Ile Asp Thr Leu Pro Lys Leu Val Asn Pro Lys Thr
                325                 330                 335

Gly Arg Ile His Ala Ser Phe His Gln Thr Gly Thr Ala Thr Gly Arg
            340                 345                 350

Leu Ser Ser Asp Pro Asn Leu Gln Asn Leu Pro Thr Lys Ser Glu
        355                 360                 365

Glu Gly Lys Glu Ile Arg Lys Ala Ile Val Pro Gln Asp Pro Asp Trp
    370                 375                 380

Trp Ile Val Ser Ala Asp Tyr Ser Gln Ile Glu Leu Arg Ile Leu Ala
385                 390                 395                 400

His Leu Ser Gly Asp Glu Asn Leu Val Lys Ala Phe Glu Glu Gly Ile
                405                 410                 415

Asp Val His Thr Leu Thr Ala Ser Arg Ile Tyr Asn Val Lys Pro Glu
            420                 425                 430

Glu Val Asn Glu Glu Met Arg Arg Val Gly Lys Met Val Asn Phe Ser
        435                 440                 445

Ile Ile Tyr Gly Val Thr Pro Tyr Gly Leu Ser Val Arg Leu Gly Ile
    450                 455                 460

Pro Val Lys Glu Ala Glu Lys Met Ile Ile Ser Tyr Phe Thr Leu Tyr
465                 470                 475                 480

Pro Lys Val Arg Ser Tyr Ile Gln Gln Val Val Ala Glu Ala Lys Glu
                485                 490                 495

Lys Gly Tyr Val Arg Thr Leu Phe Gly Arg Lys Arg Asp Ile Pro Gln
            500                 505                 510

Leu Met Ala Arg Asp Lys Asn Thr Gln Ser Glu Gly Glu Arg Ile Ala
        515                 520                 525

Ile Asn Thr Pro Ile Gln Gly Thr Ala Ala Asp Ile Ile Lys Leu Ala
    530                 535                 540

Met Ile Asp Ile Asp Glu Glu Leu Arg Lys Arg Asn Met Lys Ser Arg
545                 550                 555                 560

Met Ile Ile Gln Val His Asp Glu Leu Val Phe Glu Val Pro Asp Glu
                565                 570                 575
```

```
          Glu Lys Glu Glu Leu Val Asp Leu Val Lys Asn Lys Met Thr Asn Val
                      580                 585                 590

Val Lys Leu Ser Val Pro Leu Glu Val Asp Ile Ser Ile Gly Lys Ser
                      595                 600                 605

Trp Ser
              610

(2) INFORMATION FOR SEQ ID NO:34:

(i) SEQUENCE CHARACTERISTICS:
         (A) LENGTH: 1833 base pairs
         (B) TYPE: nucleic acid
         (C) STRANDEDNESS: double
         (D) TOPOLOGY: linear (ii) MOLECULE TYPE: DNA (genomic)

(ix) FEATURE:
         (A) NAME/KEY: CDS
         (B) LOCATION: 1..1830

(xi) SEQUENCE DESCRIPTION: SEQ ID NO:34:

ATG AAG GAA CTT CAA CTG TAC GAA GAA GCA GAA CCC ACC GGA TAC GAA           48
Met Lys Glu Leu Gln Leu Tyr Glu Glu Ala Glu Pro Thr Gly Tyr Glu
  1               5                  10                  15

ATC GTG AAG GAT CAT AAG ACC TTC GAA GAT CTC ATC GAA AAG CTG AAG           96
Ile Val Lys Asp His Lys Thr Phe Glu Asp Leu Ile Glu Lys Leu Lys
             20                  25                  30

GAG GTT CCA TCT TTT GCC CTG GCC CTT GAA ACG TCC TCC CTT GAC CCG          144
Glu Val Pro Ser Phe Ala Leu Ala Leu Glu Thr Ser Ser Leu Asp Pro
         35                  40                  45

TTC AAC TGT GAG ATA GTC GGC ATC TCC GTG TCG TTC AAA CCG AAA ACA          192
Phe Asn Cys Glu Ile Val Gly Ile Ser Val Ser Phe Lys Pro Lys Thr
     50                  55                  60

GCT TAT TAC ATT CCA CTT CAT CAC AGA AAC GCC CAG AAT CTT GAT GAA          240
Ala Tyr Tyr Ile Pro Leu His His Arg Asn Ala Gln Asn Leu Asp Glu
 65                  70                  75                  80

ACA CTG GTG CTG TCG AAG TTG AAA GAG ATC CTC GAA GAC CCG TCT TCG          288
Thr Leu Val Leu Ser Lys Leu Lys Glu Ile Leu Glu Asp Pro Ser Ser
                 85                  90                  95

AAG ATT GTG GGT CAG AAC CTG AAG TAC GCG TAC AAG GTT CTT ATG GTA          336
Lys Ile Val Gly Gln Asn Leu Lys Tyr Ala Tyr Lys Val Leu Met Val
            100                 105                 110

AAG GGT ATA TCG CCA GTT TAT CCG CAT TTT GAC ACG ATG ATA GCT GCA          384
Lys Gly Ile Ser Pro Val Tyr Pro His Phe Asp Thr Met Ile Ala Ala
        115                 120                 125

TAT TTG CTG GAG CCA AAC GAG AAA AAA TTC AAT CTC GAA GAT CTG TCT          432
Tyr Leu Leu Glu Pro Asn Glu Lys Lys Phe Asn Leu Glu Asp Leu Ser
130                 135                 140

TTG AAA TTT CTC GGA TAC AAA ATG ACG TCT TAT CAG GAA CTG ATG TCG          480
Leu Lys Phe Leu Gly Tyr Lys Met Thr Ser Tyr Gln Glu Leu Met Ser
145                 150                 155                 160

TTT TCC TCA CCA CTT TTT GGT TTC AGC TTT GCG GAT GTT CCG GTA GAC          528
Phe Ser Ser Pro Leu Phe Gly Phe Ser Phe Ala Asp Val Pro Val Asp
                165                 170                 175

AAG GCT GCG AAC TAC TCC TGC GAG GAT GCA GAC ATC ACT TAT AGG CTC          576
Lys Ala Ala Asn Tyr Ser Cys Glu Asp Ala Asp Ile Thr Tyr Arg Leu
            180                 185                 190

TAC AAG ATA CTC AGC ATG AAG CTC CAT GAA GCG GAA CTT GAG AAC GTC          624
Tyr Lys Ile Leu Ser Met Lys Leu His Glu Ala Glu Leu Glu Asn Val
        195                 200                 205
```

-continued

| | | |
|---|---|---|
| TTC TAC AGG ATA GAG ATG CCG CTT GTG AAC GTT CTT GCA CGC ATG GAA<br>Phe Tyr Arg Ile Glu Met Pro Leu Val Asn Val Leu Ala Arg Met Glu<br>210                 215                 220 | | 672 |
| TTG AAC GGG GTG TAT GTG GAC ACA GAA TTC CTG AAA AAG CTC TCG GAG<br>Leu Asn Gly Val Tyr Val Asp Thr Glu Phe Leu Lys Lys Leu Ser Glu<br>225                 230                 235                 240 | | 720 |
| GAG TAC GGC AAA AAG CTC GAG GAA CTG GCC GAA AAA ATC TAC CAG ATA<br>Glu Tyr Gly Lys Lys Leu Glu Glu Leu Ala Glu Lys Ile Tyr Gln Ile<br>                 245                 250                 255 | | 768 |
| GCA GGA GAG CCC TTC AAC ATC AAT TCT CCA AAA CAG GTT TCA AAG ATC<br>Ala Gly Glu Pro Phe Asn Ile Asn Ser Pro Lys Gln Val Ser Lys Ile<br>         260                 265                 270 | | 816 |
| CTT TTT GAG AAG CTG GGA ATA AAA CCC CGT GGA AAA ACG ACA AAA ACA<br>Leu Phe Glu Lys Leu Gly Ile Lys Pro Arg Gly Lys Thr Thr Lys Thr<br>     275                 280                 285 | | 864 |
| GGA GCG TAC TCT ACC AGG ATA GAG GTG TTG GAA GAG ATA GCG AAT GAG<br>Gly Ala Tyr Ser Thr Arg Ile Glu Val Leu Glu Glu Ile Ala Asn Glu<br>290                 295                 300 | | 912 |
| CAC GAG ATA GTA CCC CTC ATT CTC GAG TAC AGA AAG ATC CAG AAA CTG<br>His Glu Ile Val Pro Leu Ile Leu Glu Tyr Arg Lys Ile Gln Lys Leu<br>305                 310                 315                 320 | | 960 |
| AAA TCG ACC TAC ATA GAC ACC CTT CCG AAA CTT GTG AAC CCG AAA ACC<br>Lys Ser Thr Tyr Ile Asp Thr Leu Pro Lys Leu Val Asn Pro Lys Thr<br>                 325                 330                 335 | | 1008 |
| GGA AGA ATT CAT GCA TCT TTC CAC CAG ACG GGT ACC GCC ACT GGC AGG<br>Gly Arg Ile His Ala Ser Phe His Gln Thr Gly Thr Ala Thr Gly Arg<br>         340                 345                 350 | | 1056 |
| TTG AGT AGC AGT GAT CCA AAT CTT CAG AAT CTT CCG ACA AAG AGC GAA<br>Leu Ser Ser Ser Asp Pro Asn Leu Gln Asn Leu Pro Thr Lys Ser Glu<br>     355                 360                 365 | | 1104 |
| GAG GGA AAA GAA ATT AGA AAA GCG ATT GTG CCC CAG GAT CCA GAC TGG<br>Glu Gly Lys Glu Ile Arg Lys Ala Ile Val Pro Gln Asp Pro Asp Trp<br>370                 375                 380 | | 1152 |
| TGG ATC GTC AGT GCG GAT TAT TCC CAA ATA GAA CTC AGA ATC CTC GCT<br>Trp Ile Val Ser Ala Asp Tyr Ser Gln Ile Glu Leu Arg Ile Leu Ala<br>385                 390                 395                 400 | | 1200 |
| CAT CTC AGT GGT GAT GAG AAC CTT GTG AAG GCC TTC GAG GAG GGC ATC<br>His Leu Ser Gly Asp Glu Asn Leu Val Lys Ala Phe Glu Glu Gly Ile<br>                 405                 410                 415 | | 1248 |
| GAT GTG CAC ACC TTG ACT GCC TCC AGG ATC TAC AAC GTA AAG CCA GAA<br>Asp Val His Thr Leu Thr Ala Ser Arg Ile Tyr Asn Val Lys Pro Glu<br>         420                 425                 430 | | 1296 |
| GAA GTG AAC GAA GAA ATG CGA CGG GTT GGA AAG ATG GTG AAC TTC TCT<br>Glu Val Asn Glu Glu Met Arg Arg Val Gly Lys Met Val Asn Phe Ser<br>     435                 440                 445 | | 1344 |
| ATA ATA TAC GGT GTC ACA CCG TAC GGT CTT TCT GTG AGA CTT GGA ATA<br>Ile Ile Tyr Gly Val Thr Pro Tyr Gly Leu Ser Val Arg Leu Gly Ile<br>450                 455                 460 | | 1392 |
| CCG GTT AAA GAA GCA GAA AAG ATG ATT ATC AGC TAT TTC ACA CTG TAT<br>Pro Val Lys Glu Ala Glu Lys Met Ile Ile Ser Tyr Phe Thr Leu Tyr<br>465                 470                 475                 480 | | 1440 |
| CCA AAG GTG CGA AGC TAC ATC CAG CAG GTT GTT GCA GAG GCA AAA GAG<br>Pro Lys Val Arg Ser Tyr Ile Gln Gln Val Val Ala Glu Ala Lys Glu<br>                 485                 490                 495 | | 1488 |
| AAG GGC TAC GTC AGG ACT CTC TTT GGA AGA AAA AGA GAT ATT CCC CAG<br>Lys Gly Tyr Val Arg Thr Leu Phe Gly Arg Lys Arg Asp Ile Pro Gln<br>         500                 505                 510 | | 1536 |
| CTC ATG GCA AGG GAC AAG AAC ACC CAG TCC GAA GGC GAA AGA ATC GCA<br>Leu Met Ala Arg Asp Lys Asn Thr Gln Ser Glu Gly Glu Arg Ile Ala<br>     515                 520                 525 | | 1584 |

```
ATA AAC ACC CCC ATT CAG GGA ACG GCG GCA GAT ATA ATA AAA TTG GCT      1632
Ile Asn Thr Pro Ile Gln Gly Thr Ala Ala Asp Ile Ile Lys Leu Ala
    530                 535                 540

ATG ATA GAT ATA GAC GAG GAG CTG AGA AAA AGA AAC ATG AAA TCC AGA      1680
Met Ile Asp Ile Asp Glu Glu Leu Arg Lys Arg Asn Met Lys Ser Arg
545                 550                 555                 560

ATG ATC ATT CAG GTT CAT GAC GAA CTG GTC TTC GAG GTT CCC GAT GAG      1728
Met Ile Ile Gln Val His Asp Glu Leu Val Phe Glu Val Pro Asp Glu
                565                 570                 575

GAA AAA GAA GAA CTA GTT GAT CTG GTG AAG AAC AAA ATG ACA AAT GTG      1776
Glu Lys Glu Glu Leu Val Asp Leu Val Lys Asn Lys Met Thr Asn Val
            580                 585                 590

GTG AAA CTC TCT GTG CCT CTT GAG GTT GAC ATA AGC ATC GGA AAA AGC      1824
Val Lys Leu Ser Val Pro Leu Glu Val Asp Ile Ser Ile Gly Lys Ser
        595                 600                 605

TGG TCT TGA                                                          1833
Trp Ser
    610

(2) INFORMATION FOR SEQ ID NO:35:

(i) SEQUENCE CHARACTERISTICS:
        (A) LENGTH: 610 amino acids
        (B) TYPE: amino acid
        (D) TOPOLOGY: linear (ii) MOLECULE TYPE: protein (xi) SEQUENCE DESCRIPTION: SEQ ID NO:35:

Met Lys Glu Leu Gln Leu Tyr Glu Glu Ala Glu Pro Thr Gly Tyr Glu
  1               5                  10                  15

Ile Val Lys Asp His Lys Thr Phe Glu Asp Leu Ile Glu Lys Leu Lys
                 20                  25                  30

Glu Val Pro Ser Phe Ala Leu Ala Leu Glu Thr Ser Ser Leu Asp Pro
             35                  40                  45

Phe Asn Cys Glu Ile Val Gly Ile Ser Val Ser Phe Lys Pro Lys Thr
         50                  55                  60

Ala Tyr Tyr Ile Pro Leu His His Arg Asn Ala Gln Asn Leu Asp Glu
 65                  70                  75                  80

Thr Leu Val Leu Ser Lys Leu Lys Glu Ile Leu Glu Asp Pro Ser Ser
                 85                  90                  95

Lys Ile Val Gly Gln Asn Leu Lys Tyr Ala Tyr Lys Val Leu Met Val
                100                 105                 110

Lys Gly Ile Ser Pro Val Tyr Pro His Phe Asp Thr Met Ile Ala Ala
            115                 120                 125

Tyr Leu Leu Glu Pro Asn Glu Lys Lys Phe Asn Leu Glu Asp Leu Ser
130                 135                 140

Leu Lys Phe Leu Gly Tyr Lys Met Thr Ser Tyr Gln Glu Leu Met Ser
145                 150                 155                 160

Phe Ser Ser Pro Leu Phe Gly Phe Ser Phe Ala Asp Val Pro Val Asp
                165                 170                 175

Lys Ala Ala Asn Tyr Ser Cys Glu Asp Ala Asp Ile Thr Tyr Arg Leu
            180                 185                 190

Tyr Lys Ile Leu Ser Met Lys Leu His Glu Ala Glu Leu Glu Asn Val
        195                 200                 205

Phe Tyr Arg Ile Glu Met Pro Leu Val Asn Val Leu Ala Arg Met Glu
    210                 215                 220
```

```
Leu Asn Gly Val Tyr Val Asp Thr Glu Phe Leu Lys Lys Leu Ser Glu
225                 230                 235                 240

Glu Tyr Gly Lys Lys Leu Glu Leu Ala Glu Lys Ile Tyr Gln Ile
            245                 250                 255

Ala Gly Glu Pro Phe Asn Ile Asn Ser Pro Lys Gln Val Ser Lys Ile
                260                 265                 270

Leu Phe Glu Lys Leu Gly Ile Lys Pro Arg Gly Lys Thr Thr Lys Thr
            275                 280                 285

Gly Ala Tyr Ser Thr Arg Ile Glu Val Leu Glu Glu Ile Ala Asn Glu
290                 295                 300

His Glu Ile Val Pro Leu Ile Leu Glu Tyr Arg Lys Ile Gln Lys Leu
305                 310                 315                 320

Lys Ser Thr Tyr Ile Asp Thr Leu Pro Lys Leu Val Asn Pro Lys Thr
                325                 330                 335

Gly Arg Ile His Ala Ser Phe His Gln Thr Gly Thr Ala Thr Gly Arg
                340                 345                 350

Leu Ser Ser Ser Asp Pro Asn Leu Gln Asn Leu Pro Thr Lys Ser Glu
            355                 360                 365

Glu Gly Lys Glu Ile Arg Lys Ala Ile Val Pro Gln Asp Pro Asp Trp
370                 375                 380

Trp Ile Val Ser Ala Asp Tyr Ser Gln Ile Glu Leu Arg Ile Leu Ala
385                 390                 395                 400

His Leu Ser Gly Asp Glu Asn Leu Val Lys Ala Phe Glu Gly Ile
                405                 410                 415

Asp Val His Thr Leu Thr Ala Ser Arg Ile Tyr Asn Val Lys Pro Glu
                420                 425                 430

Glu Val Asn Glu Glu Met Arg Arg Val Gly Lys Met Val Asn Phe Ser
            435                 440                 445

Ile Ile Tyr Gly Val Thr Pro Tyr Gly Leu Ser Val Arg Leu Gly Ile
            450                 455                 460

Pro Val Lys Glu Ala Glu Lys Met Ile Ile Ser Tyr Phe Thr Leu Tyr
465                 470                 475                 480

Pro Lys Val Arg Ser Tyr Ile Gln Gln Val Val Ala Glu Ala Lys Glu
                485                 490                 495

Lys Gly Tyr Val Arg Thr Leu Phe Gly Arg Lys Arg Asp Ile Pro Gln
                500                 505                 510

Leu Met Ala Arg Asp Lys Asn Thr Gln Ser Glu Gly Glu Arg Ile Ala
            515                 520                 525

Ile Asn Thr Pro Ile Gln Gly Thr Ala Ala Asp Ile Ile Lys Leu Ala
            530                 535                 540

Met Ile Asp Ile Asp Glu Leu Arg Lys Arg Asn Met Lys Ser Arg
545                 550                 555                 560

Met Ile Ile Gln Val His Asp Glu Leu Val Phe Glu Val Pro Asp Glu
                565                 570                 575

Glu Lys Glu Glu Leu Val Asp Leu Val Lys Asn Lys Met Thr Asn Val
            580                 585                 590

Val Lys Leu Ser Val Pro Leu Glu Val Asp Ile Ser Ile Gly Lys Ser
            595                 600                 605

Trp Ser
    610
```

(2) INFORMATION FOR SEQ ID NO:36:

(i) SEQUENCE CHARACTERISTICS:

-continued

```
          (A) LENGTH: 1716 base pairs
          (B) TYPE: nucleic acid
          (C) STRANDEDNESS: double
          (D) TOPOLOGY: linear (ii) MOLECULE TYPE: DNA (genomic)

(ix) FEATURE:
          (A) NAME/KEY: CDS
          (B) LOCATION: 1..1713

(xi) SEQUENCE DESCRIPTION: SEQ ID NO:36:

ATG CTT GAA ACG TCC TCC CTT GAC CCG TTC AAC TGT GAG ATA GTC GGC         48
Met Leu Glu Thr Ser Ser Leu Asp Pro Phe Asn Cys Glu Ile Val Gly
 1               5                  10                  15

ATC TCC GTG TCG TTC AAA CCG AAA ACA GCT TAT TAC ATT CCA CTT CAT         96
Ile Ser Val Ser Phe Lys Pro Lys Thr Ala Tyr Tyr Ile Pro Leu His
             20                  25                  30

CAC AGA AAC GCC CAG AAT CTT GAT GAA ACA CTG GTG CTG TCG AAG TTG        144
His Arg Asn Ala Gln Asn Leu Asp Glu Thr Leu Val Leu Ser Lys Leu
         35                  40                  45

AAA GAG ATC CTC GAA GAC CCG TCT TCG AAG ATT GTG GGT CAG AAC CTG        192
Lys Glu Ile Leu Glu Asp Pro Ser Ser Lys Ile Val Gly Gln Asn Leu
 50                  55                  60

AAG TAC GAC TAC AAG GTT CTT ATG GTA AAG GGT ATA TCG CCA GTT TAT        240
Lys Tyr Asp Tyr Lys Val Leu Met Val Lys Gly Ile Ser Pro Val Tyr
 65                  70                  75                  80

CCG CAT TTT GAC ACG ATG ATA GCT GCA TAT TTG CTG GAG CCA AAC GAG        288
Pro His Phe Asp Thr Met Ile Ala Ala Tyr Leu Leu Glu Pro Asn Glu
                 85                  90                  95

AAA AAA TTC AAT CTC GAA GAT CTG TCT TTG AAA TTT CTC GGA TAC AAA        336
Lys Lys Phe Asn Leu Glu Asp Leu Ser Leu Lys Phe Leu Gly Tyr Lys
            100                 105                 110

ATG ACG TCT TAT CAG GAA CTG ATG TCG TTT TCC TCA CCA CTT TTT GGT        384
Met Thr Ser Tyr Gln Glu Leu Met Ser Phe Ser Ser Pro Leu Phe Gly
        115                 120                 125

TTC AGC TTT GCG GAT GTT CCG GTA GAC AAG GCT GCG AAC TAC TCC TGC        432
Phe Ser Phe Ala Asp Val Pro Val Asp Lys Ala Ala Asn Tyr Ser Cys
    130                 135                 140

GAG GAT GCA GAC ATC ACT TAT AGG CTC TAC AAG ATA CTC AGC ATG AAG        480
Glu Asp Ala Asp Ile Thr Tyr Arg Leu Tyr Lys Ile Leu Ser Met Lys
145                 150                 155                 160

CTC CAT GAA GCG GAA CTT GAG AAC GTC TTC TAC AGG ATA GAG ATG CCG        528
Leu His Glu Ala Glu Leu Glu Asn Val Phe Tyr Arg Ile Glu Met Pro
                165                 170                 175

CTT GTG AAC GTT CTT GCA CGC ATG GAA TTG AAC GGG GTG TAT GTG GAC        576
Leu Val Asn Val Leu Ala Arg Met Glu Leu Asn Gly Val Tyr Val Asp
            180                 185                 190

ACA GAA TTC CTG AAA AAG CTC TCG GAG GAG TAC GGC AAA AAG CTC GAG        624
Thr Glu Phe Leu Lys Lys Leu Ser Glu Glu Tyr Gly Lys Lys Leu Glu
        195                 200                 205

GAA CTG GCC GAA AAA ATC TAC CAG ATA GCA GGA GAG CCC TTC AAC ATC        672
Glu Leu Ala Glu Lys Ile Tyr Gln Ile Ala Gly Glu Pro Phe Asn Ile
    210                 215                 220

AAT TCT CCA AAA CAG GTT TCA AAG ATC CTT TTT GAG AAG CTG GGA ATA        720
Asn Ser Pro Lys Gln Val Ser Lys Ile Leu Phe Glu Lys Leu Gly Ile
225                 230                 235                 240

AAA CCC CGT GGA AAA ACG ACA AAA ACA GGA GCG TAC TCT ACC AGG ATA        768
Lys Pro Arg Gly Lys Thr Thr Lys Thr Gly Ala Tyr Ser Thr Arg Ile
                245                 250                 255

GAG GTG TTG GAA GAG ATA GCG AAT GAG CAC GAG ATA GTA CCC CTC ATT        816
Glu Val Leu Glu Glu Ile Ala Asn Glu His Glu Ile Val Pro Leu Ile
```

-continued

```
                       260                      265                      270
CTC GAG TAC AGA AAG ATC CAG AAA CTG AAA TCG ACC TAC ATA GAC ACC            864
Leu Glu Tyr Arg Lys Ile Gln Lys Leu Lys Ser Thr Tyr Ile Asp Thr
            275                      280                      285

CTT CCG AAA CTT GTG AAC CCG AAA ACC GGA AGA ATT CAT GCA TCT TTC            912
Leu Pro Lys Leu Val Asn Pro Lys Thr Gly Arg Ile His Ala Ser Phe
            290                      295                      300

CAC CAG ACG GGT ACC GCC ACT GGC AGG TTG AGT AGC AGT GAT CCA AAT            960
His Gln Thr Gly Thr Ala Thr Gly Arg Leu Ser Ser Ser Asp Pro Asn
305                      310                      315                      320

CTT CAG AAT CTT CCG ACA AAG AGC GAA GAG GGA AAA GAA ATT AGA AAA           1008
Leu Gln Asn Leu Pro Thr Lys Ser Glu Glu Gly Lys Glu Ile Arg Lys
            325                      330                      335

GCG ATT GTG CCC CAG GAT CCA GAC TGG TGG ATC GTC AGT GCG GAT TAT           1056
Ala Ile Val Pro Gln Asp Pro Asp Trp Trp Ile Val Ser Ala Asp Tyr
            340                      345                      350

TCC CAA ATA GAA CTC AGA ATC CTC GCT CAT CTC AGT GGT GAT GAG AAC           1104
Ser Gln Ile Glu Leu Arg Ile Leu Ala His Leu Ser Gly Asp Glu Asn
            355                      360                      365

CTT GTG AAG GCC TTC GAG GAG GGC ATC GAT GTG CAC ACC TTG ACT GCC           1152
Leu Val Lys Ala Phe Glu Glu Gly Ile Asp Val His Thr Leu Thr Ala
            370                      375                      380

TCC AGG ATC TAC AAC GTA AAG CCA GAA GAA GTG AAC GAA GAA ATG CGA           1200
Ser Arg Ile Tyr Asn Val Lys Pro Glu Glu Val Asn Glu Glu Met Arg
385                      390                      395                      400

CGG GTT GGA AAG ATG GTG AAC TTC TCT ATA ATA TAC GGT GTC ACA CCG           1248
Arg Val Gly Lys Met Val Asn Phe Ser Ile Ile Tyr Gly Val Thr Pro
            405                      410                      415

TAC GGT CTT TCT GTG AGA CTT GGA ATA CCG GTT AAA GAA GCA GAA AAG           1296
Tyr Gly Leu Ser Val Arg Leu Gly Ile Pro Val Lys Glu Ala Glu Lys
            420                      425                      430

ATG ATT ATC AGC TAT TTC ACA CTG TAT CCA AAG GTG CGA AGC TAC ATC           1344
Met Ile Ile Ser Tyr Phe Thr Leu Tyr Pro Lys Val Arg Ser Tyr Ile
            435                      440                      445

CAG CAG GTT GTT GCA GAG GCA AAA GAG AAG GGC TAC GTC AGG ACT CTC           1392
Gln Gln Val Val Ala Glu Ala Lys Glu Lys Gly Tyr Val Arg Thr Leu
            450                      455                      460

TTT GGA AGA AAA AGA GAT ATT CCC CAG CTC ATG GCA AGG GAC AAG AAC           1440
Phe Gly Arg Lys Arg Asp Ile Pro Gln Leu Met Ala Arg Asp Lys Asn
465                      470                      475                      480

ACC CAG TCC GAA GGC GAA AGA ATC GCA ATA AAC ACC CCC ATT CAG GGA           1488
Thr Gln Ser Glu Gly Glu Arg Ile Ala Ile Asn Thr Pro Ile Gln Gly
            485                      490                      495

ACG GCG GCA GAT ATA ATA AAA TTG GCT ATG ATA GAT ATA GAC GAG GAG           1536
Thr Ala Ala Asp Ile Ile Lys Leu Ala Met Ile Asp Ile Asp Glu Glu
            500                      505                      510

CTG AGA AAA AGA AAC ATG AAA TCC AGA ATG ATC ATT CAG GTT CAT GAC           1584
Leu Arg Lys Arg Asn Met Lys Ser Arg Met Ile Ile Gln Val His Asp
            515                      520                      525

GAA CTG GTC TTC GAG GTT CCC GAT GAG GAA AAA GAA GAA CTA GTT GAT           1632
Glu Leu Val Phe Glu Val Pro Asp Glu Glu Lys Glu Glu Leu Val Asp
            530                      535                      540

CTG GTG AAG AAC AAA ATG ACA AAT GTG GTG AAA CTC TCT GTG CCT CTT           1680
Leu Val Lys Asn Lys Met Thr Asn Val Val Lys Leu Ser Val Pro Leu
545                      550                      555                      560

GAG GTT GAC ATA AGC ATC GGA AAA AGC TGG TCT TGA                           1716
Glu Val Asp Ile Ser Ile Gly Lys Ser Trp Ser
            565                      570
```

-continued (2) INFORMATION FOR SEQ ID NO:37:

(i) SEQUENCE CHARACTERISTICS:
        (A) LENGTH: 571 amino acids
        (B) TYPE: amino acid
        (D) TOPOLOGY: linear (ii) MOLECULE TYPE: protein (xi) SEQUENCE DESCRIPTION: SEQ ID NO:37:

```
Met Leu Glu Thr Ser Ser Leu Asp Pro Phe Asn Cys Glu Ile Val Gly
 1               5                  10                  15

Ile Ser Val Ser Phe Lys Pro Lys Thr Ala Tyr Tyr Ile Pro Leu His
             20                  25                  30

His Arg Asn Ala Gln Asn Leu Asp Glu Thr Leu Val Leu Ser Lys Leu
         35                  40                  45

Lys Glu Ile Leu Glu Asp Pro Ser Ser Lys Ile Val Gly Gln Asn Leu
     50                  55                  60

Lys Tyr Asp Tyr Lys Val Leu Met Val Lys Gly Ile Ser Pro Val Tyr
 65                  70                  75                  80

Pro His Phe Asp Thr Met Ile Ala Ala Tyr Leu Leu Glu Pro Asn Glu
                 85                  90                  95

Lys Lys Phe Asn Leu Glu Asp Leu Ser Leu Lys Phe Leu Gly Tyr Lys
            100                 105                 110

Met Thr Ser Tyr Gln Glu Leu Met Ser Phe Ser Ser Pro Leu Phe Gly
        115                 120                 125

Phe Ser Phe Ala Asp Val Pro Val Asp Lys Ala Ala Asn Tyr Ser Cys
    130                 135                 140

Glu Asp Ala Asp Ile Thr Tyr Arg Leu Tyr Lys Ile Leu Ser Met Lys
145                 150                 155                 160

Leu His Glu Ala Glu Leu Glu Asn Val Phe Tyr Arg Ile Glu Met Pro
                165                 170                 175

Leu Val Asn Val Leu Ala Arg Met Glu Leu Asn Gly Val Tyr Val Asp
            180                 185                 190

Thr Glu Phe Leu Lys Lys Leu Ser Glu Glu Tyr Gly Lys Lys Leu Glu
        195                 200                 205

Glu Leu Ala Glu Lys Ile Tyr Gln Ile Ala Gly Glu Pro Phe Asn Ile
    210                 215                 220

Asn Ser Pro Lys Gln Val Ser Lys Ile Leu Phe Glu Lys Leu Gly Ile
225                 230                 235                 240

Lys Pro Arg Gly Lys Thr Thr Lys Thr Gly Ala Tyr Ser Thr Arg Ile
                245                 250                 255

Glu Val Leu Glu Glu Ile Ala Asn Glu His Glu Ile Val Pro Leu Ile
            260                 265                 270

Leu Glu Tyr Arg Lys Ile Gln Lys Leu Lys Ser Thr Tyr Ile Asp Thr
        275                 280                 285

Leu Pro Lys Leu Val Asn Pro Lys Thr Gly Arg Ile His Ala Ser Phe
    290                 295                 300

His Gln Thr Gly Thr Ala Thr Gly Arg Leu Ser Ser Asp Pro Asn
305                 310                 315                 320

Leu Gln Asn Leu Pro Thr Lys Ser Glu Glu Gly Lys Glu Ile Arg Lys
                325                 330                 335

Ala Ile Val Pro Gln Asp Pro Asp Trp Trp Ile Val Ser Ala Asp Tyr
            340                 345                 350

Ser Gln Ile Glu Leu Arg Ile Leu Ala His Leu Ser Gly Asp Glu Asn
        355                 360                 365
```

-continued

```
Leu Val Lys Ala Phe Glu Glu Gly Ile Asp Val His Thr Leu Thr Ala
    370                 375                 380
Ser Arg Ile Tyr Asn Val Lys Pro Glu Val Asn Glu Glu Met Arg
385                 390                 395                 400
Arg Val Gly Lys Met Val Asn Phe Ser Ile Ile Tyr Gly Val Thr Pro
                405                 410                 415
Tyr Gly Leu Ser Val Arg Leu Gly Ile Pro Val Lys Glu Ala Glu Lys
                420                 425                 430
Met Ile Ile Ser Tyr Phe Thr Leu Tyr Pro Lys Val Arg Ser Tyr Ile
            435                 440                 445
Gln Gln Val Val Ala Glu Ala Lys Glu Lys Gly Tyr Val Arg Thr Leu
    450                 455                 460
Phe Gly Arg Lys Arg Asp Ile Pro Gln Leu Met Ala Arg Asp Lys Asn
465                 470                 475                 480
Thr Gln Ser Glu Gly Glu Arg Ile Ala Ile Asn Thr Pro Ile Gln Gly
                485                 490                 495
Thr Ala Ala Asp Ile Ile Lys Leu Ala Met Ile Asp Ile Asp Glu Glu
                500                 505                 510
Leu Arg Lys Arg Asn Met Lys Ser Arg Met Ile Ile Gln Val His Asp
            515                 520                 525
Glu Leu Val Phe Glu Val Pro Asp Glu Glu Lys Glu Glu Leu Val Asp
    530                 535                 540
Leu Val Lys Asn Lys Met Thr Asn Val Val Lys Leu Ser Val Pro Leu
545                 550                 555                 560
Glu Val Asp Ile Ser Ile Gly Lys Ser Trp Ser
                565                 570
```

(2) INFORMATION FOR SEQ ID NO:38:

(i) SEQUENCE CHARACTERISTICS:
        (A) LENGTH: 1485 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1482

(xi) SEQUENCE DESCRIPTION: SEQ ID NO:38:

```
ATG AAG GAA CTT CAA CTG TAC GAA GAA GCA GAA CCC ACC GGA TAC GAA         48
Met Lys Glu Leu Gln Leu Tyr Glu Glu Ala Glu Pro Thr Gly Tyr Glu
1               5                   10                  15

ATC GTG AAG GAT CAT AAG ACC TTC GAA GAT CTG TCT TTG AAA TTT CTC         96
Ile Val Lys Asp His Lys Thr Phe Glu Asp Leu Ser Leu Lys Phe Leu
                20                  25                  30

GGA TAC AAA ATG ACG TCT TAT CAG GAA CTG ATG TCG TTT TCC TCA CCA        144
Gly Tyr Lys Met Thr Ser Tyr Gln Glu Leu Met Ser Phe Ser Ser Pro
            35                  40                  45

CTT TTT GGT TTC AGC TTT GCG GAT GTT CCG GTA GAC AAG GCT GCG AAC        192
Leu Phe Gly Phe Ser Phe Ala Asp Val Pro Val Asp Lys Ala Ala Asn
    50                  55                  60

TAC TCC TGC GAG GAT GCA GAC ATC ACT TAT AGG CTC TAC AAG ATA CTC        240
Tyr Ser Cys Glu Asp Ala Asp Ile Thr Tyr Arg Leu Tyr Lys Ile Leu
65                  70                  75                  80

AGC ATG AAG CTC CAT GAA GCG GAA CTT GAG AAC GTC TTC TAC AGG ATA        288
Ser Met Lys Leu His Glu Ala Glu Leu Glu Asn Val Phe Tyr Arg Ile
```

```
              85                  90                  95
GAG ATG CCG CTT GTG AAC GTT CTT GCA CGC ATG GAA TTG AAC GGG GTG      336
Glu Met Pro Leu Val Asn Val Leu Ala Arg Met Glu Leu Asn Gly Val
            100                 105                 110

TAT GTG GAC ACA GAA TTC CTG AAA AAG CTC TCG GAG GAG TAC GGC AAA      384
Tyr Val Asp Thr Glu Phe Leu Lys Lys Leu Ser Glu Glu Tyr Gly Lys
        115                 120                 125

AAG CTC GAG GAA CTG GCC GAA AAA ATC TAC CAG ATA GCA GGA GAG CCC      432
Lys Leu Glu Glu Leu Ala Glu Lys Ile Tyr Gln Ile Ala Gly Glu Pro
130                 135                 140

TTC AAC ATC AAT TCT CCA AAA CAG GTT TCA AAG ATC CTT TTT GAG AAG      480
Phe Asn Ile Asn Ser Pro Lys Gln Val Ser Lys Ile Leu Phe Glu Lys
145                 150                 155                 160

CTG GGA ATA AAA CCC CGT GGA AAA ACG ACA AAA ACA GGA GCG TAC TCT      528
Leu Gly Ile Lys Pro Arg Gly Lys Thr Thr Lys Thr Gly Ala Tyr Ser
                165                 170                 175

ACC AGG ATA GAG GTG TTG GAA GAG ATA GCG AAT GAG CAC GAG ATA GTA      576
Thr Arg Ile Glu Val Leu Glu Glu Ile Ala Asn Glu His Glu Ile Val
            180                 185                 190

CCC CTC ATT CTC GAG TAC AGA AAG ATC CAG AAA CTG AAA TCG ACC TAC      624
Pro Leu Ile Leu Glu Tyr Arg Lys Ile Gln Lys Leu Lys Ser Thr Tyr
        195                 200                 205

ATA GAC ACC CTT CCG AAA CTT GTG AAC CCG AAA ACC GGA AGA ATT CAT      672
Ile Asp Thr Leu Pro Lys Leu Val Asn Pro Lys Thr Gly Arg Ile His
210                 215                 220

GCA TCT TTC CAC CAG ACG GGT ACC GCC ACT GGC AGG TTG AGT AGC AGT      720
Ala Ser Phe His Gln Thr Gly Thr Ala Thr Gly Arg Leu Ser Ser Ser
225                 230                 235                 240

GAT CCA AAT CTT CAG AAT CTT CCG ACA AAG AGC GAA GAG GGA AAA GAA      768
Asp Pro Asn Leu Gln Asn Leu Pro Thr Lys Ser Glu Glu Gly Lys Glu
                245                 250                 255

ATT AGA AAA GCG ATT GTG CCC CAG GAT CCA GAC TGG TGG ATC GTC AGT      816
Ile Arg Lys Ala Ile Val Pro Gln Asp Pro Asp Trp Trp Ile Val Ser
            260                 265                 270

GCG GAT TAT TCC CAA ATA GAA CTC AGA ATC CTC GCT CAT CTC AGT GGT      864
Ala Asp Tyr Ser Gln Ile Glu Leu Arg Ile Leu Ala His Leu Ser Gly
        275                 280                 285

GAT GAG AAC CTT GTG AAG GCC TTC GAG GAG GGC ATC GAT GTG CAC ACC      912
Asp Glu Asn Leu Val Lys Ala Phe Glu Glu Gly Ile Asp Val His Thr
        290                 295                 300

TTG ACT GCC TCC AGG ATC TAC AAC GTA AAG CCA GAA GAA GTG AAC GAA      960
Leu Thr Ala Ser Arg Ile Tyr Asn Val Lys Pro Glu Glu Val Asn Glu
305                 310                 315                 320

GAA ATG CGA CGG GTT GGA AAG ATG GTG AAC TTC TCT ATA ATA TAC GGT     1008
Glu Met Arg Arg Val Gly Lys Met Val Asn Phe Ser Ile Ile Tyr Gly
                325                 330                 335

GTC ACA CCG TAC GGT CTT TCT GTG AGA CTT GGA ATA CCG GTT AAA GAA     1056
Val Thr Pro Tyr Gly Leu Ser Val Arg Leu Gly Ile Pro Val Lys Glu
            340                 345                 350

GCA GAA AAG ATG ATT ATC AGC TAT TTC ACA CTG TAT CCA AAG GTG CGA     1104
Ala Glu Lys Met Ile Ile Ser Tyr Phe Thr Leu Tyr Pro Lys Val Arg
        355                 360                 365

AGC TAC ATC CAG CAG GTT GTT GCA GAG GCA AAA GAG AAG GGC TAC GTC     1152
Ser Tyr Ile Gln Gln Val Val Ala Glu Ala Lys Glu Lys Gly Tyr Val
        370                 375                 380

AGG ACT CTC TTT GGA AGA AAA AGA GAT ATT CCC CAG CTC ATG GCA AGG     1200
Arg Thr Leu Phe Gly Arg Lys Arg Asp Ile Pro Gln Leu Met Ala Arg
385                 390                 395                 400

GAC AAG AAC ACC CAG TCC GAA GGC GAA AGA ATC GCA ATA AAC ACC CCC     1248
```

```
Asp Lys Asn Thr Gln Ser Glu Gly Glu Arg Ile Ala Ile Asn Thr Pro
                405                 410                 415

ATT CAG GGA ACG GCG GCA GAT ATA ATA AAA TTG GCT ATG ATA GAT ATA      1296
Ile Gln Gly Thr Ala Ala Asp Ile Ile Lys Leu Ala Met Ile Asp Ile
            420                 425                 430

GAC GAG GAG CTG AGA AAA AGA AAC ATG AAA TCC AGA ATG ATC ATT CAG      1344
Asp Glu Glu Leu Arg Lys Arg Asn Met Lys Ser Arg Met Ile Ile Gln
            435                 440                 445

GTT CAT GAC GAA CTG GTC TTC GAG GTT CCC GAT GAG GAA AAA GAA GAA      1392
Val His Asp Glu Leu Val Phe Glu Val Pro Asp Glu Glu Lys Glu Glu
        450                 455                 460

CTA GTT GAT CTG GTG AAG AAC AAA ATG ACA AAT GTG GTG AAA CTC TCT      1440
Leu Val Asp Leu Val Lys Asn Lys Met Thr Asn Val Val Lys Leu Ser
465                 470                 475                 480

GTG CCT CTT GAG GTT GAC ATA AGC ATC GGA AAA AGC TGG TCT              1482
Val Pro Leu Glu Val Asp Ile Ser Ile Gly Lys Ser Trp Ser
                485                 490

TGA                                                                   1485

(2) INFORMATION FOR SEQ ID NO:39:

(i) SEQUENCE CHARACTERISTICS:
        (A) LENGTH: 494 amino acids
        (B) TYPE: amino acid
        (D) TOPOLOGY: linear (ii) MOLECULE TYPE: protein (xi) SEQUENCE DESCRIPTION: SEQ ID NO:39:

Met Lys Glu Leu Gln Leu Tyr Glu Glu Ala Glu Pro Thr Gly Tyr Glu
1               5                   10                  15

Ile Val Lys Asp His Lys Thr Phe Glu Asp Leu Ser Leu Lys Phe Leu
                20                  25                  30

Gly Tyr Lys Met Thr Ser Tyr Gln Glu Leu Met Ser Phe Ser Ser Pro
            35                  40                  45

Leu Phe Gly Phe Ser Phe Ala Asp Val Pro Val Asp Lys Ala Ala Asn
        50                  55                  60

Tyr Ser Cys Glu Asp Ala Asp Ile Thr Tyr Arg Leu Tyr Lys Ile Leu
65                  70                  75                  80

Ser Met Lys Leu His Glu Ala Glu Leu Glu Asn Val Phe Tyr Arg Ile
                85                  90                  95

Glu Met Pro Leu Val Asn Val Leu Ala Arg Met Glu Leu Asn Gly Val
                100                 105                 110

Tyr Val Asp Thr Glu Phe Leu Lys Lys Leu Ser Glu Glu Tyr Gly Lys
            115                 120                 125

Lys Leu Glu Glu Leu Ala Glu Lys Ile Tyr Gln Ile Ala Gly Glu Pro
        130                 135                 140

Phe Asn Ile Asn Ser Pro Lys Gln Val Ser Lys Ile Leu Phe Glu Lys
145                 150                 155                 160

Leu Gly Ile Lys Pro Arg Gly Lys Thr Thr Lys Thr Gly Ala Tyr Ser
                165                 170                 175

Thr Arg Ile Glu Val Leu Glu Glu Ile Ala Asn Glu His Glu Ile Val
            180                 185                 190

Pro Leu Ile Leu Glu Tyr Arg Lys Ile Gln Lys Leu Lys Ser Thr Tyr
        195                 200                 205

Ile Asp Thr Leu Pro Lys Leu Val Asn Pro Lys Thr Gly Arg Ile His
210                 215                 220
```

```
Ala Ser Phe His Gln Thr Gly Thr Ala Thr Gly Arg Leu Ser Ser Ser
225                 230                 235                 240

Asp Pro Asn Leu Gln Asn Leu Pro Thr Lys Ser Glu Glu Gly Lys Glu
            245                 250                 255

Ile Arg Lys Ala Ile Val Pro Gln Asp Pro Trp Trp Ile Val Ser
            260                 265                 270

Ala Asp Tyr Ser Gln Ile Glu Leu Arg Ile Leu Ala His Leu Ser Gly
            275                 280                 285

Asp Glu Asn Leu Val Lys Ala Phe Glu Glu Gly Ile Asp Val His Thr
            290                 295                 300

Leu Thr Ala Ser Arg Ile Tyr Asn Val Lys Pro Glu Glu Val Asn Glu
305                 310                 315                 320

Glu Met Arg Arg Val Gly Lys Met Val Asn Phe Ser Ile Ile Tyr Gly
                325                 330                 335

Val Thr Pro Tyr Gly Leu Ser Val Arg Leu Gly Ile Pro Val Lys Glu
                340                 345                 350

Ala Glu Lys Met Ile Ile Ser Tyr Phe Thr Leu Tyr Pro Lys Val Arg
                355                 360                 365

Ser Tyr Ile Gln Gln Val Val Ala Glu Ala Lys Glu Lys Gly Tyr Val
370                 375                 380

Arg Thr Leu Phe Gly Arg Lys Arg Asp Ile Pro Gln Leu Met Ala Arg
385                 390                 395                 400

Asp Lys Asn Thr Gln Ser Glu Gly Glu Arg Ile Ala Ile Asn Thr Pro
                405                 410                 415

Ile Gln Gly Thr Ala Ala Asp Ile Ile Lys Leu Ala Met Ile Asp Ile
                420                 425                 430

Asp Glu Glu Leu Arg Lys Arg Asn Met Lys Ser Arg Met Ile Ile Gln
            435                 440                 445

Val His Asp Glu Leu Val Phe Glu Val Pro Asp Glu Glu Lys Glu Glu
    450                 455                 460

Leu Val Asp Leu Val Lys Asn Lys Met Thr Asn Val Val Lys Leu Ser
465                 470                 475                 480

Val Pro Leu Glu Val Asp Ile Ser Ile Gly Lys Ser Trp Ser
                485                 490

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

CGCCAGGGTT TTCCCAGTCA CGAC                                              24

(2) INFORMATION FOR SEQ ID NO:41:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:
```

```
ATAAGCGCCA TTGATGTTCC TCTCTACTCG AAAGTTAGAG AGGACACACC CGATCCCTAT      60

AGTGAGTCGT ATTA                                                       74
```

(2) INFORMATION FOR SEQ ID NO:42:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

```
TAATACGACT CACTATAGGG CGAAT                                           25
```

(2) INFORMATION FOR SEQ ID NO:43:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

```
GAATCGTCGT ATGCAGTGAA AACTC                                           25
```

(2) INFORMATION FOR SEQ ID NO:44:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

```
CTTGATTGAC AAGGATGGAT GGCTA                                           25
```

(2) INFORMATION FOR SEQ ID NO:45:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

```
CATGGTTTAA ATCCTGTGTG AAATTGTTAT CCG                                  33
```

(2) INFORMATION FOR SEQ ID NO:46:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

```
CGGATAACAA TTTCACACAG GATTTAAAC                                       29
```

```
(2) INFORMATION FOR SEQ ID NO:47:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

TAATACGACT CACTATAGGG CGAAT                                              25

(2) INFORMATION FOR SEQ ID NO:48:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

CATGCCATGG CATGCATTTA CGTTGACACC A                                       31

(2) INFORMATION FOR SEQ ID NO:49:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

TCCCCCGGGT TGCGCTCACT GCCCGCTTTC CAGT                                    34

(2) INFORMATION FOR SEQ ID NO:50:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

AGCTTATCGA TGGCACTTTT CGGGGAAATG TGCG                                    34

(2) INFORMATION FOR SEQ ID NO:51:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

AGCTTATCGA TAAGCGATGC CGGGAGCAGA CAAGC                                   35

(2) INFORMATION FOR SEQ ID NO:52:

(i) SEQUENCE CHARACTERISTICS:
```

```
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:52:

GGAAAGATGG TTAACTACTC TATAATATAC G                                     31

(2) INFORMATION FOR SEQ ID NO:53:

(i) SEQUENCE CHARACTERISTICS:
            (A) LENGTH: 1833 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 1..1833

(xi) SEQUENCE DESCRIPTION: SEQ ID NO:53:

ATG AAG GAA CTT CAA CTG TAC GAA GAA GCA GAA CCC ACC GGA TAC GAA        48
Met Lys Glu Leu Gln Leu Tyr Glu Glu Ala Glu Pro Thr Gly Tyr Glu
 1               5                  10                  15

ATC GTG AAG GAT CAT AAG ACC TTC GAA GAT CTC ATC GAA AAG CTG AAG        96
Ile Val Lys Asp His Lys Thr Phe Glu Asp Leu Ile Glu Lys Leu Lys
                20                  25                  30

GAG GTT CCA TCT TTT GCC CTG GCC CTT GAA ACG TCC TCC CTT GAC CCG       144
Glu Val Pro Ser Phe Ala Leu Ala Leu Glu Thr Ser Ser Leu Asp Pro
            35                  40                  45

TTC AAC TGT GAG ATA GTC GGC ATC TCC GTG TCG TTC AAA CCG AAA ACA       192
Phe Asn Cys Glu Ile Val Gly Ile Ser Val Ser Phe Lys Pro Lys Thr
         50                  55                  60

GCT TAT TAC ATT CCA CTT CAT CAC AGA AAC GCC CAG AAT CTT GAT GAA       240
Ala Tyr Tyr Ile Pro Leu His His Arg Asn Ala Gln Asn Leu Asp Glu
 65                  70                  75                  80

ACA CTG GTG CTG TCG AAG TTG AAA GAG ATC CTC GAA GAC CCG TCT TCG       288
Thr Leu Val Leu Ser Lys Leu Lys Glu Ile Leu Glu Asp Pro Ser Ser
                 85                  90                  95

AAG ATT GTG GGT CAG AAC CTG AAG TAC GCG TAC AAG GTT CTT ATG GTA       336
Lys Ile Val Gly Gln Asn Leu Lys Tyr Ala Tyr Lys Val Leu Met Val
                100                 105                 110

AAG GGT ATA TCG CCA GTT TAT CCG CAT TTT GAC ACG ATG ATA GCT GCA       384
Lys Gly Ile Ser Pro Val Tyr Pro His Phe Asp Thr Met Ile Ala Ala
            115                 120                 125

TAT TTG CTG GAG CCA AAC GAG AAA AAA TTC AAT CTC GAA GAT CTG TCT       432
Tyr Leu Leu Glu Pro Asn Glu Lys Lys Phe Asn Leu Glu Asp Leu Ser
        130                 135                 140

TTG AAA TTT CTC GGA TAC AAA ATG ACG TCT TAT CAG GAA CTG ATG TCG       480
Leu Lys Phe Leu Gly Tyr Lys Met Thr Ser Tyr Gln Glu Leu Met Ser
145                 150                 155                 160

TTT TCC TCA CCA CTT TTT GGT TTC AGC TTT GCG GAT GTT CCG GTA GAC       528
Phe Ser Ser Pro Leu Phe Gly Phe Ser Phe Ala Asp Val Pro Val Asp
                165                 170                 175

AAG GCT GCG AAC TAC TCC TGC GAG GAT GCA GAC ATC ACT TAT AGG CTC       576
Lys Ala Ala Asn Tyr Ser Cys Glu Asp Ala Asp Ile Thr Tyr Arg Leu
                180                 185                 190

TAC AAG ATA CTC AGC ATG AAG CTC CAT GAA GCG GAA CTT GAG AAC GTC       624
Tyr Lys Ile Leu Ser Met Lys Leu His Glu Ala Glu Leu Glu Asn Val
            195                 200                 205
```

```
TTC TAC AGG ATA GAG ATG CCG CTT GTG AAC GTT CTT GCA CGC ATG GAA      672
Phe Tyr Arg Ile Glu Met Pro Leu Val Asn Val Leu Ala Arg Met Glu
210                 215                 220

TTG AAC GGG GTG TAT GTG GAC ACA GAA TTC CTG AAA AAG CTC TCG GAG      720
Leu Asn Gly Val Tyr Val Asp Thr Glu Phe Leu Lys Lys Leu Ser Glu
225                 230                 235                 240

GAG TAC GGC AAA AAG CTC GAG GAA CTG GCC GAA AAA ATC TAC CAG ATA      768
Glu Tyr Gly Lys Lys Leu Glu Glu Leu Ala Glu Lys Ile Tyr Gln Ile
                245                 250                 255

GCA GGA GAG CCC TTC AAC ATC AAT TCT CCA AAA CAG GTT TCA AAG ATC      816
Ala Gly Glu Pro Phe Asn Ile Asn Ser Pro Lys Gln Val Ser Lys Ile
            260                 265                 270

CTT TTT GAG AAG CTG GGA ATA AAA CCC CGT GGA AAA ACG ACA AAA ACA      864
Leu Phe Glu Lys Leu Gly Ile Lys Pro Arg Gly Lys Thr Thr Lys Thr
        275                 280                 285

GGA GCG TAC TCT ACC AGG ATA GAG GTG TTG GAA GAG ATA GCG AAT GAG      912
Gly Ala Tyr Ser Thr Arg Ile Glu Val Leu Glu Glu Ile Ala Asn Glu
290                 295                 300

CAC GAG ATA GTA CCC CTC ATT CTC GAG TAC AGA AAG ATC CAG AAA CTG      960
His Glu Ile Val Pro Leu Ile Leu Glu Tyr Arg Lys Ile Gln Lys Leu
305                 310                 315                 320

AAA TCG ACC TAC ATA GAC ACC CTT CCG AAA CTT GTG AAC CCG AAA ACC     1008
Lys Ser Thr Tyr Ile Asp Thr Leu Pro Lys Leu Val Asn Pro Lys Thr
                325                 330                 335

GGA AGA ATT CAT GCA TCT TTC CAC CAG ACG GGT ACC GCC ACT GGC AGG     1056
Gly Arg Ile His Ala Ser Phe His Gln Thr Gly Thr Ala Thr Gly Arg
            340                 345                 350

TTG AGT AGC AGT GAT CCA AAT CTT CAG AAT CTT CCG ACA AAG AGC GAA     1104
Leu Ser Ser Ser Asp Pro Asn Leu Gln Asn Leu Pro Thr Lys Ser Glu
        355                 360                 365

GAG GGA AAA GAA ATT AGA AAA GCG ATT GTG CCC CAG GAT CCA GAC TGG     1152
Glu Gly Lys Glu Ile Arg Lys Ala Ile Val Pro Gln Asp Pro Asp Trp
370                 375                 380

TGG ATC GTC AGT GCG GAT TAT TCC CAA ATA GAA CTC AGA ATC CTC GCT     1200
Trp Ile Val Ser Ala Asp Tyr Ser Gln Ile Glu Leu Arg Ile Leu Ala
385                 390                 395                 400

CAT CTC AGT GGT GAT GAG AAC CTT GTG AAG GCC TTC GAG GAG GGC ATC     1248
His Leu Ser Gly Asp Glu Asn Leu Val Lys Ala Phe Glu Glu Gly Ile
                405                 410                 415

GAT GTG CAC ACC TTG ACT GCC TCC AGG ATC TAC AAC GTA AAG CCA GAA     1296
Asp Val His Thr Leu Thr Ala Ser Arg Ile Tyr Asn Val Lys Pro Glu
            420                 425                 430

GAA GTG AAC GAA GAA ATG CGA CGG GTT GGA AAG ATG GTT AAC TAC TCT     1344
Glu Val Asn Glu Glu Met Arg Arg Val Gly Lys Met Val Asn Tyr Ser
        435                 440                 445

ATA ATA TAC GGT GTC ACA CCG TAC GGT CTT TCT GTG AGA CTT GGA ATA     1392
Ile Ile Tyr Gly Val Thr Pro Tyr Gly Leu Ser Val Arg Leu Gly Ile
450                 455                 460

CCG GTT AAA GAA GCA GAA AAG ATG ATT ATC AGC TAT TTC ACA CTG TAT     1440
Pro Val Lys Glu Ala Glu Lys Met Ile Ile Ser Tyr Phe Thr Leu Tyr
465                 470                 475                 480

CCA AAG GTG CGA AGC TAC ATC CAG CAG GTT GTT GCA GAG GCA AAA GAG     1488
Pro Lys Val Arg Ser Tyr Ile Gln Gln Val Val Ala Glu Ala Lys Glu
                485                 490                 495

AAG GGC TAC GTC AGG ACT CTC TTT GGA AGA AAA AGA GAT ATT CCC CAG     1536
Lys Gly Tyr Val Arg Thr Leu Phe Gly Arg Lys Arg Asp Ile Pro Gln
            500                 505                 510

CTC ATG GCA AGG GAC AAG AAC ACC CAG TCC GAA GGC GAA AGA ATC GCA     1584
Leu Met Ala Arg Asp Lys Asn Thr Gln Ser Glu Gly Glu Arg Ile Ala
```

```
                515                 520                 525
ATA AAC ACC CCC ATT CAG GGA ACG GCG GCA GAT ATA ATA AAA TTG GCT    1632
Ile Asn Thr Pro Ile Gln Gly Thr Ala Ala Asp Ile Ile Lys Leu Ala
        530                 535                 540

ATG ATA GAT ATA GAC GAG GAG CTG AGA AAA AGA AAC ATG AAA TCC AGA    1680
Met Ile Asp Ile Asp Glu Glu Leu Arg Lys Arg Asn Met Lys Ser Arg
545                 550                 555                 560

ATG ATC ATT CAG GTT CAT GAC GAA CTG GTC TTC GAG GTT CCC GAT GAG    1728
Met Ile Ile Gln Val His Asp Glu Leu Val Phe Glu Val Pro Asp Glu
                565                 570                 575

GAA AAA GAA GAA CTA GTT GAT CTG GTG AAG AAC AAA ATG ACA AAT GTG    1776
Glu Lys Glu Glu Leu Val Asp Leu Val Lys Asn Lys Met Thr Asn Val
            580                 585                 590

GTG AAA CTC TCT GTG CCT CTT GAG GTT GAC ATA AGC ATC GGA AAA AGC    1824
Val Lys Leu Ser Val Pro Leu Glu Val Asp Ile Ser Ile Gly Lys Ser
        595                 600                 605

TGG TCT TGA                                                        1833
Trp Ser *
    610

(2) INFORMATION FOR SEQ ID NO:54:

(i) SEQUENCE CHARACTERISTICS:
        (A) LENGTH:  610 amino acids
        (B) TYPE: amino acid
        (D) TOPOLOGY: linear (ii) MOLECULE TYPE: protein (xi) SEQUENCE DESCRIPTION: SEQ ID NO:54:

Met Lys Glu Leu Gln Leu Tyr Glu Glu Ala Glu Pro Thr Gly Tyr Glu
  1               5                  10                  15

Ile Val Lys Asp His Lys Thr Phe Glu Asp Leu Ile Glu Lys Leu Lys
                 20                  25                  30

Glu Val Pro Ser Phe Ala Leu Ala Leu Glu Thr Ser Ser Leu Asp Pro
             35                  40                  45

Phe Asn Cys Glu Ile Val Gly Ile Ser Val Ser Phe Lys Pro Lys Thr
         50                  55                  60

Ala Tyr Tyr Ile Pro Leu His His Arg Asn Ala Gln Asn Leu Asp Glu
 65                  70                  75                  80

Thr Leu Val Leu Ser Lys Leu Lys Glu Ile Leu Glu Asp Pro Ser Ser
                 85                  90                  95

Lys Ile Val Gly Gln Asn Leu Lys Tyr Ala Tyr Lys Val Leu Met Val
            100                 105                 110

Lys Gly Ile Ser Pro Val Tyr Pro His Phe Asp Thr Met Ile Ala Ala
        115                 120                 125

Tyr Leu Leu Glu Pro Asn Glu Lys Lys Phe Asn Leu Glu Asp Leu Ser
    130                 135                 140

Leu Lys Phe Leu Gly Tyr Lys Met Thr Ser Tyr Gln Glu Leu Met Ser
145                 150                 155                 160

Phe Ser Ser Pro Leu Phe Gly Phe Ser Phe Ala Asp Val Pro Val Asp
                165                 170                 175

Lys Ala Ala Asn Tyr Ser Cys Glu Asp Ala Asp Ile Thr Tyr Arg Leu
            180                 185                 190

Tyr Lys Ile Leu Ser Met Lys Leu His Glu Ala Glu Leu Glu Asn Val
        195                 200                 205

Phe Tyr Arg Ile Glu Met Pro Leu Val Asn Val Leu Ala Arg Met Glu
    210                 215                 220
```

-continued

Leu Asn Gly Val Tyr Val Asp Thr Glu Phe Leu Lys Lys Leu Ser Glu
225                 230                 235                 240

Glu Tyr Gly Lys Lys Leu Glu Glu Leu Ala Glu Lys Ile Tyr Gln Ile
            245                 250                 255

Ala Gly Glu Pro Phe Asn Ile Asn Ser Pro Lys Gln Val Ser Lys Ile
            260                 265                 270

Leu Phe Glu Lys Leu Gly Ile Lys Pro Arg Gly Lys Thr Thr Lys Thr
        275                 280                 285

Gly Ala Tyr Ser Thr Arg Ile Glu Val Leu Glu Ile Ala Asn Glu
        290                 295                 300

His Glu Ile Val Pro Leu Ile Leu Glu Tyr Arg Lys Ile Gln Lys Leu
305                 310                 315                 320

Lys Ser Thr Tyr Ile Asp Thr Leu Pro Lys Leu Val Asn Pro Lys Thr
                325                 330                 335

Gly Arg Ile His Ala Ser Phe His Gln Thr Gly Thr Ala Thr Gly Arg
                340                 345                 350

Leu Ser Ser Asp Pro Asn Leu Gln Asn Leu Pro Thr Lys Ser Glu
        355                 360                 365

Glu Gly Lys Glu Ile Arg Lys Ala Ile Val Pro Gln Asp Pro Asp Trp
370                 375                 380

Trp Ile Val Ser Ala Asp Tyr Ser Gln Ile Glu Leu Arg Ile Leu Ala
385                 390                 395                 400

His Leu Ser Gly Asp Glu Asn Leu Val Lys Ala Phe Glu Glu Gly Ile
                405                 410                 415

Asp Val His Thr Leu Thr Ala Ser Arg Ile Tyr Asn Val Lys Pro Glu
            420                 425                 430

Glu Val Asn Glu Glu Met Arg Arg Val Gly Lys Met Val Asn Tyr Ser
        435                 440                 445

Ile Ile Tyr Gly Val Thr Pro Tyr Gly Leu Ser Val Arg Leu Gly Ile
        450                 455                 460

Pro Val Lys Glu Ala Glu Lys Met Ile Ile Ser Tyr Phe Thr Leu Tyr
465                 470                 475                 480

Pro Lys Val Arg Ser Tyr Ile Gln Gln Val Val Ala Glu Ala Lys Glu
            485                 490                 495

Lys Gly Tyr Val Arg Thr Leu Phe Gly Arg Lys Arg Asp Ile Pro Gln
        500                 505                 510

Leu Met Ala Arg Asp Lys Asn Thr Gln Ser Gly Glu Arg Ile Ala
        515                 520                 525

Ile Asn Thr Pro Ile Gln Gly Thr Ala Ala Asp Ile Ile Lys Leu Ala
        530                 535                 540

Met Ile Asp Ile Asp Glu Glu Leu Arg Lys Arg Asn Met Lys Ser Arg
545                 550                 555                 560

Met Ile Ile Gln Val His Asp Glu Leu Val Phe Glu Val Pro Asp Glu
                565                 570                 575

Glu Lys Glu Glu Leu Val Asp Leu Val Lys Asn Lys Met Thr Asn Val
            580                 585                 590

Val Lys Leu Ser Val Pro Leu Glu Val Asp Ile Ser Ile Gly Lys Ser
        595                 600                 605

Trp Ser
    610

(2) INFORMATION FOR SEQ ID NO:55:

-continued

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

GTGACCCATG GCGATGCCTG                                                  20

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

GGCGAAGCGG CATGCATTTA                                                  20

(2) INFORMATION FOR SEQ ID NO:57:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

CATCACGGTT TTGGAATGTT TACTA                                            25
```